(12) United States Patent
Lu et al.

(10) Patent No.: US 11,718,860 B2
(45) Date of Patent: Aug. 8, 2023

(54) SYNTHETIC PROMOTERS

(71) Applicant: Massachusetts Institute of Technology, Cambridge, MA (US)

(72) Inventors: Timothy Kuan-Ta Lu, Cambridge, MA (US); Lior Nissim, Cambridge, MA (US); Ming-Ru Wu, Brookline, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 572 days.

(21) Appl. No.: 16/493,340

(22) PCT Filed: Mar. 13, 2018

(86) PCT No.: PCT/US2018/022093
§ 371 (c)(1),
(2) Date: Sep. 12, 2019

(87) PCT Pub. No.: WO2018/169901
PCT Pub. Date: Sep. 20, 2018

(65) Prior Publication Data
US 2021/0171977 A1 Jun. 10, 2021

Related U.S. Application Data

(60) Provisional application No. 62/470,754, filed on Mar. 13, 2017.

(51) Int. Cl.
| | | |
|---|---|---|
| *A01N 63/00* | (2020.01) |
| *A61K 39/245* | (2006.01) |
| *C07H 21/04* | (2006.01) |
| *C12N 15/85* | (2006.01) |
| *A61K 35/763* | (2015.01) |
| *C12N 15/86* | (2006.01) |

(52) U.S. Cl.
CPC ............ *C12N 15/85* (2013.01); *A61K 35/763* (2013.01); *C12N 15/86* (2013.01); *C12N 2710/16632* (2013.01); *C12N 2710/16643* (2013.01); *C12N 2830/008* (2013.01)

(58) Field of Classification Search
CPC ................ C12N 15/86; C12N 15/8695; C12N 2510/00; C07H 21/04
See application file for complete search history.

(56) References Cited

FOREIGN PATENT DOCUMENTS

| WO | WO 2009/007980 A1 | 1/2009 |
| WO | WO 2016/179226 A1 | 11/2016 |
| WO | WO 2016/205737 A2 | 12/2016 |

OTHER PUBLICATIONS

Kannan et al., 2018, ACS Synth. Biol. vol. 7, p. 832-841.*
Fu et al., A strict-late viral promoter is a strong tumor-specific promoter in the context of an oncolytic herpes simplex virus. Gene Ther. Aug. 1, 2003;10(17):1458-64. doi: 10.1038/SJ.GT.3302029.
Gayral et al., Targeted oncolytic herpes simplex virus type 1 eradicates experimental pancreatic tumors. Human Gene Ther. Nov. 25, 2014;26(2):104-13. Epub Feb. 2015. doi: 10.1089/hum.2014.072.
Kurayoshi et al., Cancer cell specific by ARF tumor suppressor promoter constructs. Biochem Biophys Research Commun. Jun. 2, 2014;450(1):240-6. doi: 10.1016/J.BBRC.2014.05.102.
Nissim et al., Synthetic RNA-based immunomodulatory gene circuits for cancer immunotherapy. Cell. Nov. 16, 2017;171(5):1138-50. doi: 10.1016/J.CELL.2017.09.049.
Qu et al., Evaluation of MCF10A as a reliable model for normal human mammary epithelial cells. PLos One. Jul. 6, 2015;10(7):e0131285, 16 pages, doi: 10.1371/journal.pone.0131285.
Su et al., Targeting gene expression selectively in cancer cells by using the progression-elevated gene-3 promoter. PNAS. Jan. 25, 2005;102(4):1059-64. doi: 10.1073/pnas.0409141102.
Vranic et al., Update on the molecular profile of the MDA-MB-453 cell line as a model for apocrine breast carcinoma studies. Oncol Lett. Aug. 5, 2011;2(6):1131-7. doi: 10.3892/ol.2011.375.
Guye et al., Genetically engineering self-organization of human pluripotent stem cells into a liver bud-like tissue using Gata6. Nat Comm. Jan. 6, 2016; 7(10243): 1-12.
Jeyaseelan et al., Real-time detection of gene promoter activity: quantitation of toxin gene transcription. Nucleic Acids Res. Jun. 15, 2001;29(12):E58-8.
Nissim et al., Synthetic RNA-Based Immunomodulatory Gene Circuits for Cancer Immunotherapy. Cell. Nov. 16, 2017;171(5):1138-1150.e15. doi: 10.1016/j.cell.2017.09.049. Epub Oct. 19, 2017.

* cited by examiner

*Primary Examiner* — Shin Lin Chen
(74) *Attorney, Agent, or Firm* — Wolf, Greenfield & Sacks, P.C.

(57) ABSTRACT

Synthetic promoters that are differentially modulated between certain diseased cells (e.g., cancer cells) and normal cells (e.g., non-cancer cells) are described. The synthetic promoters may be used to drive expression of gene(s) of interest in a specific cell type or during a specific cellular state. These synthetic promoters are useful, for example, for targeted expression of therapeutic molecules in diseased cells.

7 Claims, 10 Drawing Sheets

Specification includes a Sequence Listing.

SYNTHETIC PROMOTERS

RELATED APPLICATION

This application is a national stage filing under 35 U.S.C. § 371 of International Patent Application Serial No. PCT/US2018/022093, filed Mar. 13, 2018, which claims the benefit under 35 U.S.C. § 119(e) of U.S. provisional application No. 62/470,754, filed Mar. 13, 2017, the contents of each of which is incorporated by reference herein in its entirety.

FEDERALLY SPONSORED RESEARCH

This invention was made with Government support under Grant No. W911NF-11-2-0056 awarded by the Army Research Office and under Grant No. P50 GM098792 awarded by the National Institutes of Health. The Government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Feb. 2, 2022, is named M065670406US01-SEQ-JRV, and is 6,068,501 bytes in size.

BACKGROUND

Targeted therapy is useful for treating a myriad of different diseases. Cell type-specific and/or cellular state-specific control of gene expression enables, for example, targeted delivery of therapeutic proteins to diseased cells (e.g., cancer cells) without adversely affecting healthy, non-diseased cells.

SUMMARY

Some aspects of the present disclosure provide synthetic promoters that have differential activities in different cell types and/or different cellular states. The synthetic promoters may be used to drive expression of gene(s) of interest in a specific cell type or during a specific cellular state. In some embodiments, a synthetic promoter is used for diagnostic purposes to drive the expression of a detectable molecule (e.g., a fluorescent protein such as GFP) in a specific cell type or at a specific cellular state. In some embodiments, a synthetic promoter is used for therapeutic purposes to drive the expression of a therapeutic molecule (e.g., a protein, such as an antibody, or a nucleic acid, such as a siRNA) in a specific cell type (e.g., a cancer cell) or during a specific cellular state.

Thus, provided herein are engineered nucleic acids comprising a promoter that comprises the following consensus sequence: TFBS-AGA-TFBS-TCG-TFBS-GAC-TFBS-CTA-TFBS-ACT-TFBS-TGC-TFBS-GTA-TFBS, wherein TFBS is a transcription factor binding site sequence of Table 5. In some embodiments, the activity of the promoter is increased in diseased cells relative to healthy cells. In some embodiments, the activity of the promoter is decreased in diseased cells relative to healthy cells.

In some embodiments, the diseased cells are selected from breast cancer cells, colon cancer cells, and ovarian cancer cells.

In some embodiments, the promoter is operably linked to a nucleotide sequence encoding a therapeutic protein.

In some embodiments, the transcription factor binding site sequence comprises the following sequence: CCACGTGC (SEQ ID NO: 12265). In some embodiments, the promoter comprises the following sequence:

(SEQ ID NO: 12266)
CCACGTGCAGACCACGTGCTCGCCACGTGCGACCCACGTGCCTACCACGT

GCACTCCACGTGCTGCCCACGTGCGTACCACGTGCG.

In some embodiments, the transcription factor binding site sequence comprises the following sequence: TGCTGAGTCAGCA (SEQ ID NO: 12267). In some embodiments, the promoter comprises the following sequence:

(SEQ ID NO: 12268)
TGCTGAGTCAGCAAGATGCTGAGTCAGCATCGTGCTGAGTCAGCAGACTG

CTGAGTCAGCACTATGCTGAGTCAGCAACTTGCTGAGTCAGCATGCTGCT

GAGTCAGCAGTATGCTGAGTCAGCAG.

Also provided herein are cells comprising an engineered nucleic acid described herein.

Further provided herein are viruses, such as lentiviruses, adenoviruses, adeno-associated viruses, and/or oncolytic viruses comprising an engineered nucleic acid described herein. In some embodiments, the oncolytic virus is an oncolytic herpes simplex virus.

The present disclosure also provides methods of delivering to a cell, optionally in a subject, an engineered nucleic acid or an oncolytic virus described herein.

In some embodiments, the engineered nucleic acids comprise a promoter that comprises a nucleotide sequence identified by any one of SEQ ID NOs: 1-12263. In some embodiments, the activity of the promoter is increased in diseased cells (e.g., ovarian cancer cells or breast cancer cells) relative to healthy cells. In some embodiments, the activity of the promoter is decreased in diseased cells relative to healthy cells. SEQ ID NOs: 1-12263 include the sequence ATCATCTCACCTTGCCTCCTG (SEQ ID NO: 12264), used to amplify promoters of interest directly from the promoter library. It will be understood that "a promoter that comprises the nucleotide sequence identified by any one of SEQ ID NOS: 1-12263," in some embodiments, does not include the 5' SEQ ID NO: 12264. Thus, SEQ ID NO: 12264 may be excluded from any one of SEQ ID NOs. 1-12263.

Also provided herein are cells comprising engineered nucleic acids that include a synthetic promoter having a nucleotide sequence identified by any one of SEQ ID NOS: 1-12263.

The present disclosure also provide delivering to a cell or delivering to a subject (e.g., directly or via a cell) an engineered nucleic acid that includes a synthetic promoter having a nucleotide sequence identified by any one of SEQ ID NOS: 1-12263.

The entire disclosure of Nissim, L. et al. *Cell* 2017; 171: 1138-1150 is incorporated herein by reference.

BRIEF DESCRIPTION OF THE DRAWINGS

The accompanying drawings are not intended to be drawn to scale. For purposes of clarity, not every component may be labeled in every drawing.

DETAILED DESCRIPTION

Figure 1:
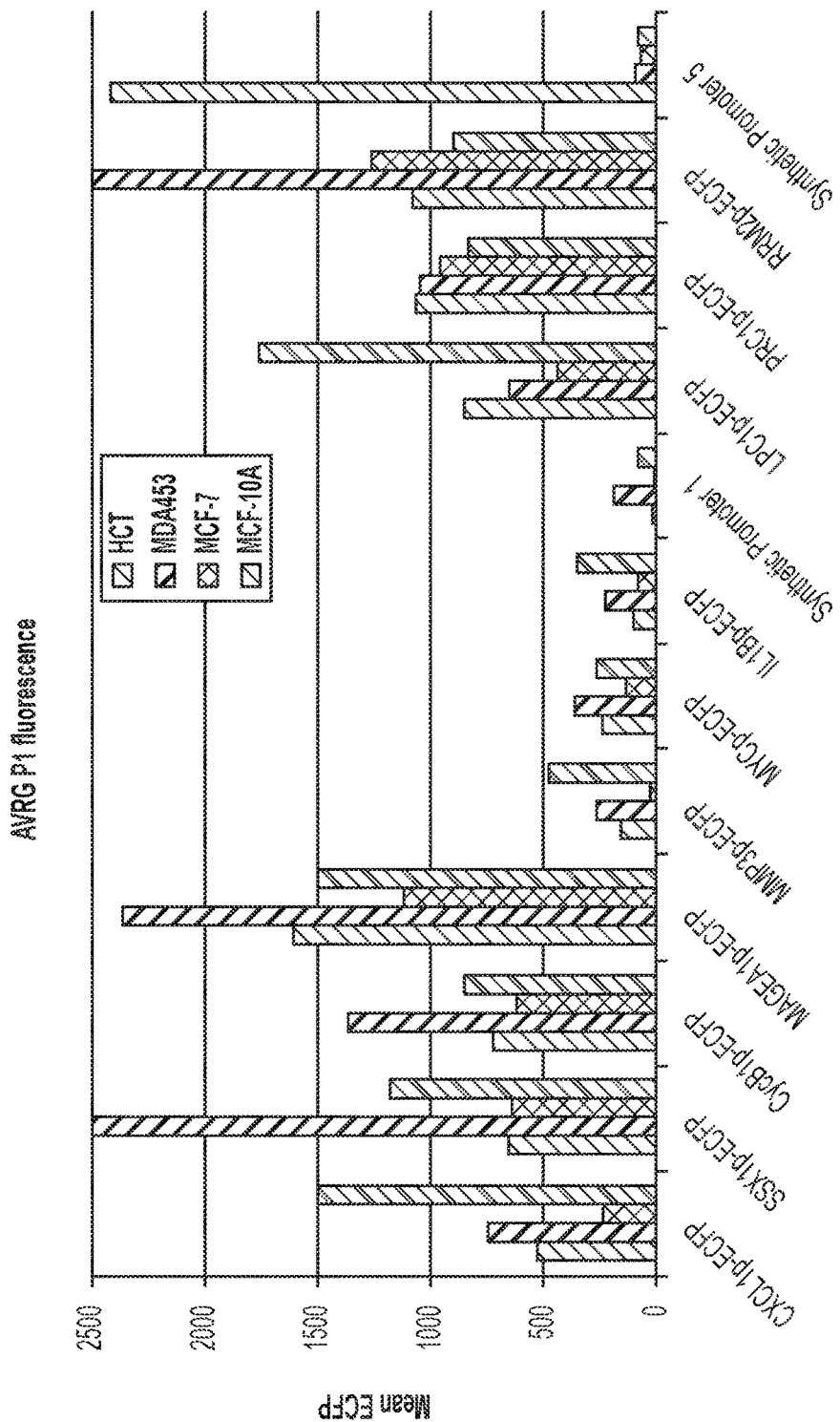
FIG. 1 is a graph showing the activities of synthetic promoters in four different cell lines: HCT, MDA-453, MCF-7, and MCF-10A.
Figure 2:
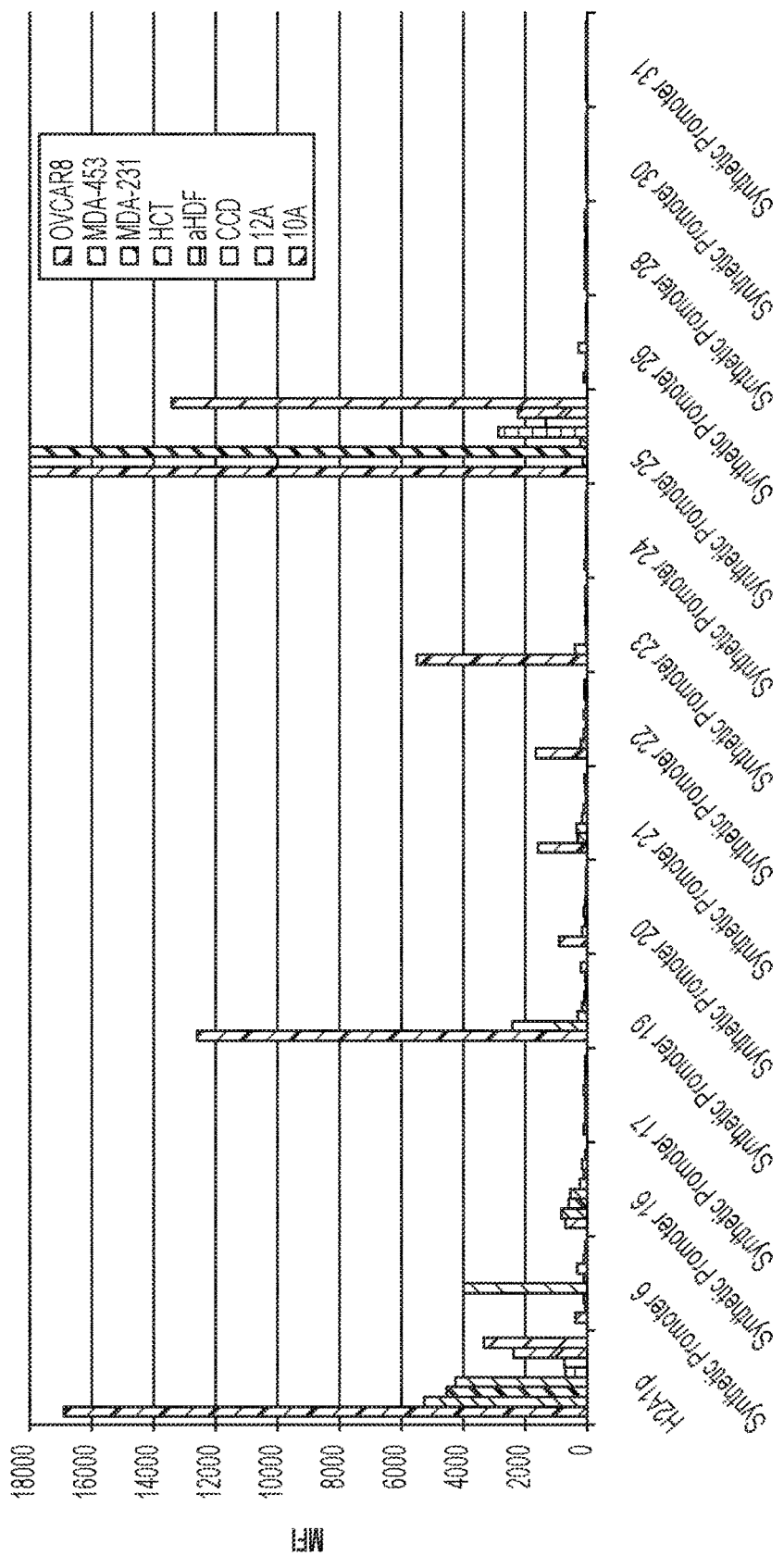
FIG. 2 is a graph showing the activities of synthetic promoters in eight different cell lines: OVCAR8, MDA-453, MDA-231, HCT, aHDF, CCD, 12A, and 10A.

Provided herein are synthetic promoters that are differentially modulated among various diseased cell types, relative to healthy (normal), non-diseased cell types. These synthetic promoters may be used for targeted expression of molecules/products of interest (e.g., therapeutic and/or diagnostic molecules) in select cell types (e.g., cancer cells or other diseased cells).

Synthetic Promoters

A "promoter" refers to a control region of a nucleic acid sequence at which initiation and rate of transcription of the remainder of a nucleic acid sequence are controlled. A promoter regulates (e.g., activates or represses) expression or transcription of the nucleic acid sequence that it is operably linked to. A promoter may also contain sub-regions at which regulatory proteins and molecules may bind, such as RNA polymerase and other transcription factors. Promoters may be constitutive, inducible, activatable, repressible, tissue-specific, cell type-specific, cell state-specific, or any combination thereof.

Promoters of the present disclosure are synthetic promoters. A synthetic promoters is a promoter that is not "naturally occurring." The synthetic promoters of the present disclosure may be produced synthetically (e.g., via chemical synthesis), or using recombinant cloning and/or nucleic acid amplification technology, including polymerase chain reaction (PCR) (see U.S. Pat. Nos. 4,683,202 and 5,928,906).

In some embodiments, a synthetic promoter may be 10-300 nucleotides long. For example, the length of a synthetic promoter may be 10-300, 10-290, 10-280, 10-270, 10-260, 10-250, 10-240, 10-230, 10-220, 10-210, 10-210, 10-200, 10-190, 10-180, 10-170, 10-160, 10-150, 10-140, 10-130, 10-120, 10-110, 10-100, 10-90, 10-80, 10-70, 10-60, 10-50, 10-40, 10-30, 10-20, 20-300, 20-290, 20-280, 20-270, 20-260, 20-250, 20-240, 20-230, 20-220, 20-210, 20-210, 20-200, 20-190, 20-180, 20-170, 20-160, 20-150, 20-140, 20-130, 20-120, 20-110, 20-100, 20-90, 20-80, 20-70, 20-60, 20-50, 20-40, 20-30, 30-300, 30-290, 30-280, 30-270, 30-260, 30-250, 30-240, 30-230, 30-220, 30-210, 30-210, 30-200, 30-190, 30-180, 30-170, 30-160, 30-150, 30-140, 30-130, 30-120, 30-110, 30-100, 30-90, 30-80, 30-70, 30-60, 30-50, 30-40, 40-300, 40-290, 40-280, 40-270, 40-260, 40-250, 40-240, 40-230, 40-220, 40-210, 40-210, 40-200, 40-190, 40-180, 40-170, 40-160, 40-150, 40-140, 40-130, 40-120, 40-110, 40-100, 40-90, 40-80, 40-70, 40-60, 40-50, 50-300, 50-290, 50-280, 50-270, 50-260, 50-250, 50-240, 50-230, 50-220, 50-210, 50-210, 50-200, 50-190, 50-180, 50-170, 50-160, 50-150, 50-140, 50-130, 50-120, 50-110, 50-100, 50-90, 50-80, 50-70, 50-60, 60-300, 60-290, 60-280, 60-270, 60-260, 60-250, 60-240, 60-230, 60-220, 60-210, 60-210, 60-200, 60-190, 60-180, 60-170, 60-160, 60-150, 60-140, 60-130, 60-120, 60-110, 60-100, 60-90, 60-80, 60-70, 70-300, 70-290, 70-280, 70-270, 70-260, 70-250, 70-240, 70-230, 70-220, 70-210, 70-210, 70-200, 70-190, 70-180, 70-170, 70-160, 70-150, 70-140, 70-130, 70-120, 70-110, 70-100, 70-90, 70-80, 80-300, 80-290, 80-280, 80-270, 80-260, 80-250, 80-240, 80-230, 80-220, 80-210, 80-210, 80-200, 80-190, 80-180, 80-170, 80-160, 80-150, 80-140, 80-130, 80-120, 80-110, 80-100, 80-90, 90-300, 90-290, 90-280, 90-270, 90-260, 90-250, 90-240, 90-230, 90-220, 90-210, 90-210, 90-200, 90-190, 90-180, 90-170, 90-160, 90-150, 90-140, 90-130, 90-120, 90-110, 90-100, 100-300, 100-290, 100-280, 100-270, 100-260, 100-250, 100-240, 100-230, 100-220, 100-210, 100-210, 100-200, 100-190, 100-180, 100-170, 100-160, 100-150, 100-140, 100-130, 100-120, 100-110, 110-300, 110-290, 110-280, 110-270, 110-260, 110-250, 110-240, 110-230, 110-220, 110-210, 110-210, 110-200, 110-190, 110-180, 110-170, 110-160, 110-150, 110-140, 110-130, 110-120, 120-300, 120-290, 120-280, 120-270, 120-260, 120-250, 120-240, 120-230, 120-220, 120-210, 120-210, 120-200, 120-190, 120-180, 120-170, 120-160, 120-150, 120-140, 120-130, 130-300, 130-290, 130-280, 130-270, 130-260, 130-250, 130-240, 130-230, 130-220, 130-210, 130-210, 130-200, 130-190, 130-180, 130-170, 130-160, 130-150, 130-140, 140-300, 140-290, 140-280, 140-270, 140-260, 140-250, 140-240, 140-230, 140-220, 140-210, 140-210, 140-200, 140-190, 140-180, 140-170, 140-160, 140-150, 150-300, 150-290, 150-280, 150-270, 150-260, 150-250, 150-240, 150-230, 150-220, 150-210, 150-210, 150-200, 150-190, 150-180, 150-170, 150-160, 160-300, 160-290, 160-280, 160-270, 160-260, 160-250, 160-240, 160-230, 160-220, 160-210, 160-210, 160-200, 160-190, 160-180, 160-170, 170-300, 170-290, 170-280, 170-270, 170-260, 170-250, 170-240, 170-230, 170-220, 170-210, 170-210, 170-200, 170-190, 170-180, 180-300, 180-290, 180-280, 180-270, 180-260, 180-250, 180-240, 180-230, 180-220, 180-210, 180-210, 180-200, 180-190, 190-300, 190-290, 190-280, 190-270, 190-260, 190-250, 190-240, 190-230, 190-220, 190-210, 190-210, 190-200, 200-300, 200-290, 200-280, 200-270, 200-260, 200-250, 200-240, 200-230, 200-220, 200-210, 200-210, 210-300, 210-290, 210-280, 210-270, 210-260, 210-250, 210-240, 210-230, 210-220, 220-300, 220-290, 220-280, 220-270, 220-260, 220-250, 220-240, 220-230, 230-300, 230-290, 230-280, 230-270, 230-260, 230-250, 230-240, 240-300, 240-290, 240-280, 240-270, 240-260, 240-250, 250-300, 250-290, 250-280, 250-270, 250-260, 260-300, 260-290, 260-280, 260-270, 270-300, 270-290, 270-280, 280-300, 280-290, or 290-300 nucleotides. Promoters may be longer than 300 nucleotides, in some embodiments. In some embodiments, a synthetic promoter may be longer than 300 nucleotide (e.g., 300, 350, 400, 450, or 500 nucleotides long or longer).

In some embodiments, the length of a synthetic promoter is 200 nucleotides or shorter. In some embodiments, a synthetic promoter may be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 nucleotides long.

In some embodiments, a synthetic promoter comprises the nucleotide sequence identified by any one of SEQ ID NOs: 1-12263 (with or without the 5' sequence identified by SEQ ID NO: 12264). In some embodiments, a synthetic promoter comprises a nucleotide sequence that is at least 95% identical to the nucleotide sequence identified by any one of SEQ ID NOs: 1-12263 (with or without the 5' sequence identified by SEQ ID NO: 12264), and is able to regulate the expression (e.g., activate or repress) the sequence to which it is operably linked. For example, a synthetic promoter may comprise a nucleotide sequence that is at least 95%, at least 96%, at least 97%, at least 98%, at least 99%, or at least 99.5% identical to the nucleotide sequence identified by any one of SEQ ID NOs: 1-12263 (with or without the 5' sequence identified by SEQ ID NO: 12264), and is able to regulate the expression (e.g., activate or repress) the sequence to which it is operably linked. In some embodiments, a synthetic promoter comprises a nucleotide sequence that is 95-99% identical to the nucleotide sequence identified by any one of SEQ ID NOs: 1-12263 (with or without the 5' sequence identified by SEQ ID NO: 12264), and is able to regulate the expression (e.g., activate or repress) the sequence to which it is operably linked. In some embodiments, a synthetic promoter comprises a nucleotide sequence that is 95%-99%, 95%-98%, 95%-97%, 95%-96%, 96%-99%, 96%-98%, 96%-97%, 97%-99%, 97%-98%, or 98%-99% identical to the nucleotide sequence identified by any one of SEQ ID NOs: 1-12263 (with or without the 5' sequence identified by SEQ ID NO: 12264), and is able to regulate the expression (e.g., activate or repress) the sequence to which it is operably linked. In some embodiments, a synthetic promoter may comprise a nucleotide sequence that is 95%, 96%, 97%, 98%, 99%, or 99.5% identical to the nucleotide sequence identified by any one of SEQ ID NOs: 1-12263 (with or without the 5' sequence identified by SEQ ID NO: 12264), and is able to regulate the expression (e.g., activate or repress) the sequence to which it is operably linked.

Other aspects of the present disclosure provide synthetic promoters having differential activities in different cell lines or different cellular states. "Having differential activities" means the activity of a synthetic promoter is higher or lower in one type of cell or at a cellular state, compare to in a different type of cell or at a different cellular state, respectfully. In some embodiments, the activity of a synthetic promoter in one cell type or a cellular state is different from (higher or lower) the activity of the synthetic promoter in another cell type or another cellular state by at least 10% (e.g., at least 10%, 20%, 30%, 40%, 50%, 60%, 70%, 80%, 90% 100%, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, or 1000-fold). In some embodiments, the activity of a synthetic promoter in one cell type or a cellular state is different from (higher or lower) the activity of the synthetic promoter in another cell type or another cellular state by 10%-100%. For example, the activity of a synthetic promoter in one cell type or a cellular state may be different from (higher or lower) the activity of the synthetic promoter in another cell type or another cellular state by 10%-100%, 10%-90%, 10%-80%, 10%-70%, 10%-60%, 10%-50%, 10%-40%, 10%-30%, 10%-20%, 20%-100%, 20%-90%, 20%-80%, 20%-70%, 20%-60%, 20%-50%, 20%-40%, 20%-30%, 30%-100%, 30%-90%, 30%-80%, 30%-70%, 30%-60%, 30%-50%, 30%-40%, 40%-100%, 40%-90%, 40%-80%, 40%-70%, 40%-60%, 40%-50%, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100%. In some embodiments, the activity of a synthetic promoter in one cell type or a cellular state is different from (higher or lower) the activity of the synthetic promoter in another cell type or another cellular state by 1-1000 fold. For example, the activity of a synthetic promoter in one cell type or a cellular state may be different from (higher or lower than) the activity of the synthetic promoter in another cell type or another cellular state by 1-1000, 1-900, 1-800, 1-700, 1-600, 1-500, 1-400, 1-300, 1-200, 1-100, 1-90, 1-80, 1-70, 1-60, 1-50, 1-40, 1-30, 1-20, 1-10, 1-9, 1-8, 1-7, 1-6, 1- 5, 1-4, 1-3, 1-2, 5-1000, 5-900, 5-800, 5-700, 5-600, 5-500, 5-400, 5-300, 5-200, 5-100, 5-90, 5-80, 5-70, 5-60, 5-50, 5-40, 5-30, 5-20, 5-10, 5-9, 5-8, 5-7, 5-6, 10-1000, 10-900, 10-800, 10-700, 10-600, 10-500, 10-400, 10-300, 10-200, 10-100, 10-90, 10-80, 10-70, 10-60, 10-50, 10-40, 10-30, 10-20, 20-1000, 20-900, 20-800, 20-700, 20-600, 20-500, 20-400, 20-300, 20-200, 20-100, 20-90, 20-80, 20-70, 20-60, 20-50, 20-40, 20-30, 30-1000, 30-900, 30-800, 30-700, 30-600, 30-500, 30-400, 30-300, 30-200, 30-100, 30-90, 30-80, 30-70, 30-60, 30-50, 30-40, 40-1000, 40-900, 40-800, 40-700, 40-600, 40-500, 40-400, 40-300, 40-200, 40-100, 40-90, 40-80, 40-70, 40-60, 40-50, 50-1000, 50-900, 50-800, 50-700, 50-600, 50-500, 50-400, 50-300, 50-200, 50-100, 50-90, 50-80, 50-70, 50-60, 60-1000, 60-900, 60-800, 60-700, 60-600, 60-500, 60-400, 60-300, 60-200, 60-100, 60-90, 60-80, 60-70, 70-1000, 70-900, 70-800, 70-700, 70-600, 70-500, 70-400, 70-300, 70-200, 70-100, 70-90, 70-80, 80-1000, 80-900, 80-800, 80-700, 80-600, 80-500, 80-400, 80-300, 80-200, 80-100, 80-90, 90-1000, 90-900, 90-800, 90-700, 90-600, 90-500, 90-400, 90-300, 90-200, 90-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-800, 600-700, 700-1000, 700-900, 700-800, 800-1000, 800-900, or 900-1000 fold. In some embodiments, the activity of a synthetic promoter in one cell type or a cellular state may be different from (higher or lower than) the activity of the synthetic promoter in another cell type or another cellular state by 10%, 20%, 30%, 40%, 50%, 60%, 70%, 80%, 90%, 100%, 2 fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100- fold, 500-fold, or 1000-fold. In some embodiments, a synthetic promoter may be inactive in one cell type and active in another. In some embodiments, a synthetic promoter may be inactive in one cellular state and active in another. Methods of measuring the activities of a promoter (e.g., a synthetic promoter) are known to those skilled in the art, e.g., as described in Jeyaseelan et al., *Nucleic Acids Research.* 29 (12), 2001; Allard et al., *Cell Notes* (21), 2008; and Zaslaver et al., *Nature Methods.* 3 (8): 623-628, 2006, each of which is incorporated herein by reference.

In some embodiments, a synthetic promoter has differential activity (higher or lower) in one type of diseased cell relative to a healthy cell or another type of diseased cell. A "diseased cell" refers to an abnormal cell that is associated with a particular disease or condition. Non-limiting examples of diseased cells include: cancer cells, diseased neurons, diseased cardiomyocytes, diseased skin cells, diseased liver cells, diseased immune cells, diseased epithelial cells, diseased eye cells, diseased astrocytes, diseased microglia, and diseased stem cells. Other diseased cell types are encompassed herein. One skilled in the art is able to identify diseased cells. A "healthy" cell, also referred to as a "non-diseased cell," refers to a normal cell that is not associated with any disease or condition.

In some embodiments, a synthetic promoter has differential activity (e.g., higher or lower) in one cellular state relative to another cellular state. Non-limiting examples of different cell types that may transition between different cellular states include: embryonic stem cells, adult stem cells, induced pluripotent stem cells, neurons, cardiomyocytes, skin cells, liver cells, immune cells, epithelial cells, eye cells, astrocytes, and microglia.

In some embodiments, a synthetic promoter as provided herein is active only in or has higher activity in cancer cells. For example, a synthetic promoter as provided herein may be activate only in in breast cancer cells and remains inactive in non-breast cancer cells, or has higher activity in breast cancer cells compared to in healthy cells or non-breast cancer cells. As another example, a synthetic promoter as provided herein may be activate only in tumor cancer cells and remains inactive in circulating cancer cells, or has higher activity in tumor cancer cells compared to circulating cancer cells.

In some embodiments, a synthetic promoter has higher activity in a breast cancer cell relative to a healthy cell or relative to other types of cancer cells.

In some embodiments, a synthetic promoter has higher activity in a ovarian cancer cell relative to a healthy cell or relative to other types of cancer cells.

In some embodiments, a synthetic promoter has higher activity in a colorectal cancer cell relative to a healthy cell or relative to other types of cancer cells.

In some embodiments, a synthetic promoter comprises at least one (one or more) sequence identified in Table 5 (a specific transcription factor binding site sequence). In some embodiments, a synthetic promoter comprises at least one (e.g., at least 2, at least 3, at least 4, or at least 5) tandem repeat of a sequence identified in Table 5. In some embodiments, a synthetic promoter comprises 1, 2, 3, 4, 5, 6, 7, 8, 9, or 10 tandem repeat(s) of a sequence identified in Table 5. A repeat sequence of Table 5 may be separated from each other by a linker sequence. In some embodiments, the linker sequences comprises or consists of three (random) nucleotides (e.g., AGA, TCG, GAC, CTA, ACT, TGC, GTA). In some embodiments, a synthetic promoter comprises the following consensus motif: TFBS-AGA-TFBS-TCG-TFBS-GAC-TFBS-CTA-TFBS-ACT-TFBS-TGC-TFBS-GTA-TFBS, wherein "TFBS" is a transcription factor binding site of Table 5.

In some embodiments, a synthetic promoter may comprise a tandem repeat of a USF1 transcription factor binding site CCACGTGC (SEQ ID NO: 12265). In some embodiments, a synthetic promoter comprises the following sequence:

(SEQ ID NO: 12266)
CCACGTGCAGA<u>CCACGTGC</u>TCG<u>CCACGTGC</u>GAC<u>CCACGTGC</u>CTA<u>CCACGT</u>

<u>GC</u>ACT<u>CCACGTGC</u>TGC<u>CCACGTGC</u>GTA<u>CCACGTGCG</u>.

In some embodiments, a synthetic promoter may comprise a tandem repeat of a MAFK transcription factor binding site TGCTGAGTCAGCA (SEQ ID NO: 12267). In some embodiments, a synthetic promoter comprises the following sequence:

(SEQ ID NO: 12268)
<u>TGCTGAGTCAGCA</u>AGA<u>TGCTGAGTCAGCA</u>TCG<u>TGCTGAGTCAGCA</u>GA<u>CTG</u>

<u>CTGAGTCAGCA</u>CTA<u>TGCTGAGTCAGCA</u>ACT<u>TGCTGAGTCAGCA</u>TGC<u>TGCT</u>

<u>GAGTCAGCA</u>GTA<u>TGCTGAGTCAGCAG</u>.

Engineered Nucleic Acids and Output Molecules

Further provided herein are engineered nucleic acids (e.g., construct) containing the synthetic promoters described herein. In some embodiments, a synthetic promoter is operably linked to a nucleotide sequence encoding a molecule (e.g., a protein or nucleic acid). A promoter is considered to be "operably linked" when it is in a correct functional location and orientation in relation to a nucleic acid sequence it regulates to control ("drive") transcriptional initiation and/or expression of that sequence.

In some embodiments, a synthetic promoter is operably linked to a nucleotide sequence encoding an output molecule, such that activation of the synthetic promoter results in expression of the output molecule. The signal of the output molecule may be detected and its intensity is an indication of the level of activation of the synthetic promoter. As such, by comparing the signal from the output molecule, the activities of a synthetic promoter in different cell types can be compared. In some embodiments, a promoter that is operably linked to a nucleotide sequence encoding an output molecule may be used for diagnostic purposes. For example, when a synthetic promoter that has higher activity in a diseased cell (e.g., a cancer cell such as a breast cancer cell) is operably linked to a nucleotide sequence encoding an output molecule, the higher signal generated from the output molecule in a cell relative to another cell indicates that the cell is a diseased cell (e.g., a cancer cell such as a breast cancer cell). The example is not meant to be limiting. The synthetic promoter described herein may be used for the diagnosis of any disease, so long as it has differential activity in the diseased cell relative to a healthy cell or to other cell types.

In some embodiments, the output molecule is a detectable protein. In some embodiments, a detectable protein is a fluorescent protein. A fluorescent protein is a protein that emits a fluorescent light when exposed to a light source at an appropriate wavelength (e.g., light in the blue or ultraviolet range). Suitable fluorescent proteins that may be used as a detectable protein in the sensor circuit of the present disclosure include, without limitation, eGFP, eYFP, eCFP, mKate2, mCherry, mPlum, mGrape2, mRaspberry, mGrape1, mStrawberry, mTangerine, mBanana, and mHoneydew. In some embodiments, a detectable protein is an enzyme that hydrolyzes an substrate to produce a detectable signal (e.g., a chemiluminescent signal). Such enzymes include, without limitation, beta-galactosidase (encoded by LacZ), horseradish peroxidase, or luciferase. In some embodiments, the output signal is a fluorescent RNA. A fluorescent RNA is an RNA aptamer that emits a fluorescent light when bound to a fluorophore and exposed to a light source at an appropriate wavelength (e.g., light in the blue or ultraviolet range). Suitable fluorescent RNAs that may be used as an output signal in the sensor circuit of the present disclosure include, without limitation, Spinach and Broccoli (e.g., as described in Paige et al., Science Vol. 333, Issue 6042, pp. 642-646, 2011, incorporated herein by reference).

In some embodiments, a synthetic promoter is operably linked to a nucleotide sequence encoding a therapeutic molecule. A "therapeutic molecule" is a molecule that has therapeutic effects on a disease or condition, and may be used to treat a diseases or condition. Therapeutic molecules of the present disclosure may be nucleic acid-based or protein or polypeptide-based. In some embodiments, the synthetic promoter drives the expression of the therapeutic molecule in a desired cell type (e.g., cancer cell) but not in other cell types, due to the synthetic promoter's cell-specific activity. As such, targeted therapy of diseases (e.g., cancer) is achieved.

In some embodiments, nucleic acid-based therapeutic molecule may be an RNA interference (RNAi) molecule (e.g., a microRNA, siRNA, or shRNA) or an nucleic acid enzyme (e.g., a ribozyme). RNAi molecules and there use in silencing gene expression are familiar to those skilled in the art. In some embodiments, the RNAi molecule targets an oncogene.

An oncogene is a gene that in certain circumstances can transform a cell into a tumor cell. An oncogene may be a gene encoding a growth factor or mitogen (e.g., c-Sis), a receptor tyrosine kinase (e.g., EGFR, PDGFR, VEGFR, or HER2/neu), a cytoplasmic tyrosine kinase (e.g., Src family kinases, Syk-ZAP-70 family kinases, or BTK family kinases), a cytoplasmic serine/threonine kinase or their regulatory subunits (e.g., Raf kinase or cyclin-dependent kinase), a regulatory GTPase (e.g., Ras), or a transcription factor (e.g., Myc). In some embodiments, the oligonucleotide targets Lipocalin (Lcn2) (e.g., a Lcn2 siRNA). One skilled in the art is familiar with genes that may be targeted for the treatment of cancer.

Non-limiting examples of protein or polypeptide-based therapeutic molecules include enzymes, regulatory proteins (e.g., immuno-regulatory proteins), antigens, antibodies or antibody fragments, and structural proteins. In some embodiments, the protein or polypeptide-based therapeutic molecules are for cancer therapy.

Suitable enzymes (for operably linking to a synthetic promoter) for some embodiments of this disclosure include, for example, oxidoreductases, transferases, polymerases, hydrolases, lyases, synthases, isomerases, and ligases, digestive enzymes (e.g., proteases, lipases, carbohydrases, and nucleases). In some embodiments, the enzyme is selected from the group consisting of lactase, beta-galactosidase, a pancreatic enzyme, an oil-degrading enzyme, mucinase, cellulase, isomaltase, alginase, digestive lipases (e.g., lingual lipase, pancreatic lipase, phospholipase), amylases, cellulases, lysozyme, proteases (e.g., pepsin, trypsin, chymotrypsin, carboxypeptidase, elastase), esterases (e.g. sterol esterase), disaccharidases (e.g., sucrase, lactase, beta-galactosidase, maltase, isomaltase), DNases, and RNases.

Non-limiting examples of antibodies and fragments thereof include: bevacizumab (AVASTIN®), trastuzumab (HERCEPTIN®), alemtuzumab (CAMPATH®, indicated for B cell chronic lymphocytic leukemia), gemtuzumab (MYLOTARG®, hP67.6, anti-CD33, indicated for leukemia such as acute myeloid leukemia), rituximab (RITUXAN®), tositumomab (BEXXAR®, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX®, indicated for ovarian cancer), edrecolomab (PANOREX®), daclizumab (ZENAPAX®), palivizumab (SYNAGIS®, indicated for respiratory conditions such as RSV infection), ibritumomab tiuxetan (ZEVALIN®, indicated for Non-Hodgkin's lymphoma), cetuximab (ERBITUX®), MDX-447, MDX-22, MDX-220 (anti-TAG-72), IOR-C5, IOR-T6 (anti-CD1), IOR EGF/R3, celogovab (ONCOSCINT® OV103), epratuzumab (LYMPHOCIDE®), pemtumomab (THERAGYN®), Gliomab-H (indicated for brain cancer, melanoma). In some embodiments, the antibody is an antibody that inhibits an immune check point protein, e.g., an anti-PD-1 antibody such as pembrolizumab (Keytruda®) or nivolumab (Opdivo®), or an anti-CTLA-4 antibody such as ipilimumab (Yervoy®). Other antibodies and antibody fragments may be operably linked to a synthetic promoter, as provided herein.

A regulatory protein may be, in some embodiments, a transcription factor or a immunoregulatory protein. Non-limiting, exemplary transcriptional factors include: those of the NFkB family, such as Rel-A, c-Rel, Rel-B, p50 and p52; those of the AP-1 family, such as Fos, FosB, Fra-1, Fra-2, Jun, JunB and JunD; ATF; CREB; STAT-1, -2, -3, -4, -5 and -6; NFAT-1, -2 and -4; MAF; Thyroid Factor; IRF; Oct-1 and -2; NF-Y; Egr-1; and USF-43, EGR1, Sp1, and E2F1. Other transcription factors may be operably linked to a synthetic promoter, as provided herein.

As used herein, an immunoregulatory protein is a protein that regulates an immune response. Non-limiting examples of immunoregulatory include: antigens, adjuvants (e.g., flagellin, muramyl dipeptide), cytokines including interleukins (e.g., IL-2, IL-7, IL-15 or superagonist/mutant forms of these cytokines), IL-12, IFN-gamma, IFN-alpha, GM-CSF, FLT3-ligand), and immunostimulatory antibodies (e.g., anti-CTLA-4, anti-CD28, anti-CD3, or single chain/antibody fragments of these molecules). Other immunoregulatory proteins may be operably linked to a synthetic promoter, as provided herein.

As used herein, an antigen is a molecule or part of a molecule that is bound by the antigen-binding site of an antibody. In some embodiments, an antigen is a molecule or moiety that, when administered to or expression in the cells of a subject, activates or increases the production of antibodies that specifically bind the antigen. Antigens of pathogens are well known to those of skill in the art and include, but are not limited to parts (coats, capsules, cell walls, flagella, fimbriae, and toxins) of bacteria, viruses, and other microorganisms. Examples of antigens that may be used in accordance with the disclosure include, without limitation, cancer antigens, self-antigens, microbial antigens, allergens and environmental antigens. Other antigens may be operably linked to a synthetic promoter, as provided herein.

In some embodiments, the antigen of the present disclosure is a cancer antigen. A cancer antigen is an antigen that is expressed preferentially by cancer cells (i.e., it is expressed at higher levels in cancer cells than on non-cancer cells) and, in some instances, it is expressed solely by cancer cells. Cancer antigens may be expressed within a cancer cell or on the surface of the cancer cell. Cancer antigens that may be used in accordance with the disclosure include, without limitation, MART-1/Melan-A, gp100, adenosine deaminase-binding protein (ADAbp), FAP, cyclophilin b, colorectal associated antigen (CRC)-C017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4 and MAGE-C5. The cancer antigen may be selected from the group consisting of GAGE-1, GAGE-2, GAGE-3, GAGE-4, GAGE-5, GAGE-6, GAGE-7, GAGE-8 and GAGE-9. The cancer antigen may be selected from the group consisting of BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100Pmel117, PRAME, NY-ESO-1, cdc27, adenomatous polyposis *coli* protein (APC), fodrin, Connexin 37, Ig-idiotype, p15, gp75, GM2 ganglioside, GD2 ganglioside, human papilloma virus proteins, Smad family of tumor antigens, lmp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20 and c-erbB-2. Other cancer antigens may be operably linked to a synthetic promoter, as provided herein.

In some embodiments, a protein or polypeptide-based therapeutic molecule is a fusion protein. A fusion protein is a protein comprising two heterologous proteins, protein domains, or protein fragments, that are covalently bound to each other, either directly or indirectly (e.g., via a linker), via a peptide bond. In some embodiments, a fusion protein is encoded by a nucleic acid comprising the coding region of a protein in frame with a coding region of an additional protein, without intervening stop codon, thus resulting in the translation of a single protein in which the proteins are fused together.

A "nucleic acid" is at least two nucleotides covalently linked together, and in some instances, may contain phosphodiester bonds (e.g., a phosphodiester "backbone"). An "engineered nucleic acid" (also referred to as a "construct") is a nucleic acid that does not occur in nature. It should be understood, however, that while an engineered nucleic acid as a whole is not naturally-occurring, it may include nucleotide sequences that occur in nature. In some embodiments, an engineered nucleic acid comprises nucleotide sequences from different organisms (e.g., from different species). For example, in some embodiments, an engineered nucleic acid includes a murine nucleotide sequence, a bacterial nucleotide sequence, a human nucleotide sequence, and/or a viral nucleotide sequence. Engineered nucleic acids include recombinant nucleic acids and synthetic nucleic acids. A "recombinant nucleic acid" is a molecule that is constructed by joining nucleic acids (e.g., isolated nucleic acids, synthetic nucleic acids or a combination thereof) and, in some embodiments, can replicate in a living cell. A "synthetic nucleic acid" is a molecule that is amplified or chemically, or by other means, synthesized. A synthetic nucleic acid includes those that are chemically modified, or otherwise modified, but can base pair with naturally-occurring nucleic acid molecules. Recombinant and synthetic nucleic acids also include those molecules that result from the replication of either of the foregoing.

In some embodiments, a nucleic acid of the present disclosure is considered to be a nucleic acid analog, which may contain, at least in part, other backbones comprising, for example, phosphoramide, phosphorothioate, phosphorodithioate, O-methylphophoroamidite linkages and/or peptide nucleic acids. A nucleic acid may be single-stranded (ss) or double-stranded (ds), as specified, or may contain portions of both single-stranded and double-stranded sequence. In some embodiments, a nucleic acid may contain portions of triple-stranded sequence. A nucleic acid may be DNA, both genomic and/or cDNA, RNA or a hybrid, where the nucleic acid contains any combination of deoxyribonucleotides and ribonucleotides (e.g., artificial or natural), and any combination of bases, including uracil, adenine, thymine, cytosine, guanine, inosine, xanthine, hypoxanthine, isocytosine and isoguanine.

Nucleic acids of the present disclosure may include one or more genetic elements. A "genetic element" refers to a particular nucleotide sequence that has a role in nucleic acid expression (e.g., promoter, enhancer, terminator) or encodes a discrete product of an engineered nucleic acid (e.g., a nucleotide sequence encoding a guide RNA, a protein and/or an RNA interference molecule, such as siRNA or miRNA).

Nucleic acids of the present disclosure may be produced using standard molecular biology methods (see, e.g., *Green and Sambrook, Molecular Cloning,* A Laboratory Manual, 2012, Cold Spring Harbor Press).

In some embodiments, nucleic acids are produced using GIBSON ASSEMBLY® Cloning (see, e.g., Gibson, D. G. et al. *Nature Methods,* 343-345, 2009; and Gibson, D. G. et al. *Nature Methods,* 901-903, 2010, each of which is incorporated by reference herein). GIBSON ASSEMBLY® typically uses three enzymatic activities in a single-tube reaction: 5' exonuclease, the 3' extension activity of a DNA polymerase and DNA ligase activity. The 5' exonuclease activity chews back the 5' end sequences and exposes the complementary sequence for annealing. The polymerase activity then fills in the gaps on the annealed regions. A DNA ligase then seals the nick and covalently links the DNA fragments together. The overlapping sequence of adjoining fragments is much longer than those used in Golden Gate Assembly, and therefore results in a higher percentage of correct assemblies.

Figure 3:
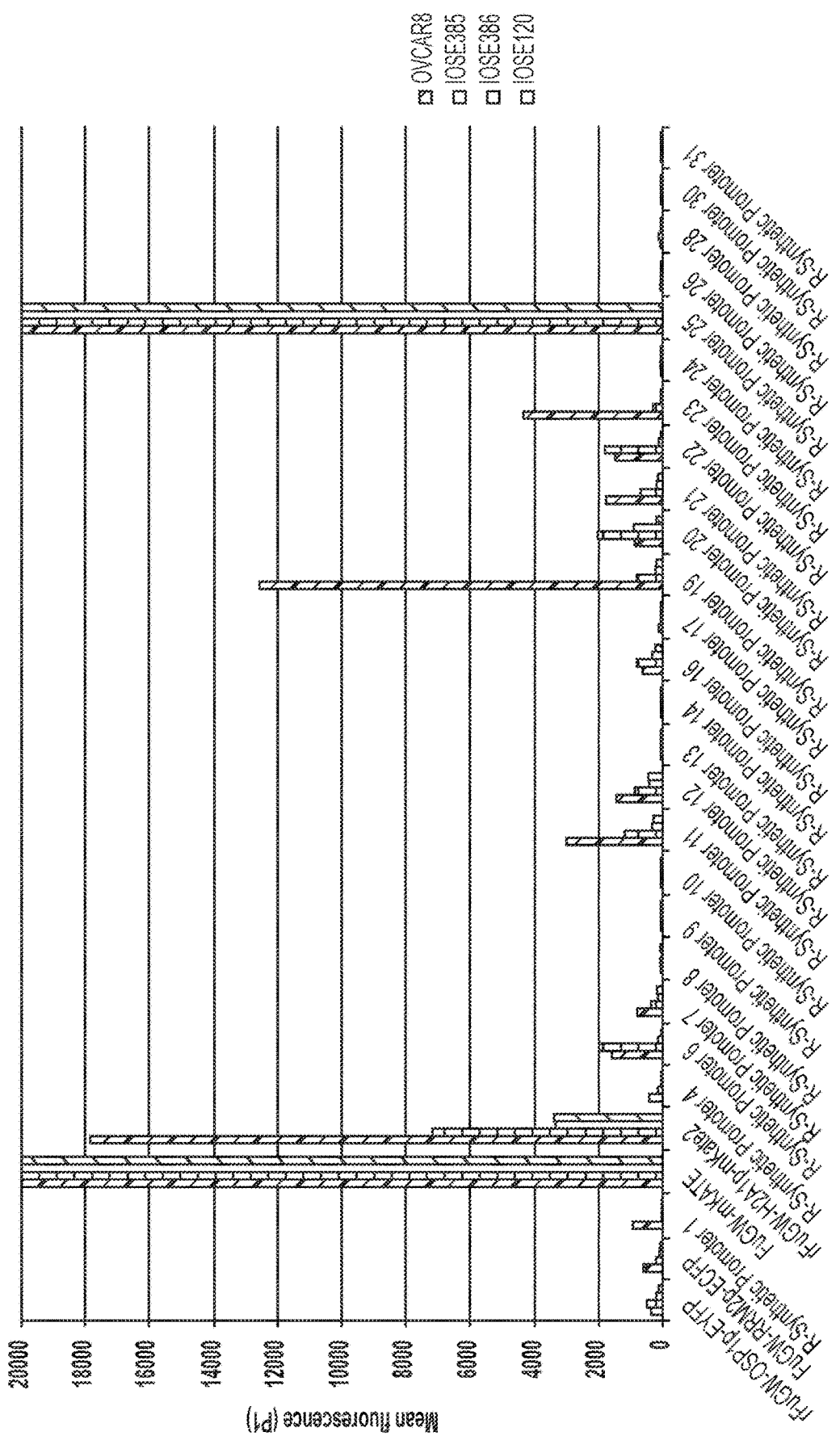
FIG. 3 is a graph showing the activities of synthetic promoters in four cell lines: OVCAR8, IOSE385, IOSE386, and IOSE120.
Figure 4:
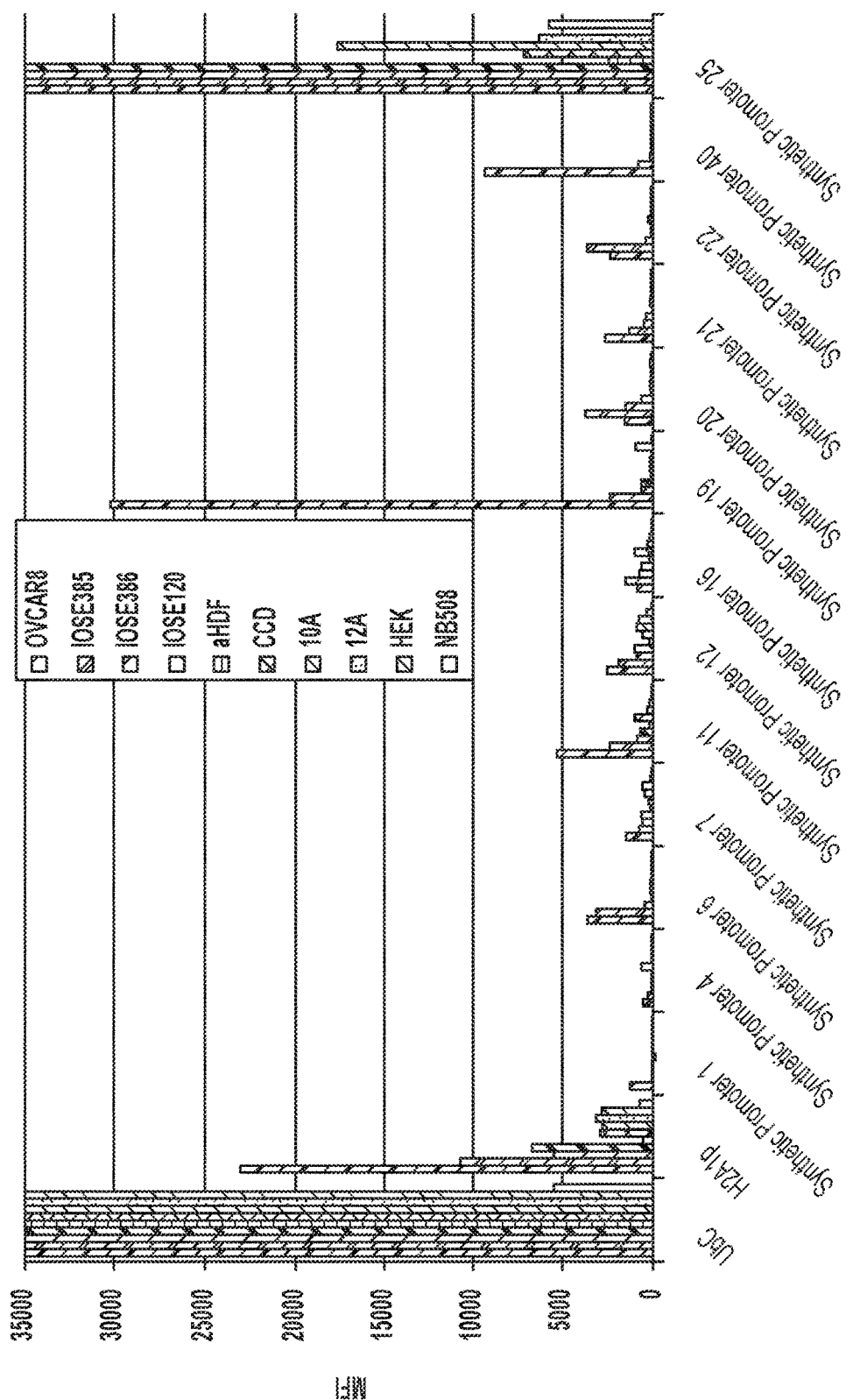
FIG. 4 is a graph showing the activities of synthetic promoters in eight different cell lines: OVCAR8, IOSE385, IOSE386, IOSE120, aHDF, CCD, 12A, 10A, HEK, and NB508.
Figure 5:
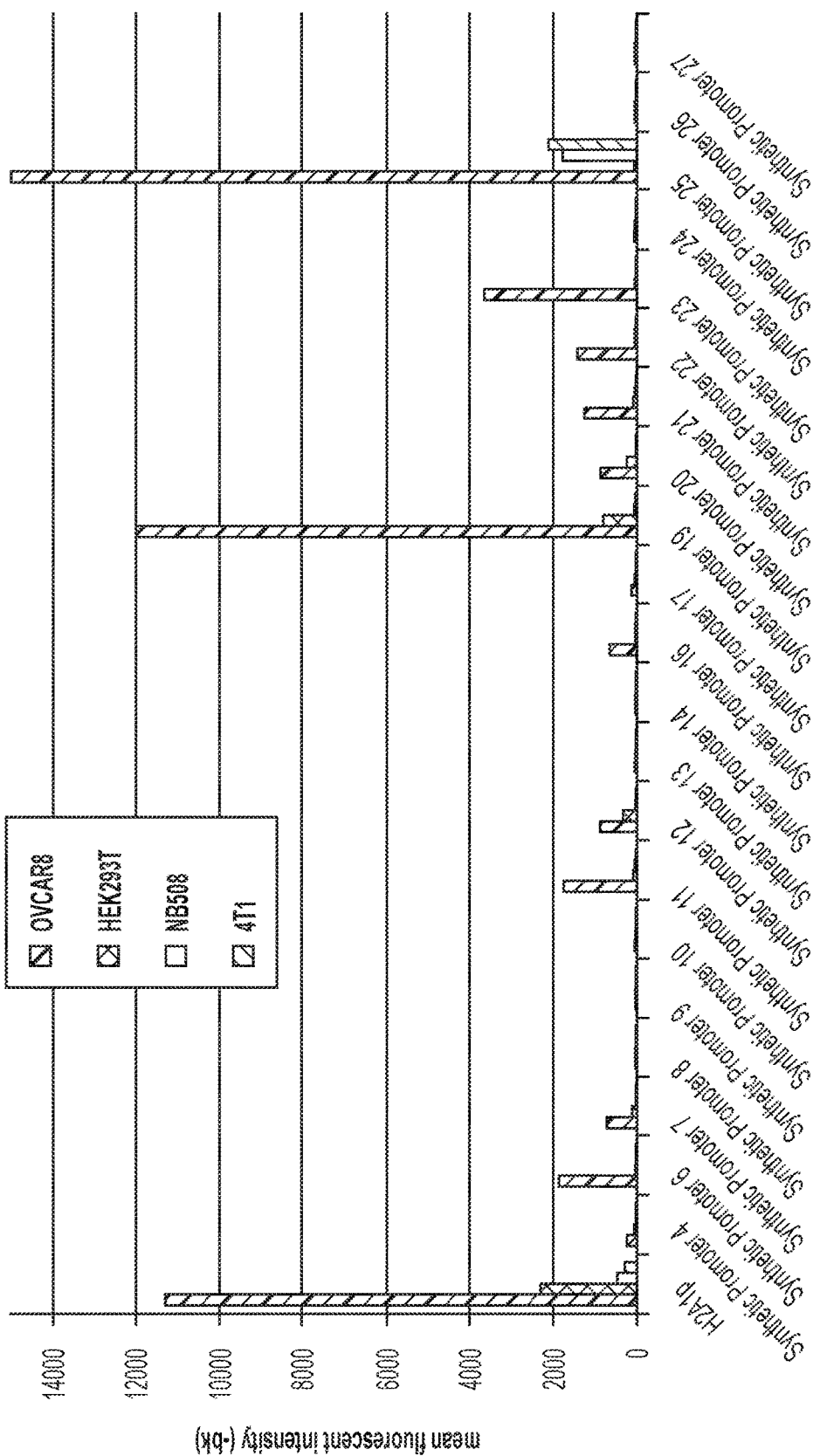
FIG. 5 is a graph showing the activities of synthetic promoters in four different cell lines: OVCAR8, HEK293T, NB508, and 4T1.
Figure 6:
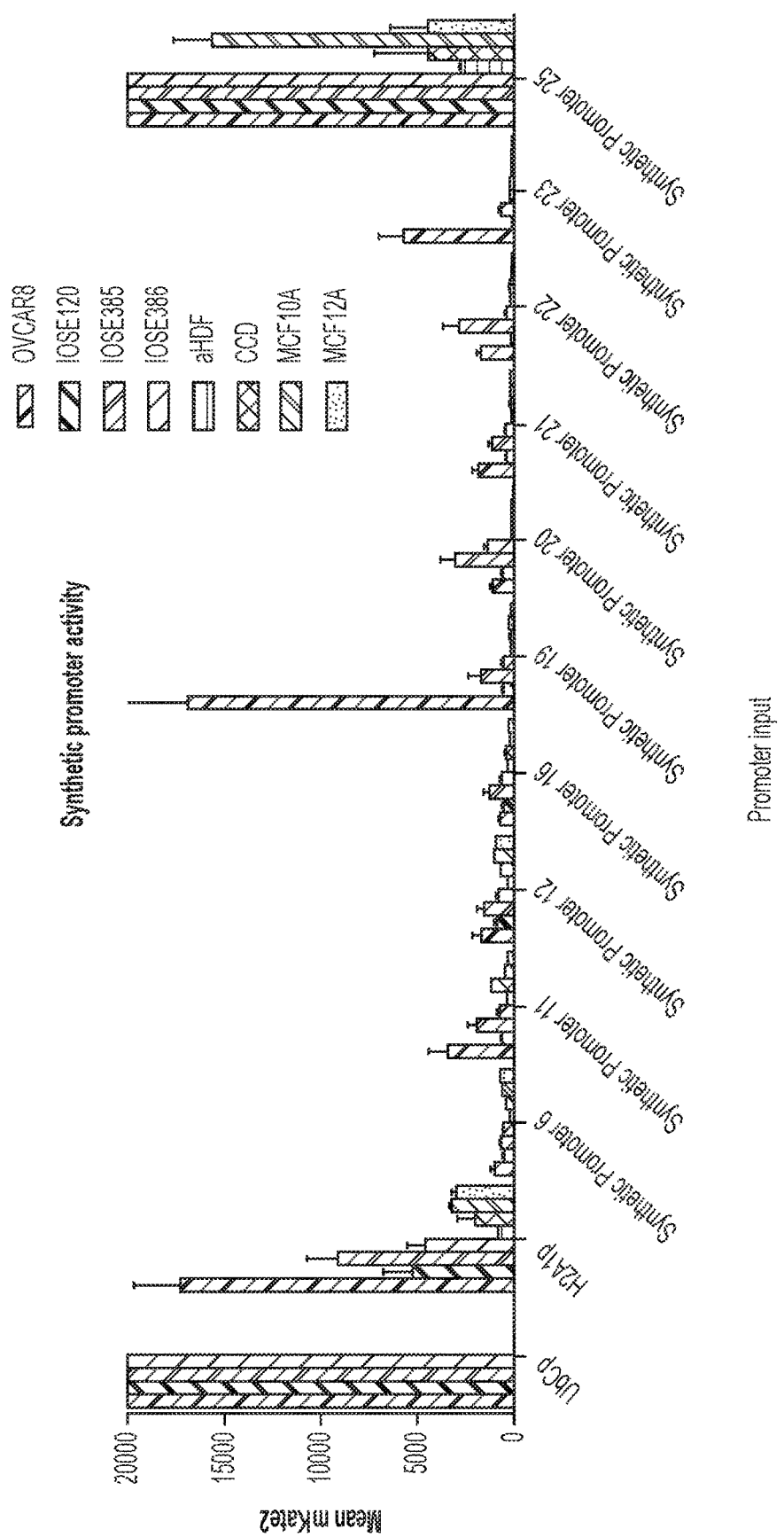
FIG. 6 is a graph showing the activities of synthetic promoters in eight different cell lines: OVCAR8, IOSE385, IOSE386, IOSE120, aHDF, CCD, MCF10A, and MCF12A.
Figure 7:
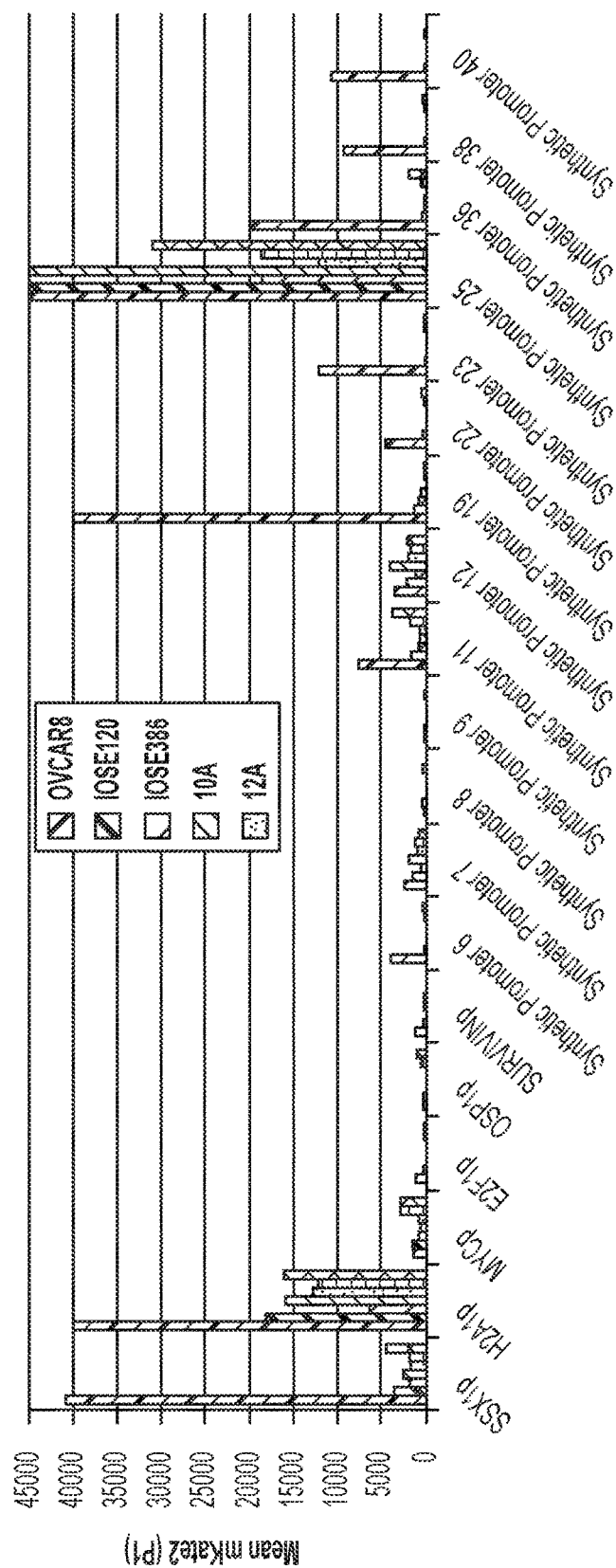
FIG. 7 is a graph showing the activities of synthetic promoters in four different cell lines: OVCAR8, IOSE386, IOSE120, 12A, and 10A.

In some embodiments, an engineered nucleic acid is delivered to a cell on a vector. A "vector" refers to a nucleic acid (e.g., DNA) used as a vehicle to artificially carry genetic material (e.g., an engineered nucleic acid) into a cell where, for example, it can be replicated and/or expressed. In some embodiments, a vector is an episomal vector (see, e.g., Van Craenenbroeck K. et al. *Eur. J. Biochem.* 267, 5665, 2000, incorporated by reference herein). A non-limiting example of a vector is a plasmid (e.g., FIG. 3). Plasmids are double-stranded generally circular DNA sequences that are capable of automatically replicating in a host cell. Plasmid vectors typically contain an origin of replication that allows for semi-independent replication of the plasmid in the host and also the transgene insert. Plasmids may have more features, including, for example, a "multiple cloning site," which includes nucleotide overhangs for insertion of a nucleic acid insert, and multiple restriction enzyme consensus sites to either side of the insert. Another non-limiting example of a vector is a viral vector, such as an oncolytic herpes simplex virus. Thus, the present disclosure provides oncolytic herpes simplex virus vectors comprising an engineered nucleic acid comprising a promoter that comprises the nucleotide sequence identified by any one of SEQ ID NOS: 1-12263, or a nucleotide sequences at least 95% identical to the nucleotide sequence identified by any one of SEQ ID NOS: 1-12263.

Cells

Cells comprising the engineered nucleic acids of the present disclosure are also provided. Engineered nucleic acids comprising the synthetic promoters described herein are, in some embodiments, delivered systemically or to a particular cell type, such as a cancerous cell, a benign tumor cell or other disease cell. In some embodiments, engineered nucleic acids are delivered to a subject having tumor cells or cancer cells, and the synthetic promoters drive the expression of the nucleotide sequence to which it is operably linked to specifically in the tumor cells or cancer cells.

A cancerous cell may be any type of cancerous cell, including, but not limited to, premalignant neoplasms, malignant tumors, metastases, or any disease or disorder characterized by uncontrolled cell growth such that it would be considered cancerous or precancerous. The cancer may be a primary or metastatic cancer. Cancers include, but are not limited to, ocular cancer, biliary tract cancer, bladder cancer, pleura cancer, stomach cancer, ovary cancer, meninges cancer, kidney cancer, brain cancer including glioblastomas and medulloblastomas, breast cancer, cervical cancer, choriocarcinoma, colon cancer, endometrial cancer, esophageal cancer, gastric cancer, hematological neoplasms including acute lymphocytic and myelogenous leukemia, multiple myeloma, AIDS-associated leukemias and adult T-cell leukemia lymphoma, intraepithelial neoplasms including Bowen's disease and Paget's disease, liver cancer, lung cancer, lymphomas including Hodgkin's disease and lymphocytic lymphomas, neuroblastomas, oral cancer including squamous cell carcinoma, ovarian cancer including those arising from epithelial cells, stromal cells, germ cells and mesenchymal cells, pancreatic cancer, prostate cancer, rectal cancer, sarcomas including leiomyosarcoma, rhabdomyosarcoma, liposarcoma, fibrosarcoma, and osteosarcoma, skin cancer including melanoma, Kaposi's sarcoma, basocellular cancer, and squamous cell cancer, testicular cancer including germinal tumors such as seminoma, non-seminoma, teratomas, choriocarcinomas, stromal tumors and germ cell tumors, thyroid cancer including thyroid adenocarcinoma and medullar carcinoma, and renal cancer including adenocarcinoma and Wilms' tumor. Commonly encountered cancers include breast, prostate, lung, ovarian, colorectal, and brain cancer. In some embodiments, the tumor is a melanoma, carcinoma, sarcoma, or lymphoma.

Engineered nucleic acids of the present disclosure may be used in a broad range of host cell types. In some embodiments, engineered nucleic acids are used in mammalian cells (e.g., human cells), bacterial cells (*Escherichia coli* cells), yeast cells, insect cells, or other types of cells. Engineered nucleic acids of the present disclosure may be used in vivo, e.g., in a subject such as a human subject.

In some embodiments, engineered nucleic acids comprising synthetic promoters are used in mammalian cells, for example, for research or therapeutic applications. For example, in some embodiments, engineered nucleic acids are used in human cells, primate cells (e.g., vero cells), rat cells (e.g., GH3 cells, OC23 cells) or mouse cells (e.g., MC3T3 cells). There are a variety of human cell lines, including, without limitation, human embryonic kidney (HEK) cells, HeLa cells, cancer cells from the National Cancer Institute's 60 cancer cell lines (NCI60), DU145 (prostate cancer) cells, Lncap (prostate cancer) cells, MCF-7 (breast cancer) cells, MDA-MB-438 (breast cancer) cells, PC3 (prostate cancer) cells, T47D (breast cancer) cells, THP-1 (acute myeloid leukemia) cells, U87 (glioblastoma) cells, SHSY5Y human neuroblastoma cells (cloned from a myeloma) and Saos-2 (bone cancer) cells. In some embodiments, engineered nucleic acids are expressed in human embryonic kidney (HEK) cells (e.g., HEK 293 or HEK 293T cells). In some embodiments, engineered nucleic acids are expressed in stem cells (e.g., human stem cells) such as, for example, pluripotent stem cells (e.g., human pluripotent stem cells including human induced pluripotent stem cells (hiPSCs)). A "stem cell" refers to a cell with the ability to divide for indefinite periods in culture and to give rise to specialized cells. A "pluripotent stem cell" refers to a type of stem cell that is capable of differentiating into all tissues of an organism, but not alone capable of sustaining full organismal development. A "human induced pluripotent stem cell" refers to a somatic (e.g., mature or adult) cell that has been reprogrammed to an embryonic stem cell-like state by being forced to express genes and factors important for maintaining the defining properties of embryonic stem cells (see, e.g., Takahashi and Yamanaka, Cell 126 (4): 663-76, 2006, incorporated by reference herein). Human induced pluripotent stem cell cells express stem cell markers and are capable of generating cells characteristic of all three germ layers (ectoderm, endoderm, mesoderm).

Additional non-limiting examples of cell lines that may be used in accordance with the present disclosure include 293-T, 293-T, 3T3, 4T1, 721, 9L, A-549, A172, A20, A253, A2780, A2780ADR, A2780cis, A431, ALC, B16, B35, BCP-1, BEAS-2B, bEnd.3, BHK-21, BR 293, BxPC3, C2C12, C3H-10T1/2, C6, C6/36, Cal-27, CGR8, CHO, CML T1, CMT, COR-L23, COR-L23/5010, COR-L23/CPR, COR-L23/R23, COS-7, COV-434, CT26, D17, DH82, DU145, DuCaP, E14Tg2a, EL4, EM2, EM3, EMT6/AR1, EMT6/AR10.0, FM3, H1299, H69, HB54, HB55, HCA2, Hepa1c1c7, High Five cells, HL-60, HMEC, HT-29, HUVEC, J558L cells, Jurkat, JY cells, K562 cells, KCL22, KG1, Ku812, KYO1, LNCap, Ma-Mel 1, 2, 3 . . . 48, MC-38, MCF-10A, MCF-7, MDA-MB-231, MDA-MB-435, MDA-MB-468, MDCK II, MG63, MONO-MAC 6, MOR/0.2R, MRC5, MTD-1A, MyEnd, NALM-1, NCI-H69/CPR, NCI-H69/LX10, NCI-H69/LX20, NCI-H69/LX4, NIH-3T3, NW-145, OPCN/OPCT Peer, PNT-1A/PNT 2, PTK2, Raji, RBL cells, RenCa, RIN-5F, RMA/RMAS, S2, Saos-2 cells, Sf21, Sf9, SiHa, SKBR3, SKOV-3, T-47D, T2, T84, THP1, U373, U87, U937, VCaP, WM39, WT-49, X63, YAC-1 and YAR cells.

Cells of the present disclosure, in some embodiments, are modified. A modified cell is a cell that contains an exogenous nucleic acid or a nucleic acid that does not occur in nature. In some embodiments, a modified cell contains a mutation in a genomic nucleic acid. In some embodiments, a modified cell contains an exogenous independently replicating nucleic acid (e.g., an engineered nucleic acid present on an episomal vector). In some embodiments, a modified cell is produced by introducing a foreign or exogenous nucleic acid into a cell. A nucleic acid may be introduced into a cell by conventional methods, such as, for example, electroporation (see, e.g., Heiser W. C. *Transcription Factor Protocols: Methods in Molecular Biology™* 2000; 130: 117-134), chemical (e.g., calcium phosphate or lipid) transfection (see, e.g., Lewis W. H., et al., *Somatic Cell Genet.* 1980 May; 6(3): 333-47; Chen C., et al., *Mol Cell Biol.* 1987 August; 7(8): 2745-2752), fusion with bacterial protoplasts containing recombinant plasmids (see, e.g., Schaffner W.

*Proc Natl Acad Sci USA*. 1980 April; 77(4): 2163-7), transduction, conjugation, or microinjection of purified DNA directly into the nucleus of the cell (see, e.g., Capecchi M. R. *Cell*. 1980 November; 22(2 Pt 2): 479-88).

In some embodiments, a cell is modified to express a reporter molecule. In some embodiments, a cell is modified to express an inducible promoter operably linked to a reporter molecule (e.g., a fluorescent protein such as green fluorescent protein (GFP) or other reporter molecule).

In some embodiments, a cell is modified to overexpress an endogenous protein of interest (e.g., via introducing or modifying a promoter or other regulatory element near the endogenous gene that encodes the protein of interest to increase its expression level). In some embodiments, a cell is modified by mutagenesis. In some embodiments, a cell is modified by introducing an engineered nucleic acid into the cell in order to produce a genetic change of interest (e.g., via insertion or homologous recombination).

In some embodiments, an engineered nucleic acid may be codon-optimized, for example, for expression in mammalian cells (e.g., human cells) or other types of cells. Codon optimization is a technique to maximize the protein expression in living organism by increasing the translational efficiency of gene of interest by transforming a DNA sequence of nucleotides of one species into a DNA sequence of nucleotides of another species. Methods of codon optimization are well-known.

Also provided herein, in some aspects, are methods that comprise introducing into a cell an (e.g., at least one, at least two, at least three, or more) engineered nucleic acids or an episomal vector (e.g., comprising an engineered nucleic acid). An engineered nucleic acid may be introduced into a cell by conventional methods, such as, for example, electroporation, chemical (e.g., calcium phosphate or lipid) transfection, fusion with bacterial protoplasts containing recombinant plasmids, transduction, conjugation, or microinjection of purified DNA directly into the nucleus of the cell.

Engineered nucleic acids of the present disclosure may be delivered to a subject (e.g., a mammalian subject, such as a human subject) by any in vivo delivery method known in the art. For example, engineered nucleic acids may be delivered intravenously. In some embodiments, engineered nucleic acids are delivered in a delivery vehicle (e.g., non-liposomal nanoparticle or liposome). In some embodiments, engineered nucleic acids are delivered systemically to a subject having a cancer or other disease and activated (transcription is activated) specifically in cancer cells or diseased cells of the subject.

Engineered nucleic acids, as discussed above, may be delivered to cells (e.g., cancer cells) of a subject using a viral delivery system (e.g., retroviral, adenoviral, adeno-association, helper-dependent adenoviral systems, hybrid adenoviral systems, herpes simplex, pox virus, lentivirus, Epstein-Barr virus) or a non-viral delivery system (e.g., physical: naked DNA, DNA bombardment, electroporation, hydrodynamic, ultrasound or magnetofection; or chemical: cationic lipids, different cationic polymers or lipid polymer) (Nayerossadat N et al. *Adv Biomed Res*. 2012; 1: 27, incorporated herein by reference). In some embodiments, the non-viral based deliver system is a hydrogel-based delivery system (see, e.g., Brandl F, et al. *Journal of Controlled Release*, 2010, 142(2): 221-228, incorporated herein by reference).

Additional Embodiments

The present disclosure further provides the additional embodiments set forth in the following numbered paragraphs:

1. An engineered nucleic acid comprising a promoter that comprises the nucleotide sequence identified by any one of SEQ ID NOS: 1-12263, or a nucleotide sequences at least 95% identical to the nucleotide sequence identified by any one of SEQ ID NOS: 1-12263.
2. The engineered nucleic acid of paragraph 1, wherein the activity of the promoter is increased in diseased cells relative to healthy cells.
3. The engineered nucleic acid of paragraph 1, wherein the activity of the promoter is decreased in diseased cells relative to healthy cells.
4. The engineered nucleic acid of paragraph 2 or 3, wherein the diseased cells are selected from breast cancer cells, colon cancer cells, and ovarian cancer cells.
5. The engineered nucleic acid of any one of paragraphs 1-4, wherein the promoter is operably linked to a nucleotide sequence encoding a therapeutic protein.
6. A cell comprising the engineered nucleic acid of any one of paragraphs 1-5.
7. A method of delivering to a cell the engineered nucleic acid of any one of paragraphs 1-5.
8. A method of delivering to a subject the engineered nucleic acid of any one of paragraphs 1-5.
9. A method of delivering to a subject the cell of paragraph 6.
10. The engineered nucleic acid of any one of paragraphs 1-5, wherein the nucleotide sequence is identified by any one of SEQ ID NO: 1-40 or a nucleotide sequences at least 95% identical to the nucleotide sequence identified by any one of SEQ ID NO: 1-40.
11. The engineered nucleic acid of paragraph 10, wherein the nucleotide sequence is identified by SEQ ID NO: 1.
12. The engineered nucleic acid of paragraph 10, wherein the nucleotide sequence is identified by SEQ ID NO: 2.
13. The engineered nucleic acid of paragraph 10, wherein the nucleotide sequence is identified by SEQ ID NO: 3.
14. The engineered nucleic acid of paragraph 10, wherein the nucleotide sequence is identified by SEQ ID NO: 4.
15. The engineered nucleic acid of paragraph 10, wherein the nucleotide sequence is identified by SEQ ID NO: 5.
16. The engineered nucleic acid of paragraph 10, wherein the nucleotide sequence is identified by SEQ ID NO: 6.
17. The engineered nucleic acid of paragraph 10, wherein the nucleotide sequence is identified by SEQ ID NO: 7.
18. The engineered nucleic acid of paragraph 10, wherein the nucleotide sequence is identified by SEQ ID NO: 8.
19. The engineered nucleic acid of paragraph 10, wherein the nucleotide sequence is identified by SEQ ID NO: 9.
20. The engineered nucleic acid of paragraph 10, wherein the nucleotide sequence is identified by SEQ ID NO: 10.
21. The engineered nucleic acid of paragraph 10, wherein the nucleotide sequence is identified by SEQ ID NO: 11.
22. The engineered nucleic acid of paragraph 10, wherein the nucleotide sequence is identified by SEQ ID NO: 12.
23. The engineered nucleic acid of paragraph 10, wherein the nucleotide sequence is identified by SEQ ID NO: 13.
24. The engineered nucleic acid of paragraph 10, wherein the nucleotide sequence is identified by SEQ ID NO: 14.
25. The engineered nucleic acid of paragraph 10, wherein the nucleotide sequence is identified by SEQ ID NO: 15.
26. The engineered nucleic acid of paragraph 10, wherein the nucleotide sequence is identified by SEQ ID NO: 16.

27. The engineered nucleic acid of paragraph 10, wherein the nucleotide sequence is identified by SEQ ID NO: 17.
28. The engineered nucleic acid of paragraph 10, wherein the nucleotide sequence is identified by SEQ ID NO: 18.
29. The engineered nucleic acid of paragraph 10, wherein the nucleotide sequence is identified by SEQ ID NO: 19.
30. The engineered nucleic acid of paragraph 10, wherein the nucleotide sequence is identified by SEQ ID NO: 20.
31. The engineered nucleic acid of paragraph 10, wherein the nucleotide sequence is identified by SEQ ID NO: 21.
32. The engineered nucleic acid of paragraph 10, wherein the nucleotide sequence is identified by SEQ ID NO: 22.
33. The engineered nucleic acid of paragraph 10, wherein the nucleotide sequence is identified by SEQ ID NO: 23.
34. The engineered nucleic acid of paragraph 10, wherein the nucleotide sequence is identified by SEQ ID NO: 24.
35. The engineered nucleic acid of paragraph 10, wherein the nucleotide sequence is identified by SEQ ID NO: 25.
36. The engineered nucleic acid of paragraph 10, wherein the nucleotide sequence is identified by SEQ ID NO: 26.
37. The engineered nucleic acid of paragraph 10, wherein the nucleotide sequence is identified by SEQ ID NO: 27.
38. The engineered nucleic acid of paragraph 10, wherein the nucleotide sequence is identified by SEQ ID NO: 28.
39. The engineered nucleic acid of paragraph 10, wherein the nucleotide sequence is identified by SEQ ID NO: 29.
40. The engineered nucleic acid of paragraph 10, wherein the nucleotide sequence is identified by SEQ ID NO: 30.
41. The engineered nucleic acid of paragraph 10, wherein the nucleotide sequence is identified by SEQ ID NO: 31.
42. The engineered nucleic acid of paragraph 10, wherein the nucleotide sequence is identified by SEQ ID NO: 32.
43. The engineered nucleic acid of paragraph 10, wherein the nucleotide sequence is identified by SEQ ID NO: 33.
44. The engineered nucleic acid of paragraph 10, wherein the nucleotide sequence is identified by SEQ ID NO: 34.
45. The engineered nucleic acid of paragraph 10, wherein the nucleotide sequence is identified by SEQ ID NO: 35.
46. The engineered nucleic acid of paragraph 10, wherein the nucleotide sequence is identified by SEQ ID NO: 36.
47. The engineered nucleic acid of paragraph 10, wherein the nucleotide sequence is identified by SEQ ID NO: 37.
48 The engineered nucleic acid of paragraph 10, wherein the nucleotide sequence is identified by SEQ ID NO: 38.
49. The engineered nucleic acid of paragraph 10, wherein the nucleotide sequence is identified by SEQ ID NO: 39.
50. The engineered nucleic acid of paragraph 10, wherein the nucleotide sequence is identified by SEQ ID NO: 40.
51. The engineered nucleic acid of any one of paragraphs 1-5, wherein the nucleotide sequence is identified by any one of SEQ ID NO: 41-49, or a nucleotide sequences at least 95% identical to the nucleotide sequence identified by any one of SEQ ID NO: 41-49.
52. The engineered nucleic acid of paragraph 51, wherein the nucleotide sequence is identified by SEQ ID NO: 41.
53. The engineered nucleic acid of paragraph 51, wherein the nucleotide sequence is identified by SEQ ID NO: 42.
54. The engineered nucleic acid of paragraph 51, wherein the nucleotide sequence is identified by SEQ ID NO: 43.
55. The engineered nucleic acid of paragraph 51, wherein the nucleotide sequence is identified by SEQ ID NO: 44.
56. The engineered nucleic acid of paragraph 51, wherein the nucleotide sequence is identified by SEQ ID NO: 45.
57. The engineered nucleic acid of paragraph 51, wherein the nucleotide sequence is identified by SEQ ID NO: 46.
58. The engineered nucleic acid of paragraph 51, wherein the nucleotide sequence is identified by SEQ ID NO: 47.
59. The engineered nucleic acid of paragraph 51, wherein the nucleotide sequence is identified by SEQ ID NO: 48.
60. The engineered nucleic acid of paragraph 51, wherein the nucleotide sequence is identified by SEQ ID NO: 49.
61. An oncolytic virus comprising the engineered nucleic acid of any one of paragraphs 1-5 or 10-60.
62. The oncolytic virus of paragraph 61, wherein the oncolytic virus is an oncolytic herpes simplex virus.

EXAMPLES

Example 1. Synthetic Promoter Activity and Specificity—Synthetic Promoters 1-40

Reporter constructs were constructed by placing the coding sequence of ECFP or mKate2 under the synthetic promoters. The reporter constructs were transfected into different cell lines as listed in Table 1. The expression of ECFP or mKate2 indicates the activity of the synthetic promoter in each cell line. The activities of a set of synthetic promoters (Table 2) were tested in different cell lines. The results are provided in FIGS. 1-7.

TABLE 1

Different Cell Lines for Testing Promoter Activity

| # | Line | Type | Tissue | Organism |
|---|---|---|---|---|
| 1 | OVCAR8 | cancer | ovarian | human |
| 2 | IOSE386 | normal | ovarian | human |
| 3 | IOSE385 | normal | ovarian | human |
| 4 | IOSE120 | normal | ovarian | human |
| 5 | HCT116 | cancer | Colorectal | human |
| 6 | CCD-841-Con | normal | Colon | human |
| 7 | SKBR3 | cancer | breast | human |
| 8 | MDA-MB-453 | cancer | breast | human |
| 9 | MDA-MB-231 | cancer | breast | human |
| 10 | MCF-7 | cancer | breast | human |
| 11 | MCF-10A | normal | breast | human |
| 12 | MCF-12A | normal | breast | human |
| 13 | aHDF | normal | adult dermal fibroblasts | human |
| 14 | NB508 | cancer | pancreatic | mouse |
| 15 | 4T1 | cancer | breast | mouse |

Examples of synthetic promoters used to regulate expression of ECFP:

TABLE 2

Synthetic Promoters 1-40

| Name | Sequence | SEQ ID NO |
|---|---|---|
| Synthetic Promoter 1 | CAGGGGATGCTTTAGGCGGGAAAGTCAGAGTTTCTGCCTCCAT TTCCCAGGGGATGCTTTAGGCGGGAAAGTCAGAGTTTCTGCCT CCATTTGTCATGCATCTCAATTACCCAGGGGATGCTTTAGGCG GGAAAGTCAGAGTTTCTGCCTCCATTTCCCAGGGGATGCTTTA GGCGGGAAAGTCAGAGTTTCTGCCTCCATTT | 1 |

TABLE 2-continued

Synthetic Promoters 1-40

| Name | Sequence | SEQ ID NO |
|---|---|---|
| Synthetic Promoter 2 | CCCGTTTCCAGCCGAAACGTAGCCGTTTCGTACTCGAGCTTTG GCGCATCCGTTTCCCGAATTCCCGAAACGTTCCTTTGGCGCTG CCCTACTGACACTGCCTGCGTTTCCAGCCGAAACGTAGCCGTT TCGTACTCGAGCTTTGGCGCATCCGTTTCCCGAATTCCCGAAA CGTTCCTTTGGCGC | 2 |
| Synthetic Promoter 3 | CCCGTTTCCAGCCGAAACGTAGCCGTTTCGTACTCGAGCTTTG GCGCATCCGTTTCCCGAATTCCCGAAACGTTCCTTTGGCGCTG CCCTACTGACACTGCCTGCGTTTCCAGCCGAAACGTAGCCGTT TCGTACTCGAGCTTTGGCGCATCCGTTTCCCGAATTCCCGAAA CGTTCCTTTGGCGCGGCGCGCCAGACGCTAGCGGGGGGCTATA AAAGGGGTGGGGGCGTTCGTCCTCACTCTAGATCTGCGATCT AAGTAAGCTTGATATCGCGGCCGCCCCTGGACACCCTTGGAAG CAAATCCCCTGCAGGCCCGTTTCCAGCCGAAACGTAGCCGTTT CGTACTCGAGCTTTGGCGCATCCGTTTCCCGAATTCCCGAAAC GTTCCTTTGGCGCTGCCCTACTGACACTGCCTGCGTTTCCAGCC GAAACGTAGCCGTTTCGTACTCGAGCTTTGGCGCATCCGTTTC CCGAATTCCCGAAACGTTCCTTTGGCGC | 3 |
| Synthetic Promoter 4 | CCGGTGACTCAGTAGCGGTGACTCAGAATCGATGACTCAGAC AGTGACTAAGTACTATGAGTCAGGTCGAATGAGTCAGCGAGT GACTCAATGGTCCATGACTCACGAATTCCTGCCCTACTGACAC TGCCTGCCGGTGACTCAGTAGCGGTGACTCAGAATCGATGACT CAGACAGTGACTAAGTACTATGAGTCAGGTCGAATGAGTCAG CGAGTGACTCAATGGTCCATGACTCAGAATATCCGC | 4 |
| Synthetic Promoter 5 | CCGGTGACTCAGTAGCGGTGACTCAGAATCGATGACTCAGAC AGTGACTAAGTACTATGAGTCAGGTCGAATGAGTCAGCGAGT GACTCAATGGTCCATGACTCACGAATTCCTGCCCTACTGACAC TGCCTGCCGGTGACTCAGTAGCGGTGACTCAGAATCGATGACT CAGACAGTGACTAAGTACTATGAGTCAGGTCGAATGAGTCAG CGAGTGACTCAATGGTCCATGACTCAGAATATCCGCGGCTTGG AAGCAAATCCCCTGCAGGCCGGTGACTCAGTAGCGGTGACTC AGAATCGATGACTCAGACAGTGACTAAGTACTATGAGTCAGG TCGAATGAGTCAGCGAGTGACTCAATGGTCCATGACTCACGAA TTCCTGCCCTACTGACACTGCCTGCCGGTGACTCAGTAGCGGT GACTCAGAATCGATGACTCAGACAGTGACTAAGTACTATGAGT CAGGTCGAATGAGTCAGCGAGTGACTCAATGGTCCATGACTCA GAATATCCGC | 5 |
| Synthetic Promoter 6 | TCCACACGTGCAAGCCGAGCACGTGGCTCATCACCACGAGTCA GACAACCACGTGCTCACTGACCACGTGCCTGTCGGCCACGTGT GAGTCCACACGTGCATCCCGAGCACGTGGCTCCGAATTCCTGC CCTACTGACACTGCCTGCCGTCCACACGTGCAAGCCGAGCACG TGGCTCATCACCACGAGTCAGACAACCACGTGCTCACTGACCA CGTGCCTGTCGGCCACGTGTGAGTCCACACGTGCATCCCGAGC ACGTGGCTCCGAATATCCGC | 6 |
| Synthetic Promoter 7 | CGTACGTGCGGCAGCCCGGACGTGCGCCATCTGCGTGAGGAC GCGCGTGACAACTCGTACGTGCGGCGTCCCGGACGTGCGCCG AGTGCGTGAGTCCGCGCGTGACACCGAATTCCTGCCCTACTGA CACTGCCTGCCGCGTACGTGCGGCAGCCCGGACGTGCGCCATC TGCGTGAGGACGCGCGTGACAACTCGTACGTGCGGCGTCCCG GACGTGCGCCGAGTGCGTGAGTCCGCGCGTGACACCGAATAT CCGC | 7 |
| Synthetic Promoter 8 | CTCATTTCAAAAAAGCCCCATTTAAGAGTATCCTCATTTCAGA TTGACTATTTGGTAAACTATATTTGGCAATGCACGTCGTATTTT GCAATGGCTGAGCTCATTTCAAAAATCCCCCATTTAAGAGTCG AATTCCTGCCCTACTGACACTGCCTGCCGCTCATTTCAAAAAA GCCCCATTTAAGAGTATCTATTTGGTAAGACCTCATTTCAGATT ACTGTATTTTGCAATGGCTGTCATATTTGGCAATGCACGAGCC CATTTAAGAGTTCCCTCATTTCAAAAACGAATATCCGC | 8 |
| Synthetic Promoter 9 | CCGCGAGGAGGCAGAGCTGACCACTAGATGGCAGTAATCTGG CCACCAGAGGGCGCGACTCGCCACTAGGTGGCGCACTTGGCC ACCAGGGGCGCCAGTCCCGCGAGGAGGCAGGAGTGGCCACC AGAGGGCGCCGAATTCCTGCCCTACTGACACTGCCTGCCGTCG CCACTAGGTGGCGCAGCTGGCCACCAGGGGGCGCCAGACCCG CGAGGAGGCAGACTTGACCACTAGATGGCAGTAGAGTGGCCA CCAGGGGGCGCCATCCTCGCCACTAGGTGGCGCCGAATATCCG C | 9 |

TABLE 2-continued

Synthetic Promoters 1-40

| Name | Sequence | SEQ ID NO |
|---|---|---|
| Synthetic Promoter 10 | CGACCATCTGGTAGCCGAACATCTGTTATCCGACCATCTGTTG ACCCACCTGCCCGACTCCAGCTGCTCGGTCCGACCATCTGGTG AGCCACCTGCCCGTCCCGACCATCTGTTCGAATTCCTGCCCTA CTGACACTGCCTGCCGCCACCTGCCCGAGCCCAGCTGCTCGAT CCGACCATCTGGTGACCGAACATCTGTTACTCCAGCTGCTCGG TCCCACCTGCCCGGAGCCAGCTGCTCGTCCCGACCATCTGGTC GAATATCCGC | 10 |
| Synthetic Promoter 11 | CTGATTGGCCAAAGCCTGATTGGCCAAATCCTGATTGGCCAAG ACCTGATTGGCCAAACTCTGATTGGCCAAGTCTCTGATTGGCC AAGGAGCTGATTGGCCAATCCCTGATTGGCCAACGAATTCCTG CCCTACTGACACTGCCTGCCGCTGATTGGCCAAAGCCTGATTG GCCAAATCCTGATTGGCCAAGACCTGATTGGCCAAACTCTGAT TGGCCAAGTCCTGATTGGCCAAGAGCTGATTGGCCAATCCCTG ATTGGCCAACGAATATCCGC | 11 |
| Synthetic Promoter 12 | AAACAGGAAGTTCGTAGCCCAACCGGAAGTATCAACCGGAAG TAGACGACCGGAAGTAACTGACCGGAAGTAGTCGACCGGAAG TGGAGAAACAGGAAGTTCGTTCCCCAACCGGAAGTCGAATTC CTGCCCTACTGACACTGCCTGCCGGACCGGAAGTAAGCAACCG GAAGTAATCGACCGGAAGTGGACAAACAGGAAGTTCGTACTC CAACCGGAAGTGTCAACCGGAAGTAGAGGACCGGAAGTATCC GACCGGAAGTGCGAATATCCGC | 12 |
| Synthetic Promoter 13 | GGCCCAGGGGATGCTTTAGGCGAGCGGCCCAGGGGATGCTTT AGGCGATCGGCCCAGGGGATGCTTTAGGCGGACGGCCCAGGG GATGCTTTAGGCGACTGGCCCAGGGGATGCTTTAGGCGGTCGA ATTCCTGCCCTACTGACACTGCCTGCCGGGCCCAGGGGATGCT TTAGGCGAGCGGCCCAGGGGATGCTTTAGGCGATCGGCCCAG GGGATGCTTTAGGCGGACGGCCAGGGGATGCTTTAGGCGGT CGGCCCAGGGGATGCTTTAGGCGCGAATATCCGC | 13 |
| Synthetic Promoter 14 | CGGTTGCCATGGCAACCGAGCCGGTTTCCATGGAAACAAATCA AGTTACTAGGCAAAAGGACCGGTTGCCATGGCAACCGACTAA GTTACTAGGCAAAAGGAGCGGTTTCCATGGAAACAATCCCGG TTGCCATGGCAACCGCGAATTCCTGCCCTACTGACACTGCCTG CCGAAGTTACTAGGCAAAAGAGCCGGTTGCCATGGCAACCGA TCCGGTTTCCATGGAAACAAGACCGGTTGCCATGGCAACCGAC TAAGTTACTAGGCAAAAGGTCCGGTTTCCATGGAAACAATCCG AATATCCGC | 14 |
| Synthetic Promoter 15 | CCCAGGGGATGCTTTAGGCGGGAAAGTCAGAGTTTCTGCCTCC ATTTCCCAGGGGATGCTTTAGGCGGGAAAGTCAGAGTTTCTGC CTCCATTTGTCATGCATCTCAATTACCCAGGGGATGCTTTAGG CGGGAAAGTCAGAGTTTCTGCCTCCATTTGGCCTGCAGG CCCAGGGGATGCTTTAGGCGGGAAAGTCAGAGTTTCTGCCTCC ATTTCCCAGGGGATGCTTTAGGCGGGAAAGTCAGAGTTTCTGC CTCCATTTGTCATGCATCTCAATTACCCAGGGGATGCTTTAGG CGGGAAAGTCAGAGTTTCTGCCTCCATTTCCCAGGGGATGCTT TAGGCGGGAAAGTCAGAGTTTCTGCCTCCATTT | 15 |
| Synthetic Promoter 16 | TAGGGTGGGCGTGGCAGCCGGGGCGGGGCATCTAGGGCGGGG CCGACGGGGGGCGGGGCCACTTAGGGTGGGCGTGGCGTCCGG GGCGGGGCGAGTAGGGCGGGGCCTCCGGGGGGCGGGGCCCGA ATTCTGCCCTACTGACACTGCCTGCCGTAGGGTGGGCGTGGCA GCCGGGGCGGGGCATCTAGGGCGGGGCCGACGGGGGGCGGG GCCACTTAGGGTGGGCGTGGCGTCCGGGGCGGGGCGAGTAGG GCGGGGCCTCCGGGGGGCGGGGCCCGAATATCCGC | 16 |
| Synthetic Promoter 17 | CGGGTGACGTCAACGGAGCGGGCTGACGTAAACGGATCTGAC GTCAGACCAATGACGTCACGACTCGGGTGACGTCAACGGGTC GGGCTGACGTAAACGGGAGTGACGTCATCCCAATGACGTCAC GCGAATTCTGCCCTACTGACACTGCCTGCCGCGGGTGACGTCA ACGGAGCGGGCTGACGTAAACGGATCTGACGTCAGACCAATG ACGTCACGACTCGGGTGACGTCAACGGGTCGGGCTGACGTAA ACGGGAGTGACGTCATCCCAATGACGTCACGCGAATATCCGC | 17 |

TABLE 2-continued

Synthetic Promoters 1-40

| Name | Sequence | SEQ ID NO |
|---|---|---|
| Synthetic Promoter 18 | CGGGTGACGTCAACGGAGCGGGCTGACGTAAACGGATCTGAC GTCAGACCAATGACGTCACGACTCGGGTGACGTCAACGGGTC GGGCTGACGTAAACGGGAGTGACGTCATCCCAATGACGTCAC GCGAATTCTGCCCTACTGACACTGCCTGCCGCGGGTGACGTCA ACGGAGCGGGCTGACGTAAACGGATCTGACGTCAGACCAATG ACGTCACGACTCGGGTGACGTCAACGGGTCGGGCTGACGTAA ACGGGAGTGACGTCATCCCAATGACGTCACGCGAATATCCGC | 18 |
| Synthetic Promoter 19 | TACGCGCGAAAACTGAGCGCGCCAAAATCGCTGAGCGCGAAA CGGACGGGGCGGGAAGACTTACGCGCGAAAACTGGTCGCGCC AAAGAGGCTGAGCGCGAAACGTCCGGGGCGGGAAGCGAATTC TGCCCTACTGACACTGCCTGCCGTACGCGCGAAAACTGAGCGC GCCAAAATCGCTGAGCGCGAAACGGACGGGGCGGGAAGACTT ACGCGCGAAAACTGGTCGCGCCAAAGAGGCTGAGCGCGAAAC GTCCGGGGCGGGAAGCGAATATCCGC | 18 |
| Synthetic Promoter 20 | TCTGATGCAATAGCGGTATGATGCAAGGAATCAGATTGTGAA ATGTGACATTGTGAAATAACTTCTGATGCAATGTCGGTATGAT GCAAGGAGAGAGATTGTGAAATGTTCCATTGTGAAATACGAA TTCTGCCCTACTGACACTGCCTGCCGTCTGATGCAATAGCGGT ATGATGCAAGGAATCAGATTGTGAAATGTGACATTGTGAAAT AACTTCTGATGCAATGTCGGTATGATGCAAGGAGAGAGATTGT GAAATGTTCCATTGTGAAATACGAATATCCGC | 20 |
| Synthetic Promoter 21 | TCAGCCAATCAGAGAGCGAGCCAATCAGAATCCCAGCCAATC AGAGACTGGGCCAATCAGAAACTTCAGCCAATCAGAGGTCGA GCCAATCAGAGAGCCAGCCAATCAGATCCTGGGCCAATCAGA ACGAATTCTGCCCTACTGACACTGCCTGCCGTCAGCCAATCAG AGAGCGAGCCAATCAGAATCCCAGCCAATCAGAGACTGGGCC AATCAGAAACTTCAGCCAATCAGAGGTCGAGCCAATCAGAGA GCCAGCCAATCAGATCCTGGGCCAATCAGAACGAATATCCGC | 21 |
| Synthetic Promoter 22 | AGCCGCACGTGACAGCAGCCGCACGTGACATCCACCCACGTG CGACCACCCACGTGCACTAGCCGCACGTGACCACAGCCGCAC GTGACGAGCACCCACGTGCTCCCACCCACGTGCCGAATTCTGC CCTACTGACACTGCCTGCCGAGCCGCACGTGACAGCAGCCGCA CGTGACATCCACCCACGTGCGACCACCCACGTGCACTAGCCGC ACGTGACCATCAGCCGCACGTGACGAGCACCCACGTGCTCCCA CCCACGTGCCGAATATCCGC | 22 |
| Synthetic Promoter 23 | GACCACGTGGAAGCGACCACGTGGAATCCGCCACGTGCGCGA CCGCCACGTGCGCACTAGACCACGTGGTCGTCAGACCACGTGG TCGAGAAAACACGTGGTTCCAAAACACGTGGTCGAATTCTGCC CTACTGACACTGCCTGCCGGACCACGTGGAAGCGACCACGTG GAATCCGCCACGTGCGCGACCGCCACGTGCGCACTAGACCAC GTGGTCGTCAGACCACGTGGTCGAGAAAACACGTGGTTCCAA AACACGTGGTCGAATATCCGCG | 23 |
| Synthetic Promoter 24 | TAGCCTGGGGCCGAGCTAGCCTGGGGCCGATCACCGCCTGAG GGGAGACACCGCCTGAGGGGAACTTGCCCTGGGGCCGTCTGC CCTGGGGCCGAGTTGCCCTAGGGCATTCCTTGCCCTAGGGCAT CGAATTCTGCCCTACTGACACTGCCTGCCGTAGCCTGGGGCCG AGCTAGCCTGGGGCCGATCACCGCCTGAGGGGAGACACCGCC TGAGGGGAACTTGCCCTGGGGCCGTCTGCCCTGGGGCCGAGTT GCCCTAGGGCATTCCTTGCCCTAGGGCATCGAATATCCGC | 24 |
| Synthetic Promoter 25 | GGGAATTCCCAGCGGGAATTCCCATCGGGGACTTTCCAGACGG GGACTTTCCAACTGGGAATTCCCGTCGGGAATTCCCGAGGGGG ACTTTCCATCCGGGGACTTTCCACGAATTCTGCCCTACTGACA CTGCCTGCCGGGGAATTCCCAGCGGGAATTCCCATCGGGGACT TTCCAGACGGGGACTTTCCAACTGGGAATTCCCGTCGGGAATT CCCGAGGGGGACTTTCCATCCGGGGACTTTCCACGAATATCCG C | 25 |
| Synthetic Promoter 26 | AGCGCATTTCCCGGAAATGATATCTATTCCAGGAACTGACTAT TCCAGGAACTACTGCATTTCCCGGAAATGATGTCGCATTTCCC GGAAATGATGAGTATTCCAGGAACTTCCTATTCCAGGAACTCG AATTCTGCCCTACTGACACTGCCTGCCGGCATTTCCCGGAAAT GATAGCGCATTTCCCGGAAATGATACTATTCCAGGAACTACTG CATTTCCCGGAAATGATGTCGCATTTCCCGGAAATGATGAGTA TTCCAGGAACTTCCTATTCCAGGAACTCGAATATCCG | 26 |

TABLE 2-continued

Synthetic Promoters 1-40

| Name | Sequence | SEQ ID NO |
|---|---|---|
| Synthetic Promoter 27 | ATGCGTGGGCGTAGCATGCGTGGGCGTATCCGCGGCGGGGGC GGAGGACCGCGGCGGGGGCGGAGACTAATGCGGGGGCGGAG TCAATGCGGGGGCGGAGAGGGGCGGGGGCGGGGCCTCCGGGC GGGGGCGGGGCCCGAATTCTGCCCTACTGACACTGCCTGCCGA TGCGTGGGCGTACATGCGTGGGCGTATCCGCGGCGGGGGCGG AGGCCGCGGCGGGGGCGGAGCTAATGCGGGGGCGGAGTCAAT GCGGGGGCGGAGAGGGGCGGGGGCGGGGCCTCCGGGCGGGG GCGGGGCCCGAATATCCGC | 27 |
| Synthetic Promoter 28 | GCGCCAAAGGAACGTTTCGGGAATTCGGGAAACGGATGCGCC AAAGCTCGAGTACGAAACGGCTACGTTTCGGCTGGAAACGCA GGCAGTGTCAGTAGGGCAGCGCCAAAGGAACGTTTCGGGAAT TCGGGAAACGGATGCGCCAAAGCTCGAGTACGAAACGGCTAC GTTTCGGCTGGAAACGGG | 28 |
| Synthetic Promoter 29 | GCGCCAAAGGAACGTTTCGGGAATTCGGGAAACGGATGCGCC AAAGCTCGAGTACGAAACGGCTACGTTTCGGCTGGAAACGCA GGCAGTGTCAGTAGGGCAGCGCCAAAGGAACGTTTCGGGAAT TCGGGAAACGGATGCGCCAAAGCTCGAGTACGAAACGGCTAC GTTTCGGCTGGAAACGCAGGCAGTGTCAGTAGGGCAGCGCCA AAGGAACGTTTCGGGAATTCGGGAAACGGATGCGCCAAAGCT CGAGTACGAAACGGCTACGTTTCGGCTGGAAACGCAGGCAGT GTCAGTAGGGCAGCGCCAAAGGAACGTTTCGGGAATTCGGGA AACGGATGCGCCAAAGCTCGAGTACGAAACGGCTACGTTTCG GCTGGAAACGGG | 29 |
| Synthetic Promoter 30 | GCGGATATTCGGCGCCACCTAGTGGCGAGGATGGCGCCCCCTG GTGGCCACTCTACTGCCATCTAGTGGTCAAGTCTGCCTCCTCG CGGGTCTGGCGCCCCTGGTGGCCAGCTGCGCCACCTAGTGGC GACGGCAGGCAGTGTCAGTAGGGCAGGAATTCGGCGCCCTCT GGTGGCCACTCCTGCCTCCTCGCGGGACTGGCGCCCCCTGGTG GCCAAGTGCGCCACCTAGTGGCGAGTCGCGCCCTCTGGTGGCC AGATTACTGCCATCTAGTGGTCAGCTCTGCCTCCTCGCGG | 30 |
| Synthetic Promoter 31 | GCGGATATTCGACCAGATGGTCGGGACGAGCAGCTGGCTCCG GGCAGGTGGGACCGAGCAGCTGGAGTAACAGATGTTCGGTCA CCAGATGGTCGGATCGAGCAGCTGGGCTCGGGCAGGTGGCGG CAGGCAGTGTCAGTAGGGCAGGAATTCGAACAGATGGTCGGG ACGGGCAGGTGGCTCACCAGATGGTCGGACCGAGCAGCTGGA GTCGGGCAGGTGGGTCAACAGATGGTCGGATAACAGATGTTC GGCTACCAGATGGTCG | 31 |
| Synthetic Promoter 32 | GACCACGTGGAAAGCGACCACGTGGAAATCGACCACGTGGAA GACGACCACGTGGAAACTGACCACGTGGAAGTCGACCACGTG GAAGAGGACCACGTGGAATCCGACCACGTGGAAGAATTCTGC CCTACTGACACTGCCTGCCGGACCACGTGGAAAGCGACCACGT GGAAATCGACCACGTGGAAGACGACCACGTGGAAACTGACCA CGTGGAAGTCGACCACGTGGAAGAGGACCACGTGGAATCCGA CCACGTGGAACGAATATCCGC | 32 |
| Synthetic Promoter 33 | TCCGCCACGTGCGCGACGACTCCGCCACGTGCGCGACGAGTCCGCC ACGTGCGCGACTCCTCCGCCACGTGCGCGACCGAATTCTGCCC TACTGACACTGCCTGCCGTCCGCCACGTGCGCGACGACTCCGC CACGTGCGCGACACTTCCGCCACGTGCGCGACGTCTCCGCCAC GTGCGCGACGAGTCCGCCACGTGCGCGACTCCTCCGCCACGTG CGCGACCGAATATCCGC | 33 |
| Synthetic Promoter 34 | AGACCACGTGGTCAGCAGACCACGTGGTCATCAGACCACGTG GTCGACAGACCACGTGGTCACTAGACCACGTGGTCGTCAGACC ACGTGGTCGAGAGACCACGTGGTCTCCAGACCACGTGGTCCG AATTCTGCCCTACTGACACTGCCTGCCGAGACCACGTGGTCAG CAGACCACGTGGTCATCAGACCACGTGGTCGACAGACCACGT GGTCACTAGACCACGTGGTCGTCAGACCACGTGGTCGAGAGA CCACGTGGTCTCCAGACCACGTGGTCCGAATATCCGC | 34 |
| Synthetic Promoter 35 | AAAACACGTGGTAGCAAAACACGTGGTATCAAAACACGTGGT GACAAAACACGTGGTACTAAAACACGTGGTGTCAAAACACGT GGTGAGAAAACACGTGGTTCCAAAACACGTGGTCGAATTCTG CCCTACTGACACTGCCTGCCGAAAACACGTGGTAGCAAAACA CGTGGTATCAAAACACGTGGTGACAAAACACGTGGTACTAAA ACACGTGGTGTCAAAACACGTGGTGAGAAAACACGTGGTTCC AAAACACGTGGTCGAATATCCGC | 35 |

TABLE 2-continued

Synthetic Promoters 1-40

| Name | Sequence | SEQ ID NO |
|---|---|---|
| Synthetic Promoter 36 | GTCCGCCACGTGCGCGACAGTCCGCCACGTGCGCGACTGGTCC GCCACGTGCGCGACCGTCCGCCACGTGCGCGACCGGTCCGCCA CGTGCGCGACCGTCCGCCACGTGCGCGACGTGTCCGCCACGTG CGCGCC | 36 |
| Synthetic Promoter 37 | TTCCGCCACGTGGCGGAAGTTCCGCCACGTGGCGGAATTCCGC CACGTGGCGGAAATTCCGCCACGTGGCGGAATTCCGCCACGTG GCGGAATTTCCGCCACGTGGCGGAATTCCGCCACGTGGCGGA ACC | 37 |
| Synthetic Promoter 38 | GCCACGTGAGCGCCACGTGATCGCCACGTGGACGCCACGTGA CTGCCACGTGAGTGCCACGTGGTCGCCACGTGGATGCCACGTG GCTGCCACGTG | 38 |
| Synthetic Promoter 39 | GCGGATATTCGACCACGTGTTTTGGAACCACGTGTTTTCTCGA CCACGTGGTCTGACGACCACGTGGTCTAGTGCGCACGTGGCGG TCGCGCACGTGGCGGATTCCACGTGGTCGCTTCCACGTGGTCC GGCAGGCAGTGTCAGTAGGGCAGAATTCGACCACGTGTTTTGG AACCACGTGTTTTCTCGACCACGTGGTCTGACGACCACGTGGT CTAGTGCGCACGTGGCGGTCGCGCACGTGGCGGATTCCACGTG GTCGCTTCCACGTGGTCC | 39 |
| Synthetic Promoter 40 | GGCCGCCCTGCACCTGCAGGGACCACGTGGAAGCGACCACGT GGAATCCGCCACGTGCGCGACCGCCACGTGCGCACTAGACCA CGTGGTCGTCAGACCACGTGGTCGAGAAAACACGTGGTTCCA AAACACGTGGTCGAATTCTGCCCTACTGACACTGCCTGCCGGA CCACGTGGAAGCGACCACGTGGAATCCGCCACGTGCGCGACC GCCACGTGCGCACTAGACCACGTGGTCGTCAGACCACGTGGTC GAGAAAACACGTGGTTCCAAAACACGTGGTCGAATATCCGCG GCGCGCCAGACGTGCAGGGACCACGTGGAAGCGACCACGTGG AATCCGCCACGTGCGCGACCGCCACGTGCGCACTAGACCACGT GGTCGTCAGACCACGTGGTCGAGAAAACACGTGGTTCCAAAA CACGTGGTCGAATTCTGCCCTACTGACACTGCCTGCCGGACCA CGTGGAAGCGACCACGTGGAATCCGCCACGTGCGCGACCGCC ACGTGCGCACTAGACCACGTGGTCGTCAGACCACGTGGTCGA GAAAACACGTGGTTCCAAAACACGTGGTCGAATATCCGCGGC GCGCCAGAC | 40 |

Example 2. Synthetic Promoter Activity and Specificity—Synthetic Promoters 41-49

Reporter constructs were created by placing the coding sequence of mKate2 under the control of selected promoters from the library (synthetic promoters 41-49). The reporter constructs were transfected into different cell lines as listed in Table 3. P119 are negative control cells and p153 are mKate2 positive cells expressing mKate2 under the strong hUbC promoter.

Figure 8:
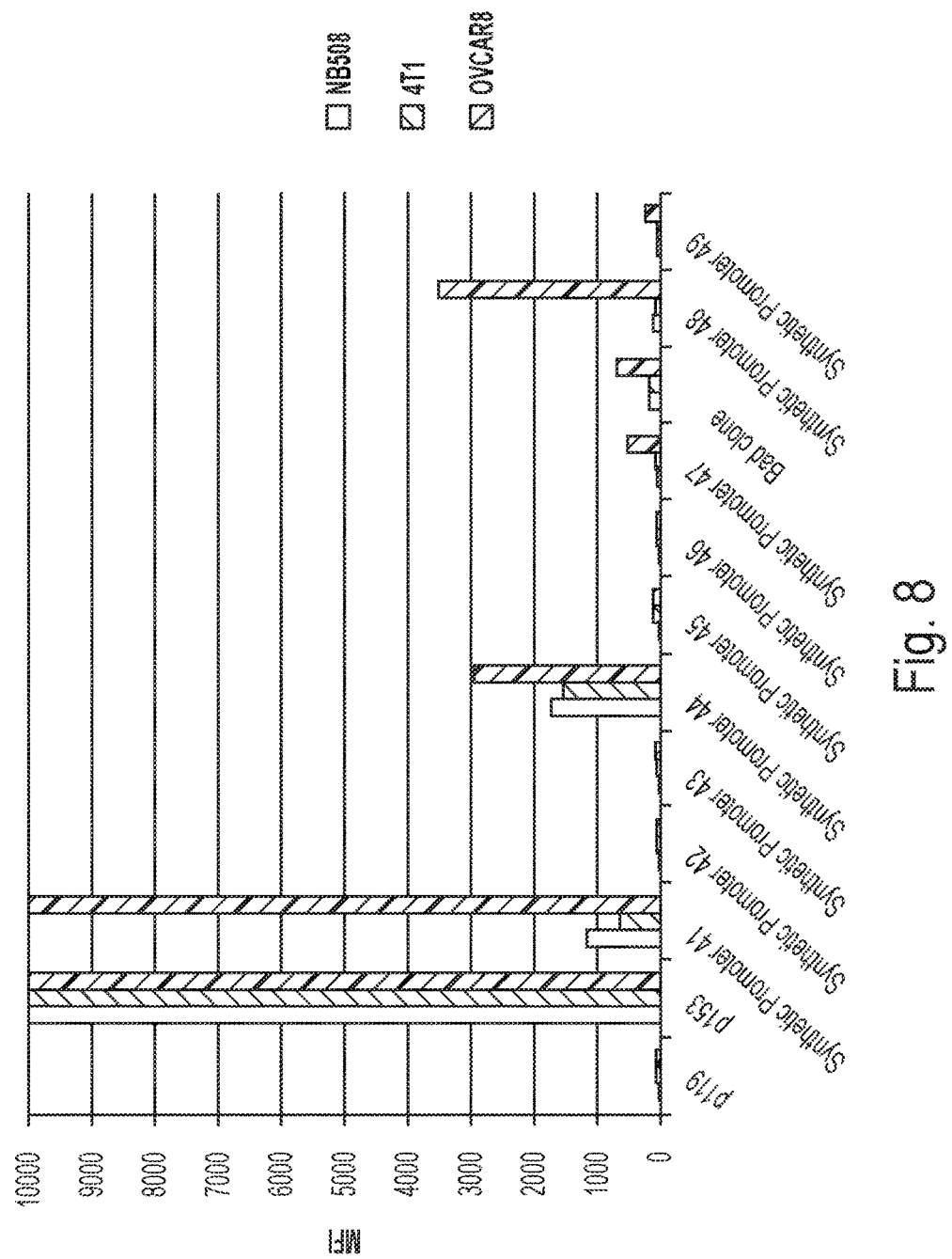
FIG. 8 is a graph showing the activities of synthetic promoters in three different cell lines: NB508, 4T1, and OVCAR8.

The expression of mKate2 indicates the activity of a synthetic promoter in each cell line. The results were provided in FIG. 8 and Table 2. Synthetic promoters 41 and 44 were found to be more active than other synthetic promoters tested in tumor cell lines. Interestingly, both synthetic promoter 41 and 44 have binding motifs for tumor-specific TFs, including CREB, EGR1, SP1 and E2F1. The activities of another set of synthetic promoters were tested in different cell lines, as indicated in Table 3.

TABLE 3

Synthetic Promoter Activity in Different Cell Lines

|  | NB508 AVRG mKate2 | 4T1 AVRG mKate2 | OVCAR8 AVRG mKate2 |
|---|---|---|---|
| p119 | 35 | 56 | 50 |
| p153 | 21200 | 14200 | 79800 |
| Synthetic Promoter 41 | 1203 | 677 | 13400 |
| Synthetic Promoter 42 | 39 | 60 | 73 |
| Synthetic Promoter 43 | 42 | 62 | 93 |
| Synthetic Promoter 44 | 1743 | 1555 | 2956 |
| Synthetic Promoter 45 | 42 | 59 | 137 |
| Synthetic Promoter 46 | 39 | 54 | 75 |
| Synthetic Promoter 47 | 72 | 82 | 507 |
| Synthetic Promoter 48 | 139 | 110 | 3553 |
| Synthetic Promoter 49 | 53 | 64 | 246 |

TABLE 4

Synthetic Promoters 41-49

| Name | Sequence | SEQ ID NO. |
| --- | --- | --- |
| Synthetic Promoter 41 | GACGCCATGACGCATGACGCCATGACGCCATGACGCCA TGACGCCATGACGCCATGACGCATGACGCCATGACGCC ATGACGCCATTACGCCAT | 41 |
| Synthetic Promoter 42 | GGGGGTCCAGCGGGGGTCCATCGGGGGTCCGACGGGGG TCCACTGGGGGTCCAGTGGGGGTCCGTCGGGGGTCCGAT GGGGGTCCGCTGGGGGTCC | 42 |
| Synthetic Promoter 43 | AGTGGGGTAGCAGTGGGTATCAGTGGGGTGACAGTGGG GTACTAGTGGGGTAGTAGTGGGGTGTCAGTGGGGTGAT AGTGGGGTGCTAGTGGGGT | 43 |
| Synthetic Promoter 44 | GTGCCCGCGTAATCCCGCCCGCGTAGACCCGCCCGCGTA ACTCCGCCCGCGTAAGTCCGCCCGCGTAGTCCCGCCCGC GTAGATCCGCCCGCGTA | 44 |
| Synthetic Promoter 45 | GAGACATAGAGACATAGAGACATAGAGACATAGAGACA TAGAGACATAGAGACATAGAGACATAGAGACATAGAGA CATAGAGACATAGAGACATA | 45 |
| Synthetic Promoter 46 | CACTGGGTCACGGGGTCACGGGGTCACGGGGTCACGGG GTCACGGGGTCACGGGGTCACGGGGTCACGGGGTCACG GGGTCACGGGGT | 46 |
| Synthetic Promoter 47 | GGGAATGAGGGAATGAGGGAATGAGGGAATGAGGGAA TGAGGGAATGAGGGAATGAGGGAATGAGGGAATGTGGG AATGTGGGAATGTGGGAATGT | 47 |
| Synthetic Promoter 48 | GAAGGCAGGAAGGCAGGAAGGCAGGAAGGCAGGAAGG CAGGAAGGCAGGAAGGCAGGAAGGCAGGAAGGCAGGA AGGCAGGAAGGCAGGAAGGCAG | 48 |
| Synthetic Promoter 49 | GGGCCAAATGGATCGGGCCAAATGGGACGGGGCAAATG GACTGGGCAAATGGAGTGGGGCAAATGGGTCGGGCAAA TGGGATGGGGCAAATGG | 49 |

Example 3. MDA-MB-453-Specific Promoter Expression

Figure 9:
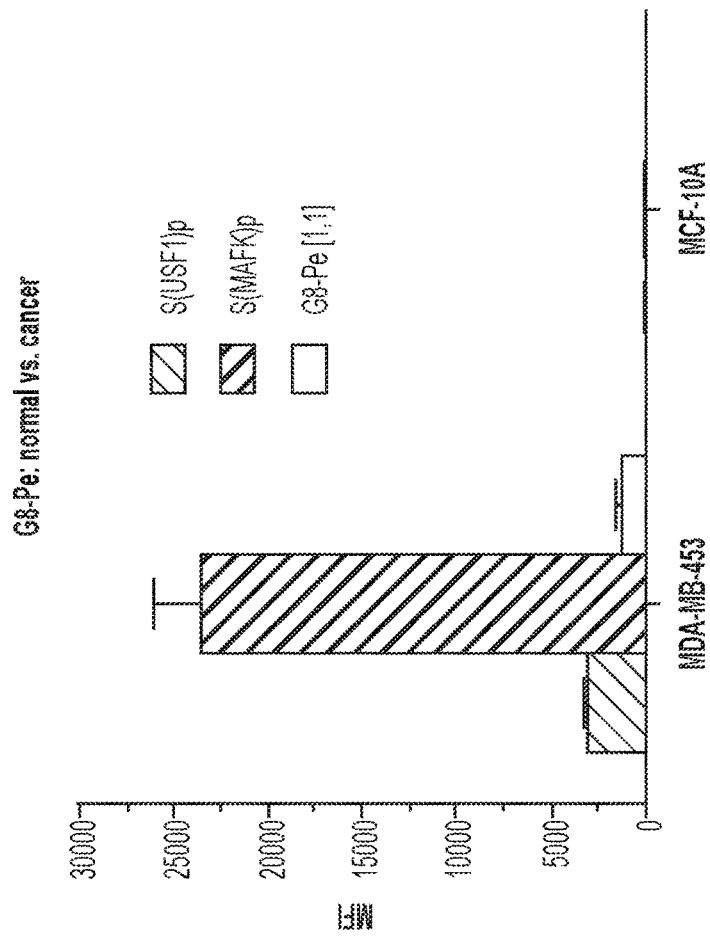
FIG. 9 is a graph showing the activities of synthetic promoters in two different cell lines: 10A and MDA.

Two synthetic promoters, S(USF1)p and S(MAFK)p, were designed to specifically target the MDA-MB-453 breast cancer cell line, but not the MCF-10A non-tumorigenic mammary epithelial cell line. mKate2 outputs generated by each promoter individually were compared to a control (G8-Pe) in both cell lines. S(USF1)p and S(MAFK)p generated a high output only in MDA-MB-453 cells (FIG. 9) (see also Nissim, L. et al. *Cell* 2017; 171: 1138-1150 is incorporated herein by reference).

S(USF1)p
(SEQ ID NO: 12266)
CCACGTGCAGACCACGTGCTCGCCACGTGCGACCCACGTGCCTACCACGT

GCACTCCACGTGCTGCCCACGTGCGTACCACGTGCG

S(MAFK)p
(SEQ ID NO: 12268)
TGCTGAGTCAGCAAGATGCTGAGTCAGCATCGTGCTGAGTCAGCAGACTG

CTGAGTCAGCACTATGCTGAGTCAGCAACTTGCTGAGTCAGCATGCTGCT

GAGTCAGCAGTATGCTGAGTCAGCAG

Example 4. Synthetic Promoter Activity and Specificity

Figure 10:
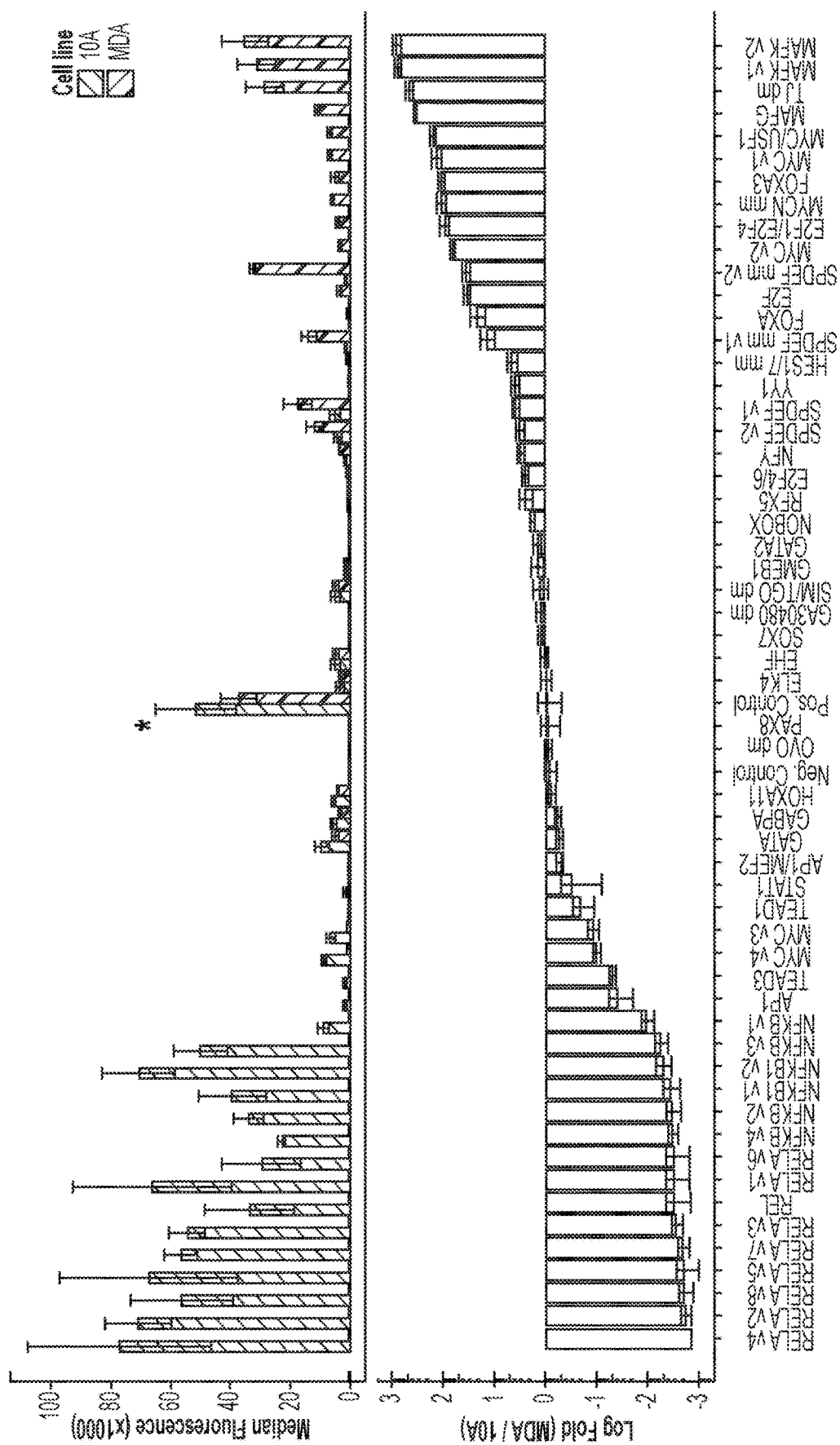
FIG. 10 is a graph showing the activities of synthetic promoters in two different cell lines: 10A and MDA.

Reporter constructs were created by placing the coding sequence of mKate2 under the control of selected promoters from the library (see FIG. 10). The reporter constructs were transfected into different cell lines: 10A (normal breast tissue cells) or MDA (cancerous breast tissue cells).

The expression of mKate2 indicates the activity of a synthetic promoter in each cell line. The results are provided in FIG. 10. A subset of the synthetic promoters was found to be more active in the tumor cell line than the other synthetic promoters tested.

Example 5

The synthetic promoter library was tested in a human induced pluripotent stem cell line (GATA6-hiPSCs) that forms a liver bud-like organoid upon doxycycline-inducible GATA6 expression (Guye, P. et al. Nature Communications, 2016, incorporated herein by reference). 2D organoids were prepared by seeding 25,000 GATA6-hiPSCs/cm$^2$ in a flat-bottom, matrigel-coated tissue-culture plate. Differentiation followed the previously described protocol (Guye, P. et al. Nature Communications, 2016) and was initiated by addition of 1000 ng/mL doxycycline (dox) for 5 days. On day 5, organoids were transduced with an equimolar mix of the synthetic promoter library and a transduction control. The viral titer was qualitatively adjusted such that <15% of the population expressed the transduction marker. Differentiation continued for a total of 16 days after which organoids were washed with PBS and dissociated with Accutase to a single cell suspension. Cells were centrifuged (3 min at 300×g) and resuspended in APEL 2 Medium (StemCell Technologies). The resuspended cells were sorted by FACS (BD FACS Aria, BD Biosciences) into an mKate positive and negative population with manually defined gates. Extraction of genomic DNA (gDNA) was done as for all other samples.

Using the gDNA from the mKate positive population, we amplified the synthetic promoters by PCR as described for the other samples with the exception that 50 cycles were necessary. The amplified promoter library and pLN490 were digested with AscI and SbfI and gel purified. The digested and purified promoters and pLN490 backbone were ligated and transformed into E. coli and selected for by ampicillin. Colonies were picked and submitted for Sanger sequencing to identify synthetic promoters that led to mKate expression in the organoids. Candidate promoters identified from Sanger sequencing were verified in triplicate. Verification was done by transducing undifferentiated GATA6-hiPSCs with a lentivirus expressing the particular promoter upstream of mKate2. Transductions were done with 2 μg/mL polybrene and qualitatively assessed to lead to mKate2 expression in more than 90% of the GATA6-hiPSCs. Organoids were differentiated as above and imaged daily for 20 days using a Leica TCS SP5 II confocal microscope. Each promoter was also expressed in GATA6-hiPSCs that were kept undifferentiated for >5 days by culturing cells in mTeSR1 without the addition of dox.

Expression of the synthetic promoter library in a liver bud-like organoid derived through GATA6 expression in hiPSCs, led to the identification of 37 different candidate promoters from a pool of 1396 mKate positive cells. Each promoter was individually verified by transduction of GATA6-hiPSCs with the particular promoter and repeating the differentiation to a liver bud-like organoid. We verified 18 of these promoters in triplicate and found 7 of them to be mKate2 positive in all samples. 2 of the promoters were only mKate2 positive in duplicate. Among these 9 promoters with mKate2 activity, 8 also had detectable activity in undifferentiated GATA6-hiPSCs (activity could be verified in triplicate for 4 promoters, duplicate for 1, and single sample only for 3 promoters). However, their activity in GATA6-hiPSCs were generally limited to clusters of with few cells, indicating that there might be subtle differences in the transcription factor profile of these undifferentiated stem cell.

The synthetic promoters with RELA, STAT_disc5, HIF1A and TP53 binding sites showed consistent behavior across all triplicates. The activity and pattern of these promoters changed between days, implying cell type-specific promoter activity. Moreover, the pattern, strength and number of cells in which the promoter was active also varied. For instance, the HIF1A promoter appeared active in large globular similar to previously identified ectoderm-derived cells (P. Guye, 2016). Moreover, the signal shows a pattern within these globular structures, indicating further cell type-specificity. The mKate2 expression appeared suddenly late in organoid development (≈day 15) and gradually disappear. As the signal faded from the putative ectoderm regions, it would begin to appear in nearby regions of the organoid that favored a flat structure.

TP53, and STAT_disc5 were both active early on during organoid development and with no apparent preference for morphologically distinct cells. TP53 was widely active in hiPSCs and the early (day 2) organoid. The frequency of mKate2 positive cells faded over time, albeit the signal remained strong in the few positive cells that remained. STAT_disc5 was not active in hiPSCs, but turned on around day 3 and peaked at day 4/5. It then gradually turned off as the organoid matured and had effectively disappeared on day 12.

RELA turned on strongly, first in a few cells around day 4, but continuously spread to a larger fraction of the cell population over the duration of the experiment. The promoter appeared to favor certain regions with a flat morphology. Moreover, several cells—based on their mKate2 fluorescence—showed a long, thin shape which is morphologically distinct from the pattern observed from other promoters.

Overall, verification of mKate2 expression from the candidate promoters also revealed heterogeneous expression of the promoters that generally required screening multiple regions of each organoid to identify an mKate positive region. This implies that morphologically similar regions might still show subtle differences in TF profiles that affects transcription from the synthetic promoter. Altogether, the replicated temporal, spatial and morphological observations indicate a non-random preference for certain cell types that appear and mature during development of a liver bud-like organoid.

The previously described method to differentiate hiPSCs to a liver bud-like organoid results in a heterogeneous and diverse cell composition within the organoid with cell lineages arising from all three different germ layers. This cell type heterogeneity made the organoid ideal as a platform to test the cell-type preference of the synthetic promoter library.

Changes in the TF profile of a specific cells is quintessential to cell differentiation and maturation, and the synthetic promoters are expected to exploit this change, thereby providing a platform for cell-type specific gene regulation. Indeed, we find that a few candidate promoters show temporal specificity towards certain morphologically distinct regions within the organoid. However, the promoter activity often differs between morphologically similar regions implying the promoters may be very sensitive towards changes in TF activity between cell types. With thorough screening and a more targeted search for specific cell populations, the synthetic promoters are a powerful tool for regulating gene networks in subpopulations of heterogeneous cell populations.

TABLE 5

Transcription Factor Binding Sites of Synthetic Promoters

| Name | Binding Site Sequence | Reverse Complement |
| --- | --- | --- |
| EOMES_EOMES_f1_HocoMoco | ATTTCGTATCCCCG | CGGGGATACGAAAT |
| LHX9_LHX2_2_SELEX\|LHX2_3 | TAATTACGCTAATTA | TAATTAGCGTAATTA |
| HOXC5_Zen_Cell_FBgn0004053_B1H | CCCTAATGA | TCATTAGGG |

TABLE 5-continued

Transcription Factor Binding Sites of Synthetic Promoters

| Name | Binding Site Sequence | Reverse Complement |
|---|---|---|
| BARHL2_MA0171.1_B1H\|NKX2-5_MA0063.1_SELEX\|ISL2_MA0248.1_B1H\|BARHL2_MA0168.1_B1H\|HMX1_Hmx_SOLEXA_FBgn0085448_B1H\|BSX_MA0214.1_B1H\|ISL2_Tup_SOLEXA_FBgn0003896_B1H\|SHOX_PRRX2_f1_HocoMoco\|SHOX_MA0250.1_B1H\|HMX1_Hmx_Cell_FBgn0085448_B1H\|ISL2_Isl2_3430_PBM\|BARHL2_MA0169.1_B1H\|HMX1_MA0192.1_B1H\|NKX2-5_4 | CAATTAA | TTAATTG |
| NKX2-5_NKX28_f1_HocoMoco | GTCCTTGAA | TTCAAGGAC |
| EN2_V$EN1_01_Transfac\|EN1_1 | CAATTAC | GTAATTG |
| NR1I3_NR1I3_f2_HocoMoco | CTGAACTTTCCTGACCCC | GGGGTCAGGAAAGTTCAG |
| MSX1_Msx1_3031_PBM\|GBX2_Gbx2_3110_PBM | CAATTAG | CTAATTG |
| GATA2_MA0536.1_ChIP-chip | AACTATCGATA | TATCGATAGTT |
| DLX2_1 | CTGAAGTAATTATTCC | GGAATAATTACTTCAG |
| VSX2_VSX1_2_SELEX\|VSX1_3 | GCTAATTAGCC | GGCTAATTAGC |
| SIX5_Six4_SOLEXA_2_FBgn0027364_B1H | ATGATACC | GGTATCAT |
| SIX5_Six4_Cell_FBgn0027364_B1H | ATTTGATAC | GTATCAAAT |
| OVOL2_1 | CCCCCGC | GCGGGGG |
| ELF1_known1 | ATAAGAGGAAAT | ATTTCCTCTTAT |
| HNF1A_HNF1B_f1_HocoMoco | GGTTAATGATTAAC | GTTAATCATTAACC |
| RXRA_known7 | GTAGGGCAAAGGTCA | TGACCTTTGCCCTAC |
| NFKB1_V$NFKB_C_Transfac\|NFKB_known5 | GGGGACTTTCCA | TGGAAAGTCCCC |
| NR5A1_ftz-f1_FlyReg_FBgn0001078_B1H | CAGTCCGAAGGTCACCGC | GCGGTGACCTTCGGACTG |
| KLF4_SRP000217_Klf4_ChIP-seq | GGCCCCACCCA | TGGGTGGGGCC |
| SOX9_SOX10_si_HocoMoco | ACAAAGA | TCTTTGT |
| DMBX1_DRGX_1_SELEX\|DRGX_1 | CTAATCTAATTAA | TTAATTAGATTAG |
| DMBX1_pTH5511_PBM\|DRGX_CRX_si_HocoMoco | CTAATCCC | GGGATTAG |
| NFYA_V$NFY_C_Transfac\|NFY_known2 | ACTAACCAATCAGA | TCTGATTGGTTAGT |
| HNF4G_Hnf4_SANGER_10_FBgn0004914_B1H | TGACCCCGCCAACAA | TTGTTGGCGGGGTCA |
| POU6F2_PO6F1_f1_HocoMoco | CATAATTTATGCA | TGCATAAATTATG |
| HOXC5_HXC6_f1_HocoMoco | AAAGTAATAAATCAT | ATGATTTATTACTTT |
| VSX2_pTH5821_PBM\|SHOX_pTH5474_PBM\|EN2_inv_SOLEXA_2_FBgn0001269_B1H\|POU3F3_pTH9216_PBM | CTAATTAAC | GTTAATTAG |
| DMRTC2_pTH3205_PBM | AACATGTATAAA | TTTTATACATGTT |
| MLX_MLX_1_SELEX\|MLXIPL_MLXIPL_1_SELEX\|MLX_MIx_1_SELEX\|MLXIPL_1\|MLX_1\|MLX_2 | ATCACGTGAT | ATCACGTGAT |
| SNAI2_wor_SOLEXA_2.5_FBgn0001983_B1H | CCACCTGC | GCAGGTGG |
| SOX1_SRP000712_Sox2_ChIP-seq\|BX088580.2_SRP000217_Oct4_ChIP-seq\|SOX1_SRP000217_Sox2_ChIP-seq | CCATTGTTATGCAAA | TTTGCATAACAATGG |
| TGIF1_MA0252.1_B1H\|TGIF1_MA0207.1_B1H\|PKNOX2_MA0227.1_B1H | CTGTCA | TGACAG |
| POU3F3_V$POU3F2_01_Transfac\|POU3F2_2 | ATGAATTAATGCAT | ATGCATTAATTCAT |

TABLE 5-continued

Transcription Factor Binding Sites of Synthetic Promoters

| Name | Binding Site Sequence | Reverse Complement |
|---|---|---|
| HOXA4_MA0228.1_B1H\|SHOX_Prrx2_3072_PBM\|DMBX1_Alx3_3418_PBM\|PROP1_Prop1_3949_PBM\|UNCX_MA0198.1_B1H\|UNCX_Odsh_Cell_FBgn0026058_B1H\|SHOX_MA0200.1_B1H\|LHX1_Lhx4_1719_PBM\|EN2_En1_3123_PBM\|LHX9_MA0209.1_B1H\|ALX1_MA0202.1_B1H\|ALX1_MA0184.1_B1H | CTAATTA | TAATTAG |
| SOX5_3 | ATTTTATTGTTCTAAA | TTTAGAACAATAAAAT |
| BHLHE40_BHLHB2_1_SELEX\|SREBF2_Srebf1_1_SELEX\|MITF_TFEB_1_SELEX\|MITF_TFE3_1_SELEX\|USF1_USF1_1_SELEX\|SREBF2_SREBF2_1_SELEX\|MITF_TFEC_1_SELEX\|BHLHE40_known3\|SREBP_known5\|SREBP_known6\|TFE3_1\|TFEB_1\|MYC_known22\|TFEC_1 | ATCACGTGAC | GTCACGTGAT |
| ZNF187_Zfp187_2626_PBM | ATTAGTAC | GTACTAAT |
| SIX2_MA0246.1_B1H\|SIX5_MA0204.1_B1H | GTATCA | TGATAC |
| GLIS3_GLIS3_1_SELEX\|GLIS3_1 | CTTCGTGGGGGTC | GACCCCCACGAAG |
| ENSG00000250096_MA0002.2_ChIP-seq\|RUNX1_9 | AAACCACAGAC | GTCTGTGGTTT |
| SOX1_SOX2_1_SELEX\|SOX2_2 | GAACAATACCATTGTTC | GAACAATGGTATTGTTC |
| LMX1A_1 | CGAATTAATTAAAAACC | GGTTTTTAATTAATTCG |
| RORB_V$RORA2_01_Transfac\|RORA_2 | ATAAGTAGGTCAA | TTGACCTACTTAT |
| HSF1_MA0486.1_ChIP-seq | AGAACCTTCTAGAAG | CTTCTAGAAGGTTCT |
| NKX6-3_V$NKX61_01_Transfac\|NKX6-1_1 | AACCAATTAAAAA | TTTTTAATTGGTT |
| ENSG00000250096_RUNX2_f1_HocoMoco | ACAAACCACAG | CTGTGGTTTGT |
| FOXD1_V$FREAC4_01_Transfac\|FOXD1_1 | CCATTGTTTACTTAAG | CTTAAGTAAACAATGG |
| DDIT3::CEBPA_1 | AGATGCAATCCCC | GGGGATTGCATCT |
| LHX1_Lhx5_2279_PBM\|LHX1_Lhx1_2240_PBM | AATTAATTA | TAATTAATT |
| TCF7L1_TCF7L1_1_SELEX\|TCF7L2_Tcf7_1_SELEX\|TCF7L1_2\|TCF7_2 | AAAGATCAAAGG | CCTTTGATCTTT |
| MEF2_known2 | AAGCTATAAATAGACT | AGTCTATTTATAGCTT |
| PAX9_PAX5_si_HocoMoco | CCTCAGCC | GGCTGAGG |
| SP9_K562_SP2_HudsonAlpha_ChIP-seq | GCCTAGAGCGGCCCC | GGGGCCGCTCTAGGC |
| SIX2_Six2_2307_PBM | GGGTATCA | TGATACCC |
| ZNF589_ZN589_f1_HocoMoco | CCCACGGTTACTGCCG | CGGCAGTAACCGTGGG |
| ETS_disc7 | GGACTACAGCTCCC | GGGAGCTGTAGTCC |
| LIN54_pTH8566_PBM | AATTCAAAT | ATTTGAATT |
| PDX1_2 | GAGTCTAATGACCCA | TGGGTCATTAGACTC |
| ESR2_1 | CAAGGTCACGGTGACCTG | CAGGTCACCGTGACCTTG |
| SOX21_1 | CTTAATTATAATTAAA | TTTAATTATAATTAAG |
| STAT_known11 | GGATTCCC | GGGAATCC |
| PRKRIR_pTH9190_PBM | ATCTCGTTTGGA | TCCAAACGAGAT |
| TCF3_3 | CGGCACCTGCC | GGCAGGTGCCG |
| TET1_pTH9605_PBM | ATCGCGTTA | TAACGCGAT |
| SPDEF_SPDEF_5_SELEX\|SPDEF_6 | ATGATCCGGGACCAC | GTGGTCCCGGATCAT |
| EBF1_MA0154.2_ChIP-seq | GTCCCCAGGGA | TCCCTGGGGAC |

TABLE 5-continued

Transcription Factor Binding Sites of Synthetic Promoters

| Name | Binding Site Sequence | Reverse Complement |
|---|---|---|
| ARID5A_1 | CTAATATTGCTAAA | TTTAGCAATATTAG |
| EBF1_COE1_f2_HocoMoco | GTCCCCAGGGAC | GTCCCTGGGGAC |
| DBX2_1 | GAATTAATTAATTAAA | TTTAATTAATTAATTC |
| IRF2_V$IRF2_01_Transfac\|IRF1_V$IRF1_01_Transfac\|IRF_known1\|IRF_known2 | GAAAAGTGAAACC | GGTTTCACTTTTC |
| SRF_MA0331.1_COMPILED | CCCAATTAGGAA | TTCCTAATTGGG |
| ELF1_ELF2_f1_HocoMoco | AGTCACTTCCTGCTA | TAGCAGGAAGTGACT |
| MYOD1_pTH5099_PBM | AACAGCTGA | TCAGCTGTT |
| ETV5_MA0076.2_ChIP-seq | CCACTTCCGGC | GCCGGAAGTGG |
| EGR3_EGR1_2_SELEX\|EGR3_EGR1_1_SELEX\|EGR1_known8\|EGR1_known9 | AATGCGTGGGCGTA | TACGCCCACGCATT |
| REST_disc2\|BCL_disc3 | ACCATGGACA | TGTCCATGGT |
| ALX1_RAX_1_SELEX\|RAX_2 | GCCAATTAAC | GTTAATTGGC |
| SPIC_SPIC_1_SELEX\|SPIC_1 | AAAAGAGGAAGTA | TACTTCCTCTTTTT |
| RORB_pTH3469_PBM | GGTGACCTA | TAGGTCACC |
| EMX2_ems_FlyReg_FBgn0000576_B1H | TGTCATAA | TTATGACA |
| SP1_disc2 | AAAGGGGC | GCCCCTTT |
| E2F7 _E2F7_f1_HocoMoco | AAAGGCGCGAAAA | TTTTCGCGCCTTT |
| FOXD1_MA0032.1_SELEX\|FOXC1_2 | GGTAAGTA | TACTTACC |
| TCF4_Tcfe2a_3865_PBM | GCACCTGC | GCAGGTGC |
| HINFP_HINFP_f1_HocoMoco | GCGCTAGCGGACGTTA | TAACGTCCGCTAGCGC |
| EGR3_Egr1_1_SELEX\|EGR1_known12 | AATTGAGTGGGCGTAG | CTACGCCCACTCAATT |
| POU1F1_2 | AATTCATAATTATACACA | TGTGTATAATTATGAATT |
| SPI1_known3 | TAACTTCCTCTTAA | TTAAGAGGAAGTTA |
| MIXL1_MIXL1_1_SELEX\|MIXL1_1 | GTTAATTAGA | TCTAATTAAC |
| GCM1_GCM1_f1_HocoMoco | AATACCCGCATGTG | CACATGCGGGTATT |
| HLTF_HLTF_f1_HocoMoco | TAGGGCTGCAAA | TTTGCAGCCCTA |
| SMAD3_2 | CAAATCCAGACATCAGA | TCTGATGTCTGGATTTG |
| SPIC_SPI1_si_HocoMoco | AAAAGAGGAAGTGAAA | TTTCACTTCCTCTTTTT |
| POU6F1_2 | GACGATAATGAGGTTGC | GCAACCTCATTATCGTC |
| NR2C2_HepG2b_TR4_UCD_ChIP-seq | AACCGCTTCCGGGTC | GACCCGGAAGCGGTT |
| PRDM4_PRDM4_1_SELEX\|PRDM4_1 | GGGGGCCTTGAAA | TTTCAAGGCCCCC |
| NEUROG1_NEUROD2_1_SELEX\|NEUROD2_1 | ACCATATGGC | GCCATATGGT |
| HOXC5_Hoxa5_3415_PBM\|MEOX2_Meox1_2310_PBM\|HOXA4_Gsh2_3990_PBM\|HOXC5_Hoxa7_3750_PBM\|VAX1_Vax1_3499_PBM\|HOXB2_Hoxa1_3425_PBM\|HOXC5_Hoxa6_1040_PBM\|HOXC5_Hoxa4_3426_PBM | GGTAATTAA | TTAATTACC |
| MYC_known13 | AACCACGTGCTC | GAGCACGTGGTT |
| POU5F1_PP5F1_do_HocoMoco | ATTTGCATAACAAAGG | CCTTTGTTATGCAAAT |

TABLE 5-continued

Transcription Factor Binding Sites of Synthetic Promoters

| Name | Binding Site Sequence | Reverse Complement |
|---|---|---|
| MYBL1_V$CMYB_01_Transfac\|MYB_1 | CCCAACGGCGGTTGGGGG | CCCCCAACCGCCGTTGGG |
| HOXC10_1 | ACGTTTTACGACTTTA | TAAAGTCGTAAAACGT |
| HOXC10_HXD10_a_HocoMoco | AATTAAAGCA | TGCTTTAATT |
| SHOX_Hbn_SOLEXA_FBgn0008636_B1H\|HOXC5_Pb_Cell_FBgn0051481_B1H\|EMX2_E5_Cell_FBgn0008646_B1H\|UNCX_Odsh_SOLEXA_FBgn0026058_B1H\|EVX2_Eve_SOLEXA_FBgn0000606_B1H\|ALX1_CG33980_SOLEXA_FBgn0053980_B1H\|LBX2_Lb1_SOLEXA_FBgn0008651_B1H\|EN2_En_Cell_FBgn0000577_B1H\|TLX3_C15_Cell_FBgn0004863_B1H | GTTAATTA | TAATTAAC |
| BHLHA15_BHLHA15_1_SELEX\|MSC_pTH5112_PBM\|OLIG2_OLIG2_2_SELEX\|NEUROG1_pTH5270_PBM\|BHLHA15_1\|OLIG2_2 | ACCATATGGT | ACCATATGGT |
| SRF_MA0083.2_ChIP-seq | CATGCCCAAATAAGGCAA | TTGCCTTATTTGGGCATG |
| TFCP2_TFCP2_2_SELEX\|TFCP2_5 | ACCGGTTTAAACCGGT | ACCGGTTTAAACCGGT |
| IRX4_1 | AATATACATGTAAAACA | TGTTTTACATGTATATT |
| RUNX_1 | AAGTCTGTGGTTAGC | GCTAACCACAGACTT |
| CREB3_1 | CGATGACGTCATCA | TGATGACGTCATCG |
| FOXO3_2 | AATTTGTTTACA | TGTAAACAAATT |
| FOSL1_K562_FOSL1_HudsonAlpha_ChIP-seq | ATGAGTCACCC | GGGTGACTCAT |
| PAX2_V$PAX2_02_Transfac\|PAX2_2 | AATAAACTC | GAGTTTATT |
| IRF_disc1\|E2F_disc4 | CAGCCAATCA | TGATTGGCTG |
| PRDM1_known1 | AGGAAGGGAAAGGA | TCCTTTCCCTTCCT |
| EGR3_MA0162.2_ChIP-seq | CCCCCGCCCCGCC | GGCGGGGCGGGGG |
| MEF2B_GM12878_MEF2A_HudsonAlpha_ChIP-seq | ATGCCAAAAATAGAA | TTCTATTTTTGGCAT |
| GFI1B_sens-2_SANGER_2.5_FBgn0051632_B1H | ATAAATCACAGCACTC | GAGTGCTGTGATTTAT |
| GFI1B_V$GFI1_01_Transfac | ACAAAATAAATCACAGCATATGCC | GGCATATGCTGTGATTTATTTTGT |
| NR3C1_disc2\|TFAP2_disc1 | GGTGAGTCAC | GTGACTCACC |
| TP63_MA0525.1_ChIP-seq | AGACATGCCCAGACATGCCC | GGGCATGTCTGGGCATGTCT |
| GFI1B_GFI1B_f1_HocoMoco | AAATCACTGCA | TGCAGTGATTT |
| ITGB2_1 | CTGACCCC | GGGGTCAG |
| ETV5_GABPA_f1_HocoMoco | CCACTTCCGGTTC | GAACCGGAAGTGG |
| CPHX_1 | ATGATCGAATCAAA | TTTGATTCGATCAT |
| MBD2_MBD2_si_HocoMoco | CCTCCGGCCCG | CGGGCCGGAGG |
| HMGA2_pTH8863_PBM | CAAATATTTG | CAAATATTTG |
| SOX15_1 | AAATCTATTGTTCACTA | TAGTGAACAATAGATTT |
| CTCF_ProgFib_CTCF_UT-A_ChIP-seq\|CTCF_GM12878_CTCF_Stanford_ChIP-seq\|CTCF_SK-N-SH_RA_UW_ChIP-seq\|CTCF_HCFaa_CTCF_UW_ChIP-seq | CGCCCCCTGGTGGCC | GGCCACCAGGGGGCG |
| TBX1_TBX20_4_SELEX\|TBX20_4 | CTTCACACCTA | TAGGTGTGAAG |
| EN2_MA0027.1_SELEX\|EN1_2 | AAGTAGTGCCC | GGGCACTACTT |
| EGR1_disc1 | CCGCCCCCGC | GCGGGGGCGG |

TABLE 5-continued

Transcription Factor Binding Sites of Synthetic Promoters

| Name | Binding Site Sequence | Reverse Complement |
|---|---|---|
| GLIS2_Glis2_1757_PBM | AGACCCCCAC | GTGGGGGTCT |
| REST_known2 | GGCGCTCTCCGTGGTGCTGAA | TTCAGCACCACGGAGAGCGCC |
| HMG20B_pTH8555_PBM | ATATATAATAA | TTATTATATAT |
| SOX11_1 | ATAAGAACAAAGGACTA | TAGTCCTTTGTTCTTAT |
| MAFA_V$VMAF_01_Transfac | AAATGCTGACTCAGCACAA | TTGTGCTGAGTCAGCATTT |
| HAND2_HAND1_si_HocoMoco | AATGCCAGACCC | GGGTCTGGCATT |
| RREB1_RREB1_si_HocoMoco | ACCCCAAACCACCCCCCCCCC | GGGGGGGGGGTGGTTTGGGGT |
| PAX4_V$PAX4_02_Transfac\|PAX4_2 | GAATAATTACC | GGTAATTATTC |
| SCRT2_CG12605_SOLEXA_5_FBgn0035481_B1H\|SCRT2_scrt_SOLEXA_2.5_1_FBgn0004880_B1H | CCACCTGTTGCAC | GTGCAACAGGTGG |
| HOXB13_pTH5808_PBM | GCCCATAAAA | TTTTATGGGC |
| SRY_SRY_2_SELEX\|SRY_6 | AACAATATTCATTGTT | AACAATGAATATTGTT |
| RORA_3 | TAAATAGGTCA | TGACCTATTTA |
| MAFK_MAFF_1_SELEX\|MAFF_1 | TTGCTGACTCAGCAA | TTGCTGAGTCAGCAA |
| RARG_RARG_do_HocoMoco | GGGGGTCACCCAGAGGTCAC | GTGACCTCTGGGTGACCCCC |
| SPDEF_Ets98B_SANGER_10_FBgn0005659_B1H | ACCCGGATC | GATCCGGGT |
| E2F_disc7 | CCGCGCCGCC | GGCGGCGCGG |
| NR3C1_known8 | GTTGCGGGTACAGAGTGTTCTAGGGAA | TTCCCTAGAACACTCTGTACCCGCAAC |
| TCF12_disc3 | AGGTGCGG | CCGCACCT |
| GATA_disc1 | CCTTATCTGC | GCAGATAAGG |
| THRB_THA_f1_HocoMoco | CTGACCTGAA | TTCAGGTCAG |
| GSC_1 | AATCGTTAATCCCTTTA | TAAAGGGATTAACGATT |
| PAX5_disc5 | GCGCGCGCGC | GCGCGCGCGC |
| NKX2-5_MA0211.1_B1H | CACTTAA | TTAAGTG |
| NR4A2_NR4A2_2_SELEX\|NR4A_known3 | TGACCTTTAAAGGTCA | TGACCTTTAAAGGTCA |
| FOXD1_V$XFD1_01_Transfac | CATGTAAATAATGC | GCATTATTTACATG |
| FOXD1_FOXC2_3_SELEX\|FOXC2_3 | TAAGTAAACAAA | TTTGTTTACTTA |
| IRX3_1 | AAAATACATGTAATACT | AGTATTACATGTATTTT |
| NOBOX_NOBOX_si_HocoMoco\|BARHL2_Barhl2_3868_PBM\|BARHL2_Barhl1_2590_PBM | ACCAATTAG | CTAATTGGT |
| SOX17_Sox17_1_SELEX\|SOX17_4 | AACAATGCAATTGTT | AACAATTGCATTGTT |
| PKNOX2_Pknox1_2364_PBM | ACCTGTCA | TGACAGGT |
| E2F4_E2F4_2_SELEX\|E2F1_E2F1_2_SELEX\|E2F_known28\|E2F_known30 | TTTGGCGCCAAA | TTTGGCGCCAAA |
| SNAI3_SNAI1_f1_HocoMoco | CCACCTGG | CCAGGTGG |

TABLE 5-continued

Transcription Factor Binding Sites of Synthetic Promoters

| Name | Binding Site Sequence | Reverse Complement |
|---|---|---|
| SREBF2_MA0595.1_ChIP-seq | ATCACCCCAC | GTGGGGTGAT |
| NR2E1_NR2E1_2_SELEX\|NR2E1_Nr2e1_2_SELEX\|NR2E1_2\|NR2E1_4 | AAGTCAATAAGTCA | TGACTTATTGACTT |
| CDX2_CDX2_f1_HocoMoco | ATTTATGG | CCATAAAT |
| ALX1_MA0180.1_B1H\|ALX1_CG33980_SOLEXA_2_10_FBgn0053980_B1H\|ALX1_CG33980_Cell_FBgn0053980_B1H | CTAATTAAA | TTTAATTAG |
| BCL11B_GM12878_BCL11A_HudsonAlpha_ChIP-seq | AAGAGGAAGTGAAAC | GTTTCACTTCCTCTT |
| TGIF2_1 | AACTAGCTGTCAATAC | GTATTGACAGCTAGTT |
| SREBF2_MA0596.1_ChIP-seq | ATCACCCCAT | ATGGGGTGAT |
| ARID3C_pTH4425_PBM | ATATTAATTAA | TTAATTAATAT |
| EGR1_disc7 | CACGCACGCA | TGCGTGCGTG |
| EN2_inv_SOLEXA_5_FBgn0001269_B1H | CTAATTAAG | CTTAATTAG |
| IRX3_Irx4_2242_PBM | AATTACAA | TTGTAATT |
| NKX2-5_V$NKX25_02_Transfac\|ISL2_Tup_Cell_FBgn0003896_B1H\|NKX2-5_2 | CAATTAAG | CTTAATTG |
| MAX_H1-hESC_MAX_UCD_ChIP-seq | AGAGCACGTGG | CCACGTGCTCT |
| ARID3C_pTH5118_PBM | CAATTAAA | TTTAATTG |
| CRX_1 | GTGGGATTAGTGA | TCACTAATCCCAC |
| GSC_GSC_1_SELEX\|GSC_2 | GCTAATCCCC | GGGGATTAGC |
| COMP1_1 | GGCCTTTTGTTGTCAATCAAAACA | TGTTTTGATTGACAACAAAAGGCC |
| ETS1_ETS1_si_HocoMoco | ACAGGAAGT | ACTTCCTGT |
| RFX5_known4 | CTGTTGCCA | TGGCAACAG |
| DLX1_pTH5506_PBM | AGTAATTAGC | GCTAATTACT |
| KIAA0415_YNL068C_830_DeBoer11 | TCATCTTTGTTTACTTTTAA | TTAAAAGTAAACAAAGATGA |
| ZBTB33_KAISO_f1_HocoMoco | CTCGCAGGAAGA | TCTTCCTGCGAG |
| T_TBX19_1_SELEX\|TBX19_1 | TTTCACACCTAGGTGTGAAA | TTTCACACCTAGGTGTGAAA |
| NEUROG1_NDF1_f1_HocoMoco | CGGCAGATGGCC | GGCCATCTGCCG |
| SP9_pTH5576_PBM | ACCGCTTC | GAAGCGGT |
| MYOD1_MA0500.1_ChIP-seq | CTGCAGCTGTC | GACAGCTGCAG |
| RORB_V$RORA1_01_Transfac\|RORA_1 | ATATCAAGGTCAT | ATGACCTTGATAT |
| RAD21_disc7 | GCCAGCAGCTGGCGC | GCGCCAGCTGCTGGC |
| POU3F3_V$BRN2_01_Transfac | GCTCATTACGAATGAC | GTCATTCGTAATGAGC |
| HNF4_known4 | ATGAACTTTGACC | GGTCAAAGTTCAT |
| PRDM1_Mv110_ChIP-seq | ACTTTCAC | GTGAAAGT |
| CTCF_CTCF_1_SELEX\|CTCF_known2 | AGCGCCACCTAGTGGTA | TACCACTAGGTGGCGCT |
| BPTF_V$FAC1_01_Transfac | ACCCACAACACATA | TATGTGTTGTGGGT |
| NFE2_NFE2_1_SELEX\|NFE2_known2 | CATGACTCATC | GATGAGTCATG |

TABLE 5-continued

Transcription Factor Binding Sites of Synthetic Promoters

| Name | Binding Site Sequence | Reverse Complement |
|---|---|---|
| HNF4_known3 | GGGGGCAAAGGTCAC | GTGACCTTTGCCCCC |
| HIF1A_2 | GCGTACGTGCGGCA | TGCCGCACGTACGC |
| BDP1_disc1 | CCCGGAGGGCTTCCTGGAGGAGG | CCTCCTCCAGGAAGCCCTCCGGG |
| PAX6_MA0069.1_SELEX\|PAX6_3 | AACTCATGCGTGAA | TTCACGCATGAGTT |
| FOXJ3_1 | AAAAAGTAAACAAACCC | GGGTTTGTTTACTTTTT |
| AP1_disc1 | ATGACGTCAC | GTGACGTCAT |
| NPAS3_HIF1A_si_HocoMoco | CCGCACGTACGC | GCGTACGTGCGG |
| CTCF_N H-A_CTCF_Broad_ChIP-seq | TAGTGCCCCCTAGTGGCCAAA | TTTGGCCACTAGGGGGCACTA |
| ATF3_known12 | GCGCTGACGTAACC | GGTTACGTCAGCGC |
| MEF2B_V$MEF2_04_Transfac\|MEF2_known5 | ACTGTTACTAAAATAGAAACT | AGTTTCTATTTTTAGTAACAGT |
| SOX7_SOX7_2_SELEX\|SOX7_3 | AAACAATGCAATTGTTT | AAACAATTGCATTGTTT |
| NFIA_NFIA_2_SELEX | ACTTGGCACC | GGTGCCAAGT |
| TATA_disc2 | ATGACGTCAT | ATGACGTCAT |
| OVOL1_ovo_SANGER_5_FBgn0003028_B1H | AGTACCGTTAT | ATAACGGTACT |
| ZIC5_Opa_SANGER_5_FBgn0003002_B1H | ATCCCCCCACCG | CGGTGGGGGGAT |
| ENSG00000250096_RUNX2_3_SELEX\|RUNX2_6 | AAACCGCAA | TTGCGGTTT |
| CUX1_7 | TAATGATGATCACTA | TAGTGATCATCATTA |
| YY1_disc5 | CTCCCCTGCCGC | GCGGCAGGGGAG |
| BATF3_BATF3_1_SELEX\|BATF_known1 | TGATGACGTCATCA | TGATGACGTCATCA |
| EBF1_disc2 | CAGCTCCCCAGGG | CCCTGGGGAGCTG |
| ZNF75C_ZNF75A_1_SELEX\|ZNF75A_1 | GCTTTTCCCACA | TGTGGGAAAAGC |
| CHD2_disc3 | CTCCTCGCCCC | GGGGCGAGGAG |
| OSR2_sob_SANGER_10_FBgn0004892_B1H | GAAACACAGTAGC | GCTACTGTGTTTC |
| NFAT5_pTH9263_PBM\|NFATC1_pTH8401_PBM\|NFATC1_pTH8315_PBM\|NFATC1_pTH9196_PBM\|NFATC1_pTH8557_PBM\|NFATC1_pTH9005_PBM\|NFATC1_pTH9192_PBM | AATGGAAAAT | ATTTTCCATT |
| SIX5_known 7 | AATAGGGTATCAATATT | AATATTGATACCCTATT |
| NKX3-1_4 | CATTTAAGTACTTAGTA | TACTAAGTACTTAAATG |
| MSC_MSC_1_SELEX\|ASCL2_Ascl2_2654_PBM\|MYOD1_MYF6_1_SELEX\|MYF6_2\|MSC_1 | AACAGCTGTT | AACAGCTGTT |
| FOXP3_FOXP3_f1_HocoMoco | AAACAAATT | AATTTGTTT |
| STAT_known17 | CATTTCCCGGAAACC | GGTTTCCGGGAAATG |
| AR_ANDR_do_HocoMoco | AAGAACATCCTGTTCC | GGAACAGGATGTTCTT |
| E2F2_E2F2_1_SELEX\|E2F3_E2F3_1_SELEX\|E2F2_2\|E2F_known24 | AAAAATGGCGCCAAAATG | CATTTTGGCGCCATTTTT |
| USF1_V$USF_02_Transfac\|MYC_known4 | AAATCACGTGATAT | ATATCACGTGATTT |
| PITX1_1 | ATTGTTAATCCCTCTAA | TTAGAGGGATTAACAAT |
| KLF4_pTH3086_PBM\|KLF4_Klf7_0974_PBM\|KLF4_pTH0977_PBM | GCCACGCCCA | TGGGCGTGGC |

TABLE 5-continued

Transcription Factor Binding Sites of Synthetic Promoters

| Name | Binding Site Sequence | Reverse Complement |
| --- | --- | --- |
| RHOXF1_7 | CGCTGTTAA | TTAACAGCG |
| LMX1A_MA0182.1_B1H | CAATAAA | TTTATTG |
| PTF1A_PTF1A_f1_HocoMoco | CAGGAAACTGAACAGCTGTCC | GGACAGCTGTTCAGTTTCCTG |
| FOXD1_V$XFD2_01_Transfac | AATATAAACATACA | TGTATGTTTATATT |
| NANOG_known1 | GGAAATGGGCCC | GGGCCCATTTCC |
| SOX9_SOX9_5_SELEX|SOX9_7 | AAACAATTGCAGTGTTT | AAACACTGCAATTGTTT |
| CUX1_6 | ACCGGTTGATCACCTGA | TCAGGTGATCAACCGGT |
| YY1_known4 | CAAGATGGC | GCCATCTTG |
| ATF1_pTH5002_PBM | TATGACGTAA | TTACGTCATA |
| UBP1_MA0145.2_ChIP-seq|TFCP2L1_1 | CCAGTTCAAACCAG | CTGGTTTGAACTGG |
| MEF2_known10 | GGCTATTTTAA | TTAAAATAGCC |
| IKZF1_V$IK2_01_Transfac|IKZF2_1 | GTATTCCCAAAC | GTTTGGGAATAC |
| NANOG_disc2 | GCCTTTGTTTTGCAA | TTGCAAAACAAAGGC |
| BACH1_V$BACH1_01_Transfac|BACH1_1 | ACGATGAGTCATGCT | AGCATGACTCATCGT |
| GATA2_V$GATA2_01_Transfac|GATA_known2 | CGCTATCCGC | GCGGATAGCG |
| MZF1_V$MZF1_02_Transfac|MZF1_2 | GGGTGAGGGGGAA | TTCCCCCTCACCC |
| OSR2_Osr1_3033_PBM|OSR2_pTH9150_PBM | ACGGTAGCA | TGCTACCGT |
| RFX8_pTH9285_PBM | CATAGCAAC | GTTGCTATG |
| ENSG00000250096_RUNX3_si_HocoMoco | AACCACAAACCCCA | TGGGGTTTGTGGTT |
| RORB_pTH3464_PBM | CTAGGTCA | TGACCTAG |
| POU2F2_known4 | ATATAATTATGCAAATTAAAAGA | TCTTTTAATTTGCATAATTATAT |
| ATF5_ATF5_si_HocoMoco | CCTTCTTCCTTA | TAAGGAAGAAGG |
| ETV5_ELK3_f1_HocoMoco | CCCAGGAAGTGC | GCACTTCCTGGG |
| MYC_known18|MYCN_2 | CGCACGTGGC | GCCACGTGCG |
| ZIC4_Zic3_1_SELEX|ZIC4_ZIC4_1_SELEX|ZIC4_1|ZIC3_4 | GACCCCCGCTGTGC | GCACAGCGGGGGTC |
| CTCF_HMEC_CTCF_Broad_ChIP-seq | ATAGCGCCCCTGGTGGCCA | TGGCCACCAGGGGCGCTAT |
| USF1_K562_USF1_HudsonAlpha_ChIP-seq | CGGCCACGTGACCC | GGGTCACGTGGCCG |
| PITX3_1 | AGGGGGATTAGCTGCC | GGCAGCTAATCCCCCT |
| LBX1_pTH5994_PBM|SHOX_UNCX_2_SELEX|LBX1_pTH5672_PBM|ALX1_pTH6195_PBM|DMBX1_Cart1_0997_PBM|HOXC5_pTH6140_PBM|DRGX_Pax6_3838_PBM|DMBX1_Arx_1738_PBM|LMX1A_LMX16_2_SELEX|VENTX_pTH5490_PBM|POU3F3_pTH9342_PBM|LBX2_Lbx2_3869_PBM|EVX2_pTH6104_PBM|ALX1_PRRX1_1_SELEX|SHOX_Prrx2_1_SELEX|LHX9_Lhx2_0953_PBM|HESX1_pTH6156_PBM|HOXD1_pTH6251_PBM|LHX9_Lhx9_3492_PBM|LBX2_pTH6404_PBM|SHOX_SHOX_1_SELEX|SHOX_Shox2_1_SELEX|SHOX_Uncx_2_SELEX|ALX1_ISX_3_SELEX|ISX_4|LMX16_3|NKX6-2_2|NKX6-2_3|PRRX1_2|PRRX2_5|SHOX_1|SHOX2_3|UNCX_3|UNCX_5 | CTAATTAA | TTAATTAG |
| HOXC5_PDX1_2_SELEX|VAX1_VAX1_1_SELEX|HOXC5_pTH6215_PBM|VAX1_VAX2_1_SELEX|PDX1_6|VAX1_2|VAX2_2 | CTAATTAC | GTAATTAG |

TABLE 5-continued

Transcription Factor Binding Sites of Synthetic Promoters

| Name | Binding Site Sequence | Reverse Complement |
| --- | --- | --- |
| PAX4_PAX4_2_SELEX\|ALX1_VSX2_1_SELEX\|PAX4_PAX4_1_SELEX\|EN2_EN1_3_SELEX\|LHX8_Lhx8_2_SELEX\|PAX4_7\|PAX4_8\|EN1_6\|LHX8_3\|VSX2_2 | CTAATTAG | CTAATTAG |
| RHOXF2_1 | GAGCATTAATTAAGGCA | TGCCTTAATTAATGCTC |
| MYC_known11 | GACCACGTGACA | TGTCACGTGGTC |
| ZIC4_Zic3_3119_PBM\|ZIC4_Zic2_2895_PBM\|ZIC4_Zic1_0991_PBM | CACAGCGGGG | CCCCGCTGTG |
| ETV5_K562_ETS1_HudsonAlpha_ChIP-seq | CCTGCTGGGAGTTGTAGTCCC | GGGACTACAACTCCCAGCAGG |
| FOXD1_Foxk1_1_SELEX\|FOXK1_3 | CGGACACAATC | GATTGTGTCCG |
| AL662830.5_exd_SOLEXA_2_FBgn0000611_B1H | ATATCAAA | TTTGATAT |
| CREB3L2_pTH5024_PBM | ACACGTGGC | GCCACGTGT |
| GATA2_Mf28_ChIP-seq | ACCCCCTTATCAGACTAT | ATAGTCTGATAAGGGGGT |
| TEF_DBP_si_HocoMoco | GTTATGTAACA | TGTTACATAAC |
| ENSG00000234254_Tgif2_3451_PBM\|PKNOX2_Pknox2_3077_PBM | ACCTGTCAAT | ATTGACAGGT |
| AL662834.13_Zbtb12_2932_PBM | ATCTAGAACA | TGTTCTAGAT |
| SRY_4 | GAATATTATAATTATA | TATAATTATAATATTC |
| DMBX1_Alx1_1_SELEX\|DMBX1_ALX3_2_SELEX\|ALX3_3\|ALX1_4 | TCTAATTAAA | TTTAATTAGA |
| DLX1_Dlx2_1_SELEX\|DLX2_3 | GCAATTAA | TTAATTGC |
| YY2_pho_SANGER_10_FBgn0002521_B1H | CAAAATGGCGGC | GCCGCCATTTTG |
| TFAP2A_Tcfap2a_2337_PBM | CCCTGAGGCA | TGCCTCAGGG |
| CR936877.3_RXRB_f1_HocoMoco | TGAGGTCACA | TGTGACCTCA |
| RBPJ_MA0085.1_COMPILED | ATCTCGTTTCCCACAG | CTGTGGGAAACGAGAT |
| ETV5_HepG2_GABP_HudsonAlpha_ChIP-seq | CCACTTCCGGTTCCG | CGGAACCGGAAGTGG |
| NKX2-5_Bap_Cell_FBgn0004862_B1H | CCACTTAAGA | TCTTAAGTGG |
| CUX1_CUX1_1_SELEX\|CUX1_8 | ATCGATAACTGATCGAT | ATCGATCAGTTATCGAT |
| DMBX1_ALX4_1_SELEX\|DMBX1_Alx1_2_SELEX\|DMBX1_Arx_1_SELEX\|SHOX_Uncx_1_SELEX\|ALX4_3\|ALX1_5\|ARX_3\|UNCX_4 | CTAATTAAATTAA | TTAATTTAATTAG |
| RELA_GM12892_N FKB_Stanford_ChIP-seq\|RELA_GM19193_NFKB_Stanford_ChIP-seq | AGGGGATTTCCAAGG | CCTTGGAAATCCCCT |
| HNF4_known1 | ACAGGGTCAAAGGTCAAGA | TCTTGACCTTTGACCCTGT |
| SHOX_UNCX_1_SELEX\|UNCX_2 | CTAATTAAATTAG | CTAATTTAATTAG |
| NKX2-6_Tin_SOLEXA_FBgn0004110_B1H\|NKX2-5_Bap_SOLEXA_FBgn0004862_B1H | CACTTAAG | CTTAAGTG |
| CDX2_cad_FlyReg_FBgn0000251_B1H | ATCATAAAA | TTTTATGAT |
| BCL_disc10 | CCTCCGCCGC | GCGGCGGAGG |
| SIX5_known 1 | AATAGGGTATCATATAT | ATATATGATACCCTATT |
| HOXC5_1 | AGTAATTAATTAATTCG | CGAATTAATTAATTACT |
| ZNF423_ZN423_a_HocoMoco | GCACCCTTGGGTGCC | GGCACCCAAGGGTGC |

TABLE 5-continued

Transcription Factor Binding Sites of Synthetic Promoters

| Name | Binding Site Sequence | Reverse Complement |
| --- | --- | --- |
| REST_disc3 | GGACAGCGCC | GGCGCTGTCC |
| IRF7_IRF7_2_SELEX\|IRF_known18 | AAAACGAAAATCGATTT | AAATCGATTTTCGTTTT |
| THRB_V$T3R_01_Transfac | GATTGAGGTCACGCCA | TGGCGTGACCTCAATC |
| POU3F3_pTH3819_PBM\|ALX1_Vsx1_1728_PBM | CTAATTATC | GATAATTAG |
| SREBP_known2 | GATCACCCCAC | GTGGGGTGATC |
| MLX_pTH2882_PBM | CACGTGATC | GATCACGTG |
| ZNF32_pTH3120_PBM | ATATATATA | TATATATAT |
| PAX9_sv_SOLEXA_5_FBgn0005561_B1H | ATTGGTGCGTGACGG | CCGTCACGCACCAAT |
| RELA_MA0101.1_SELEX\|RELA_V$CREL_01_Transfac\|REL1\|REL2 | GGAAATCCCC | GGGGATTTCC |
| CTCF_A549_CTCF_HudsonAlpha_ChIP-seq | ACAGCGCCCCTGGTGGCCAC | GTGGCCACCAGGGGGCGCTGT |
| CR936877.3_MA0512.1_ChIP-seq | CAAAGGTCAGA | TCTGACCTTTG |
| THAP1_disc1 | CCGCCATCTTGGTTAAGGCAGAGG | CCTCTGCCCTTAACCAAGATGGCGG |
| IRF7_IRF7_1_SELEX\|IRF_known17 | ACGAAAGCGAAAGT | ACTTTCGCTTTCGT |
| SP9_Sp4_1011_PBM | AGGGGGCGGG | CCCGCCCCCT |
| BX088580.2_H1-hESC_POU5F1_HudsonAlpha_ChIP-seq | ATTTGCATAACAAAGGA | TCCTTTGTTATGCAAAT |
| HOXC10_HOXC10_1_SELEX\|HOXC10_2 | CCCATAAAAA | TTTTTATGGG |
| HBP1_Hbp1_2241_PBM | GTGAATGA | TCATTCAC |
| ATF1_pTH5005_PBM | ATGACGTA | TACGTCAT |
| RFX8_pTH10021_PBM | CATAGCAACC | GGTTGCTATG |
| PAX4_V$PAX4_04_Transfac\|PAX4_4 | AAAAATTAACCCAAAATCCAACCTCACCCC | GGGGTGAGGTTGGATTTTGGGTTAATTTTT |
| RFX8_Rfxdc2_3516_PBM | CATAGCAACG | CGTTGCTATG |
| GLIS3_GLIS3_f1_HocoMoco | GTGGGGGTA | TACCCCCAC |
| PAX5_disc4 | AGAGGAAGTG | CACTTCCTCT |
| TEAD1_TEAD1_2_SELEX\|TEAD1_4 | ACATTCCTGACATTCCA | TGGAATGTCAGGAATGT |
| E2F_known17 | GTTTGGCGCGA | TCGCGCCAAAC |
| ZNF274_NT2-D1_ZNF274_UCD_ChIP-seq | TCATACTGGAGAGAA | TTCTCTCCAGTATGA |
| TFAP2A_Tcfap2a_2_SELEX\|TFAP2A_TFAP2A_2_SELEX\|TFAP2_known12\|TFAP2_known21 | CGCCTCAGGCA | TGCCTGAGGCG |
| OVOL1_OVOL1_f1_HocoMoco | ACAGTTACA | TGTAACTGT |
| ESRRG_Esrra_2190_PBM | ATGACCTTG | CAAGGTCAT |
| PAX4_3 | AATCCCCACCCC | GGGGTGGGGATT |
| IRF1_IRF1_si_HocoMoco | ACTTTCACTTTC | GAAAGTGAAAGT |
| POU2F2_known1 | ATCAATATGCAAATTCGG | CCGAAATTTGCATATTGAT |
| PAX4_V$PAX4_03_Transfac | AATCCCCACCCG | CGGGTGGGGATT |
| POU3F3_V$OCT1_02_Transfac\|POU2F2_known2 | ATGAATATGCATATA | TATATGCATATTCAT |
| ARHGEF12_1 | ATTTACGACAAATAGC | GCTATTTGTCGTAAAT |

TABLE 5-continued

Transcription Factor Binding Sites of Synthetic Promoters

| Name | Binding Site Sequence | Reverse Complement |
|---|---|---|
| EOMES_TBX21_3_SELEX\|TBX21_3 | TCACACCTTAAAGGTGTGA | TCACACCTTTAAGGTGTGA |
| MAX_MAX_1_SELEX\|MYC_known20 | CACGTGCTAACCACGTG | CACGTGGTTAGCACGTG |
| HSFY1_HSFY2_3_SELEX\|HSFY2_3 | TTCGAACCGTTCGAA | TTCGAACGGTTCGAA |
| CEBPA_HeLa-S3_CEBPB_Stanford_ChIP-seq | AGGATTGTGCAATA | TATTGCACAATCCT |
| RFX8_pTH8587_PBM | ATAGCAAC | GTTGCTAT |
| CEBPA_pTH3208_PBM | ATTACGCAAT | ATTGCGTAAT |
| FOXM1_pTH8652_PBM | AAAAACAA | TTGTTTTT |
| PDX1_1 | GAATTAATGACC | GGTCATTAATTC |
| E2F1_MA0024.2_ChIP-seq | CCTCCCGCCCG | CGGGCGGGAGG |
| ALX1_ISX_1_SELEX\|ISX_2 | TTAATCTAATTAA | TTAATTAGATTAA |
| TWIST2_pTH5033_PBM\|OLIG2_OLIG3_1_SELEX\|OLIG2_pTH5267_PBM\|OLIG2_BHLHE23_1_SELEX\|OLIG2_OLIG2_1_SELEX\|BHLHE23_1\|OLIG2_1\|OLIG3_1 | AACATATGGT | ACCATATGTT |
| GFI1B_sens_SOLEXA_5_FBgn0002573_B1H | AAATAAATCACAGCA | TGCTGTGATTTATTT |
| FOXN1_1 | AAAGCGTCGTT | AACGACGCTTT |
| SHOX_PHOX2A_1_SELEX\|PROP1_PROP1_1_SELEX\|SHOX_PHOX26_2_SELEX\|SHOX_PHOX26_1_SELEX\|PHOX2A_2\|PHOX26_2\|PHOX26_3\|PROP1_2 | TAATTAAATTA | TAATTTAATTA |
| POU2F2_known11\|POU2F2_known12 | TATGCAAATCA | TGATTTGCATA |
| ATOH7_pTH5074_PBM | AACATATGGC | GCCATATGTT |
| FOXD1_MA0546.1_ChIP-seq | AAAGTAAACA | TGTTTACTTT |
| NR2E1_pTH6281_PBM | AGAGGTCAAT | ATTGACCTCT |
| AHR_AHR_si_HocoMoco | GCACGCAAC | GTTGCGTGC |
| GATA2_V$GATA1_02_Transfac\|GATA_known4 | GTAAAGATAGGGGA | TCCCCTATCTTTAC |
| AP1_known3 | ACTGAGTCATC | GATGACTCAGT |
| STAT1_V$STAT1_03_Transfac | CGGAAATC | GATTTCCG |
| HDAC2_disc6 | AAGAAAAGAAAAAA | TTTTTTCTTTTCTT |
| SIN3A_disc7 | CCCCGGACAGCGCC | GGCGCTGTCCGGGG |
| TEF_V$HLF_01_Transfac\|TEF_V$VBP_01_Transfac\|HLF_I | ATTACGTAAC | GTTACGTAAT |
| ZEB1_GM12878_ZEB1_HudsonAlpha_ChIP-seq\|ZEB1_disc1 | CAGGTGAG | CTCACCTG |
| KLF4_KLF3_f1_HocoMoco | AGCCACACCCAGGCA | TGCCTGGGTGTGGCT |
| EP300_disc1\|RXRA_disc3 | AATGAGTCAT | ATGACTCATT |
| HNFIA_HNF1B_1_SELEX\|HNF1B_3 | GTTAATCATTAAC | GTTAATGATTAAC |
| LMX1A_CG32105_Cell_FBgn0052105_B1H | ATTAATTAG | CTAATTAAT |
| RBPJ_1 | CGTGGGAA | TTCCCACG |
| NKX6-3_Nkx6-1_2825_PBM\|NKX6-3_N_kx6-3_3446_PBM | ATTAATTAC | GTAATTAAT |
| OSR2_sob_SOLEXA_5_FBgn0004892_B1H | AAAAACAGTAGCCG | CGGCTACTGTTTTT |
| FOXP4_CG2052_SOLEXA_2.5_FBgn0039905_B1H | AAAAAAAAAAAACC | GGTTTTTTTTTTTT |
| TCF12_disc5 | CCAGCTGCCCC | GGGGCAGCTGG |

TABLE 5-continued

Transcription Factor Binding Sites of Synthetic Promoters

| Name | Binding Site Sequence | Reverse Complement |
|---|---|---|
| USF1_V$USF_C_Transfac\|MYC_known7 | CCACGTGC | GCACGTGG |
| BDP1_disc3 | CCCACAGCCTCGTC | GACGAGGCTGTGGG |
| THRB_THA_f2_HocoMoco | CTGACCTGAAGTGACCC | GGGTCACTTCAGGTCAG |
| AR_V$GR_Q6_Transfac\|NR3C1_known1 | CTAGAACACAGTGTACCCA | TGGGTACACTGTGTTCTAG |
| TEAD3_TEAD3_2_SELEX\|TEAD3_2 | ACATTCCA | TGGAATGT |
| SREBF2_pTH4327_PBM | TCACGCGA | TCGCGTGA |
| MAFK_MAFK_4_SELEX\|MAF_known9 | ATGCTGAGTCAGCGA | TCGCTGACTCAGCAT |
| ATF3_HepG2_ATF3_HudsonAlpha_ChIP-seq\|ATF3_GM12878_ATF3_HudsonAlpha_ChIP-seq\|USF1_HeLa-S3_USF2_Stanford_ChIP-seq\|ATF3_H1-hESC_ATF3_HudsonAlpha_ChIP-seq | GGTCACGTGAC | GTCACGTGACC |
| MYC_K562_CMYC_Stanford_ChIP-seq\|MYC_HepG2_CMYC_UT-A_ChIP-seq\|MYC_MYC_f1_HocoMoco | GAGCACGTGGC | GCCACGTGCTC |
| DPRX_DPRX_1_SELEX\|DPRX_1 | ACGGATTAGC | GCTAATCCGT |
| MNX1_1 | CGCCACTAATTAGTAC | GTACTAATTAGTGGCG |
| HMGA2_pTH3046_PBM | CCGCAATAAA | TTTATTGCGG |
| NRF1_disc1 | CACTGCGCATGCGCA | TGCGCATGCGCAGTG |
| PBX3_disc1 | AGCCAATGAG | CTCATTGGCT |
| TEF_TEF_2_SELEX\|NFIL3_NFIL3_1_SELEX\|NFIL3_3\|TEF_3 | TATTACATAACA | TGTTATGTAATA |
| SP1_known5 | AGGGGGCGGGCC | GGCCCGCCCCCT |
| NKX6-1_3 | AGTAATTAATTACTTC | GAAGTAATTAATTACT |
| KLF4_MA0599.1_ChIP-seq\|TATA_disc4\|SP1_known4 | GCCCCGCCCC | GGGGCGGGGC |
| NKX2-5_5 | AAATTCAAGTGGCTTA | TAAGCCACTTGAATTT |
| KLF4_luna_SOLEXA_5_FBgn0040765_B1H | AAATGGGCGTGGCC | GGCCACGCCCATTT |
| PAX9_PAX5_1_SELEX\|PAX5_known5 | CGTCACGCATGAGTGCTC | GAGCACTCATGCGTGACG |
| DLX1_Dlx2_2273_PBM\|DLX1_Dlx3_1030_PBM\|DLX1_Dlx1_1741_PBM | ATAATTGCC | GGCAATTAT |
| NAIF1_pTH8560_PBM | CTTACGCAA | TTGCGTAAG |
| NR3C1_known9 | AGGGGAGGTACACGGTGTTCTTTTGGG | CCCAAAAGAACACCGTGTACCTCCCCT |
| DOBOX4_1 | TAAATAGATACCCCATA | TATGGGGTATCTATTTA |
| ALX4_2 | CGCATTAATTAATTACC | GGTAATTAATTAATGCG |
| MTF1_1 | GGGCCGTGTGCAGA | TCTGCACACGGCCC |
| TCF12_disc2 | TGAGTAAACA | TGTTTACTCA |
| TFAP2A_MA0003.2_ChIP-seq | CATTGCCTCAGGGCA | TGCCCTGAGGCAATG |
| FOXO6_pTH3846_PBM\|FOXD1_pTH5334_PBM\|FOXD1_FOXB1_4_SELEX\|FOXB1_4 | TGTAAACAA | TTGTTTACA |
| ATF3_disc4 | CCCCGCGCCC | GGGCGCGGGG |
| SPDEF_1 | AAAATCCGGATGTAC | GTACATCCGGATTTT |
| RFX8_V$RFX1_02_Transfac\|RFX5_known2 | TAGTAGCCATGGCAACAA | TTGTTGCCATGGCTACTA |

TABLE 5-continued

Transcription Factor Binding Sites of Synthetic Promoters

| Name | Binding Site Sequence | Reverse Complement |
|---|---|---|
| MAFA_MAFA_f1_HocoMoco | CGAAGGCTGCGGGGTCAGCAC | GTGCTGACCCCGCAGCCTCG |
| IRF_disc2 | ATGACTCATA | TATGAGTCAT |
| PKNOX2_MA0498.1_ChIP-seq | AGCTGTCACTCACCT | AGGTGAGTGACAGCT |
| JUN_JUNB_f1_HocoMoco\|MYC_disc3 | ATGACTCATC | GATGAGTCAT |
| ZFP161_Zfp161_2858_PBM | CGCGCGCAC | GTGCGCGCG |
| GATA_disc4 | ATCTGATA | TATCAGAT |
| STAT2_STAT2_f1_HocoMoco | GGAAAACGAAACTGA | TCAGTTTCGTTTTCC |
| IKZF2_2 | TATAGGGATAA | TTATCCCTATA |
| MAX_Max_3864_PBM\|MAX_pTH4381_PBM\|MAX_Max_3863_PBM | ACCACGTGG | CCACGTGGT |
| HNF4G_HNF4A_3_SELEX\|HNF4_known18 | ATTGGACTTTGGACCC | GGGTCCAAAGTCCAAT |
| MAX_MA0058.2_ChIP-seq\|MYC_MA0147.2_ChIP-seq | AAGCACATGG | CCATGTGCTT |
| RFX8_HepG2_RFX5_Stanford_ChIP-seq | CTGTTGCTAGGCAGA | TCTGCCTAGCAACAG |
| ZEB1_V$AREB6_03_Transfac\|ZEB1_known3 | CTGCACCTGTGC | GCACAGGTGCAG |
| GCM1_I$GCM_01_Transfac | AAACCCGCATATT | AATATGCGGGTTT |
| CTCF_disc6 | ACCTAGTG | CACTAGGT |
| ESRRG_T-47D_ERALPHA_HudsonAlpha_ChIP-seq | CAAGGTCAGGGTGACCTGG | CCAGGTCACCCTGACCTTG |
| VTN_pTH6379_PBM | AATTAATTAG | CTAATTAATT |
| LHX3_1 | AATTAATTA | TTAATTAATT |
| IRF_known3 | CAGTTTCACTTTCCC | GGGAAAGTGAAACTG |
| GLIS2_GLIS2_1_SELEX\|GLIS2_2 | CTTCGCGGGGGTC | GACCCCCGCGAAG |
| THRB_THRB_2_SELEX\|THRB_2 | GTGACCTTAATAAGGTCAC | GTGACCTTATTAAGGTCAC |
| HOXA4_pTH5887_PBM | CCTAATGAG | CTCATTAGG |
| YY2_NT2-D1_YY1_UCD_ChIP-seq | CAAGATGGCGGCC | GGCCGCCATCTTG |
| TFAP4_TFAP4_si_HocoMoco | CCGCAGCTGGC | GCCAGCTGCGG |
| AL662830.5_GM12878_PBX3_HudsonAlpha_ChIP-seq | CTCTGATTGGCCGGC | GCCGGCCAATCAGAG |
| TATA_disc10 | CCGCGGCGGC | GCCGCCGCGG |
| SIX6_Optix_Cell_FBgn0025360_B1H\|SIX6_Optix_SOLEXA_FBgn0025360_B1H | AAGTGATA | TATCACTT |
| HNF1A_Tcf2_0913_PBM | CTGGTTAA | TTAACCAG |
| ETV5_MA0474.1_ChIP-seq\|ETV5_MA0475.1_ChIP-seq | ACAGGAAGTGG | CCACTTCCTGT |
| CEBPB_known3 | GCCTTACCAAATA | TATTTGGTAAGGC |
| SOX15_SOX15_2_SELEX\|SOX15_3 | ATCAATAACATTGAT | ATCAATGTTATTGAT |
| STAT_disc3 | AGTTTCATTTTC | GAAAATGAAACT |
| MAFB_MAFB_f1_HocoMoco | CCGTCAGCA | TGCTGACGG |
| TFAP4_V$AP4_01_Transfac\|TFAP4_1 | AGAACCAGCTGCGGTCAG | CTGACCGCAGCTGGTTCT |
| ATF7_pTH5083_PBM | AATGACGTCA | TGACGTCATT |

TABLE 5-continued

Transcription Factor Binding Sites of Synthetic Promoters

| Name | Binding Site Sequence | Reverse Complement |
| --- | --- | --- |
| SOX9_SOX10_5_SELEX\|SOX10_7 | TGAATGTTCAGTCA | TGACTGAACATTCA |
| NRF1_NRF1_f1_HocoMoco | CTGCGCATGCGC | GCGCATGCGCAG |
| BCL6B_1 | CAAATTCCTCGAAAGA | TCTTTCGAGGAATTTG |
| E2F2_1 | ATAAAGGCGCGCGAT | ATCGCGCGCCTTTAT |
| NR2C2_HeLa-53_TR4_UCD_ChIP-seq | ACCACTTCCGGGTCA | TGACCCGGAAGTGGT |
| VSX1_1 | AATTATTAATTAACTCG | CGAGTTAATTAATAATT |
| MYCN_V$NMYC_01_Transfac\|MYCN_1 | TCCCACGTGTCA | TGACACGTGGGA |
| TCF7L2_MA0237.2_ChIP-chip | ATCAAAGGAGCCGA | TCGGCTCCTTTGAT |
| MYC_disc5 | GCTGATGCAA | TTGCATCAGC |
| SOX18_SOX18_3_SELEX\|SOX18_4 | ATGAATGGAATTCAT | ATGAATTCCATTCAT |
| DLX1_DLX1_1_SELEX\|DLX1_2 | CCTAATTATC | GATAATTAGG |
| SMAD2_SMAD2_si_HocoMoco | CAGACGGACAC | GTGTCCGTCTG |
| CDX1_1 | TAAGGTAATAAAATTA | TAATTTTATTACCTTA |
| NR2C2_pTH6019_PBM | AAGGTCAA | TTGACCTT |
| NR4A_known1 | AAGGTCAC | GTGACCTT |
| RBPJ_2 | ACCGTGGGAAA | TTTCCCACGGT |
| MEOX2_MEOX2_2_SELEX\|MEOX2_2 | GTAATTACCGTAATTAA | TTAATTACGGTAATTAC |
| MYC_disc7 | AACACGTG | CACGTGTT |
| CTCF_disc5 | CCAGCAGGGGCGG | CCGCCCCTGCTGG |
| KLF4_V$AP2REP_01_Transfac\|KLF12_1 | CAGTGGG | CCCACTG |
| NR5A1_pTH5709_PBM | AAGGTCAT | ATGACCTT |
| MLXIPL_MLXPL_f1_HocoMoco | CCACGGCGGTGTCACATGC | GCATGTGACACCGCCGTGG |
| IRF_disc6 | AAGTTTCA | TGAAACTT |
| CTCF_HepG2_CTCF_Broad_ChIP-seq | ATAGCGCCCCTGGTGGC | GCCACCAGGGGCGCTAT |
| NFE2_known1 | GTGACTCAGCA | TGCTGAGTCAC |
| GATA2_V$GATA2_02_Transfac\|GATA2_V$GATA3_02_Transfac\|GATA2_V$GATA2_03_Transfac | AGAGATAAGA | TCTTATCTCT |
| CTCF_HUVEC_CTCF_UT-A_ChIP-seq | AGTGCCATCTAGTGG | CCACTAGATGGCACT |
| HIF1A_1 | CGTACGTGCGGC | GCCGCACGTACG |
| THRB_THRB_3_SELEX\|THRB_3 | GTGACCTTACATAAGGTCAC | GTGACCTTATGTAAGGTCAC |
| SRF_K562_SRF_HudsonAlpha_ChIP-seq | AGTTGCCTTATATGGTC | GACCATATAAGGCAACT |
| ARID5A_Arid5a_3770_PBM | GATAATATTGA | TCAATATTATC |
| MYB_V$VMYB_01_Transfac | AATAACGGAA | TTCCGTTATT |
| TCF4_pTH5071_PBM | AACACCTGG | CCAGGTGTT |
| TATA_disc6 | CCAATCAGAA | TTCTGATTGG |
| POU1F1_1 | ATGAATAAAT | ATTTATTCAT |
| IRX6_1 | AAAATACATGTAAAAAT | ATTTTTACATGTATTTT |

TABLE 5-continued

Transcription Factor Binding Sites of Synthetic Promoters

| Name | Binding Site Sequence | Reverse Complement |
|---|---|---|
| ALX4_1 | CCTGAGAATAATC | GATTATTCTCAGG |
| E2F3_E2F3_2_SELEX\|E2F_known25 | AAAAATGGCGCCATTTTT | AAAAATGGCGCCATTTTT |
| NR1I3_NR1I3_si_HocoMoco | AAGTTCAT | ATGAACTT |
| POU6F1_3 | AAACATAATGAGGTTGC | GCAACCTCATTATGTTT |
| NR1I2_NR1I2_si_HocoMoco | AAGTTCAC | GTGAACTT |
| SOX9_SOX9_f1_HocoMoco | AGAACAATGGG | CCCATTGTTCT |
| PLAGL1_1 | CTAGGGGCGCCCCCAA | TTGGGGGCGCCCCTAG |
| EP300_V$P300_01_Transfac\|EP300_known1 | ACAGGGAGTGAGTG | CACTCACTCCCTGT |
| IRF4_IRF4_1_SELEX\|IRF4_2 | CCGAAACCGAAACTA | TAGTTTCGGTTTCGG |
| SRF_F$MCM1_01_Transfac | TTACCTGATTAGGAAA | TTTCCTAATCAGGTAA |
| BSX_Bsx_3483_PBM | ACCCATTAA | TTAATGGGT |
| STAT3_V$STAT3_02_Transfac | GGCTTCCC | GGGAAGCC |
| FOXD1_V$HFH3_01_Transfac\|FOXI1_1 | GGATGTTTGTTTA | TAAACAAACATCC |
| AHR::ARNT::HIF1A_1 | CCGCACGCA | TGCGTGCGG |
| NKX2-8_1 | AATTTAAGTACTTAAAA | TTTTAAGTACTTAAATT |
| MEF2B_Mv88_Ch\|P-seq\|MEF2_known11 | CTATAAATAG | CTATTTATAG |
| EMX2_pTH5673_PBM\|HOXC5_PDX1_do_HocoMoco\|EVX2_Evx1_3952_PBM\|HOXA4_Hoxa2_3079_PBM\|EVX2_pTH6436_PBM\|VAX1_Vax2_3500_PBM | CTAATTACC | GGTAATTAG |
| NKX2-5_Nkx2-2_2823_PBM | GCACTTAAA | TTTAAGTGC |
| STAT3_GM12878_STAT3_Stanford_ChIP-seq | CAGGTGATTTCCGGGAAATG | CATTTCCCGGAAATCACCTG |
| MYF6_1 | CGGACACCTGTTCTTC | GAAGAACAGGTGTCCG |
| ALX1_V$CHX10_01_Transfac\|VSX2_1 | GGCTAATTAGCGAA | TTCGCTAATTAGCC |
| CEBPA_V$CEBP_01_Transfac | AACTTACCAAACA | TGTTTGGTAAGTT |
| DMBX1_ALX1_si_Hoco Moco | ATAATTGGATTA | TAATCCAATTAT |
| TAL1_known5 | AACAGATGGTCG | CGACCATCTGTT |
| FOXP4_MA0593.1_ChIP-seq | AAGTAAACAAA | TTTGTTTACTT |
| FOXD1_MA0041.1_SELEX\|FOXD3_2 | AAACAAACATTC | GAATGTTTGTTT |
| TCF7L2_LEF1_1_SELEX\|TCF7L2_known7 | AAAGATCAAAGGGTT | AACCCTTTGATCTTT |
| AR_GCR_si_HocoMoco\|AR_PRGR_f1_HocoMoco | AGAACAG | CTGTTCT |
| TAL1_known2 | GTCACCATCTGTTCGA | TCGAACAGATGGTGAC |
| NFY_known6 | CTCAGCCAATCAGCGC | GCGCTGATTGGCTGAG |
| TCF4_sc_da_SANGER_10_FBgn0000413_B1H\|TCF4_ac_da_SANGER_5_FBgn0000413_B1H | ACACCTGC | GCAGGTGT |
| DBX2_MA0174.1_B1H | TAATAAA | TTTATTA |
| TCF4_H1-hESC_TCF12_HudsonAlpha_ChIP-seq\|TCF12_disc1 | ACACCTGG | CCAGGTGT |
| ENSG00000234254_Tgif1_2342_PBM | AGCTGTCAAT | ATTGACAGCT |
| NR3C1_disc6 | CTCCCTGTCCCCTC | GAGGGGACAGGGAG |

TABLE 5-continued

Transcription Factor Binding Sites of Synthetic Promoters

| Name | Binding Site Sequence | Reverse Complement |
|---|---|---|
| STAT_known12 | GATTTCCA | TGGAAATC |
| MAFK_MA0496.1_ChIP-seq | AAATTGCTGACTCAG | CTGAGTCAGCAATTT |
| SPIC_GM12878_PU1_HudsonAlpha_ChIP-seq | AAAAAGAGGAAGTGAAACT | AGTTTCACTTCCTCTTTTT |
| HES4_HES1_f1_HocoMoco | CCGCCACGAGCCC | GGGCTCGTGGCGG |
| SNAI3_pTH2340_PBM | AGCTGTCAAA | TTTGACAGCT |
| AL662828.6_ATF6A_si_HocoMoco | CCACGTCACCAC | GTGGTGACGTGG |
| RFX5_known5 | ACCGTTGCTATGGTA | TACCATAGCAACGGT |
| ESRRG_ESRRA_2_SELEX\|ESRRG_ESRRA_5_SELEX\|ESRRA_known8 | AAGGTCATTCAAGGTCA | TGACCTTGAATGACCTT |
| MYBL2_MYBB_f1_HocoMoco | TCAACCTGCA | TGCAGGTTGA |
| NAIF1_pTH9299_PBM | TTACGCAAA | TTTGCGTAA |
| FOSL1_FOSB_f1_HocoMoco | CTGACTCATC | GATGAGTCAG |
| SPIC_MA0081.1_SELEX\|SPIB_1 | AGAGGAA | TTCCTCT |
| STAT_disc1 | TTCCAGGAAA | TTTCCTGGAA |
| LHX1_Lhx3_3431_PBM | ATTTAATTA | TAATTAAAT |
| ZBTB7C_ZBT7A_a_HocoMoco | AGCAGTGGGTCCCCAG | CTGGGGGACCCACTGCT |
| TP53_Tp53_2_SELEX\|TP53_6 | ACATGTCATAGACATGT | ACATGTCTATGACATGT |
| HSF_disc1 | GTTATGCAAC | GTTGCATAAC |
| ZNF8_1 | TCTTTGGCGTACCCTAA | TTAGGGTACGCCAAAGA |
| CDX2_CDX1_f1_HocoMoco | ACATAAAT | ATTTATGT |
| HOXB13_1 | AACCCAATAAAATTCG | CGAATTTTATTGGGTT |
| PITX2_1 | TGTAATCCCAA | TTGGGATTACA |
| PROX1_PROX1_1_SELEX\|PROX1_1 | CAAGACGCCTTA | TAAGGCGTCTTG |
| FOXM1_1 | AGATGGACT | AGTCCATCT |
| TATA_disc3 | ACCGGAAG | CTTCCGGT |
| BPTF_BPTF_si_HocoMoco | GAACACAACAAA | TTTGTTGTTC |
| ARID3C_pTH5119_PBM | TAATCAAA | TTTGATTA |
| IRF9_IRF9_1_SELEX\|IRF_known21 | AACGAAACCGAAACT | AGTTTCGGTTTCGTT |
| BARX1_BARX1_1_SELEX\|BARX1_2 | CAATTAAATACCGATTA | TAATCGGTATTTAATTG |
| FOXD1_bin_FlyReg_FBgn0045759_B1H | TAAACAAGA | TCTTGTTTA |
| HLX_1 | CCATAATTAATTACA | TGTAATTAATTATGG |
| STAT3_MA0144.2_ChIP-seq | CTTCTGGGAAA | TTTCCCAGAAG |
| HSF1_HSF1_2_SELEX\|HSF2_HSF2_1_SELEX\|HSF1_HSF4_1_SELEX\|HSFLHSF1_1_SELEX\|HSF_known4\|HSF_known5\|HSF2_2\|HSF4_1 | GAACGTTCTAGAA | TTCTAGAACGTTC |
| STAT1_K562_STAT1_Stanford_ChIP-seq | TTTCCCGGAAA | TTTCCGGGAAA |
| EGR1_disc4 | AACTACAATTCCCAGAATGCCCCGC | GCGGGGCATTCTGGGAATTGTAGTT |
| GBX_Gbx2_1_SELEX\|GBX2_GBX2_3_SELEX\|GBX2_GBX2_1_SELEX\|GBX2_2\|GBX2_4\|GBX2_5 | ACCAATTAGC | GCTAATTGGT |

TABLE 5-continued

Transcription Factor Binding Sites of Synthetic Promoters

| Name | Binding Site Sequence | Reverse Complement |
|---|---|---|
| ISL2_1 | AAATTAATTGATTTTG | CAAAATCAATTAATTT |
| TFAP4_TFAP4_2_SELEX\|TFAP4_TFAP4_1_SELEX\|TFAP4_5\|TFAP4_6 | AACAGCTGAT | ATCAGCTGTT |
| CTCF_HSMMtube_CTCF_Broad_ChIP-seq | GGCCACCAGGGGGCGCTA | TAGCGCCCCTGGTGGCC |
| BARHL1_1 | AACAACCAATTAATTC | GAATTAATTGGTTGTT |
| EOMES_pTH2659_PBM | GAGGTGTAA | TTCACACCTC |
| ZBED1_ZBED1_1_SELEX\|ZBED1_1 | CTATCGCGACATA | TATGTCGCGATAG |
| FOXJ3_MA0296.1_PBM | TCCTCTTTGTTTACAATTCA | TGAATTGTAAACAAGAGGA |
| RAD21_disc3 | ACAAGAGGGC | GCCCTCTTGT |
| RFX8_MA0509.1_ChIP-seq | GTTGCCATGGCAAC | GTTGCCATGGCAAC |
| AL662830.5_pTH6425_PBM | CACATCAA | TTGATGTG |
| IRF_disc5 | AGGAAGTGAA | TTCACTTCCT |
| SRF_disc1 | CCTTATAAGG | CCTTATAAGG |
| E2F_known10\|E2F_known11\|E2F_known13 | GCGGGAAA | TTTCCCGC |
| REST_GM12878_NRSF_HudsonAlpha_ChIP-seq | TCCATGGTGCTGAA | TTCAGCACCATGGA |
| ATF1_CREB1_f1_HocoMoco\|ATF3_known14 | GTGACGTCA | TGACGTCAC |
| PROP1_PROP1_f1_HocoMoco | GAGAAATTAATATAA | TTATATTAATTTCTC |
| ARNT2_V$ARNT_02_Transfac\|ARNT_2 | CAAAGGTCACGTGACCTTTG | CAAAGGTCACGTGACCTTTG |
| TEAD3_TEAD3_si_HocoMoco | GATATTTCTGCTCTA | TAGAGCAGAAATATC |
| BCL6_BCL6_f1_HocoMoco | AAAAGCTTTCTAGGAA | TTCCTAGAAAGCTTTT |
| E2F_disc3 | CTTTCCCGCCCCC | GGGGGCGGGAAAG |
| USF1_USF1_f1_HocoMoco\|MAX_K562_MAX_Stanford_ChIP-seq\|MITF_pTH5465_PBM\|MITF_pTH5065_PBM\|MITF_pTH5057_PBM\|MXI1_known1 | CCACGTGACC | GGTCACGTGG |
| DMBX1_ALX3_3_SELEX\|ALX3_4 | CTAATTTAATTAA | TTAATTAAATTAG |
| PLAG1_MA0163.1_B1H\|PLAG1_1 | CCCCCTTGGGCCCC | GGGGCCCAAGGGGG |
| SPI1_disc3 | AGGAGGGGCAGTG | CACTGCCCCCTCCT |
| HOXC9_MA0165.1_B1H | TCATAAA | TTTATGA |
| REST_REST_f1_HocoMoco | GGGCGCTGTCCATGGTGCTGAA | TTCAGCACCATGGACAGCGCCC |
| HOXC10_MA0594.1_ChIP-seq | GCCATAAATCA | TGATTTATGGC |
| TBPL2_Spt15_PBM | AATATAT | ATATATT |
| LHX9_LHX2_1_SELEX\|LHX2_2 | ACTAATTAAC | GTTAATTAGT |
| MAFA_NRL_1_SELEX\|NRL_1 | AATTTGCTGAC | GTCAGCAAATT |
| HNF4_disc1 | AGGTCAAAGTCCA | TGGACTTTGACCT |
| BDP1_disc2 | GGATTCGAAC | GTTCGAATCC |
| YY2_GM12891_YY1_HudsonAlpha_ChIP-seq | AAGATGGCGGC | GCCGCCATCTT |

TABLE 5-continued

Transcription Factor Binding Sites of Synthetic Promoters

| Name | Binding Site Sequence | Reverse Complement |
|---|---|---|
| BRCA1_HeLa-S3_BRCA1_Stanford_ChIP-seq | CAAATCTCGCGAGA | TCTCGCGAGATTTG |
| ATF3_known8 | CGTTGACGTCAC | GTGACGTCAACG |
| FIGLA_FIGLA_1_SELEX\|TCF4_dei_da_SANGER_5_FBgn0000413_B1H\|FIGLA_1 | AACAGGTGGT | ACCACCTGTT |
| ZIC4_ZIC1_1_SELEX\|ZIC1_3 | CACAGCGGGGGTC | GACCCCCGCTGTG |
| E2F4_E2F4_1_SELEX\|E2F_kn0wn29 | AATGGCGCCAAA | TTTGGCGCCATT |
| EVX2_Eve_Cell_FBgn0000606_B1H\|EVX2_Evx2_2645_PBM | GCTAATGA | TCATTAGC |
| ZBTB3_1 | AATCGCACTGCATTCCG | CGGAATGCAGTGCGATT |
| MLX_pTH5070_PBM | CCACGTGATC | GATCACGTGG |
| AL662830.5_Exd_Cell_FBgn0000611_B1H\|AL662830.5_Exd_SOLEXA_FBgn0000611_B1H\|AL662830.5_MA0222.1_B1H | TGTCAAAA | TTTTGACA |
| ETS_known10 | CAATACCGGAAGTGTAA | TTACACTTCCGGTATTG |
| UBP1_UBIP1_f1_HocoMoco | GCAGAGA | TCTCTGC |
| EGR3_Egr1_2580_PBM | CGCCCCCGCA | TGCGGGGGCG |
| HOXA9_1 | ACGGCCATAAAATTAAT | ATTAATTTTATGGCCGT |
| POU3F3_pTH9225_PBM | CTAATTATAC | GTATAATTAG |
| SPZ1_SPZ1_f1_HocoMoco | CCCAGGGTAACAGCCG | CGGCTGTTACCCTGGG |
| BHLHE40_pTH5060_PBM | ACACGTGCC | GGCACGTGT |
| SIX5_known6 | AATAGGGTATCAATTAT | ATAATTGATACCCTATT |
| MAF_known5 | AAGTCAGCATTTTTA | TAAAAATGCTGACTT |
| HOXC5_Hoxb8_3780_PBM\|HOXC5_Hoxa7_2668_PBM | GGCCATTAA | TTAATGGCC |
| HOXA7_2 | CGAGTTAATTAATAAGC | GCTTATTAATTAACTCG |
| ARID5A_V$MRF2_01_Transfac\|ARID56_1 | AACCACAATACCAA | TTGGTATTGTGGTT |
| TCF7L2_disc2 | ACATCAAAGG | CCTTTGATGT |
| IRF7_V$IRF7_01_Transfac\|RF_known4 | CCAACTTTCGATTCCTA | TAGGAAATCGAAAGTTGG |
| SOX30_1 | AATTCCATTGTTCAAT | ATTGAACAATGGAATT |
| PITX2_PITX1_2_SELEX\|PITX2_PITX1_1_SELEX\|PITX2_PITX3_1_SELEX\|PITX1_2\|PITX1_3\|PITX3_2 | CTTAATCCC | GGGATTAAG |
| PRDM1_disc2 | ATGACTCACC | GGTGAGTCAT |
| SMAD3_1 | AGACAGACA | TGTCTGTCT |
| ELF1_MA0026.1_SELEX | CCGGAAG | CTTCCGG |
| SOX1_Sox1_4_SELEX\|SOX1_5 | TGAATAGTCATTCA | TGAATGACTATTCA |
| FOXA_known1 | TAAATAAATATTTCA | TGAAATATTTATTTA |
| LCOR_pTH9275_PBM | ATTTTGGG | CCCAAAAT |
| DMBX1_Alx4_1_SELEX\|ALX4_4 | ATAATTAAATTAA | TTAATTTAATTAT |
| CREB3L2_Creb3l2_1_SELEX\|CREB3L2_1 | TGATGACGTGGCA | TGCCACGTCATCA |
| HOXC6_HXC8_f1_HocoMoco | GGGCATCAATCAAA | TTTGATTGATGCCC |
| BATF_disc1 | GAAATGAGTCA | TGACTCATTTC |
| DDIT3_DDIT3_f1_HocoMoco | AAATGCAATCCCC | GGGGATTGCATTT |

TABLE 5-continued

Transcription Factor Binding Sites of Synthetic Promoters

| Name | Binding Site Sequence | Reverse Complement |
| --- | --- | --- |
| CUX1_CUX2_2_SELEX\|CUX1_CUX1_3_SELEX\|CUX1_10\|CUX2_2 | TAATCGATAA | TTATCGATTA |
| ZBTB12_1 | CTAAGGTTCTAGATCAC | GTGATCTAGAACCTTAG |
| ISX_pTH6551_PBM\|ALX1_pTH6221_PBM | AATTAATTAGT | ACTAATTAATT |
| NFAT5_N FAT5_1_SELEX\|N FAT5_1 | ATGGAAAATTACAG | CTGTAATTTTCCAT |
| HNF4_known12 | CCCCCTGACCTTTGCCCTCTGCC | GGCAGAGGGCAAGGTCAGGGGG |
| TBPL2_V$TATA_C_Transfac\|TATA_known1 | CTTTTATAGA | TCTATAAAAG |
| HOXA4_Zen2_Cell_FBgn0004054_B1H | TAATTAAGA | TCTTAATTA |
| GATA_disc6 | AGCTGACT | AGTCAGCT |
| SRY_MA0084.1_SELEX\|SRY_3 | ATTGTTTAC | GTAAACAAT |
| ETV5_FEV_f1_HocoMoco | CAGGAAATAA | TTATTTCCTG |
| HOXC10_HOXD11_1_SELEX\|HOXD11_2 | GTCGTAAAAA | TTTTTACGAC |
| ZBTB7B_Zbtb7b_1054_PBM | AGCCCCCAA | TTGGGGGCT |
| ZFY_MA0146.2_ChIP-seq\|ZFX_1 | CAGGCCTCGGCCCC | GGGGCCGAGGCCTG |
| NR4A2_N R4A2_1_SELEX\|NR4A_known2 | AGGTCAAACTGTGACCT | AGGTCACAGTTTGACCT |
| GFI1B_MA0038.1_SELEX\|GFI1_3 | CAAATCACTG | CAGTGATTTG |
| ATF1_V$TAXCREB_01_Transfac\|ATF3_known4 | GGGGGTTGACGCAGA | TCTGCGTCAACCCCC |
| HOXB13_Hoxd13_2_SELEX\|HOXB13_HOXD13_2_SELEX\|HOXB13_HOXA13_2_SELEX\|HOXA13_3\|HOXD13_3\|HOXD13_5 | GCTCGTAAAAC | GTTTTACGAGC |
| HOXB13_HOXB13_2_SELEX\|HOXB13_HOXC13_2_SELEX\|HOXB13_3\|HOXC13_3 | GCTCGTAAAAA | TTTTTACGAGC |
| MYOD1_MYOD1_f1_HocoMoco | GACAGCTGC | GCAGCTGTC |
| USF1_GM12878_USF1_HudsonAlpha_ChIP-seq | CCCGCCACGTGACCC | GGGTCACGTGGCGGG |
| PKNOX2_1 | AAGCACCTGTCAATAT | ATATTGACAGGTGCTT |
| ENSG00000234254_TGIF1_f1_HocoMoco | CAGGTGACACCTGACA | TGTCAGGTGTCACCTG |
| EGR3_EGR1_f2_HocoMoco | CCGCCCCCGCA | TGCGGGGGCGG |
| IKZF1_IKZF1_f1_HocoMoco | TCTCCCAA | TTGGGAGA |
| MYBL1_V$MYB_Q6_Transfac | GCCAGTTGAC | GTCAACTGGC |
| TBX3_pTH9289_PBM\|TBX3_pTH3998_PBM | AAGGTGTCAA | TTGACACCTT |
| PAX5_MA0239.1_B1H\|OVOL1_MA0126.1_SELEX | ACTGTTACT | AGTAACAGT |
| SPZ1_V$SPZ1_01_Transfac\|SPZ1_1 | GCAGGAGGGTATGGC | GCCATACCCTCCTGC |
| PPARA_V$PPARG_01_Transfac | CGGATGACCTTTGACCCCTGA | TCAGGGGTCAAAGGTCATCCG |
| ZNF263_K562b_ZNF263_UCD_ChIP-seq | CTCCTCCCCTCCCTCCTCCC | GGGGAGGAGGGAGGGGAGGAG |
| KIAA0415_Fkh2_PBM\|FOXD1_pTH2846_PBM\|FOXJ3_Fkh1_PBM\|FOXD1_pTH6641_PBM\|FOXD1_pTH6108_PBM | ATGTAAACAA | TTGTTTACAT |
| RFX8_pTH9199_PBM\|RFX8_pTH9385_PBM\|RFX8_Rfx4_3761_PBM\|MYC_disc4 | CCATGGCAAC | GTTGCCATGG |
| OTX2_1 | GACAATTAATCCCTACA | TGTAGGGATTAATTGTC |

TABLE 5-continued

Transcription Factor Binding Sites of Synthetic Promoters

| Name | Binding Site Sequence | Reverse Complement |
|---|---|---|
| MAFK_MAFK_1_SELEX\|MAF_known6 | AAATTTGCTGAC | GTCAGCAAATTT |
| MYC_known6 | GCCACGTGAC | GTCACGTGGC |
| ELF5_1 | AAGGAAGTA | TACTTCCTT |
| SCRT2_CG12605_SANGER_10_FBgn0035481_B1H | CAACAGGTG | CACCTGTTG |
| BCL_disc7 | ACAGCTCCC | GGGAGCTGT |
| HMGA1_2 | AATGCAATTTTTGA | TCAAAAATTGCATT |
| BRCA1_GM12878_BRCA1_Stanford_ChIP-seq | AAATCTCGCGAGAAC | GTTCTCGCGAGATTT |
| TCF3_4 | CCACCTGCCGCAGG | CCTGCGGCAGGTGG |
| RARG_RARG_4_SELEX\|RARG_4 | GAGGTCAAAAGGTCAC | GTGACCTTTTGACCTC |
| NR2F2_NR2F1_2_SELEX\|HNF4_known24 | GAGGTCAAAAGGTCAA | TTGACCTTTTGACCTC |
| IRX3_Ara_SOLEXA_FBgn0015904_B1H\|IRX3_Mirr_SOLEXA_FBgn0014343_B1H\|IRX3_Caup_SOLEXA_FBgn0015919_B1H | ATAACA | TGTTAT |
| ARNT2_ARNT_f1_HocoMoco\|BHLHE40_pTH4330_PBM\|ID4_pTH5068_PBM | GCACGTGA | TCACGTGC |
| SIN3A_disc4 | ACAGCTCCT | AGGAGCTGT |
| ETS_disc9 | CGCCGCCCCGC | GCGGGGCGGCG |
| SOX1_SOX2_4_SELEX\|SOX2_5 | GAACAATAACATTGTTC | GAACAATGTTATTGTTC |
| E2F2_E2F2_f1_HocoMoco\|E2F_known21 | GGCGCGAAAC | GTTTCGCGCC |
| CUX1_V$CDPCR3HD_01_Transfac\|CUX1_5 | GATCGATCCC | GGGATCGATC |
| HOXC10_HOXA10_1_SELEX\|HOXA10_2 | ATTTTTACGACC | GGTCGTAAAAAT |
| DUX4_1 | CACCGTTGATTGGGTCG | CGACCCAATCAACGGTG |
| NR1H_2 | GGGTTACTGGCGGTCA | TGACCGCCAGTAACCC |
| SPDEF_Spdef_0905_PBM | ACATCCGGGT | ACCCGGATGT |
| ATF3_known16 | ACGATGACGTCATCGA | TCGATGACGTCATCGT |
| POU1F1_pTH4326_PBM | ATTATTAATA | TATTAATAAT |
| SIX2_pTH5690_PBM | AGGGTATCA | TGATACCCT |
| SP9_pTH0978_PBM | CCCGCCCCC | GGGGGCGGG |
| NKX2-6_tin_FlyReg_FBgn0004110_B1H | GGCCACTTGAGA | TCTCAAGTGGCC |
| E2F_disc8 | GCAGGCGCCGC | GCGGCGCCTGC |
| TCF4_MA0522.1_ChIP-seq | CACAGCTGCAG | CTGCAGCTGTG |
| HOXB6_1 | AAGGTAATTACCAATA | TATTGGTAATTACCTT |
| GATA_HUVEC_GATA2_UCD_ChIP-seq\|GATA2_MA0035.3_ChIP-seq\|GATA_known15 | ACAGATAAGAA | TTCTTATCTGT |
| FOSL2_MA0478.1_ChIP-seq\|JUN_MA0490.1_ChIP-seq | ATGAGTCATCC | GGATGACTCAT |
| DMBX1_1 | TGAACCGGATTAATGAA | TTCATTAATCCGGTTCA |
| MEOX2_MEOX2_1_SELEX\|HOXC5_Hoxd3_1_SELEX\|HOXB2_HOXB2_1_SELEX\|HOXB2_1\|HOXD3_2\|MEOX2_1 | AGTAATTAAC | GTTAATTACT |

TABLE 5-continued

Transcription Factor Binding Sites of Synthetic Promoters

| Name | Binding Site Sequence | Reverse Complement |
|---|---|---|
| TP53_Tp53_3_SELEX\|TP53_7 | AACATGCCCGGGCATGTC | GACATGCCCGGGCATGTT |
| HEY1_HEY2_2_SELEX\|HEY1_HEY2_1_SELEX\|HEY1_HEY1_1_SELEX\|NPAS2_pTH5457_PBM\|HEY1_known1\|HEY2_1\|HEY2_2 | GACACGTGCC | GGCACGTGTC |
| RFX8_pTH9223_PBM\|RFX8_pTH9226_PBM | CCTTAGCAAC | GTTGCTAAGG |
| ETV5_MA0028.1_SELEX\|ETS_known7 | CTTCCGGCTC | GAGCCGGAAG |
| GCM1_pTH8653_PBM | ATGCGGGTAC | GTACCCGCAT |
| ZNF263_MA0528.1_ChIP-seq | GGAGGAGGAGGGGAGGAGGA | TCCTCCTCCCCCTCCTCC |
| BX088580.2_GSE11329_bioOct4_ChIP-seq | TTTGCATAACAAAA | TTTTGTTATGCAAA |
| SRF_HepG2_SRF_HudsonAlpha_ChIP-seq | CATGCCCATATAAGGCAA | TTGCCTTATATGGGCATG |
| TGIF1_Achi_Cell_FBgn0033749_B1H | TGTCAAA | TTTGACA |
| BX088580.2_MA0142.1_ChIP-seq\|POU5F1_known3 | ATTTGCATAACAAAG | CTTTGTTATGCAAAT |
| SRF_known7 | CCATATATGGGC | GCCCATATATGG |
| TATA_disc7 | GAAGGAAGCGGAAGA | TCTTCCGCTTCCTTC |
| MSX1_MA0188.1_B1H | CCAATTA | TAATTGG |
| NR2C2_pTH6174_PBM\|RARG_pTH5430_PBM | AGGTCACG | CGTGACCT |
| OTP_OTX2_si_HocoMoco | CTTTAATCCCTTAAC | GTTAAGGGATTAAAG |
| TBX1_pTH3822_PBM | AGGTGTGAAGA | TCTTCACACCT |
| HDAC2_disc3 | GGTGCTGTCCGTGGTGCTGA | TCAGCACCACGGACAGCACC |
| SREBF2_SRBP2_f1_HocoMoco | CCTCACCCCACCC | GGGTGGGGTGAGG |
| SREBP_known4 | GCGATCACCCCA | TGGGGTGATCGC |
| ONECUT3_pTH8982_PBM | AATCGATAA | TTATCGATT |
| ZBTB42_ZNF238_2_SELEX\|ZBTB18_3 | CATCCAGATGTTC | GAACATCTGGATG |
| E2F4_E2F5_do_HocoMoco | CGCGCCAAAC | GTTTGGCGCG |
| TOPORS_V$LUN1_01_Transfac\|TOPORS_1 | TCCCAAAGTAGCTGGGA | TCCCAGCTACTTTGGGA |
| FOXJ3_pTH5634_PBM | GTAAACAAC | GTTGTTTAC |
| FOXD1_pTH6497_PBM\|FOXD1_pTH3043_PBM\|FOXD1_pTH6591_PBM | GTAAACAAA | TTTGTTTAC |
| RFX8_RFX3_2_SELEX\|RFX3_3 | CGTTGCTAGGCAACC | GGTTGCCTAGCAACG |
| NKX1-1_Nkx1-2_3214_PBM\|ALX1_Rax_3443_PBM | CCAATTAGC | GCTAATTGG |
| HOXC5_V$HOXA3_01_Transfac\|HOXA3_1 | CCAATTAGG | CCTAATTGG |
| NR2E1_pTH5714_PBM | AAATTGACCTCA | TGAGGTCAATTT |
| FOSL1_MA0477.1_ChIP-seq | CATGAGTCACC | GGTGACTCATG |
| LBX2_MA0231.1_B1H | TAACTA | TAGTTA |
| AHR_V$AHR_01_Transfac | CCCCGGGCTTGCGTGAGA | TCTCACGCAAGCCCGGGG |
| GMEB2_GMEB2_4_SELEX\|ATF7_V$CREBP1_01_Transfac\|ZHX1_pTH5688_PBM\|ATF2_1\|GMEB2_4 | TTACGTAA | TTACGTAA |

TABLE 5-continued

Transcription Factor Binding Sites of Synthetic Promoters

| Name | Binding Site Sequence | Reverse Complement |
|---|---|---|
| ZNF274_HepG2b_ZNF274_UCD_ChIP-seq | GGTTTCTCTCCAGTA | TACTGGAGAGAAACC |
| NFATC1_NFAC2_f1_HocoMoco | AATTTTCCA | TGGAAAATT |
| TCF4_TFE2_f2_HocoMoco | ACCAGATGGTC | GACCATCTGGT |
| ETV6_ETV6_1_SELEX\|ETV6_1 | CACTTCCGCTTCCGG | CCGGAAGCGGAAGTG |
| HOXC5_Hoxb7_3953_PBM\|HOXC5_Hoxd8_2644_PBM | GCCATTAA | TTAATGGC |
| AR_A549_GR_HudsonAlpha_ChIP-seq | GAACAGAATGTTCC | GGAACATTCTGTTC |
| EBF1_disc1 | TCCCCGGGGA | TCCCCGGGGA |
| SMAD4_SMAD4_si_HocoMoco | GGCCAGACA | TGTCTGGCC |
| ARNT2_pTH5064_PBM\|BHLHE40_HepG2_BHLHE40_HudsonAlpha_ChIP-seq | GCACGTGACC | GGTCACGTGC |
| EGR3_pTH9317_PBM\|EGR3_Zif268_PBM | CGCCCACG | CGTGGGCG |
| RFX8_V$RFX1_01_Transfac\|RFX5_known 1 | TAGTAGCCTGGCAACAA | TTGTTGCCAGGCTACTA |
| GATA2_Mv75_ChIP-seq | AGATATTATC | GATAATATCT |
| VDR_4 | GGGTCAACGAGTTCA | TGAACTCGTTGACCC |
| NR4A2_pTH3467_PBM\|NR2F2_Mv102_ChIP-seq | AAAGGTCA | TGACCTTT |
| XBP1_pTH2852_PBM | ACACGTCATC | GATGACGTGT |
| SOX2_SOX21_4_SELEX\|SRY_SRY_4_SELEX\|SOX21_5\|SRY_8 | TGAATAACATTCA | TGAATGTTATTCA |
| FOXD1_GSE15244_FoxA1_ChIP-seq | AAAGCAAACA | TGTTTGCTTT |
| HOXC5_Ftz_Cell_FBgn0001077_B1H | GTTAATGA | TCATTAAC |
| GATA2_GATA5_f1_HocoMoco | ATCTAAGTTATCTCTTA | TAAGAGATAACTTAGAT |
| E4F1_1 | GCTACGTCAC | GTGACGTAGC |
| POU3F3_MA0453.1_B1H | CTAATTTGCATA | TATGCAAATTAG |
| YY2_V$YY1_01_Transfac | GATCTCCATTTTTGGAC | GTCCAAAAATGGAGATC |
| NR3C1_disc5\|FOXA_disc3 | CCTGCTGA | TCAGCAGG |
| PAX9_V$PAX5_02_Transfac\|PAX5_known2 | AAACAGATACCTGAAGCGTGACCATACA | TGTATGGTCACGCTTCAGGTATCTGTTT |
| ZEB1_V$AREB6_01_Transfac\|ZEB1_known1 | ACACAGGTAAGTA | TACTTACCTGTGT |
| FOX06_V$FOXO4_01_Transfac\|FOXO4_1 | ATAAACAAGCC | GGCTTGTTTAT |
| SOX9_SOX10_4_SELEX\|SOX9_Sox10_3_SELEX\|SOX10_6\|SOX10_10 | ATGAATTGCAGTCAT | ATGACTGCAATTCAT |
| ZNF683_HeLa-53_PRDM1_Stanford_ChIP-seq\|PRDM_PRDM1_1_SELEX\|PRDM1_MA0508.1_ChIP-seq\|PRDM1_known2 | AGAAAGTGAAAGTGA | TCACTTTCACTTTCT |
| MEOX2_MEOX2_3_SELEX\|MEOX2_3 | CTAATCATCATTAA | TTAATGATGATTAG |
| MYB_5 | CAACGGCC | GGCCGTTG |
| CTCF_disc4 | CACTAGATGGCAGC | GCTGCCATCTAGTG |
| THRB_THRB_1_SELEX\|THRB_1 | GTGACCTTATAAGGTCAC | GTGACCTTATAAGGTCAC |
| NFYA_MA0060.2_ChIP-seq | AGAGTGCTGATTGGTCCA | TGGACCAATCAGCACTCT |
| PAX9_PAX5_f1_HocoMoco | GAGGGCAGTGAAGCGTGAC | GTCACGCTTCACTGCCCTC |

TABLE 5-continued

Transcription Factor Binding Sites of Synthetic Promoters

| Name | Binding Site Sequence | Reverse Complement |
| --- | --- | --- |
| TCF7L2_known6 | ATTTCCTTTGATCTATA | TATAGATCAAAGGAAAT |
| NFE2L2_1 | ACCGGAAGAG | CTCTTCCGGT |
| TCF4_V$E47_02_Transfac | ATTAACAGGTGTTCAC | GTGAACACCTGTTAAT |
| VDR_VDR_1_SELEX\|VDR_5 | GAGTTCATTGAGTTCA | TGAACTCAATGAACTC |
| MYBL2_MYBL2_4_SELEX\|MYBL2_4 | AACCGTTAAACGGTC | GACCGTTTAACGGTT |
| MEF2_disc3\|AP1_known5 | ATGAGTCAG | CTGACTCAT |
| MYBL1_1 | AAATTAACGGTTTTCAA | TTGAAAACCGTTAATTT |
| RORB_pTH6589_PBM | ACTGACCTCG | CGAGGTCAGT |
| POU3F3_POU2F1_2_SELEX\|POU2F2_known16 | CATGAATATTCATA | TATGAATATTCATG |
| FOXD1_FOXL1_2_SELEX\|FOXL1_5 | TGTAAATAAACAA | TTGTTTATTTACA |
| HDAC2_disc5 | AAAGTCCAG | CTGGACTTT |
| ZNF143_known1 | GATTTCCCATAATGCCTTGC | GCAAGGCATTATGGGAAATC |
| HSF1_V$HSF1_01_Transfac\|HSF2_V$HSF2_01_Transfac\|HSF_known1 | AGAATGTTCG | CGAACATTCT |
| LM02_V$LMO2COM_02_Transfac\|LMO2_2 | CAGATAGGG | CCCTATCTG |
| RREB1_MA0073.1_SELEX | CCCCAAACCACCCCCCCCC | GGGGGGGGGGTGGTTTGGGG |
| RREB1_2 | CCCCAAACCACCCCCCCCA | TGGGGGGGGGTGGTTTGGGG |
| EGR3_pTH3091_PBM | CGCCCACGCA | TGCGTGGGCG |
| SOX9_SOX10_2_SELEX\|SOX10_4 | AACAATGTTCAGTGTT | AACACTGAACATTGTT |
| FOXD1_V$HFH8_01_Transfac\|FOXF1_1 | CATATAAACAATG | CATTGTTTATATG |
| HMGA2_pTH8216_PBM | CCGGAAAAA | TTTTTCCGG |
| FOXO6_FOXO3_si_HocoMoco | AGGTAAACAAACA | TGTTTGTTTACCT |
| NKX1-2_1 | GTGCACTAATTAGTGCA | TGCACTAATTAGTGCAC |
| SMAD_2 | CTGTCTGGCTA | TAGCCAGACAG |
| TCF7L2_Tcf7_0950_PBM | AACATCAAA | TTTGATGTT |
| FOXA_known4 | GACTAAGCAAACAATGAA | TTCATTGTTTGCTTAGTC |
| MYOD1_nau_SANGER_5_FBgn0002922_B1H | AACAGCTGACGC | GCGTCAGCTGTT |
| IRX3_IRX5_1_SELEX\|IRX3_IRX2_1_SELEX\|IRX2_2\|IRX5_2 | CATGTCATGTAA | TTACATGACATG |
| TCF3_1 | ACGGCAGGTGTCCCC | GGGGACACCTGCCGT |
| YY1_disc2 | AAACATGGCG | CGCCATGTTT |
| NFATC1_NFAC1_do_HocoMoco | ATGGAAATTCCA | TGGAAATTCCAT |
| ARNT_MA0004.1_SELEX\|MYC_known10\|ARNT_3 | CACGTG | CACGTG |
| MAFB_Mafb_1_SELEX\|MAF_disc2\|MAF_known10 | AAAATGCTGACT | AGTCAGCATTTT |
| TBPL2_Tbp_pr781_PBM | ATATAAA | TTTATAT |
| E2F_known23 | ATAAGGGCGCGCGAT | ATCGCGCGCCCTTAT |
| GATA2_pTH1049_PBM | CAGATAAGG | CCTTATCTG |
| BBX_Bbx_3753_PBM | TCAATGAA | TTCATTGA |

TABLE 5-continued

Transcription Factor Binding Sites of Synthetic Promoters

| Name | Binding Site Sequence | Reverse Complement |
|---|---|---|
| SRF_SRF_do_HocoMoco | ATGCCCATATATGGA | TCCATATATGGGCAT |
| PAX8_1 | ACAGTCATGCGTGAGTTA | TAACTCACGCATGACTGT |
| CACD_1 | CAACCCCTGGGTGTGG | CCACACCCAGGGGTTG |
| ELF3_1 | TACAAGGAAGTAA | TTACTTCCTTGTA |
| LHX1_1 | CATTATTAATTAATTCG | CGAATTAATTAATAATG |
| SRF_SRF_2_SELEX\|SRF_known10 | TGACCATATATGGTCA | TGACCATATATGGTCA |
| MEF2B_V$MEF2_01_Transfac\|MEF2_known1 | AGAGTTATTTTTAGAG | CTCTAAAAATAACTCT |
| ZNF143_V$STAF_01_Transfac | GGCGCAATGCATTGTGGTAAA | TTTACCCACAATGCATTGCGCC |
| TRIM28_disc2 | AGAGAAACC | GGTTTCTCT |
| PITX2_Ptx1_SOLEXA_FBgn0020912_B1H | GGATTAAC | GTTAATCC |
| ZNF202_pTH3075_PBM | AAGGGGGGCA | TGCCCCCCTT |
| RHOXF1_2 | AGGACGCTGTAAAGGGA | TCCCTTTACAGCGTCCT |
| TFAP2A_V$AP2ALPHA_01_Transfac\|TFAP2A_V$AP2GAMMA_01_Transfac\|TFAP2_known2\|TFAP2_known3\|TFAP2_known8 | CCCCCGGGC | GCCCGGGGG |
| NKX2-5_MA0264.1_PBM | ACCACTTGAAA | TTTCAAGTGGT |
| EGR3_H1-hESC_EGR1_HudsonAlpha_ChIP-seq | CCCCGCCCCGCACC | GGTGCGGGGCGGGG |
| BARHL2_BARHL2_1_SELEX\|BARHL2_2 | ACCGTTTAAC | GTTAAACGGT |
| FOXP3_1 | GAAATGTTGTTTCAGAC | GTCTGAAACAACATTTC |
| NFKB2_N_FKB2_f1_HocoMoco | AGGGAGATTCC | GGAATCTCCCT |
| ELF1_HepG2_ELF1_HudsonAlpha_ChIP-seq | CCACTTCCGGGTTC | GAACCCGGAAGTGG |
| HMX1_Hmx2_3424_PBM\|TLX3_pTH6482_PBM | AACCAATTAA | TTAATTGGTT |
| HOXA7_3 | GTAGTAATTAATGGAA | TTCCATTAATTACTAC |
| ZNF784_ZNF784_1_SELEX\|ZNF784_1 | AGGTAGGTAC | GTACCTACCT |
| TCF4_TCF3_1_SELEX\|TCF3_7 | AACACCTGCT | AGCAGGTGTT |
| SP9_MA0516.1_ChIP-seq\|SP1_disc3 | GCCCCGCCCCTCCC | GGGAGGGGCGGGGC |
| HES4_pTH5259_PBM | GCACGTGTCGTTA | TAACGACACGTGC |
| NR2F2_pTH2193_PBM | AAAGGTCAAG | CTTGACCTTT |
| ZNF219_ZN219_f1_HocoMoco | GAGGGGGGCGGA | TCCGCCCCCTC |
| FOXO6_FOXO4_3_SELEX\|FOXO6_FOXO1_3_SELEX\|FOXO1_5\|FOXO4_5 | CGTGTGGGAAA | TTTCCCCACACG |
| CR936877.3_RXRB_1_SELEX\|CR936877.3_RXRA_3_SELEX\|CR936877.3_RXRG_3_SELEX\|CR936877.3_RXRA_1_SELEX\|CR936877.3_RXRG_1_SELEX\|CR936877.3_Rxrb_1_SELEX\|CR936877.3_Rxra_1_SELEX\|HNF4G_HNF4A_4_SELEX\|HNF4_known19\|RXRA_known10\|RXRA_known12\|RXRB_1\|RXRG_1\|RXRG_3\|RXRA_known14\|RXRB_2 | GGGGTCAAGGTCA | TGACCTTTGACCCC |
| FOXP4_MA0481.1_ChIP-seq | CAAAAGTAAACAAAG | CTTTGTTTACTTTTG |
| THAP1_MA0597.1_ChIP-seq | CTGCCCGCA | TGCGGGCAG |
| TFAP2_known5 | CCGCCCCAGGCC | GGCCTGGGGCGG |

TABLE 5-continued

Transcription Factor Binding Sites of Synthetic Promoters

| Name | Binding Site Sequence | Reverse Complement |
|---|---|---|
| EP300_disc2 | AAAGATGATGCAATA | TATTGCATCATCTTT |
| MYC_disc6 | AAGTCACGT | ACGTGACTT |
| TATA_disc5\|NRF1_disc2 | AAGCGGAA | TTCCGCTT |
| FOXO6_FOXO4_f1_HocoMoco | AATAAACAA | TTGTTTATT |
| POU6F2_POU6F2_2_SELEX\|POU6F2_2 | TTAATGAGCTAATTAA | TTAATTAGCTCATTAA |
| NKX6-3_Hgtx_Cell_FBgn0040318_B1H\|POU3F3_MA0197.1_B1H\|TLX3_C15_SOLEXA_FBgn0004863_B1H\|SHOX_Otp_Cell_FBgn0015524_B1H\|NKX1-1_Slou_Cell_FBgn0002941_B1H\|HOXC5_MA0094.2_B1H\|LMX1A_CG4328_SOLEXA_FBgn0036274_B1H\|RAX2_Repo_Cell_FBgn0011701_B1H\|LMX1A_CG32105_SOLEXA_FBgn0052105_B1H\|HOXC5_Ubx_Cell_FBgn0003944_B1H\|NKX6-3_Hgtx_SOLEXA_FBgn0040318_B1H | TAATTAAA | TTTAATTA |
| TAL1_known4 | AGCAGCTGGA | TCCAGCTGCT |
| NR3C1_known11 | CTGTTCTTTC | GAAAGAACAG |
| AR_Ar_1_SELEX\|NR3C1_known17 | CGGTACACCGTGTACCC | GGGTACACGGTGTACCG |
| MNX1_Hlxb9_3422_PBM | AAGCAATTAG | CTAATTGCTT |
| MITF_HLH30_PBM | TCACGTGA | TCACGTGA |
| NR2F2_NR2F6_1_SELEX\|NR2F2_Nr2f6_1_SELEX\|NR2F6_1\|NR2F6_4 | GAGGTCAAAAGGTCA | TGACCTTTTGACCTC |
| STAT_disc7 | CTCTCCCTTTCCC | GGGAAAGGGAGAG |
| NKX2-3_2\|NKX2-3_3 | ACCACTTGAA | TTCAAGTGGT |
| NR2F2_NR2F1_1_SELEX\|HNF4_known23 | GAGGTCAAAGGTCAA | TTGACCTTTGACCTC |
| SIX5_Mv121_ChIP-seq\|SMARC_disc2 | ACTACAACTC | GAGTTGTAGT |
| ARID3C_Arid3a_3875_PBM | CAATTAAAA | TTTTAATTG |
| HNF4_known15 | CTTCAGGGGTCAATTGA | TCAATTGACCCCTGAAG |
| NKX2-5_Vnd_Cell_FBgn0003986_B1H\|NKX2-5_MA0253.1_B1H | CACTTGAAA | TTTCAAGTG |
| ZIC4_pTH2818_PBM | CCGGGGGTC | GACCCCCGG |
| EVX1_1 | AGAACTAATTAGTGGAC | GTCCACTAATTAGTTCT |
| NKX2-5_Mw138_ChIP-seq | AATCGATA | TATCGATT |
| SOX9_SOX9_4_SELEX\|SOX9_6 | ATGAATGTGCAGTCAT | ATGACTGCACATTCAT |
| VDR_VDR_f2_HocoMoco | GGGTCAACGAGTTCAC | GTGAACTCGTTGACCC |
| FOSL1_FOSL1_f2_HocoMoco | AACGTGACTCAGCA | TGCTGAGTCACGTT |
| ZSCAN4_1 | ACGTATGTGCACATCTG | CAGATGTGCACATACGT |
| GFI1B_MA0483.1_ChIP-seq | AAATCACAGCA | TGCTGTGATTT |
| SOX12_Sox12_3957_PBM | AAGAACAATG | CATTGTTCTT |
| ZBTB14_1 | AAGCGCGCCCCG | CGGGGCGCGCTT |
| PRDM_16_V$EVI1_02_Transfac\|RUNX1_3 | AGACAAGATAA | TTATCTTGTCT |
| NFATC1_NFATC1_3_SELEX\|NFATC1_3 | TTTTCCATGGAAAA | TTTTCCATGGAAAA |
| FOXD1_FOXJ3_3_SELEX\|FOXD1_Foxj3_4_SELEX\|FOXD1_FOXJ2_3_SELEX\|FOXJ2_5\|FOXJ3_4\|FOXJ3_8 | GTAAACATAAACA | TGTTTATGTTTAC |

TABLE 5-continued

Transcription Factor Binding Sites of Synthetic Promoters

| Name | Binding Site Sequence | Reverse Complement |
|---|---|---|
| ZNF410_Zfp410_3034_PBM | CCATCCCA | TGGGATGG |
| SPIC_Sfpi1_PBM | AAGGGGAAGT | ACTTCCCCTT |
| DBX1_1 | TAATTAATTAATAATTA | TAATTATTAATTAATTA |
| USF1_MA0093.2_ChIP-seq\|USF1_HepG2_USF1_HudsonAlpha_ChIP-seq | GCCACGTGACC | GGTCACGTGGC |
| NKX3-1_MA0124.1_SELEX\|NKX3-1_2 | ATACTTA | TAAGTAT |
| NR2C2_Mv98_ChIP-seq | TCAGAGGTCA | TGACCTCTGA |
| IRX3_Caup_Cell_FBgn0015919_B1H | CAATAACA | TGTTATTG |
| LIN54_pTH9366_PBM | AATTTAAATT | AATTTAAATT |
| NR2E1::NFIC_1 | TGGCACCATGCCAA | TTGGCATGGTGCCA |
| FOXD1_MA0031.1_SELEX\|FOXD1_2 | ATGTTTAC | GTAAACAT |
| PRRX1_1 | AGTAGTTAATTAGTTAC | GTAACTAATTAACTACT |
| FOXO6_V$FOXO3_01_Transfac\|FOXO3_1 | TATGTAAACAACAA | TTGTTGTTTACATA |
| TP73_GSE18650_TP73_ChIP-seq | CATGTCGGGACATGC | GCATGTCCCGACATG |
| HNF1A_V$HNF1_C_Transfac\|HNF1_2 | AGTTAATTATTAACCAA | TTGGTTAATAATTAACT |
| SOX9_Sox10_2_SELEX\|SOX9_SOX10_3_SELEX\|SOX10_5\|SOX10_9 | ATCAATTGCAGTGAT | ATCACTGCAATTGAT |
| FOXD1_HepG2_FOXA1_HudsonAlpha_ChIP-seq | CTAAGTAAACA | TGTTTACTTAG |
| HOXC5_HX68_do_HocoMoco | GCATTAATCAA | TTGATTAATGC |
| POU4F1_PO4F2_si_HocoMoco | CAGCTCATTAATA | TATTAATGAGCTG |
| ATF3_disc3 | AACCCGGCC | GGCCGGGTT |
| LHX3_3 | ATTATTTAATTAATTAC | GTAATTAATTAAATAAT |
| ZNF274_HeLa-53_ZNF274_UCD_ChIP-seq | TTCATACTGGAGAGAAA | TTTCTCTCCAGTATGAA |
| SMAD1_MA0535.1_ChIP-chip | CAGGCGCCGCCGCCG | CGGCGGCGGCGCCTG |
| CEBPA_V$CEBP_C12_Transfac\|CEBPB_known4 | ACATTGCATAATTA | TAATTATGCAATGT |
| SOX17_GSE19026_Sox17_XENcells_ChIP-seq | AAACAATGGAA | TTCCATTGTTT |
| NFYB_MA0502.1_ChIP-seq | AAATGGACCAATCAG | CTGATTGGTCCATTT |
| NKX6-1_2 | CGAAGTAATTAATTTC | GAAATTAATTACTTCG |
| SMAD2_Smad3_3805_PBM | ATTCCAGACA | TGTCTGGAAT |
| GCM1_pTH9283_PBM | ACCCGCATGA | TCATGCGGGT |
| CEBPB_known6 | AAATTTGGCAAA | TTTGCCAAATTT |
| CEBPA_2 | ATTGCGAAA | TTTCGCAAT |
| FOX_1 | GATTGTTTATTTA | TAAATAAACAATC |
| SRF_Mcm1_PBM | CGAATAGGGA | TCCCTATTCG |
| T_byn_FlyReg_FBgn0011723_B1H | AAGTGCGA | TCGCACTT |
| CTCF_disc10 | ACCTGCAGG | CCTGCAGGT |
| TFAP2_known6 | ACCGCCTGAGGGGAT | ATCCCCTCAGGCGGT |
| HOXC11_1 | CTATTTTACGACTTTA | TAAAGTCGTAAAATAG |
| ZNF524_ZNF524_1_SELEX\|ZNF524_1 | ACCCTCGAACCC | GGGTTCGAGGGT |

TABLE 5-continued

Transcription Factor Binding Sites of Synthetic Promoters

| Name | Binding Site Sequence | Reverse Complement |
| --- | --- | --- |
| NKX2-5_pTH2842_PBM | AAGCACTTAA | TTAAGTGCTT |
| BCL_disc1 | CACTTCCGGC | GCCGGAAGTG |
| LHX8_Lhx8_3_SELEX\|LHX8_4 | TAATTGCAATCA | TGATTGCAATTA |
| PAX2_PAX2_1_SELEX\|PAX2_4 | CGTCACGCTTGACTGCTC | GAGCAGTCAAGCGTGACG |
| LHX9_ap_FlyReg_FBgn0000099_B1H | TAATAA | TTATTA |
| KLF4_Klf12_1_SELEX\|KLF12_2 | AATAAGGGCGTGGTC | GACCACGCCCTTATT |
| LHX8_LHX6_2_SELEX\|LHX6_4 | TAATTAGCGCTAATTA | TAATTAGCGCTAATTA |
| MYC_disc10 | CCCCCCGCCTC | GAGGCGGGGGG |
| RORB_RORA_2_SELEX\|RORA_7 | TAACTAGGTTAGTAGGTCA | TGACCTACTAACCTAGTTA |
| HDX_1 | AAGGCGAAATCATCGCA | TGCGATGATTTCGCCTT |
| TCF7L2_LEF1_f1_HocoMoco | ATCAAAG | CTTTGAT |
| HOXC9_Abd-B_FlyReg_FBgn0000015_B1H | TCATAAAA | TTTTATGA |
| PKNOX2_Hth_Cell_FBgn0001235_B1H\|TGIF1_Vis_Cell_FBgn0033748_B1H | TGACA | TGTCA |
| BX088580.2_POU3F4_1_SELEX\|POU3F4_POU2F3_1_SELEX\|BX088580.2_POU5F1P1_1_SELEX\|POU3F3_PO2F1_f1_HocoMoco\|POU2F2_P02F2_si_HocoMoco\|POU2F3_2\|POU3F4_2\|POU5F1_known4\|POU2F2_5 | ATTTGCATA | TATGCAAAT |
| VDR_Vdr_1_SELEX\|VDR_6 | GAGTTCATCGGGTTCA | TGAACCCGATGAACTC |
| TFAP2A_Tcfap2e_3713_PBM | CCTCAGGCGA | TCGCCTGAGG |
| CEBPG_CEBPG_si_HocoMoco | ATTTTGCAATCTG | CAGATTGCAAAAT |
| MYC_MCF-7_CMYC_UT-A_ChIP-seq | ACCACGTG | CACGTGGT |
| JUN_pTH5462_PBM\|AP1_known8 | ATGACTCAA | TTGAGTCAT |
| ZNF354C_MA0130.1_SELEX\|ZNF354C_1 | ATCCAC | GTGGAT |
| HOXC5_I$FTZ_01_Transfac | AAAGCAATTAAG | CTTAATTGCTTT |
| SHOX_Phox2b_3948_PBM\|LHX9_Ap_Cell_FBgn0000099_B1H\|LBX2_Lbl_Cell_FBgn0008651_B1H\|SHOX_Otp_3496_PBM\|ALX1_Prrx1_3442_PBM\|SHOX_Phox2a_3947_PBM\|GBX2_Gbx1_2883_PBM\|ALX1_Rx_Cell_FBgn0020617_B1H\|EN2_En2_0952_PBM\|HOXD1_Hoxd1_3448_PBM | GCTAATTA | TAATTAGC |
| JUN_pTH8562_PBM\|ATF3_JDP2_3_SELEX\|JUN_JUN_f1_HocoMoco\|ATF3_Jdp2_1_SELEX\|ATF3_Jdp2_1_SELEX\|JDP2_2\|JDP2_4\|JDP2_6 | ATGACTCAT | ATGAGTCAT |
| GCM_1 | AATGCGGGTGTG | CACACCCGCATT |
| FOXD1_V$FOXJ2_01_Transfac\|FOXJ2_1 | TTATAAATAAACATTCAA | TTGAATGTTTATTTATAA |
| SPIC_Spic_PBM | AAGCGGAAG | CTTCCGCTT |
| TBPL2_TBP_f1_HocoMoco | GAATTTATACC | GGTATAAATTC |
| FIGLA_pTH5105_PBM | ACCACCTGG | CCAGGTGGT |
| ZSCAN4_2 | TACATGTGCACATAAAA | TTTTATGTGCACATGTA |
| ZNF143_MA0088.1_COMPILED | GATTTCCCATCATGCCTTGC | GCAAGGCATGATGGGAAATC |
| ZNF333_ZN333_f1_HocoMoco | CGATAATGA | TCATTATCG |

TABLE 5-continued

Transcription Factor Binding Sites of Synthetic Promoters

| Name | Binding Site Sequence | Reverse Complement |
|---|---|---|
| SHOX_V$S8_01_Transfac | AGGTTAATTGAGTAAA | TTTACTCAATTAACCT |
| KLF4_pTH9072_PBM | CCACGCCCA | TGGGCGTGG |
| ZFY_pTH2933_PBM | TAGGCCACA | TGTGGCCTA |
| RHOXF1_RHOXF1_3_SELEX\|RHOXF1_RHOXF1_1_SELEX\|RHOXF1_3\|RHOXF1_5 | GGATAATCC | GGATTATCC |
| DPRX_DPRX_2_SELEX\|DPRX_2 | GGGATAATCCC | GGGATTATCCC |
| ENSG00000250542_pTH5459_PBM | AAACGTAG | CTACGTTT |
| SOX13_pTH3862_PBM | ATTGTTTTG | CAAAACAAT |
| SOX15_Sox15_3457_PBM | ATTGTTTTA | TAAAACAAT |
| THAP1_K562_THAP1_HudsonAlpha_ChIP-seq | CGCCATCTTGGATGAGGGCAG | CTGCCCTCATCCAAGATGGCG |
| HSF1_HSF1_f2_HocoMoco | AGAAAGTTCTAGAA | TTCTAGAACTTTCT |
| LHX9_LHX2_f1_HocoMoco | CACTTTTAATTAG | CTAATTAAAAGTG |
| MEF2B_MA0497.1_ChIP-seq | ATGCTAAAATAGAA | TTCTATTTTAGCAT |
| ATF3_known13 | CGATGACGTCA | TGACGTCATCG |
| ELF3_Elf5_1_SELEX\|ELF3_ELF5_1_SELEX\|ELF3_ELF5_2_SELEX\|ELF5_2\|ELF5_3\|ELF5_4 | ACCCGGAAGTA | TACTTCCGGGT |
| HOXC10_MA0485.1_ChIP-seq | GGCCATAAATCAC | GTGATTTATGGCC |
| ELF1_K562_ELF1_HudsonAlpha_ChIP-seq | ACCCGGAAGTG | CACTTCCGGGT |
| GBX2_GBX2_2_SELEX\|GBX2_3 | TAATTGGCCAATTA | TAATTGGCCAATTA |
| MYCN_MYCN_si_HocoMoco\|MXI1_Mv94_ChIP-seq | CCACGTGG | CCACGTGG |
| HSF_known2 | GAAACCTCTGGAA | TTCCAGAGGTTTC |
| SOX30_Sox30_2781_PBM | ATTGTTCTGC | GCAGAACAAT |
| SRF_YMR043W_831_DeBoer11 | CATTTCCGAATTGGGAACA | TGTTTCCCAATTCGGAAATG |
| NKX2-5_3 | TCAAGTGGGA | TCCCACTTGA |
| SNAI2_SNAI2_1_SELEX\|SNAI2_1 | AACAGGTGT | ACACCTGTT |
| NFKB1_V$NFKB_Q6_Transfac\|NFKB_known4 | AGGGGAATTTCCCC | GGGGAAATTCCCCT |
| DRGX_Otx1_2_SELEX\|DRGX_OTX1_2_SELEX\|OTX1_3\|OTX1_5 | CGGATTAA | TTAATCCG |
| FOXD1_FOXC2_f1_HocoMoco | GTTTGTTTTGCCAGA | TCTGGCAAAACAAAC |
| ETV5_Elk3_1_SELEX\|ETV5_GABPA_1_SELEX\|ETV5_ELK3_1_SELEX\|ETV5_ELK1_2_SELEX\|ETV5_ELK1_1_SELEX\|ETV5_ETV4_1_SELEX\|ETV5_ETV1_1_SELEX\|ETS1_V$CETS1P54_01_Transfac\|ETS_known3\|ETS_known11\|ETS_known12\|ELK3_1\|ETV1_1\|ETV4_2\|ELK3_2\|ETS_known18 | ACCGGAAGTA | TACTTCCGGT |
| LHX4_1 | CAAAGCTAATTAGTTTA | TAAACTAATTAGCTTTG |
| POU4F3_1 | AGTTATTAATGAGGTC | GACCTCATTAATAACT |
| ETS1_ETS1_3_SELEX\|ENSG00000235187_ETV3_1_SELEX\|ETV5_ERG_1_SELEX\|ETV5_ELK4_1_SELEX\|ETV5_ETV5_1_SELEX\|EN5G00000235187_ERF_1_SELEX\|ETV5_FLI1_3_SELEX\|ETV5_ERG_3_SELEX\|ETS1_ETS1_1_SELEX\|ELF1_ELF1_g_HocoMoco\|ETV5_FEV_1_SELEX\|ETV5_FLI1_1_SELEX\|ETS_disc2\|EGR1_disc2\|ELK4_2\|ERF_1\|ERG_1\|ERG_3\|ETS_known14\|ETS_known16\|ETV3_1\|ETV5_1\|FEV_2\|FLI1_1\|FLI1_3 | ACCGGAAGTG | CACTTCCGGT |

TABLE 5-continued

Transcription Factor Binding Sites of Synthetic Promoters

| Name | Binding Site Sequence | Reverse Complement |
|---|---|---|
| AP1_known10 | TGACTCA | TGAGTCA |
| TFCP2_TFCP2_f1_HocoMoco | GCCTGAACTGGCCAGA | TCTGGCCAGTTCAGGC |
| DBX2_Dbx2_3487_PBM\|DLX1_Dlx5_3419_PBM | GCAATTA | TAATTGC |
| BHLHE40_BHE41_f1_HocoMoco | ACCGGGTCACGTGCAGAAGC | GCTTCTGCACGTGACCCGGT |
| EHF_1 | AGGACCCGGAAGTAA | TTACTTCCGGGTCCT |
| NHLH2_HLH4C_SANGER_5_FBgn0011277_B1H | GGCACCAGCTGCGCC | GGCGCAGCTGGTGCC |
| HOXB2_HXA1_f1_HocoMoco | CATCCATCAA | TTGATGGATG |
| BX088580.2_POU5F1P1_2_SELEX\|POU3F4_POU2F3_2_SELEX\|POU2F3_3\|POU5F1_known5 | ATGAATATGCAA | TTGCATATTCAT |
| E2F_known15 | CGCGCC | GGCGCG |
| STAT1_Mv124_ChIP-seq | TTCCCGGAAA | TTTCCGGGAA |
| BRCA1_MA0133.1_SELEX\|BRCA1_known2 | ACAACAC | GTGTTGT |
| ETS_1 | AACCACTTCCTG | CAGGAAGTGGTT |
| IRF5_IRF5_1_SELEX\|IRF_known15 | AGTTTCGGTTTCGG | CCGAAACCGAAACT |
| IRF8_IRF8_2_SELEX\|IRF_known20 | AGTTTCGGTTTCGA | TCGAAACCGAAACT |
| CDX2_V$CDXA_02_Transfac | ATTAATA | TATTAAT |
| TAL2_TAL1_f2_HocoMoco | AACAGATGGTCGCCCAACCACTGGA | TCCAGTGGTTGGGCGACCATCTGTT |
| FOXA_disc2 | AATATTGACA | TGTCAATATT |
| SP2_disc3 | AAGGGGCGGG | CCCGCCCCTT |
| MAX_NB4_MAX_Stanford_ChIP-seq | CCACGTGATCC | GGATCACGTGG |
| ATF4_1 | CATTGCGTCAGG | CCTGACGCAATG |
| SP9_V$SP1_C16_Transfac\|SP1_known2 | GGCCCCGCCCCC | GGGGGCGGGGCC |
| HOXB13_HOXA13_4_SELEX\|HOXA13_5 | TCTCGTAAAAA | TTTTTACGAGA |
| GATA2_srp_SANGER_5_FBgn0003507_B1H | CCTTATCA | TGATAAGG |
| NEUROG1_tap_da_SANGER_5_2_FBgn0015550_B1H\|TCF4_tap_da_SANGER_5_2_FBgn0000413_B1H | CCAGATGTCA | TGACATCTGG |
| FOXO6_V$FOXO4_02_Transfac\|FOXO4_2 | AACGTAAACAACAT | ATGTTGTTTACGTT |
| GATA_known17 | ATCTTCTTATCAGTTTA | TAAACTGATAAGAAGAT |
| MYBL2_MYBL2_2_SELEX\|MYBL2_2 | ACCGTTAAAACCGTTA | TAACGGTTTTAACGGT |
| WT1_WT1_f1_HocoMoco | CCCCCGCCCCCGC | GCGGGGCGGGGG |
| SOX13_1 | AAATTATTGTTCTTAA | TTAAGAACAATAATTT |
| SNAI2_SNAI2_f1_HocoMoco | CACCTGG | CCAGGTG |
| TBX3_TBX2_1_SELEX\|MGA_MGA_3_SELEX\|MGA_3\|TBX2_1 | GGTGTGAAATTTCACACC | GGTGTGAAATTTCACACC |
| E2F8_E2F8_1_SELEX\|E2F8_1 | TTTCCCGCCAAA | TTTGGCGGGAAA |
| TCF4_nau_da_SANGER_5_FBgn0000413_B1H\|MYOD1_nau_da_SANGER_5_FBgn0002922_B1H | CACCTGTC | GACAGGTG |
| CEBPZ_CEBPZ_si_HocoMoco | AGCCAATCAGC | GCTGATTGGCT |
| ATF1_pTH5080_PBM | GTGACGTAA | TTACGTCAC |

TABLE 5-continued

Transcription Factor Binding Sites of Synthetic Promoters

| Name | Binding Site Sequence | Reverse Complement |
|---|---|---|
| ATF1_V$CREB_C14_Transfac\|ATF3_known7 | GGTGACGTAACC | GGTTACGTCACC |
| RAD21_disc8 | CACCAGGGGGCAGC | GCTGCCCCCTGGTG |
| OBOX2_1\|OBOX3_1 | ATAGTTAATCCCCCTCA | TGAGGGGGATTAACTAT |
| SRY_V$SRY_02_Transfac\|SRY_2 | GTAAACAATAGA | TCTATTGTTTAC |
| ZBTB33_disc3 | AACTCTCGCG | CGCGAGAGTT |
| HOXD12_HOXD12_2_SELEX\|HOXD12_3 | AGTCGTAAAAA | TTTTTACGACT |
| BACH1_Mv47_ChIP-seq | AAATGCTGA | TCAGCATTT |
| EN2_1 | TGCACTAATTAGTGGAA | TTCCACTAATTAGTGCA |
| SOX3_2 | AATCAATAACATTGATC | GATCAATGTTATTGATT |
| SRY_SRY_f1_HocoMoco | AAAACAAAA | TTTTGTTTT |
| ZNF281_1 | GGGGGGGGGGGGGA | TCCCCCCCCCCCCC |
| SP2_disc2 | ATTGGCCAGCGTGGCTGTCAGTCA | TGACTGACAGCCACGCTGGCCAAT |
| SP9_SP8_1_SELEX\|SP8_1 | AGTGGGCGTGGC | GCCACGCCCACT |
| SPDEF_Spdef_PBM | AAACCGGATA | TATCCGGTTT |
| ESRRA_disc3 | AAGGTGACCT | AGGTCACCTT |
| CDX2_MA0216.2_ChIP-chip | GGCCATAAAAA | TTTTTATGGCC |
| SCRT2_SCRT1_1_SELEX\|SCRT1_1 | AACCACCTGTTGCTC | GAGCAACAGGTGGTT |
| NANOGP1_pTH5685_PBM | AGCGATTAA | TTAATCGCT |
| HNF4G_Hnf4a_2640_PBM | AGGGTTCAAA | TTTGAACCCT |
| ESRRG_ESRRB_1_SELEX\|ESRRB_2 | TATGACCTTGA | TCAAGGTCATA |
| PAX6_2 | CTGACCTGGAACTC | GAGTTCCAGGTCAG |
| ESR2_Mv66_ChIP-seq | AGGTCAGGGTGACCTGGA | TCCAGGTCACCCTGACCT |
| SRF_pTH5539_PBM | CCAAATCGGG | CCCGATTTGG |
| SP9_SP3_f1_HocoMoco | CCCCGGCCCCGCCCCCCCC | GGGGGGGGGCGGGCCGGGG |
| TFAP2A_Tcfap2a_1_SELEX\|TFAP2A_TFAP2A_1_SELEX\|TFAP2_known11\|TFAP2_known20 | TGCCCCCGGGCA | TGCCCGGGGGCA |
| ETV5_ETV4_f1_HocoMoco | ACTTCCTG | CAGGAAGT |
| TFAP2_known7 | ACCGCCTCAGGCGGT | ACCGCCTGAGGCGGT |
| ETS_2 | ACTTCCTC | GAGGAAGT |
| NR2E3_NR2E3_f1_HocoMoco | AAAGTCAAAGTCA | TGACTTTGACTTT |
| PAX6_PAX6_f1_HocoMoco | TCAAGCGTGAA | TTCACGCTTGA |
| TCF7L1_1\|TCF7_1 | TATAGATCAAAGGAAAA | TTTTCCTTTGATCTATA |
| JUN_H1-hESC_CJUN_Stanford_ChIP-seq | CATTCCTGAGGGATGACTTA | TAAGTCATCCCTCAGGAATG |
| DMRTA2_pTH10777_PBM | ACTGTATCAA | TTGATACAGT |
| NR2C2_NR2C1_si_HocoMoco | CTGACCTCTGGCC | GGCCAGAGGTCAG |
| RORB_RORG_f1_HocoMoco | AAAAGTAGGTCAG | CTGACCTACTTTT |
| ESRRG_ESRRA_4_SELEX | TTCAAGGTCAA | TTGACCTTGAA |

TABLE 5-continued

Transcription Factor Binding Sites of Synthetic Promoters

| Name | Binding Site Sequence | Reverse Complement |
|---|---|---|
| TFAP4_pTH5067_PBM | ATCAGCTGG | CCAGCTGAT |
| GMEB1_pTH8671_PBM | TACGTCA | TGACGTA |
| NFE2L1_1 | CTTCCAAAATGAC | GTCATTTTGGAAG |
| RELA_V$NFKAPPAB65_01_Transfac\|RELA_MA0107.1_SELEX\|NFKB_disc1\|NFKB_known2\|NFKB_known3\|NFKB_known7\|NFKB_known9 | GGAAATTCCC | GGGAATTTCC |
| ELF3_ELF5_f1_HocoMoco | ATAAGGAAGTA | TACTTCCTTAT |
| TFAP4_HLH11_PBM | ATCAGCTGA | TCAGCTGAT |
| POU4F1_POU4F1_1_SELEX\|POU4F1_1 | ATGAATAATTAATG | CATTAATTATTCAT |
| FEV_1 | ATTTCCTG | CAGGAAAT |
| XBP1_XBP1_2_SELEX\|XBP1_4 | AATGCCACGTCATC | GATGACGTGGCATT |
| POU3F3_PO3F2_si_HocoMoco | ATTATTTATG | CATAAATAAT |
| OTX_1 | AATTAATC | GATTAATT |
| SOX9_MA0077.1_SELEX\|SOX9_SOX9_1_SELEX\|SOX9_2\|SOX9_3 | CCATTGTTC | GAACAATGG |
| SOX3_3 | CATGAATACCATTCATC | GATGAATGGTATTCATG |
| NKX1-1_1 | TCCCACTAATTAGCGCA | TGCGCTAATTAGTGGGA |
| NKX6-2_1 | GAAATAATTACC | GGTAATTATTTC |
| KLF4_KLF8_f1_HocoMoco | CACCCCCTG | CAGGGGGTG |
| ZNF423_2 | GCACCCCTGGGTGCC | GGCACCCAGGGGTGC |
| GATA2_Mw144_ChIP-seq | AGATGCTTATC | GATAAGCATCT |
| NFKB1_V$NFKAPPAB50_01_Transfac\|NFKB_known1 | GGGAATCCCC | GGGGATTCCC |
| CTCF_HEK293_CTCF_UW_ChIP-seq\|CTCF_K562_CTCF_Broad_ChIP-seq\|CTCF_HBM EC_CTCF_UW_ChIP-seq | GGCGCCCCTGGTGGCCA | TGGCCACCAGGGGCGCC |
| ALX1_VSX2_si_HocoMoco | TAATTAGCTAA | TTAGCTAATTA |
| VAX1_1 | ACGTTAATTAACCCAG | CTGGGTTAATTAACGT |
| ETV5_Etv1_PBM\|ETV5_Etv4_PBM\|ETV5_Gm5454_PBM | ACTTCCGGTC | GACCGGAAGT |
| AP1_disc3 | ATGAGTCACC | GGTGACTCAT |
| HOXA4_pTH5479_PBM | CTTAATTACC | GGTAATTAAG |
| EGR3_MA0472.1_ChIP-seq | CCCCCGCCCACGCAC | GTGCGTGGGCGGGG |
| NKX2-2_2 | AATTTTCAAGTGGTTAA | TTAACCACTTGAAAATT |
| TCF4_pTH3866_PBM\|TCF12_HTF4_f1_HocoMoco | ACACCTGCT | AGCAGGTGT |
| SPDEF_SPDEF_2_SELEX\|SPDEF_3 | ATAATCCGGGACCAC | GTGGTCCCGGATTAT |
| DLX4_1 | GTCGGTAATTATAGCGA | TCGCTATAATTACCGAC |
| AIRE_1 | ATTTAACCATTATAACCAATTAATAA | TTATTAATTGGTTATAATGGTTAAAT |
| NFAT5_NFAT5_f1_HocoMoco | CATGGAGTTTCCAC | GTGGAAACTCCATG |
| POU3F3_1 | AAAATATGCATAATAAA | TTTATTATGCATATTTT |
| MESP2_MESP1_1_SELEX\|MESP1_1 | AACACCTGTG | CACAGGTGTT |
| SIN3A_disc6 | CCGCTCAGCCGC | GCGGCTGAGCGG |

TABLE 5-continued

Transcription Factor Binding Sites of Synthetic Promoters

| Name | Binding Site Sequence | Reverse Complement |
|---|---|---|
| NKX2-8_2 | CCACTTGAG | CTCAAGTGG |
| ESRRA_disc4 | CAGGGTCAGAGCGG | CCGCTCTGACCCTG |
| RARG_Rarb_2_SELEX\|RARB_2 | AAAGGTCACCAGAGGTCA | TGACCTCTGGTGACCTTT |
| HSF2_pTH9010_PBM | ATATAGAACATTC | GAATGTTCTATAT |
| GATA2_K562b_GATA2_UCD_ChIP-seq | CCTTATCTGCCCCCCCCA | TGGGGGGGGCAGATAAGG |
| ZNF148_GSE11329_zfp281_ChIP-seq\|ZNF148_ZN148_si_HocoMoco | CCCCTCCCCCACCCC | GGGGTGGGGAGGGG |
| CEBPA_CEBPD_f1_HocoMoco | AATTGTGCAAT | ATTGCACAATT |
| HOMEZ_HOMEZ_LSELEX\|HOMEZ_2 | AAAACGATTATA | TATAATCGTTTT |
| ISL2_ISL1_f1_HocoMoco | CATTAAC | GTTAATG |
| ATF7_ATF7_1_SELEX\|ATF7_1 | CGATGACGTCATCG | CGATGACGTCATCG |
| HOXA4_HOXA2_1_SELEX\|EMX2_pTH5677_PBM\|HOXA2_2 | CCTAATTACC | GGTAATTAGG |
| CR936877.3_Rxra_2_SELEX\|RXRA_known15 | GGGTCATGACCC | GGGTCATGACCC |
| STAT_known15 | GACTTTTCTGGGA | TCCCAGAAAAGTC |
| GATA2_PBDE_GATA1_UCD_ChIP-seq | CTGGGGGGGCAGATAAG | CTTATCTGCCCCCCCCAG |
| GATA2_K562_GATA2_HudsonAlpha_ChIP-seq | CTGGTGGGGCAGATAAG | CTTATCTGCCCCACCAG |
| TRIM28_disc1 | TGAGTCATCA | TGATGACTCA |
| EWSR1::FLI1_1 | CCTTCCTTCCTTCCTTCC | GGAAGGAAGGAAGGAAGG |
| ARNT2_BMAL1_f1_HocoMoco | GGGTCACGTGTCCA | TGGACACGTGACCC |
| SP9_SP1_1_SELEX\|SP1_known8 | ACCCCGCCCCC | GGGGGCGGGGT |
| PAX9_Mv109_ChIP-seq | AGCGTGACCG | CGGTCACGCT |
| STAT4_STAT4_si_HocoMoco | CTTTTCTGGGAAA | TTTCCCAGAAAAG |
| CEBPB_known7 | AAATTGTGCAAT | ATTGCACAATTT |
| ARNT2_tgo_sima_SANGER_5_FBgn0015014_B1H | GTACGTGAC | GTCACGTAC |
| ENSG00000250096_RUNX2_1_SELEX\|ENSG00000250096_RUNX3_1_SELEX\|RUNX2_4\|RUNX3_1 | TAACCGCAAACCGCAA | TTGCGGTTTGCGGTTA |
| POU3F1_1\|POU3F4_1 | AATTAATTAATTAATTC | GAATTAATTAATTAATT |
| EP300_disc9 | CCGCTCCCAGCGGCTGC | GCAGCCGCTGGGAGCGG |
| HOXC5_Mw154_ChIP-seq | CATCAATC | GATTGATG |
| TFAP4_crp_SANGER_10_FBgn0001994_B1H | ATCAGCTGGTC | GACCAGCTGAT |
| CR936877.3_HepG2_RXRA_HudsonAlpha_ChIP-seq | CCCTGACCTTTGCCC | GGGCAAAGGTCAGGG |
| PLAG1_PLAG1_si_HocoMoco | AGAGGGGCCCTA | TAGGGCCCCTCT |
| NR2C2_K562b_TR4_UCD_ChIP-seq | AGTACTTCCGGGTCA | TGACCCGGAAGTACT |
| PAX5_pTH10794_PBM | ACGCGTGACG | CGTCACGCGT |
| E2F_disc6 | AGATTTGAAT | ATTCAAATCT |
| RUNX1_V$AML1_01_Transfac\|RUNX2_1\|RUNX1_7 | ACCACA | TGTGGT |

TABLE 5-continued

Transcription Factor Binding Sites of Synthetic Promoters

| Name | Binding Site Sequence | Reverse Complement |
| --- | --- | --- |
| SOX8_1 | TAAAGAACAATAGATAA | TTATCTATTGTTCTTTA |
| AP1_disc7 | CATGACTCAGAC | GTCTGAGTCATG |
| SOX1_MA0143.3_ChIP-seq\|SOX11_Sox4_PBM | AACAAAGG | CCTTTGTT |
| JUN_JUND_f1_HocoMoco\|JUN_HeLa-S3_CJUN_Stanford_ChIP-seq\|JUN_K562_CJUN_Stanford_ChIP-seq | GATGACTCATC | GATGAGTCATC |
| PAX3_1 | AAATTTCGTCACGGTTAAGGT | ACCTTAACCGTGACGAAATT |
| RFX8_RFX5_2_SELEX\|RFX8_RFX5_3_SELEX\|RFX5_known9 | CGTTACCATGGCAACG | CGTTGCCATGGTAACG |
| BATF_GM12878_BATF_HudsonAlpha_ChIP-seq | TCTCGATATGACTCA | TGAGTCATATCGAGA |
| NR1H_1 | TGACCGCCAGTGACCCCA | TGGGGTCACTGGCGGTCA |
| RFX8_MA0365.1_PBM,\|RFX8_YLR176C_496_DeBoer11 | GGTTGCCA | TGGCAACC |
| PTF1A_1 | GCTGTGGTTTTCCC | GGGAAAACCACAGC |
| ZNF423_V$ROAZ_01_Transfac\|ZNF423_1 | GCACCCAAGGGTGC | GCACCCTTGGGTGC |
| TFAP2A_TFAP2A_3_SELEX\|TFAP2_known13 | TGCCCCCGGGGCA | TGCCCCGGGGGCA |
| TFAP2A_HeLa-S3_AP2GAMMA_UCD_ChIP-seq | AGCCTCAGGGCATGG | CCATGCCCTGAGGCT |
| NR2F2_COT1_f1_HocoMoco | GGTCAAAGGTCA | TGACCTTTGACC |
| AHR_1 | CCCCCGGCTAGCGTGAGA | TCTCACGCTAGCCGGGGG |
| ARID5A_pTH4426_PBM | CAATATCG | CGATATTG |
| RFX8_pTH3516_PBM | CCATAGCAAC | GTTGCTATGG |
| FOXD1_V$XFD3_01_Transfac | TGAGTAAACAAAAA | TTTTTGTTTACTCA |
| GATA_disc3 | GCAGGAAATGA | TCATTTCCTGC |
| RXRA_known3 | AGAGTTCA | TGAACTCT |
| YBX1_pTH8991_PBM | TAGGATAGA | TCTATCCTA |
| TATA_disc8 | CGGAAGTCGC | GCGACTTCCG |
| SHOX2_1 | CACAATTAATTAACGCG | CGCGTTAATTAATTGTG |
| DRGX_Otx1_1_SELEX\|DRGX_OTX1_1_SELEX\|OTP_OTX2_1_SELEX\|OTX1_2\|OTX2_2\|OTX1_4 | GTTAATCCGATTAAC | GTTAATCGGATTAAC |
| SP1_known3 | AGCCTTGGGGAGGG | CCCTCCCCAAGGCT |
| DLX1_Dlx4_3488_PBM | ATAATTGC | GCAATTAT |
| DMBX1_Pax7_3783_PBM | ATAATTGG | CCAATTAT |
| POU3F2_1 | GCCATCCAAAATGAAC | GTTCATTTTGGATGGC |
| CEBPA_MA0102.3_ChIP-seq | ATTGCACAATA | TATTGTGCAAT |
| MEIS1::HOXA9_1 | TCGTAAAACTGTCA | TGACAGTTTTACGA |
| MYBL1_MYBL1_4_SELEX\|MYBL1_5 | GGCCGTTATAACCGTTA | TAACGGTTATAACGGCC |
| MSX2_2 | AAATTAATTGGTTTTG | CAAAACCAATTAATTT |
| SOX4_1 | AGAAGAACAAAGGACTA | TAGTCCTTTGTTCTTCT |
| MYC_HeLa-53_CMYC_Stanford_ChIP-seq\|MAX_K562_MAX_HudsonAlpha_ChIP-seq | CCACGTGCTC | GAGCACGTGG |

TABLE 5-continued

Transcription Factor Binding Sites of Synthetic Promoters

| Name | Binding Site Sequence | Reverse Complement |
|---|---|---|
| RXRA_known4 | GGAGTTCA | TGAACTCC |
| ZNF219_1 | CGCCCCCCCCCC | GGGGGGGGGGCG |
| PBX1_3 | ACATCAATCAAA | TTTGATTGATGT |
| BCL6B_Bcl6b_0961_PBM | GTCTTTCTAGAA | TTCTAGAAAGAC |
| GATA2_SH-SY5Y_GATA2_UCD_ChIP-seq | CAGATAAGAA | TTCTTATCTG |
| HMX1_HMX2_1_SELEX\|HMX2_2 | ACCAATTAAAA | TTTTAATTGGT |
| HOXA4_2 | CAAGTTAATTAATAATC | GATTATTAATTAACTTG |
| HNF1A_Tcf1_2666_PBM | CCTGGTTAA | TTAACCAGG |
| ZBTB14_2 | CCGCGCGC | GCGCGCGG |
| OBOX6_1 | AAAAACGGATTATTG | CAATAATCCGTTTTT |
| CTCF_disc3 | ACTAGAGGG | CCCTCTAGT |
| ENSG00000234254_TG\|F1_si_HocoMoco | CTGTCAC | GTGACAG |
| SOX9_SOX9_6_SELEX\|SOX9_8 | AATCAATTTCAGTGATT | AATCACTGAAATTGATT |
| PKNOX2_Meis2_1_SELEX\|PKNOX2_MEIS1_1_SELEX\|PKNOX2_Meis3_1_SELEX\|MEIS1_4\|MEIS2_3\|MEIS3_4 | CTGTCAA | TTGACAG |
| TFAP2A_TFAP2C_5_SELEX\|TFAP2A_Tcfap2a_3_SELEX\|TFAP2A_TFAP2B_3_SELEX\|TFAP2A_TFAP2A_6_SELEX\|TFAP2A_TFAP2C_3_SELEX\|TFAP26_4\|TFAP2_known16\|TFAP2_known18\|TFAP2_known22 | TGCCCTCAGGGCA | TGCCCTGAGGGCA |
| SIX6_Six6_2267_PBM | GGTATCA | TGATACC |
| ALX1_A1_SOLEXA_FBgn0000061_B1H | CGCTAATTA | TAATTAGCG |
| FOXO6_MA0480.1_ChIP-seq | TCCTGTTTACA | TGTAAACAGGA |
| NFATC2_1 | TGGAAAA | TTTTCCA |
| FOXP1_1 | ATAAAAACAACACAAATAA | TTATTTGTGTTGTTTTTAT |
| EN2_en_SOLEXA_2_FBgn0000577_B1H | CTAATTAAGA | TCTTAATTAG |
| E2F2_E2F2_2_SELEX\|E2F2_3 | AATTTTGGCGCCAAAATG | CATTTTGGCGCCAAAATT |
| HINFP_HINFP1_1_SELEX\|HINFP_2 | CAACGTCCGCGG | CCGCGGACGTTG |
| USF1_GM12878_USF2_Stanford_ChIP-seq | CCGGGCCACGTGACC | GGTCACGTGGCCCGG |
| ETV5_pTH6345_PBM\|ETV5_pTH6450_PBM\|EP300_disc4 | ACTTCCGG | CCGGAAGT |
| CCNT2_disc2 | CCCCACCCCC | GGGGGTGGGG |
| HOXA6_1 | AAGGTAATTACCTAAT | ATTAGGTAATTACCTT |
| SMARCC1_HeLa-S3_BAF155_Stanford_ChIP-seq | GATGAGTCACCCCCC | GGGGGGTGACTCATC |
| ISX_1 | ACGACTAATTAGGAGT | ACTCCTAATTAGTCGT |
| HINFP_H\|NFP1_3_SELEX\|HINFP_4 | GCGGACGTTCAACGTCCGC | GCGGACGTTGAACGTCCGC |
| ATF1_V$CREB_02_Transfac\|ATF3_known3 | CGGGTGACGTCC | GGACGTCACCCG |
| ZNF384_ZN384_f1_HocoMoco | CCGATTTTTCC | GGAAAAATCGG |
| FOXD1_pTH3802_PBM | AATGTAAACATA | TATGTTTACATT |
| E2F_known2\|E2F_known3\|E2F_known4\|E2F_known5\|E2F_known6\|E2F_known8\|E2F_known12\|E2F_known14 | GCGCGAAA | TTTCGCGC |

TABLE 5-continued

Transcription Factor Binding Sites of Synthetic Promoters

| Name | Binding Site Sequence | Reverse Complement |
|---|---|---|
| KLF15_KLF15_a_HocoMoco | GCCCCCACCTCCCCGCC | GGCGGGGAGGTGGGGGC |
| REST_HeLa-S3_NRSF_HudsonAlpha_ChIP-seq | AGCACCATGGACAGCG | CGCTGTCCATGGTGCT |
| DDIT3::CEBPA_2 | AGATGCAATCCC | GGGATTGCATCT |
| REST_K562_NRSF_HudsonAlpha_ChIP-seq | CTGTCCATGGTGCTGA | TCAGCACCATGGACAG |
| HOXD12_HOXD12_3_SELEX\|HOXC10_HOXC11_3_SELEX\|HOXC10_HOXC11_1_SELEX\|HOXC11_2\|HOXC11_4 | ATTTTACGACC | GGTCGTAAAAT |
| POU3F3_V$OCT1_04_Transfac | TCTTTTAATTTGCATAATCATAA | TTATGATTATGCAAATTAAAAGA |
| CTCF_disc9 | GCCCACTAGAGGGCAC | GTGCCCTCTAGTGGGC |
| CEBPA_V$CEBP_C_Transfac\|CEBPB_known5 | GGTATTTGGCAATGCACA | TGTGCATTGCCAAATACC |
| HNF4_known11 | GGGGCA | TGCCCC |
| FOXD1_FOXI1_1_SELEX\|FOXD1_Foxg1_3_SELEX\|FOXD1_Foxk1_2_SELEX\|FOXD1_bin_SANGER_5_FBgn0045759_B1H\|FOXO6_FOXO6_2_SELEX\|FOXD1_FOXD3_2_SELEX\|FOXD1_FOXL1_1_SELEX\|FOXD1_FOXD2_2_SELEX\|FOXO6_FOXO4_2_SELEX\|KIAA0415_MA0297.1_PBM,\|FOXP3_FOXP3_1_SELEX\|FOXD2_2\|FOXD3_4\|FOXI1_3\|FOXL1_4\|FOXO4_4\|FOXO6_2\|FOXP3_2\|FOXG1_5\|FOXK1_4 | GTAAACA | TGTTTAC |
| ZIC4_V$ZIC1_01_Transfac\|ZIC4_ZIC3_f1_HocoMoco\|ZIC4_V$Z1C3_01_Transfac\|ZIC1_1\|ZIC3_1 | GACCACCCA | TGGGTGGTC |
| SIX5_known5 | ATAAATGACACCTATCA | TGATAGGTGTCATTTAT |
| ZIC4_V$Z1C2_01_Transfac\|ZIC4_ZIC1_f1_HocoMoco\|ZIC4_ZIC2_f1_HocoMoco\|ZIC2_1 | GACCACCCC | GGGGTGGTC |
| TFAP2_known1 | CGCCCGCCGGCG | CGCCGGCGGGCG |
| TEF_TEF_f1_HocoMoco | CATTTACATAAACA | TGTTTATGTAAATG |
| HOXA7_pTH6498_PBM | AAGTAATTACT | AGTAATTACTT |
| AR1D3A_2 | GAATTTTAATTAAACCC | GGGTTTAATTAAAATTC |
| STAT6_MA0520.1_ChIP-seq | ATTTCTCAGGAAATG | CATTTCCTGAGAAAT |
| HIC1_2 | GAGGGGTGCCCGCAGGCC | GGCCTGCGGGCACCCCTC |
| IRF_known6 | AAGTGAA | TTCACTT |
| HOXC5_I$DFD_01_Transfac | ACCAAGTAATTCCTAG | CTAGGAATTACTTGGT |
| TCF4_pTH5101_PBM | CACACCTGG | CCAGGTGTG |
| SP9_SP2_si_HocoMoco | GAGGGGGGCGGGCTAA | TTAGCCCGCCCCCCTC |
| THRB_THRA_1_SELEX\|THRA_1 | GTGACCTCATAAGGTCAC | GTGACCTTATGAGGTCAC |
| GBX1_1 | TACACTAATTAGTGGCA | TGCCACTAATTAGTGTA |
| BPTF_1 | AACCACAACACATA | TATGTGTTGTGGTT |
| SIX2_So_Cell_FBgn0003460_B1H | AATGATA | TATCATT |
| STAT6_V$STAT6_02_Transfac\|STAT_known14 | AGGAAGTC | GACTTCCT |
| ELF3_MA0598.1_ChIP-seq | CAGGAAGG | CCTTCCTG |
| PRDM1_PRDM1_a_HocoMoco | GAAAGTGAAAGTGA | TCACTTTCACTTTC |

TABLE 5-continued

Transcription Factor Binding Sites of Synthetic Promoters

| Name | Binding Site Sequence | Reverse Complement |
| --- | --- | --- |
| DBP_1 | AGCAAAC | GTTTGCT |
| FOXA_disc4 | AAATTCCT | AGGAATTT |
| ZEB1_V$DELTAEF1_01_Transfac | TCTCACCTGAA | TTCAGGTGAGA |
| CTCF_HUVEC_CTCF_Broad_ChIP-seq | CCCGGCGCCCCCTGGTGGCCG | CGGCCACCAGGGGGCGCCGGG |
| AR_AR_2_SELEX\|NR3C1_known16 | GGGAACACGGTGTACCC | GGGTACACCGTGTTCCC |
| ZNF384_1 | GAAAAAATC | GATTTTTTC |
| MSX1_MSX2_1_SELEX\|MSX1_MSX1_1_SELEX\|MSX1_Msx3_1_SELEX\|MSX1_3\|MSX2_3\|MSX2_5 | GCAATTAAAAACCAATTA | TAATTGGTTTTTAATTGC |
| NFIA_MA0161.1_High-throughput\|NFIC_4 | TGCCAA | TTGGCA |
| ATFLCREM_f1_HocoMoco | CACTGACGTCA | TGACGTCAGTG |
| HIC1_1 | CCCCGGGCACCCGGG | CCCGGGTGCCCGGGG |
| POU6F1_pTH6519_PBM | ATTAATTAAT | ATTAATTAAT |
| POU3F3_V$OCT1_03_Transfac\|POU2F2_known3 | ACCTCATTACGAG | CTCGTAATGAGGT |
| PAX9_Poxm_SOLEXA_5_FBgn0003129_B1H | CAAAAGCAATCAACCGTGA | TCACGGTTGATTGCTTTTG |
| RFX8_Rfx3_3961_PBM\|RFX8_pTH9278_PBM\|RFX8_pTH9194_PBM\|RFX8_pTH9269_PBM | CGTTGCTAAG | CTTAGCAACG |
| ELF2_1 | GTGACCTACTTCCTGGCA | TGCCAGGAAGTAGGTCAC |
| ETV5_MA0062.2_ChIP-seq\|ETS_known9 | CCGGAAGTGGC | GCCACTTCCGG |
| POU2F2_POU2F2_2_SELEX\|POU2F2_3 | CATGCATATGCAAA | TTTGCATATGCATG |
| EOMES_TBX21_4_SELEX\|TBX21_4 | GGTGTGATATCACACC | GGTGTGATATCACACC |
| NHLH2_V$HEN1_01_Transfac | GAGGGGCGCAGCTGCGCCCCAA | TTGGGGCGCAGCTGCGCCCCTC |
| NR2F2_NR2F6_a_HocoMoco | AGGACAAAGTTCACTTGA | TCAAGTGAACTTTGTCCT |
| E2F1_E2F1_4_SELEX | AAATGGCGCCATTT | AAATGGCGCCATTT |
| MAFK_HepG2_MAFF_Stanford_ChIP-seq | TGCTGACTCAGCAAA | TTTGCTGAGTCAGCA |
| PPARA_PPARG_si_HocoMoco\|NR2F2_COT1_si_HocoMoco | CAAAGGTCA | TGACCTTTG |
| IRX3_pTH6408_PBM | ATTACAAG | CTTGTAAT |
| ENSG00000187728_pTH5087_PBM | AACATATGG | CCATATGTT |
| CEBPD_1 | AATTGCGTCACT | AGTGACGCAATT |
| RELA_SRP001843_p65_Input_LPSstim_ChIP-seq\|RELA_TF65_f2_HocoMoco\|NFKB1_MA0105.3_ChIP-seq | GGGAAATTCCC | GGGAATTTCCC |
| RFX8_pTH9249_PBM | CCCTGGCAAC | GTTGCCAGGG |
| STAT_disc2\|BCL_disc2 | AATGACTCAT | ATGAGTCATT |
| SREBP_disc1 | CGTCGCCATGGCAAC | GTTGCCATGGCGACG |
| SPI1_known2 | ACTTCCT | AGGAAGT |
| GLIS1_GLIS1_1_SELEX\|GLIS1_1 | AGACCCCCACGAAGC | GCTTCGTGGGGGTCT |
| NFAT_1 | ATTTTTCCTCTG | CAGAGGAAAAAT |

TABLE 5-continued

Transcription Factor Binding Sites of Synthetic Promoters

| Name | Binding Site Sequence | Reverse Complement |
|---|---|---|
| HMX1_HMX1_1_SELEX\|H MX1_2 | AGCAATTAAAA | TTTTAATTGCT |
| HOXB5_1 | ACGGTAATTAGCTCAT | ATGAGCTAATTACCGT |
| CDC5L_V$CDC5_01_Transfac\|CDC5L1 | GATTTAACATAA | TTATGTTAAATC |
| MEF2B_Mv90_ChIP-seq | AAAATAGC | GCTATTTT |
| USF1_A549_USF1_HudsonAlpha_ChIP-seq | CCCGGTCACGTGACC | GGTCACGTGACCGGG |
| POU2F2_POU2F2_1_SELEX\|POU2F2_2 | AATTTGCATAT | ATATGCAAATT |
| MECP2_pTH3054_PBM | AATGACACTA | TAGTGTCATT |
| LHX8_Lhx8_2247_PBM | CCAATCAGC | GCTGATTGG |
| HOXA1_1\|HOXA5_3 | ACGGTAATTAGCTCAG | CTGAGCTAATTACCGT |
| MSX1_Dr_SOLEXA_FBgn0000492_B1H\|HOXC5_Ubx_FlyReg_FBgn0003944_B1H | CAATTA | TAATTG |
| GATA2_V$GATA1_05_Transfac\|GATA_known8 | GCAGATAACA | TGTTATCTGC |
| CEBPG_pTH5257_PBM | GATTGCGTAA | TTACGCAATC |
| SMARC_disc1 | CTGAGTCACC | GGTGACTCAG |
| XBP1_2 | ATTAAATGACACGTCATCTTTCAG | CTGAAAGATGACGTGTCATTTAAT |
| VAX2_1 | GTCTTAATTAGTGCAC | GTGCACTAATTAAGAC |
| NFIL3_V$E4BP4_01_Transfac\|NFIL3_1 | CGTTACATAACG | CGTTATGTAACG |
| FOXD1_V$FREAC2_01_Transfac\|FOXF2_1 | CAAACGTAAACAATCC | GGATTGTTTACGTTTG |
| ENO1_ENOA_si_HocoMoco | CACCACGTGGGCA | TGCCCACGTGGTG |
| ZBTB42_V$RP58_01_Transfac\|ZBTB18_1 | GAAACATCTGGA | TCCAGATGTTTC |
| IKZF1_V$IK3_01_Transfac\|IKZF3_1 | GGTATTCCCAGTA | TACTGGGAATACC |
| THAP1_disc2 | AACATGGCGG | CCGCCATGTT |
| SRF_Srf_3509_PBM | CCAAATTTGG | CCAAATTTGG |
| FOXA_disc5 | AAAGGTCAA | TTGACCTTT |
| NR4A2_NR4A2_si_HocoMoco\|NR4A2_NR4A1_f1_HocoMoco | AAAGGTCAC | GTGACCTTT |
| HES1_1 | AAGCCTCGTGGCCAG | CTGGCCACGAGGCTT |
| REST_disc5 | CAGCACCCCGG | CCGGGGTGCTG |
| TCF12_known1 | CAGCTGGC | GCCAGCTG |
| CTCFL_K562_CTCFL_HudsonAlpha_ChIP-seq | CCGCCAGGGGGCGCC | GGCGCCCCTGGCGG |
| CTCF_HeLa-S3_CTCF_UW_ChIP-seq | CCACCAGGGGCGCCG | CCGGCGCCCCTGGTGG |
| IRX3_pTH5976_PBM | AAACATGTACT | AGTACATGTTT |
| HOXC10_Hoxa11_2_SELEX\|HOXA11_3 | ATTTTATGGCC | GGCCATAAAAT |
| FOXO6_pTH8995_PBM | TTGTAAACAA | TTGTTTACAA |
| ALX1_3 | CGCATTAATTAATTGGC | GCCAATTAATTAATGCG |
| ZNF274_K562b_ZNF274_UCD_ChIP-seq | CCAGTATGAATTCTC | GAGAATTCATACTGG |
| BACH1_Mv46_ChIP-seq\|MAFK_MAFK_si_HocoMoco\|MAF_disc1 | TGACTCAGCA | TGCTGAGTCA |
| HOXC5_HXA7_f1_HocoMoco | AATCAATAGATTGGA | TCCAATCTATTGATT |

TABLE 5-continued

Transcription Factor Binding Sites of Synthetic Promoters

| Name | Binding Site Sequence | Reverse Complement |
| --- | --- | --- |
| ZFHX3_pTH6494_PBM | ACTAATTAG | CTAATTAGT |
| NR2F2_pTH5882_PBM | AGAGGTCAC | GTGACCTCT |
| CR936877.3_usp_SANGER_5_FBgn0003964_B1H | AGAGGTCAA | TTGACCTCT |
| STAT_known1 | TTCCCGGAA | TTCCGGGAA |
| IRX3_Irx2_0900_PBM | ATTACATGA | TCATGTAAT |
| EGR3_K562_EGR1_HudsonAlpha_ChIP-seq | CCCCCCCCCCGCCCACGCA | TGCGTGGGCGGGGGGGGGG |
| MEF2B_MEF26_1_SELEX\|MEF2B_1 | GCTATAAATAGC | GCTATTTATAGC |
| HAND2_Hand_da_SANGER_5_FBgn0032209_B1H\|TCF4_Hand_da_SANGER_5_FBgn0000413_B1H | CACATGGCC | GGCCATGTG |
| HOXC10_HXD9_f1_HocoMoco | AGTTTTATTG | CAATAAAACT |
| ETV5_ELK4_f1_HocoMoco | CACCGGAAGTA | TACTTCCGGTG |
| JUN_K562_JUND_Stanford_ChIP-seq | GATGACGTCACCCC | GGGGTGACGTCATC |
| MTF1_MTF1_1_SELEX\|MTF1_3 | GTGCCGTGTGCAAA | TTTGCACACGGCAC |
| ZBTB7A_disc1 | AGCGCCCCT | AGGGGGCGCT |
| FOXD1_Foxj1_3125_PBM | AATAAACAAACA | TGTTTGTTTATT |
| USF1_K562_USF2_Stanford_ChIP-seq\|USF1_HepG2_USF2_Stanford_ChIP-seq | GGGTCACGTGACC | GGTCACGTGACCC |
| PKNOX2_Hth_SOLEXA_FBgn0001235_B1H\|TG\|F1_Vis_SOLEXA_FBgn0033748_B1H\|TG\|F1_Achi_SOLEXA_FBgn0033749_B1H | TGTCAA | TTGACA |
| KLF4_CG12029_SOLEXA_5_FBgn0035454_B1H | CCAGCCACACCCACC | GGTGGGTGTGGCTGG |
| TP53_3 | AGACAAGTCC | GGACTTGTCT |
| GATA2_V$GATA1_01_Transfac\|GATA_known1 | CCCTATCACG | CGTGATAGGG |
| HIVEP3_ZEP1_f1_HocoMoco | GGGGATTTCCCA | TGGGAAATCCCC |
| CDX_1 | TACAAACAAAGTAATAAA | TTTATTACTTTGTTTGTA |
| NFIC_1 | CACCTGTTCAATTTGGCACGGAGCCAACA | TGTTGGCTCCGTGCCAAATTGAACAGGTG |
| POU3F3_pTH9381_PBM | ATAATGCATA | TATGCATTAT |
| E2F2_pTH9195_PBM\|E2F2_pTH9291_PBM\|E2F3_pTH9382_PBM | TTGGCGCCAA | TTGGCGCCAA |
| PRRX2_3 | AAAGCTAATTAGCGAAA | TTTCGCTAATTAGCTTT |
| STAT6_STAT6_do_HocoMoco | AAATTCCTGGGAA | TTCCCAGGAATTT |
| EGR3_EGR2_si_HocoMoco | CCGCCCACGCC | GGCGTGGGCGG |
| NR6A1_NR6A1_do_HocoMoco | AAGTTCAAGGTCA | TGACCTTGAACTT |
| TAL1_disc1 | CCTTATCTGCCCCCACCAG | CTGGTGGGGCAGATAAGG |
| ARID5A_ARI5B_f1_HocoMoco | CACAATACTAACC | GGTTAGTATTGTG |
| FOXD1_FoxI1_2809_PBM | AATGTAAACA | TGTTTACATT |
| FOXD1_Foxc1_1_SELEX\|FOXD1_FOXC2_2_SELEX\|FOXC2_2\|FOXC1_6 | GTAAATAAACA | TGTTTATTTAC |
| RAR_1 | AAGGACAGG | CCTGTCCTT |

TABLE 5-continued

Transcription Factor Binding Sites of Synthetic Promoters

| Name | Binding Site Sequence | Reverse Complement |
|---|---|---|
| STAT4_V$STAT4_01_Transfac | AAGAAATC | GATTTCTT |
| PRDM1_disc1 | AGTGAAAGTG | CACTTTCACT |
| STAT5B_V$STAT5A_04_Transfac | AAGAAATG | CATTTCTT |
| TEAD1_1 | CATTCC | GGAATG |
| NR3C1_known13 | ATAAGAACACCCTGTACCCGCC | GGCGGGTACAGGGTGTTCTTAT |
| ZNF713_ZNF713_1_SELEX\|ZNF713_1 | TAGAAAATGCCACGAA | TTCGTGGCATTTTCTA |
| EGR3_EGR4_1_SELEX\|EGR4_2 | AAATGCGTGGGCGTAA | TTACGCCCACGCATTT |
| HNF1A_HNF1A_f1_HocoMoco | GGTTAATAATTAACC | GGTTAATTATTAACC |
| NFIC_3 | TCTTGGCAAGTATCCAA | TTGGATACTTGCCAAGA |
| SP1_disc1 | ACCCCCCTTCTGATTGGCTGA | TCAGCCAATCAGAAGGGGGGT |
| EGR3_EGR4_2_SELEX | AAATGCGTGGGCGTAT | ATACGCCCACGCATTT |
| MEF2B_MEF2C_f1_HocoMoco | TCTATTTATAGAA | TTCTATAAATAGA |
| CACD_2 | CCACACCC | GGGTGTGG |
| ELF1_disc3 | CCCCGGCCTCCGC | GCGGAGGCCGGGG |
| NR3C1_known5 | AGAACAGA | TCTGTTCT |
| PTF1A_Fer3_da_SANGER_5_FBgn0037937_B1H\|TCF4_Fer3_da_SANGER_5_FBgn0000413_B1H | CAGCTGTTAC | GTAACAGCTG |
| BHLHE40_disc1 | AGTCACGTGA | TCACGTGACT |
| HERPUD1_1 | CAGTTGCTAGGCAACGG | CCCGTTGCCTAGCAACTG |
| HBP1_1 | ACTATGAATGAATGAT | ATCATTCATTCATAGT |
| REST_disc8 | CCTCGGACAGCTGC | GCAGCTGTCCGAGG |
| SOX11_Sox11_2266_PBM | ATTGTTCTC | GAGAACAAT |
| JUN_H1-hESCJUND_HudsonAlpha_ChIP-seq | ATGACTCACCC | GGGTGAGTCAT |
| MNT_MNT_1_SELEX\|MNT_1 | ACCACGTGCC | GGCACGTGGT |
| TFAP4_3 | ACCAGCTGTG | CACAGCTGGT |
| OSR2_bowl_SANGER_5_FBgn0004893_B1H | CCAGTAGC | GCTACTGG |
| HOXB13_HXD13_f1_HocoMoco | TCCCTAATAAA | TTTATTAGGGA |
| SPIC_GM12891_PU1_HudsonAlpha_ChIP-seq | AAAGAGGAAGTGAAACTAG | CTAGTTTCACTTCCTCTTT |
| RELA_GM18951_NFKB_Stanford_ChIP-seq | GGGGATTTCCA | TGGAAATCCCC |
| NKX2-8_3 | CCACTTGAA | TTCAAGTGG |
| TCF4_sage_da_SANGER_5_FBgn0000413_B1H | AAAACACCTGT | ACAGGTGTTTT |
| ATF7_V$CREBP1_Q2_Transfac\|ATF2_2 | AGTTACGTCACC | GGTGACGTAACT |
| AR_GCR_do_HocoMoco | CCGGGACAGTCTGTTCTC | GAGAACAGACTGTCCCGG |
| OVOL1_I$OVO_01_Transfac | GTGACTGTTACTATA | TATAGTAACAGTCAC |
| CTCF_WERI-Rb-1_CTCF_UW_ChIP-seq\|CTCF_GM12873_CTCF_UW_ChIP-seq\|CTCF_GM12864_CTCF_UW_ChIP- | CCACCAGGGGCGCC | GGCGCCCCTGGTGG |

TABLE 5-continued

Transcription Factor Binding Sites of Synthetic Promoters

| Name | Binding Site Sequence | Reverse Complement |
|---|---|---|
| seq\|CTCF_Gliobla_CTCF_UT-A_ChIP-seq\|CTCF_T-47D_CTCF_HudsonAlpha_ChIP-seq\|CTCF_AG04450_CTCF_UW_ChIP-seq | | |
| OLIG2_pTH5164_PBM | CCATATGGTAC | GTACCATATGG |
| KLF4_KLF6_si_HocoMoco | CCGCCCCC | GGGGGCGG |
| RORB_pTH6612_PBM | ACTGACCTCT | AGAGGTCAGT |
| EOMES_EOMES_1_SELEX\|EOMES_2 | AAGGTGTGAAAAT | ATTTTCACACCTT |
| SOX9_SOX8_3_SELEX\|SOX8_4 | GAACAATTGCAGTGTTC | GAACACTGCAATTGTTC |
| ESRRG_Esrra_2_SELEX\|ESRRG_ESRRA_1_SELEX\|ESRRA_known7\|ESRRA_known11 | ATGACCTTGAA | TTCAAGGTCAT |
| SOX9_SOX9_7_SELEX\|SOX9_9 | AATGAATTGCAGTCATT | AATGACTGCAATTCATT |
| VDR_3 | AAACGGTTCAGGAAGTTCATC | GATGAACTTCCTGAACCGTTT |
| POU6F2_POU6F2_1_SELEX\|POU6F1_Pou6f1_1731_PBM\|POU6F1_Pou6f1_3733_PBM\|POU6F2_1 | AGCTCATTAT | ATAATGAGCT |
| RAD21_disc10 | CCAGGGGCAG | CTGCCCCTGG |
| IRF7_IRF7_f1_HocoMoco | GAAAGTGAAA | TTTCACTTTC |
| HOXC5_zen_FlyReg_FBgn0004053_B1H | AATTTTAATG | CATTAAAATT |
| PATZ1_V$MAZR_01_Transfac\|PATZ1_1 | GGGGGGGGGGCCA | TGGCCCCCCCCCC |
| FOXO3_3 | TGTAAACA | TGTTTACA |
| HOXC10_HXA10_f1_HocoMoco | GATGATTTATGA | TCATAAATCATC |
| YY1_disc4 | GCAGCCGGCGCCGCC | GGCGGCGCCGGCTGC |
| SOX7_SOX7_1_SELEX\|SOX7_2 | AACAATGAACATTGTT | AACAATGTTCATTGTT |
| MITF_pTH5072_PBM\|BACH1_Mv45_ChIP-seq\|ATF3_Mv41_ChIP-seq | CACGTGAC | GTCACGTG |
| HNF4G_HNF4A_2_SELEX\|HNF4_known17 | AATGGACTTTGACCCC | GGGGTCAAAGTCCATT |
| BARX2_1 | TAAGTAATTAGTTATA | TATAACTAATTACTTA |
| PAX3_PAX7_1_SELEX\|PAX3_PAX7_2_SELEX\|PAX3_PAX3_1_SELEX\|PAX3_3\|PAX7_2\|PAX7_3 | TAATCGATTA | TAATCGATTA |
| LHX9_pTH5812_PBM | CTAATTAGTA | TACTAATTAG |
| MYBL2_MYBL2_1_SELEX\|MYBL2_1 | AACCGTTAACCGTT | AACGGTTAACGGTT |
| FOSL1_FOS_si_HocoMoco | GACCAATCAGAA | TTCTGATTGGTC |
| EMX2_Emx2_3420_PBM | CTAATTAGC | GCTAATTAG |
| CTCF_disc7 | CCACCAGGGG | CCCCTGGTGG |
| SIX6_MA0199.1_B1H | TATCA | TGATA |
| TEAD4_TEAD4_f1_HocoMoco | AAAAATAGCCCT | AGGGCTATTTTT |
| SOX_1 | CTCTTTGTTACGA | TCGTAACAAAGAG |
| C11orf9_pTH8554_PBM | CCGTACCACC | GGTGGTACGG |
| TBX5_2 | TAACACCTCA | TGAGGTGTTA |
| SP9_V$SP1_01_Transfac\|SP1_known1 | ACCCCGCCCC | GGGGCGGGGT |

TABLE 5-continued

Transcription Factor Binding Sites of Synthetic Promoters

| Name | Binding Site Sequence | Reverse Complement |
| --- | --- | --- |
| OSR1_1 | TTTTACAGTAGCAAAA | TTTTGCTACTGTAAAA |
| ETV5_pnt_SANGER_5_FBgn0003118_B1H\|ETV5_Ets21c_SANGER_5_FBgn0005660_B1H | ACCGGAAAT | ATTTCCGGT |
| AP3_1 | AATTTAGA | TCTAAATT |
| SIX2_So_SOLEXA_FBgn0003460_B1H | ATATGATA | TATCATAT |
| FOXD1_FOXD3_1_SELEX\|FOXD3_3 | AGTAAATATTAACT | AGTTAATATTTACT |
| PAX5_disc2 | CAAGCGTGAC | GTCACGCTTG |
| NR2F2_MA0017.1_COMPILED\|HNF4_known2\|HNF4_known13 | AGGTTCAAAGGTCA | TGACCTTTGAACCT |
| NFIC_2 | TCTTGGCAAGAAGCCAAA | TTTGGCTTCTTGCCAAGA |
| MAX_MXL3_PBM\|CLOCK::ARNTL1 | ACACGTGG | CCACGTGT |
| NPAS2_Clk_cyc_SANGER_5_FBgn0023076_B1H\|ARNT2_Clk_cyc_SANGER_5_FBgn0023094_B1H | ACACGTGA | TCACGTGT |
| BCL_disc6 | GGGAAAGCCC | GGGCTTTCCC |
| MLX1P_pTH5466_PBM | ACACGTGC | GCACGTGT |
| MYC_known16 | ACCACGTGGTC | GACCACGTGGT |
| FOXD1_MA0148.3_ChIP-seq | CAAAGTAAACATGGA | TCCATGTTTACTTTG |
| EN2_EN2_1_SELEX\|EN2_2 | GTTAATTGGA | TCCAATTAAC |
| FOXD1_MA0047.2_ChIP-seq\|FOXA_known6 | CCTAAGTAAACA | TGTTTACTTAGG |
| MEF2B_MA0052.2_ChIP-seq | AGCTAAAAATAGCAT | ATGCTATTTTTAGCT |
| RBPJ_I$SUH_01_Transfac | ACTGTGGGAAACG | CGTTTCCCACAGT |
| PAX8_2 | ACTCACGCAATACTG | CAGTATTGCGTGAGT |
| CEBPG_1 | CTCATTTCAAAAA | TTTTTGAAATGAG |
| MEIS3_1 | AATTACCTGTCAATAC | GTATTGACAGGTAATT |
| AR_pTH5924_PBM | ATGTTCCCA | TGGGAACAT |
| NKX6-3_1 | CAAAGTAATTAATTATC | GATAATTAATTACTTTG |
| FEZF2_CG31670_SANGER_5_FBgn0031375_B1H | AAATGAGCAAC | GTTGCTCATTT |
| TWIST2_twi_da_SANGER_5_FBgn0003900_B1H\|TCF4_twi_da_SANGER_5_FBgn0000413_B1H | AACATCTGGT | ACCAGATGTT |
| MYBL1_MYBL1_3_SELEX\|MYBL1_4 | AAAACCGTTAA | TTAACGGTTTT |
| MYB_2 | CTCAACTGGC | GCCAGTTGAG |
| TP73_Tp73_1_SELEX\|TP73_1 | GACATGTCCAGACATGTC | GACATGTCTGGACATGTC |
| JUN_GM12878_JUND_Stanford_ChIP-seq | AGTTTCGATATGAGTCATC | GATGACTCATATCGAAACT |
| HOXB13_HOXA13_1_SELEX\|HOXB13_HOXB13_1_SELEX\|HOXA13_2\|HOXB13_2 | CCAATAAAAC | GTTTTATTGG |
| HOXB13_HOXC13_1_SELEX\|HOXB13_HOXA13_3_SELEX\|HOXB13_Hoxd13_1_SELEX\|HOXB13_HOXD13_1_SELEX\|HOXA13_4\|HOXC13_2\|HOXD13_2\|HOXD13_4 | CCAATAAAAA | TTTTTATTGG |
| IRX3_Irx5_2385_PBM | AATTACATG | CATGTAATT |
| NFKB_disc4 | AAAGTCCCC | GGGGACTTT |

TABLE 5-continued

Transcription Factor Binding Sites of Synthetic Promoters

| Name | Binding Site Sequence | Reverse Complement |
|---|---|---|
| POU3F3_V$OCT1_C16_Transfac | CTGATTTGCATATTC | GAATATGCAAATCAG |
| TEAD1_TEAD1_1_SELEX\|TEAD4_TEAD4_1_SELEX\|TEAD1_3\|TEAD4_1 | ATGGAATGTG | CACATTCCAT |
| ZNF589_1 | CCAGGGTATCAGCCG | CGGCTGATACCCTGG |
| NANOG_disc3 | CCACAGCAGG | CCTGCTGTGG |
| FOXD1_FOXD3_f1_HocoMoco | AAACAAACA | TGTTTGTTT |
| CTCF_AG09319_CTCF_UW_ChIP-seq | GCCACCAGAGGGCGC | GCGCCCTCTGGTGGC |
| CEBPB_disc2 | AGCCAATCA | TGATTGGCT |
| CUX1_V$CLOX_01_Transfac\|CUX1_V$CDP_02_Transfac\|CUX1_2 | AAATAATCGATATA | TATATCGATTATTTT |
| MEIS1_pTH6524_PBM | AAATGACAGCTC | GAGCTGTCATTT |
| BARHL2_Barhl1_3_SELEX\|BARHL1_4 | CATTTAGCAGCAATTA | TAATTGCTGCTAAATG |
| HOXC9_1 | ATAATTAATGACCTCC | GGAGGTCATTAATTAT |
| BHLHE40_known1 | CCGTCACGTGACCA | TGGTCACGTGACGG |
| PBX3_PBX3_f2_HocoMoco | CCAGCCAATCAGAG | CTCTGATTGGCTGG |
| RFX8_GM12878_RFX5_Stanford_ChIP-seq | CCTAGCAACAGGTGA | TCACCTGTTGCTAGG |
| TCF4_HLH4C_da_SANGER_5_FBgn0000413_B1H\|NHLH2_HLH4C_da_SANGER_5_FBgn0011277_B1H | AAAAACACCTGCGCC | GGCGCAGGTGTTTTT |
| MAX_HUVEC_MAX_Stanford_ChIP-seq | GGCCACGTGACCC | GGGTCACGTGGCC |
| NR5A1_MA0505.1_ChIP-seq | AAGTTCAAGGTCAGC | GCTGACCTTGAACTT |
| SP9_pTH5422_PBM | GTACCCTA | TAGGGTAC |
| ATOH7_ato_da_SANGER_5_3_FBgn0010433_B1H\|TCF4_ato_da_SANGER_5_3_FBgn0000413_B1H | CCACCTGCC | GGCAGGTGG |
| EN1_3 | GCATTAATTAGTTCGC | GCGAACTAATTAATGC |
| CIC_Cic_3454_PBM | AGTCAGCAAA | TTTGCTGACT |
| MSX1_MSX1_3_SELEX\|MSX1_5 | CCAATTAG | CTAATTGG |
| CTCF_Fibrobl_CTCF_UT-A_ChIP-seq | CGGCCACCAGGGGC | GCCCCCTGGTGGCCG |
| NHLH2_V$HEN1_02_Transfac\|NHLH1_1 | AGGGGACGCAGCTGCGCCCCCT | AGGGGGCGCAGCTGCGTCCCCT |
| SOX13_V$SOX5_01_Transfac\|SOX5_1 | GTATTGTTAA | TTAACAATAC |
| USF1_V$USF_01_Transfac\|MYC_known3 | AGATCACGTGATCT | AGATCACGTGATCT |
| SOX15_SOX15_a_HocoMoco | AACAATG | CATTGTT |
| IRF4_GM12878_IRF4_HudsonAlpha_ChIP-seq | AATGTGGAAATGAGTCAG | CTGACTCATTTCCACATT |
| NKX2-5_NKX25_f1_HocoMoco\|NKX2-5_V$NKX25_01_Transfac\|NKX2-5_1 | CACTTGA | TCAAGTG |
| SOX13_Sox13_1718_PBM | GAACAATA | TATTGTTC |
| ZKSCAN1_pTH2280_PBM | ATGTGCACAT | ATGTGCACAT |
| VENTX_VENTX_1_SELEX\|VENTX_1 | ACCGATTAG | CTAATCGGT |
| MYC_K562_CMYC_UT-A_ChIP-seq | GCCACGTGGCC | GGCCACGTGGC |
| UNCX_1 | CATAATTAATTAACGCG | CGCGTTAATTAATTATG |

TABLE 5-continued

Transcription Factor Binding Sites of Synthetic Promoters

| Name | Binding Site Sequence | Reverse Complement |
| --- | --- | --- |
| SREBF2_SRBP1_f2_HocoMoco | CTCACCCCACC | GGTGGGGTGAG |
| NR2E1_dsf_SANGER_5_FBgn0015381_B1H\|NR2E1_tll_NAR_FBgn0003720_B1H\|NR2E1_MA0459.1_B1H | AAAAGTCAAA | TTTGACTTTT |
| HNF1A_Tcf1_2666_PBM\|HMBOX1_Hmbox1_2674_PBM | CTAGTTAA | TTAACTAG |
| CXXC1_CXXC1_si_HocoMoco | CGTTGGC | GCCAACG |
| PAX6_V$PAX6_01_Transfac\|PAX6_1 | AATTTTCACGCATGAGTCAC | GTGAACTCATGCGTGAAAATT |
| NR2F2_pTH6747_PBM | AGGGGTCA | TGACCCCT |
| STAT3_HeLa-S3_STAT3_Stanford_ChIP-seq | CATTTCCCGGAAG | CTTCCGGGAAATG |
| ATF3_known1 | CTCTGACGTCACCC | GGGTGACGTCAGAG |
| TCF7L2_known2 | CTTTGA | TCAAAG |
| T_MA0009.1_SELEX\|T_2 | CTAGGTGTGAA | TTCACACCTAG |
| FOXD1_FOXJ2_f1_HocoMoco | TAAATAAACA | TGTTTATTTA |
| FOSL1_HeLa-S3_CFOS_Stanford_ChIP-seq | GATGACTCACACA | TGTGTGAGTCATC |
| NFATC1_NFAC4_a_HocoMoco | AAATTTTCCT | AGGAAAATTT |
| TFAP2A_Tcfap2c_2912_PBM | CGCCCGAGGC | GCCTCGGGCG |
| SOX2_1 | CCTTTGTTATGCAAA | TTTGCATAACAAAGG |
| TBX1_TBX1_1_SELEX\|TBX1_1 | AGGTGTGAAAAAGGTGTGA | TCACACCTTTTTCACACCT |
| BHLHE40_known2 | GGAAGAGTCACGTGACCAATAC | GTATTGGTCACGTGACTCTTCC |
| EGR3_V$NGF1C_01_Transfac\|EGR4_1 | ATGCGTGGGCGG | CCGCCCACGCAT |
| ATOH7_ato_da_SANGER_5_2_FBgn0010433_B1H\|TCF4_ato_da_SANGER_5_2_FBgn0000413_B1H\|OLIG2_Oli_da_SANGER_5_3_FBgn0032651_B1H\|TCF4_Oli_da_SANGER_5_3_FBgn0000413_B1H | ACATCTGTC | GACAGATGT |
| REST_U87_N_RSF_HudsonAlpha_ChIP-seq | ACCATGGACAGCGCC | GGCGCTGTCCATGGT |
| RXRA_known6 | AAAGGTCAAAGGTCAAC | GTTGACCTTTGACCTTT |
| ETV6_ETV7_si_HocoMoco | GCCACAGGAAGTAACAC | GTGTTACTTCCTGTGGC |
| TCF4_Oli_da_SANGER_5_1_FBgn0000413_B1H\|OLIG2_Oli_da_SANGER_5_1_FBgn0032651_B1H | CACCATATGGC | GCCATATGGTG |
| RUNX2_3 | ACCACAA | TTTGTGGT |
| STAT_disc6 | AGGCAGGAA | TTCCTGCCT |
| NR5A1_NR5A2_f1_HocoMoco | TGGCCTTGAA | TTCAAGGCCA |
| NKX2-6_MA0247.2_ChIP-chip | CCACTTGAAA | TTTCAAGTGG |
| ZFY_ZFX_a_HocoMoco | GCCGAGGCCTGGGGCCCCC | GGGGGCCCCAGGCCTCGGC |

TABLE 5-continued

Transcription Factor Binding Sites of Synthetic Promoters

| Name | Binding Site Sequence | Reverse Complement |
|---|---|---|
| CTCF_SAEC_CTCF_UW_ChIP-seq\|CTCF_HPF_CTCF_UW_ChIP-seq | CCACCAGGGGGCG | CGCCCCCTGGTGG |
| NHLH1_2 | ATGGGGCGCAGCTGCGCCCCTC | GAGGGGCGCAGCTGCGCCCCAT |
| E2F6_K562_E2F6_HudsonAlpha_ChIP-seq | CTTCCCGCCCC | GGGGCGGGAAG |
| CTCF_H1-hESC_CTCF_Broad_ChIP-seq\|CTCF_MCF-7_CTCF_UT-A_ChIP-seq\|CTCF_N_HEK_CTCF_Broad_ChIP-seq\|CTCF_H1-hESC_CTCF_HudsonAlpha_ChIP-seq\|CTCF_GM12874_CTCF_UW_ChIP-seq\|CTCF_GM12872_CTCF_UW_ChIP-seq\|CTCF_Caco-2_CTCF_UW_ChIP-seq\|CTCF_GM12865_CTCF_UW_ChIP-seq\|CTCF_HA-sp_CTCF_UW_ChIP-seq\|CTCF_K562_CTCF_UT-A_ChIP-seq\|CTCF_GM12875_CTCF_UW_ChIP-seq\|CTCF_AoAF_CTCF_UW_ChIP-seq\|CTCF_K562_CTCF_UW_ChIP-seq\|CTCF_HRE_CTCF_UW_ChIP-seq\|CTCF_BJ_CTCF_UW_ChIP-seq\|SMC3_disc1 | GCCACCAGGGGCGC | GCGCCCCTGGTGGC |
| POU3F3_V$OCT1_05_Transfac\|POU2F2_known5 | AATATGCAAATTAT | ATAATTTGCATATT |
| GMEB2_pTH9211_PBM | TACGTAA | TTACGTA |
| ESR2_HepG2_ERRA_Stanford_ChIP-seq | GGCCCAAGGTCACA | TGTGACCTTGGGCC |
| DLX1_DLX3_do_HocoMoco | GATAATTACA | TGTAATTATC |
| REST_disc7 | ACAGCGTC | GACGCTGT |
| POU1F1_POU1F1_2_SELEX\|POU1F1_5 | AATATGCAAATTAG | CTAATTTGCATATT |
| NR6A1_V$GCNF_01_Transfac\|N_R6A1_1 | CTCAAGTTCAAGTTCAC | GGTGAACTTGAACTTGAG |
| FOXD1_FOXC2_1_SELEX\|FOXD1_FOXC1_2_SELEX\|FOXC1_4\|FOXC2_1 | TGTAAATATTGACA | TGTCAATATTTACA |
| JUN_MA0488.1_ChIP-seq | AAGATGATGTCAT | ATGACATCATCTT |
| ZIC2_2\|Z1C3_2 | ACCCCCCCGGGGGGG | CCCCCCCGGGGGGGT |
| GATA2_pnr_SANGER_5_FBgn0003117_B1H | CAGATAA | TTATCTG |
| MEF2_disc1 | TGCTAAAAATAGCAA | TTGCTATTTTTAGCA |
| MEF2B_GM12878_MEF2C_HudsonAlpha_ChIP-seq | ATGCCAAAATAGCA | TGCTATTTTGGCAT |
| BARHL2_BARHL2_3_SELEX\|BARHL2_4 | CATTTAACACCAATTA | TAATTGGTGTTAAATG |
| RFX8_RFX2_1_SELEX\|RFX8_RFX5_1_SELEX\|RFX8_RFX3_1_SELEX\|RFX8_RFX4_1_SELEX\|RFX2_1\|RFX3_2\|RFX5_known6\|RFX5_known8 | CGTTGCCATGGCAACG | CGTTGCCATGGCAACG |
| RFX8_Rfx3_1_SELEX\|RFX8_Rfx2_1_SELEX\|RFX8_YLR176C_1478_DeBoer11\|RFX2_3\|RFX3_4 | CGTTGCCATGGCAACC | GGTTGCCATGGCAACG |
| ZEB1_V$AREB6_04_Transfac\|ZEB1_known4 | CTGAAACAG | CTGTTTCAG |
| GSX2_1 | AGGTTAATTAGCTGAT | ATCAGCTAATTAACCT |
| STAT5B_STA5B_f1_HocoMoco | AATTCCCAGAAAA | TTTTCTGGGAATT |
| GATA2_GATA3_2_SELEX\|GATA_known20 | AGATAAGG | CCTTATCT |
| GATA2_GATA3_1_SELEX\|GATA2_GATA5_1_SELEX\|GATA2_MA0037.2_ChIP-seq\|GATA2_GATA4_1_SELEX\|GATA_known19\|GATA_known21\|GATA_known22 | AGATAAGA | TCTTATCT |
| CTCF_Osteobl_CTCF_Broad_ChIP-seq | AGCGCCCCTGGTGGCA | TGGCCACCAGGGGCGCT |

TABLE 5-continued

Transcription Factor Binding Sites of Synthetic Promoters

| Name | Binding Site Sequence | Reverse Complement |
|---|---|---|
| RORB_RORA_f1_HocoMoco | AAAACTAGGTCA | TGACCTAGTTTT |
| GATA_disc5 | AGCCAAACC | GGTTTGGCT |
| CACBP_1 | CCCACCCTC | GAGGGTGGG |
| STAT_known16 | CTTCCTGGAA | TTCCAGGAAG |
| IRF8_IRF8_si_HocoMoco | CAGTTTCAGTTTCTC | GAGAAACTGAAACTG |
| HOXD12_HOXD12_1_SELEX\|HOXD12_HOXC12_1_SELEX\|HOXD12_HOXD12_4_SELEX\|HOXC12_21HOXD12_2 | GTAATAAAA | TTTTATTAC |
| HOXB13_Hoxd13_2356_PBM\|HOXB13_Hoxa13_3126_PBM | CTCATAAAA | TTTTATGAG |
| AIRE_2 | GGTTATTAATTGGTTATATTGGTTA | TAACCAATATAACCAATTAATAACC |
| SMC3_disc4 | CTGGTGGC | GCCACCAG |
| MYC_known1 | CGACCACGTGGTCA | TGACCACGTGGTCG |
| BHLHE40_BHLHB3_1_SELEX\|BHLHE41_1 | GGCACGTGAC | GTCACGTGCC |
| FOXD1_I$CROC_01_Transfac | AAAAATAAATATAAGG | CCTTATATTTATTTTT |
| TBX3_pTH9182_PBM1TBX3_pTH9244_PBM | GAGGTGTCAA | TTGACACCTC |
| CEBPA_V$CEBPB_01_Transfac\|CEBPB_known1 | ACATTGCACAATCT | AGATTGTGCAATGT |
| MAX_dm_Max_SANGER_10_FBgn0017578_B1H | ACCACGTGTC | GACACGTGGT |
| FOSL1_HUVEC_CFOS_UCD_ChIP-seq | ATGACTCACTC | GAGTGAGTCAT |
| SOX11_Sox4_2941_PBM | AGAACAATG | CATTGTTCT |
| GLI_1 | CCTGGGTGGTCC | GGACCACCCAGG |
| STAT1_V$STAT1_01_Transfac\|STAT_known2 | CCCCATTTCCCGGAAATCACC | GGTGATTTCCGGGAAATGGGG |
| HOXC10_Hoxa9_2622_PBM | GCCATAAA | TTTATGGC |
| GMEB2_GMEB2_1_SELEX\|GMEB2_1 | GTACGTAA | TTACGTAC |
| ESR2_ESR1_do_HocoMoco | AGGTCACGGTGACCTGGG | CCCAGGTCACCGTGACCT |
| HOXA4_GSX1_1_SELEX1GSX1_1 | CCTAATTAAA | TTTAATTAGG |
| PITX2_Pitx1_2312_PBM\|DMBX1_Dmbx1_2277_PBM | GGGGATTAA | TTAATCCCC |
| RORB_pTH6142_PBM\|NR2F2_Nr2f2_2192_PBM\|NR2F2_pTH3811_PBM\|RARG_Rara_1051_PBM | GAGGTCAC | GTGACCTC |
| NR2C2_pTH3466_PBM | GAGGTCAA | TTGACCTC |
| ETV5_HEK293b_ELK4_UCD_ChIP-seq | CCACTTCCGG | CCGGAAGTGG |
| CREB3L2_CREB3L1_6_SELEX\|CREB3L2_CREB3L1_4_SELEX\|CREB3L2_CREB3L1_1_SELEX\|CREB3L1_1\|CREB3L1_4 | ATGCCACGTCATCA | TGATGACGTGGCAT |
| ATF5_Atf4_1_SELEX\|ATF4_3 | AGGATGATGCAATC | GATTGCATCATCCT |
| FOXO6_FOXO1_si_HocoMoco | AAAAGTAAACAAACC | GGTTTGTTTACTTTT |
| ONECUT3_HNF6_f1_HocoMoco | AAAAAATCAATAAA | TTTATTGATTTTTT |
| BACH1_V$BACH2_01_Transfac\|BACH2_1 | CGTGAGTCATC | GATGACTCACG |
| HOXA10_1 | TAGGTAATAAAATTCA | TGAATTTTATTACCTA |
| TFAP2A_AP2C_f1_HocoMoco | GCCCCAGGC | GCCTGGGGC |
| CRX_2 | AGGCTAATCCCCAACG | CGTTGGGGATTAGCCT |

TABLE 5-continued

Transcription Factor Binding Sites of Synthetic Promoters

| Name | Binding Site Sequence | Reverse Complement |
|---|---|---|
| HOXD13_1 | AGAATTTTATTGGTAG | CTACCAATAAAATTCT |
| HIF1A::ARNT_1 | GCACGTCC | GGACGTGC |
| SOX2_SOX21_1_SELEX\|SOX21_2 | AACAATGGTAGTGTT | AACACTACCATTGTT |
| ZNF350_ZN350_f1_HocoMoco | ACGGGGCGCAGGGATTTGTTGCCC | GGGCAACAAATCCCTGCGCCCCGT |
| HOXC5_ftz_FlyReg_FBgn0001077_B1H | GGCAATTA | TAATTGCC |
| YY1_disc3 | CGCCGCCGCC | GGCGGCGGCG |
| TFAP4_V$AP4_C15_Transfac\|TFAP4_V$AP4_C16_Transfac\|TFAP4_2 | ACCAGCTGAG | CTCAGCTGGT |
| TFAP2A_AP2B_f1_HocoMoco | GCCCCGGGC | GCCCGGGGC |
| ZNF350_1 | AAAGGGCTGCGGCCC | GGGCCGCAGCCCTTT |
| LCOR_pTH9220_PBM | AATTTTGGCA | TGCCAAAATT |
| YBX1_YBOX1_f2_HocoMoco | GGCCAATCCCC | GGGGATTGGCC |
| JUN_K562_JUNB_UChicago_ChIP-seq | AAGGATGAGTCACCG | CGGTGACTCATCCTT |
| USF1_H1-hESC_USF2_Stanford_ChIP-seq | CGCGGTCACGTGACCC | GGGTCACGTGACCGCG |
| DMRTA1_1 | AAATTGTTACATT | AATGTAACAATTT |
| LCOR_pTH8649_PBM | AATTTTGGCT | AGCCAAAATT |
| IKZF1_V$LYF1_01_Transfac\|IKZF1_2 | TCTCCCAAA | TTTGGGAGA |
| SPIC_K562_PU1_HudsonAlpha_ChIP-seq\|SPIC_SRP005406_SPI1_ChIP-seq | AAAAAGAGGAAGTGG | CCACTTCCTCTTTTT |
| CTCF_MA0139.1_ChIP-seq\|CTCF_CTCF_f2_HocoMoco\|CTCF_known1 | TAGCGCCCCTGGTGGCCA | TGGCCACCAGGGGGCGCTA |
| ZBTB6_ZBTB6_si_HocoMoco | AGATGATAGAGCC | GGCTCTATCATCT |
| POU4F1_pTH8341_PBM | ATATGCAT | ATGCATAT |
| GATA2_MA0036.2_ChIP-seq | ACAGATAAGAATCT | AGATTCTTATCTGT |
| ESR2_Mv67_ChIP-seq | CCAAGGTCAC | GTGACCTTGG |
| NFIL3_pTH3041_PBM | ACGTAATA | TATTACGT |
| ASCL2_1 | CAGGAGCAGCTGCTGAG | CTCAGCAGCTGCTCCTG |
| RFX5_disc1 | CCCTAGCAAC | GTTGCTAGGG |
| RFX8_RFX3_f1_HocoMoco | GGTTGCCATGGTAA | TTACCATGGCAACC |
| GBX2_Unpg_Cell_FBgn0015561_B1H | CTTAATTA | TAATTAAG |
| TLX3_TLX1_J2_HocoMoco | CCTTGGCAACTTGCCAG | CTGGCAAGTTGCCAAGG |
| CUX1_CUX1_f1_HocoMoco | AGGGGGATCGATGG | CCATCGATCCCCCT |
| GATA2_Gata3_1024_PBM | CTTATCTCTA | TAGAGATAAG |
| KLF4_MA0493.1_ChIP-seq | GGCCACACCCA | TGGGTGTGGCC |
| EVX2_EVX1_1_SELEX\|EVX2_EVX2_1_SELEX\|EVX1_2\|EVX2_2 | GCTAATTACC | GGTAATTAGC |
| OSR2_1 | ATGTACAGTAGCAAAG | CTTTGCTACTGTACAT |
| FOXD1_Mv69_ChIP-seq | CTAAGTAAACAAG | CTTGTTTACTTAG |
| NKX2-5_pTH5945_PBM | AACCACTTAAG | CTTAAGTGGTT |

TABLE 5-continued

Transcription Factor Binding Sites of Synthetic Promoters

| Name | Binding Site Sequence | Reverse Complement |
| --- | --- | --- |
| LHX6_1 | GAGCGTTAATTAATGTA | TACATTAATTAACGCTC |
| NFKB1_NFKB1_f1_HocoMoco\|NFKB_known8 | GGGGAATCCCC | GGGGATTCCCC |
| MXI1_Mv93_ChIP-seq | GGTTGCCATGGCGAC | GTCGCCATGGCAACC |
| RARG_Rarg_3_SELEX\|RARG_9 | AAGGTCACGAAAGGTCA | TGACCTTTCGTGACCTT |
| HOXA3_2 | GTTAATTACCTCCA | TGGAGGTAATTAAC |
| MYOD1_Myf6_3824_PBM | ACACCTGTC | GACAGGTGT |
| HNF4G_HNF4A_6_SELEX\|HNF4_known21 | GGGTCAAAGGTCAA | TTGACCTTTGGACCC |
| RELA_GM10847_NFKB_Stanford_ChIP-seq | AGGGGATTTCCCAG | CTGGGAAATCCCCT |
| TATA_known4 | GTATAAA | TTTATAC |
| FOXD1_FOXK1_1_SELEX\|FOXK1_2 | ATTGTGTCCG | CGGACACAAT |
| ATF5_pTH1014_PBM | AGTTACGTAATTG | CAATTACGTAACT |
| ZBTB7C_ZBTB7C_1_SELEX\|ZBTB7B_ZBTB76_1_SELEX\|ZBTB7A_known4\|ZBTB7C_1 | GCGACCACCGAA | TTCGGTGGTCGC |
| RARG_Rarg_1_SELEX\|RARG_7 | AAGGTCAAAGGTCAA | TTGACCTTTGACCTT |
| SOX10_2 | ACAAAG | CTTTGT |
| FOXO6_FOXO4_1_SELEX\|FOXO6_FOXO1_2_SELEX\|FOXO6_FOXO3_1_SELEX\|FOXO6_FOXO6_1_SELEX\|FOXO1_4\|FOXO3_4\|FOXO4_3\|FOXO6_1 | GTAAACATGTTTAC | GTAAACATGTTTAC |
| BCL_disc9 | CTGCACCCGCTGCC | GGCAGCGGGTGCAG |
| HDAC2_disc1 | CAGATAAGGC | GCCTTATCTG |
| USF2_MA0526.1_ChIP-seq | GGTCACATGAC | GTCATGTGACC |
| FOSL1_pTH5108_PBM\|ATF3_pTH5018_PBM | ACGTCATC | GATGACGT |
| ESRRG_ERR_SANGER_5_FBgn0035849_B1H\|ESRRG_pTH3841_PBM\|NR5A1_pTH3468_PBM\|NR5A1_Mw160_ChIP-seq\|NR5A1_1 | CAAGGTCA | TGACCTTG |
| AHR_2 | CTTGCGTGAGA | TCTCACGCAAG |
| E2F3_E2F2_1022_PBM | ACGCGCCAAA | TTTGGCGCGT |
| PAX6_4 | GTCAATTAATTAATCA | TGATTAATTAATTGAC |
| HES4_pTH5059_PBM\|HES7_pTH5260_PBM | GACGCGTGCC | GGCACGCGTC |
| BARX1_BARX1_2_SELEX\|BARX1_3 | CTAATTGC | GCAATTAG |
| HESX1_HESX1_f1_HocoMoco | AGGCCACGTGCCGGAT | ATCCGGCACGTGGCCT |
| SRF_V$SRF_C16_Transfac\|SRF_known2 | GGCCATATAAGGAC | GTCCTTATATGGCC |
| ZNF410_ZNF410_1_SELEX\|ZNF410_2 | GAGTATTATGGGATGGA | TCCATCCCATAATACTC |
| NKX3-1_3 | ATCCTTAAGTGGTTAAG | CTTAACCACTTAAGGAT |
| ETS_known4 | ACAGGAAGTGATTGC | GCAATCACTTCCTGT |
| NR4A2_NR4A2_3_SELEX\|NR4A_known4 | TGACCTTTAAA | TTTAAAGGTCA |
| HOXC10_HOXC11_4_SELEX\|HOXC10_HOXC11_2_SELEX\|HOXC11_3\|HOXC11_5 | AGCAATAAAAA | TTTTTATTGCT |
| TBX1_TBX1_2_SELEX\|TBX1_TBX20_2_SELEX\|TBX22_TBX15_1_SELEX\|TBX15_1\|TBX1_2\|TBX20_2 | AGGTGTGAAATTCACACCT | AGGTGTGAATTTCACACCT |

TABLE 5-continued

Transcription Factor Binding Sites of Synthetic Promoters

| Name | Binding Site Sequence | Reverse Complement |
|---|---|---|
| BCL_disc5 | CTGATAAG | CTTATCAG |
| POU2F2_MA0507.1_ChIP-seq | ATATGCAAATGAA | TTCATTTGCATAT |
| IRX3_Irx3_0920_PBM | ATCATGTAAT | ATTACATGAT |
| MYB_6 | AAAATAACGGTTTCCAT | ATGGAAACCGTTATTTT |
| POU3F3_GM12891_POU2F2_HudsonAlpha_ChIP-seq\|POU3F3_GM12891_OCT2_HudsonAlpha_ChIP-seq | ATATGCAAATGAG | CTCATTTGCATAT |
| GSC_GSC2_1_SELEX\|GSC2_1 | CCTAATCCGC | GCGGATTAGG |
| SRF_known5 | CATCTCCTTATATGG | CCATATAAGGAGATG |
| LHX1_pTH6478_PBM | CTAATTACGC | GCGTAATTAG |
| AR_NR3C2_1_SELEX\|NR3C2_1 | GGGAACACAATGTTCCC | GGGAACATTGTGTTCCC |
| KLF4_MA0039.2_ChIP-seq\|KLF4_1 | GCCCCACCCA | TGGGTGGGGC |
| LIN54_pTH8399_PBM | ATTCAAAT | ATTTGAAT |
| BCL6_SRP001843_Bc16_IgG_LPSstim_ChIP-seq | AGGAGAGAAGGGGAA GGGAAGAAAGGGAGA | TCTCCCTTTCTTCCCTTCC CCTTCTCTCCT |
| RREB1_V$RREB1_01_Transfac\|RREB1_1 | CCCCAAACCACCCC | GGGGTGGTTTGGGG |
| SOX7_1 | AATAAAGAACAATAGAA TTTCA | TGAAATTCTATTGTTCTT TATT |
| HIC1_5 | ATGCCAACC | GGTTGGCAT |
| BSX_1 | CAGGTAATTACCTCAG | CTGAGGTAATTACCTG |
| AP1_disc8 | AAGGAAATGA | TCATTTCCTT |
| POU3F3_POU3F3_1_SELEX\|POU3F3_2 | AAATTAGCATAAT | ATTATGCTAATTT |
| SRF_known8 | TTCCATATATGGAA | TTCCATATATGGAA |
| PURA_PURA_f1_HocoMoco | CCCTGCCCCCCCCTTCC | GGAAGGGGGGGCAG GG |
| HMX2_1\|HMX3_2 | ACAAGCAATTAAAGAAT | ATTCTTTAATTGCTTGT |
| SCRT2_SCRT2_1_SELEX\|SCRT2_1 | ATGCAACAGGTGG | CCACCTGTTGCAT |
| C11orf9_pTH8654_PBM\|C11orf9_pTH9310_PBM | TGGTACCA | TGGTACCA |
| SOX9_SOX8_7_SELEX\|SOX9_SOX8_2_SELEX\|SOX8_3\|SOX8_8 | ATGAATTGCAGTC | GACTGCAATTCAT |
| SETDB1_disc2 | GCGCACGCGC | GCGCGTGCGC |
| PBX3_disc3 | AGTGACAGGCCCGCCG GCCAA | TTGGCCGGCGGGCCTGT CACT |
| E2F6_MA0471.1_ChIP-seq\|E2F4_MA0470.1_ChIP-seq | CCTTCCCGCCC | GGGCGGGAAGG |
| ATF3_JDP2_4_SELEX\|ATF3_Jdp2_2_SELEX\|XBP1_XBP1_1_SELEX\|ATF3_JDP2_2_SELEX\|JDP2_3\|JDP2_5\|JDP2_7\|XBP1_3 | GATGACGTCATC | GATGACGTCATC |
| HOXC5_HXB6_f1_HocoMoco | AATGATTGATGCA | TGCATCAATCATT |
| KLF14_KLF14_1_SELEX\|KLF14_1 | AAGGGGGCGTGGCC | GGCCACGCCCCCTT |
| FOXK1_1 | AAAATGTAAACAAACAG | CTGTTTGTTTACATTTT |
| HOXC10_Hoxc10_1_SELEX\|HOXC10_5 | GTCATAAAAA | TTTTTATGAC |
| YY1_pho1_SOLEXA_5_FBgn0035997_B1H | AACAAATGGCGGCC | GGCCGCCATTTGTT |
| ESR2_V$ER_C16_Transfac\|ESRRA_known1 | ACAGGTCACTGTGACCT GA | TCAGGTCACAGTGACCT GT |

TABLE 5-continued

Transcription Factor Binding Sites of Synthetic Promoters

| Name | Binding Site Sequence | Reverse Complement |
|---|---|---|
| RARG_Rara_1_SELEX\|RARA_8 | AAAGGTCAAGAGAGGTCA | TGACCTCTCTTGACCTTT |
| EGR1_known5 | CCGCCCACGCA | TGCGTGGGCGG |
| CENPB_CENPB_1_SELEX\|CENPB_1 | CCCGCATACAACGAA | TTCGTTGTATGCGGG |
| BATF_disc2 | AAGTTTCAC | GTGAAACTT |
| TCF4_Fer1_da_SANGER_10_FBgn0000413_B1H\|PTF1A_Fer1_da_SANGER_10_FBgn0037475_B1H | AACACCTGTCA | TGACAGGTGTT |
| IRF_disc3 | AAGTGAAAGTGAAAG | CTTTCACTTTCACTT |
| MNT_pTH4588_PBM | GCACGTGCA | TGCACGTGC |
| RXRA_disc5 | AGAGGGCG | CGCCCTCT |
| POU3F3_POU2F1_1_SELEX\|POU2F2_known15 | AATATGCAAATT | AATTTGCATATT |
| PBX3_disc2 | CTGTCACTCA | TGAGTGACAG |
| RELA_GM12891_NFKB_Stanford_ChIP-seq | CTGGGAAATCCCCTA | TAGGGGATTTCCCAG |
| NR2C2_disc1 | TGACCCGGAA | TTCCGGGTCA |
| CUX1_CUX2_1_SELEX\|CUX2_1 | ATCGATAAAATTATCGAT | ATCGATAATTTTATCGAT |
| ZNF143_ZN143_si_HocoMoco | GCAAGGCATTCTGGGAAGTGTA | TACACTTCCCAGAATGCCTTGC |
| MSX1_Dr_Cell_FBgn0000492_B1H | GACCAATTA | TAATTGGTC |
| ATF3_K562_ATF3_Harvard_ChIP-seq | GGTGACGTGA | TCACGTCACC |
| MYC_known12 | CACGTGC | GCACGTG |
| SP2_disc1 | AGCCAATGGGA | TCCCATTGGCT |
| ETV5_HeLa-53_GABP_HudsonAlpha_ChIP-seq | GAACCGGAAGTGGC | GCCACTTCCGGTTC |
| NFY_disc1 | ACCAGCCAATCAGAG | CTCTGATTGGCTGGT |
| TFAP4_4 | ACCAGCTGC | GCAGCTGGT |
| PAX9_GM12891_PAX5C20_HudsonAlpha_ChIP-seq | CAGCCAAGCGTGACC | GGTCACGCTTGGCTG |
| FOXO6_V$FOXO1_01_Transfac\|FOXO1_1 | CATAAACAAA | TTTGTTTATG |
| SPI1_known1 | AGAGGAAG | CTTCCTCT |
| BARX1_BARX2_si_HocoMoco | CAATTAATGA | TCATTAATTG |
| MAX_MAX_2_SELEX\|MYC_known21 | ACCACGTGCT | AGCACGTGGT |
| HSF1_HepG2_HSF1_Stanford_ChIP-seq | GGGATTCGAACCCGGAC | GTCCCGGGTTCGAATCCC |
| RELA_GM18526_NFKB_Stanford_ChIP-seq | AAGGGGATTTCCAAA | TTTGGAAATCCCCTT |
| STAT_known13 | CATTTCTA | TAGAAATG |
| VDR_VDR_f1_HocoMoco\|RARG_RARA_f1_HocoMoco\|RARG_RARGJ1_HocoMoco\|RORB_pTH5508_PBM | GAGGTCA | TGACCTC |
| RELA_GM18505_NFKB_Stanford_ChIP-seq | AAGGGGATTTCCAAG | CTTGGAAATCCCCTT |
| FOXP4_FOXP2_si_HocoMoco | AGTAAACAA | TTGTTTACT |
| CTCF_AG10803_CTCF_UW_ChIP-seq | GCCACTAGAGGGC | GCCCTCTAGTGGC |
| NFATC1_NFAC3_f1_HocoMoco | AGTTTTCCA | TGGAAAACT |
| HOXA4_GSX2_1_SELEX\|GSX2_2\|HOXB5_2 | ACTAATTAAA | TTTAATTAGT |

TABLE 5-continued

Transcription Factor Binding Sites of Synthetic Promoters

| Name | Binding Site Sequence | Reverse Complement |
|---|---|---|
| HOXC5_HOXB5_1_SELEX | ACTAATTAAG | CTTAATTAGT |
| TP73_GSE15704_TP73_vehicle_ChIP-seq | GGACATGCCCAGGCATGCC | GGCATGCCTGGGCATGTCC |
| FOXJ1_2 | AAAGTAAACAAAAATT | AATTTTTGTTTACTTT |
| ZNF740_Zfp740_0925_PBM | CCCCCCCACG | CGTGGGGGGG |
| ZNF740_pTH2857_PBM | CCCCCCCACA | TGTGGGGGGG |
| YY2_pho_FlyReg_FBgn0002521_B1H | GAAGCCATAACGGC | GCCGTTATGGCTTC |
| FOXD1_FOXB1_2_SELEX\|FOXB1_2 | TATGTAAATATTGACATA | TATGTCAATATTTACATA |
| E2F_known16\|E2F_known20 | CGCGCCAAA | TTTGGCGCG |
| ENSG00000250096_RUNX3_2_SELEX\|ENSG00000250096_RUNX3_4_SELEX\|RUNX3_2\|RUNX3_4 | AAACCGCAAA | TTTGCGGTTT |
| RFX8_MA0600.1_ChIP-seq | CCGCGGTTGCCATGGCAAC | GTTGCCATGGCAACCGCGG |
| KLF4_CG12029_SANGER_10_FBgn0035454_B1H | GCCACACCCAC | GTGGGTGTGGC |
| XBP1_pTH5019_PBM | ACACGTCAC | GTGACGTGT |
| HMX1_HMX3_1_SELEX\|HMX3_3 | AGCAATTAACA | TGTTAATTGCT |
| NRF1_known1 | CGCATGCGCA | TGCGCATGCG |
| AP1_disc10 | CCCGCCCCC | GGGGGCGGG |
| USF2_USF2_f1_HocoMoco | GCCCACGTGAC | GTCACGTGGGC |
| NFE2_N_F2L2_si_HocoMoco | CATGACTCAGCA | TGCTGAGTCATG |
| ETV4_1 | ACATCCT | AGGATGT |
| CR936877.3_RXRGJ1_HocoMoco | GGTCAAAGGTCAC | GTGACCTTTGACC |
| REST_disc1 | GTCCATGGTGCTGAA | TTCAGCACCATGGAC |
| ZBTB1_pTH2366_PBM | GTCCCGCAAC | GTTGCGGGAC |
| OVOL1_ovo_SOLEXA_5_FBgn0003028_B1H | AGTACCGTTATTTG | CAAATAACGGTACT |
| PAX9_PAX9_1_SELEX\|PAX9_PAX1_1_SELEX\|PAX1_2\|PAX9_1 | CGTCACGCATGACTGCA | TGCAGTCATGCGTGACG |
| STAT2_K562_STAT2_Stanford_ChIP-seq | GAAAATGAAACTGAA | TTCAGTTTCATTTTC |
| PTEN_1 | CCCCAAGTGAAGG | CCTTCACTTGGGG |
| RARG_RARG_3_SELEX\|RARG_3 | AAGGTCACCAGAGGTCA | TGACCTCTGGTGACCTT |
| TFAP2A_TFAP2C_2_SELEX\|TFAP2A_TFAP2C_6_SELEX\|TFAP2A_TFAP26_2_SELEX\|TFAP26_3\|TFAP2_known15\|TFAP2_known19 | AGCCTCAGGCA | TGCCTGAGGCT |
| LBX2_LBX2_1_SELEX\|LBX2_2 | CTCGACCTAATTA | TAATTAGGTCGAG |
| PAX9_pTH8679_PBM | CAGTCAAGCG | CGCTTGACTG |
| NR3C1_known10 | CCCCCAAGAACACCATGTCCCCCCCCC | GGGGGGGGGACATGGTGTTCTTGGGGG |
| GFI16_1 | TAAATCACTGCA | TGCAGTGATTTA |
| FOXD1_Foxg1_2_SELEX\|FOXG1_4 | CCGGACACAATC | GATTGTGTCCGG |
| DMBX1_ARX_1_SELEX\|DMBX1_CART1_1_SELEX\|ARX_2\|ALX1_6 | TTAATTAAATTAA | TTAATTTAATTAA |

TABLE 5-continued

Transcription Factor Binding Sites of Synthetic Promoters

| Name | Binding Site Sequence | Reverse Complement |
|---|---|---|
| REST_MA0138.2_ChIP-seq\|REST_PANC-1_NRSF_HudsonAlpha_ChIP-seq\|REST_known4 | GGCGCTGTCCATGGTGCTGAA | TTCAGCACCATGGACAGCGCC |
| RFX8_HeLa-S3_RFX5_Stanford_ChIP-seq | CCTAGCAACAGATGA | TCATCTGTTGCTAGG |
| SIX5_Six4_SOLEXA_FBgn0027364_B1H | AATTGATA | TATCAATT |
| TP63_P63_si_HocoMoco | GAGACATGTCC | GGACATGTCTC |
| HINFP_MA0131.1_SELEX\|HINFP_1 | GCGGACGTTA | TAACGTCCGC |
| MITF_MITF_f1_HocoMoco | ATCACATGAC | GTCATGTGAT |
| PAX9_V$PAX5_01_Transfac\|PAX5_known1 | GGGGCGGCTACGCATCATTGCGCCTCGA | TCGAGGCGCAATGATGCGTAGCCGCCCC |
| NR3C1_known12 | TCGTGCTCA | TGAGCACGA |
| BHLHE40_Blhb2_2_SELEX | AGCACGTGAC | GTCACGTGCT |
| FOXD1_T-47D_FOXA1_HudsonAlpha_ChIP-seq | CTGAGTAAACA | TGTTTACTCAG |
| LMO2_1 HMX1_Hmx1_3423_PBM | CGCCAGGTGCAG AAGCAATTAA | CTGCACCTGGCG TTAATTGCTT |
| BHLHE40_disc2 | CAGCAGCCGCCGGCGCG | CGCGCCGGCGGCTGCTG |
| IRX2_1 | AATTTTACATGTATTTA | TAAATACATGTAAAATT |
| ESR2_pTH6055_PBM | CAGGTCAA | TTGACCTG |
| TCF4_pTH4580_PBM | GAACACCTGC | GCAGGTGTTC |
| HOXC5_I$UBX_01_Transfac | ACGAAGCCATTAAGCCCTC | GAGGGCTTAATGGCTTCGT |
| STAT_known10 | GATTTCCC | GGGAAATC |
| EGR3_EGR3_1_SELEX\|EGR3_EGR2_2_SELEX\|EGR1_known11\|EGR3_2 | AGTGCGTGGGCGTAG | CTACGCCCACGCACT |
| E2F3_E2F3_3_SELEX\|E2F_known26 | AATTTTGGCGCCAAAACT | AGTTTTGGCGCCAAAAT T |
| IRF6_1 | ACTTTGGTTTCGATCAG | CTGATCGAAACCAAAGT |
| NFATC1_NFATC1_1_SELEX\|NFATC1_1 | AATGGAAAATTATTTTCCCT | AGGGAAAATAATTTTCCATT |
| NROB1_NROB1_si_HocoMoco | GCGTGGGAGA | TCTCCCACGC |
| HIC1_HIC1_si_HocoMoco | GGGCAACCC | GGGTTGCCC |
| TCF4_net_da_SANGER_10_FBgn0000413_B1H\|ATOH8_net_da_SANGER_10_FBgn0002931_B1H\|SCRT1_CG17181_SANGER_5_FBgn0035144_B1H | ACAGGTGGT | ACCACCTGT |
| CREB3L1_CREB3_2_SELEX\|CREB3_2 | GTGCCACGTCATCA | TGATGACGTGGCAC |
| CEBPA_pTH5250_PBM | ATTGCGTAA | TTACGCAAT |
| TBX3_TBX2_f1_HocoMoco | GTCGCTTCTCACACCTCTGATGGCA | TGCCATCAGAGGTGTGAGAAGCGAC |
| NR3C1_known14 | GGGAACATTATGTCCTAA | TTAGGACATAATGTTCCC |
| XBP1_V$XBP1_01_Transfac\|XBP1_1 | ATAGGACACGTCATCAT | ATGATGACGTGTCCTAT |
| ESR2_pTH3510_PBM | GAGGTCATGC | GCATGACCTC |

TABLE 5-continued

Transcription Factor Binding Sites of Synthetic Promoters

| Name | Binding Site Sequence | Reverse Complement |
|---|---|---|
| TEAD1_TEAD1_f1_HocoMoco | CACATTCCTGCGCC | GGCGCAGGAATGTG |
| EMX2_EMX1_2_SELEX\|EMX2_E MX2_2_SELEX\|EMX1_2\|EMX2_3 | TAATTAGCTAATTA | TAATTAGCTAATTA |
| YY2_YY2_1_SELEX\|YY2_1 | GTCCGCCATTA | TAATGGCGGAC |
| NKX2-5_vnd_FlyReg_FBgn0003986_B1H | GCACTTGAGC | GCTCAAGTGC |
| ESR2_MA0258.2_ChIP-seq\|ESRRA_disc1 | AGGTCACCCTGACCT | AGGTCAGGGTGACCT |
| EGR3_pTH5337_PBM | ATGCGTGGG | CCCACGCAT |
| GATA2_Gata6_3769_PBM\|GATA2_GATA2_si_HocoMoco\|HMGN3_disc2 | CAGATAAG | CTTATCTG |
| POU1F1_POU1F1_1_SELEX\|POU1F1_4 | CATTAATTATGCATGAG | CTCATGCATAATTAATG |
| YY2_H1-hESC_YY1_HudsonAlpha_ChIP-seq | CAAGATGGCGGCCCC | GGGGCCGCCATCTTG |
| HNF1A_HNF1B_2_SELEX\|HNF1A_HNF1A_1_SELEX\|HNF1A_4\|HNF1B_4 | AGTTAATCATTAACT | AGTTAATGATTAACT |
| FOSL1_HepG2_FOSL2_HudsonAlpha_ChIP-seq | CAGGATGAGTCACC | GGTGACTCATCCTG |
| IRF6_Irf6_3803_PBM | GACCGAAACC | GGTTTCGGTC |
| MSX1_Msx3_3206_PBM\|MSX1_Msx2_3449_PBM\|NOBOX_MA0125.1_SELEX\|NOBOX_1 | ACCAATTA | TAATTGGT |
| NKX2-5_Ceh-22_PBM\|ISL2_ISL2_1_SELEX\|ISL2_2 | GCACTTAA | TTAAGTGC |
| FOXD1_MA0042.1_SELEX\|FOXI1_2 | AAACAAACATCC | GGATGTTTGTTT |
| TFAP2E_1 | ATCGCCTCAGGCAAT | ATTGCCTGAGGCGAT |
| ARID3C_ARI3A_f1_HocoMoco | AATTAAA | TTTAATT |
| CUX1_V$CDPCR3_01_Transfac\|CUX1_4 | CACCAATATGTATGG | CCATACATATTGGTG |
| MYC_known14 | GACCACGTGGTC | GACCACGTGGTC |
| TBX3_SRP001585_Tbx2_ChIP-seq | AAACTACAATTCCCAGAATGC | GCATTCTGGGAATTGTAGTTT |
| POU3F2_4 | CAAACTAATTAATTATC | GATAATTAATTAGTTTG |
| USF1_pTH5265_PBM | ACCACGTGAT | ATCACGTGGT |
| HES4_dpn_SANGER_10_FBgn0010109_B1H | GGCACGTGCCA | TGGCACGTGCC |
| MYBL1_Mybl1_1717_PBM | TAACGGTCA | TGACCGTTA |
| KIAA0415_pTH9655_PBM | ATTGTAAACAA | TTTGTTTACAAT |
| TCF4_MA0521.1_ChIP-seq | AACAGCTGCAG | CTGCAGCTGTT |
| ETV5_HeLa-53_ELK4_UCD_ChIP-seq | CACTTCCGGCC | GGCCGGAAGTG |
| NKX2-5_Vnd_SOLEXA_FBgn0003986_B1H\|NKX-6_Tin_Cell_FBgn0004110_B1H | CACTTGAG | CTCAAGTG |
| SOX18_SOX18_1_SELEX\|SOX18_2 | AACAATGAAATTGTT | AACAATTTCATTGTT |
| TCF7L2_known5 | AATCCCTTTGATCTATC | GATAGATCAAAGGGATT |
| HNF4G_HNF4A_1_SELEX\|HNF4_known16 | GAGTCCAAAGTCCATC | GATGGACTTTGGACTC |
| GMEB2_GME B2_3_SELEX\|GMEB2_3 | TACGTAACTGACGTA | TACGTCAGTTACGTA |
| HOXC5_Hoxd3_1742_PBM\|HOXC10_Hoxc10_2779_PBM | GTCATTAA | TTAATGAC |

TABLE 5-continued

Transcription Factor Binding Sites of Synthetic Promoters

| Name | Binding Site Sequence | Reverse Complement |
| --- | --- | --- |
| ATF7_Creb5_1_SELEX\|CREB5_1 | AATGACGTCACC | GGTGACGTCATT |
| CR936877.3_I$CF1_02_Transfac\|CR936877.3_I$CF1_01_Transfac | CGTGACCCC | GGGGTCACG |
| VDR_2 | CCCGGTGAACCC | GGGTTCACCGGG |
| GATA2_GATA3_si_HocoMoco | CTTATCTC | GAGATAAG |
| LHX1_MA0135.1_SELEX\|LHX3_2 | AAATTAATTAATC | GATTAATTAATTT |
| GMEB1_pTH9026_PBM\|GMEB1_pTH8745_PBM | CGTACGTCA | TGACGTACG |
| SMAD4_1 | AGGTGGCTGCCCCAC | GTGGGGCAGCCACCT |
| ETS_disc8 | AACGGAAG | CTTCCGTT |
| FUBP1_FUBP1_f1_HocoMoco | AAAAAAACACAA | TTGTGTTTTTTT |
| ZNF143_GM12878_ZNF143_Stanford_ChIP-seq | CTGGGAATTGTAGTC | GACTACAATTCCCAG |
| NKX3-1_V$NKX3A_01_Transfac\|NKX3-1_1 | AAATAAGTATAT | ATATACTTATTT |
| NR2E1_pTH2936_PBM | AAAGTCAATT | AATTGACTTT |
| ZBTB7A_known1 | AGGGCCCCC | GGGGGCCCT |
| MSX1_2 | GAATTAATTAGTTGCA | TGCAACTAATTAATTC |
| HOXD10_1 | AATGCAATAAAATTTAT | ATAAATTTTATTGCATT |
| ETS_disc6 | AAATCTCGCG | CGCGAGATTT |
| TFAP2_known4 | CCCTCCGCCTGGGGC | GCCCCCAGGCGGAGGG |
| TBX20_pTH9340_PBM | AGGTGTCA | TGACACCT |
| FOXJ3_YIL131C_2002_DeBoer11 | ATGTAAACAAGC | GCTTGTTTACAT |
| SOX1_SOX2_3_SELEX\|SOX2_4 | CATCAATAACATTGATC | GATCAATGTTATTGATG |
| CTCF_GM12878_CTCF_UW_ChIP-seq | GCCACCAGGGGCGCCA | TGGCGCCCCTGGTGGC |
| GATA2_GATA1_si_HocoMoco | ACAGATAAGG | CCTTATCTGT |
| RAD21_disc2 | CCACTAGA | TCTAGTGG |
| GATA2_K562_GATA2_UChicago_ChIP-seq | ACAGATAAGA | TCTTATCTGT |
| NKX2-1_2 | CCCTCAAGAGCC | GGCTCTTGAGGG |
| SNAI2_wor_SANGER_2.5_FBgn0001983_B1H\|ASCL2_I_1_sc_da_SANGER_5_FBgn0002561_B1H\|TCF4_ase_da_SANGER_10_FBgn0000413_B1H\|TCF4_I_1_sc_da_SANGER_5_FBgn0000413_B1H | CACCTGC | GCAGGTG |
| HOXB7_1 | GTAGTAATTAATGCAA | TTGCATTAATTACTAC |
| POU5F1_disc2 | ATGAATATGC | GCATATTCAT |
| FOXD1_FOXG1_1_SELEX\|FOXG1_1 | ATAAACAATTGTAAACA | TGTTTACAATTGTTTAT |
| HAND1_2 | ATGCCAGACC | GGTCTGGCAT |
| AR_pTH1739_PBM | TAGGAACATA | TATGTTCCTA |
| FOXP4_CG16899_SANGER_5_FBgn0037735_B1H | GATAAACAA | TTGTTTATC |
| HNF1_3 | ACTGTTAATTATTAACCA | TGGTTAATAATTAACAGT |
| SREBF2_pTH0914_PBM | ATCACGCGAT | ATCGCGTGAT |
| IRF_known13 | CAAAATCGAAACTAA | TTAGTTTCGATTTTG |

TABLE 5-continued

Transcription Factor Binding Sites of Synthetic Promoters

| Name | Binding Site Sequence | Reverse Complement |
| --- | --- | --- |
| TCF4_ITF2_f1_HocoMoco | CCAGGTGCA | TGCACCTGG |
| NFKB_disc3 | AAATCCCTC | GAGGGGATTT |
| OSR2_Osr2_1727_PBM | AACGGTAGCA | TGCTACCGTT |
| NR1H3_NR1H4_f1_HocoMoco | AGGGTCAATGACCT | AGGTCATTGACCCT |
| IRF_known5 | AAAATGAAACTG | CAGTTTCATTTT |
| HMGA2_pTH9279_PBM | AGAAAAAT | ATTTTTCT |
| EGR3_EGR2_1_SELEX\|EGR1_known10 | ACGCCCACGCA | TGCGTGGGCGT |
| NR2E1_pTH5561_PBM | AATTGACAT | ATGTCAATT |
| PITX2_2 | GATGATTAATCCCTTCA | TGAAGGGATTAATCATC |
| POU3F3_pTH9365_PBM | ATAATGAA | TTCATTAT |
| TCF4_HLH54F_da_SANGER_5_FBgn0000413_B1H\|MSC_HLH54F_da_SANGER_5_FBgn0022740_B1H | AACACCTGTTG | CAACAGGTGTT |
| HBP1_HBP1_f1_HocoMoco | ACTCATTGA | TCAATGAGT |
| HNF4G_Hnf4_SANGER_5_FBgn0004914_B1H\|NR2F2_NR2F1_3_SELEX\|HNF4_known25 | GGGGTCAA | TTGACCCC |
| TFAP2B_1 | ATGCCCTAGGGCAA | TTGCCCTAGGGCAT |
| CR936877.3_pTH2861_PBM\|CR936877.3_pTH2880_PBM\|NR2F2_pTH5516_PBM | GGGGTCAC | GTGACCCC |
| AFP_1 | ATTAACTACAC | GTGTAGTTAAT |
| OLIG2_Oli_da_SANGER_5_2_FBgn0032651_B1H\|TCF4_Oli_da_SANGER_5_2_FBgn0000413_B1H | ACCGCACCATCTGTC | GACAGATGGTGCGGT |
| NFATC1_NFAC1_si_HocoMoco | AATTTTCCATTG | CAATGGAAAATT |
| ETV5_V$ELK1_02_Transfac\|ETS_known2 | CCAACCGGAAGTCC | GGACTTCCGGTTGG |
| TCF4_tap_da_SANGER_5_FBgn0000413_B1H\|NEUROG1_tap_da_SANGER_5_FBgn0015550_B1H | CCATATGTCAC | GTGACATATGG |
| GFI1_2 | CGAAATCACGGCC | GGCCGTGATTTCG |
| NKX2-5_MA0122.1_SELEX\|N KX3-2_1 | TCCACTTAA | TTAAGTGGA |
| MXI1_HeLa-S3_MXI1_Stanford_ChIP-seq | CACGTGGTTCC | GGAACCACGTG |
| EVX2_1 | AACGCTAATTAGCGGTG | CACCGCTAATTAGCGTT |
| ETV5_MA0098.2_ChIP-seq | CCCACTTCCTGTCTC | GAGACAGGAAGTGGG |
| RXRA_disc2 | CGGCCACCAGGGGCGCCGGA | TCCGGCGCCCCTGGTGGCCG |
| MEIS1::HOXA9_2 | CCATAAAACTGTCA | TGACAGTTTTATGG |
| IRX3_Irx6_2623_PBM | ATTACAA | TTGTAAT |
| SOX13_MA0515.1_ChIP-seq | AAAACAATGG | CCATTGTTTT |
| OBOX5_1 | GAAATTTAATCCCTCTA | TAGAGGGATTAAATTTC |
| ZNF410_1 | TATTATGGGATGGATAA | TTATCCATCCCATAATA |
| GATA_known18 | CAATTCTTATCTCTATA | TATAGAGATAAGAATTG |
| MITF_Mitf_SANGER_5_FBgn0263112_B1H | CACGTGA | TCACGTG |

TABLE 5-continued

Transcription Factor Binding Sites of Synthetic Promoters

| Name | Binding Site Sequence | Reverse Complement |
|---|---|---|
| SCXA_CG33557_da_SANGER_5_FBgn0053557_B1H\|TCF4_CG33557_da_SANGER_5_FBgn0000413_B1H | CCAGATGGCACGGACACAACA | TGTTGTGTCCGTGCCATCTGG |
| SMC3_disc3 | CCAGGGGCGC | GCGCCCCTGG |
| ALX1_PRRX1_3_SELEX\|PROP1_PROP1_2_SELEX\|PROP1_31PRRX1_4 | TAATCTAATTA | TAATTAGATTA |
| ZBTB42_ZN238_a_HocoMoco | GCGAAACATCTGGA | TCCAGATGTTTCGC |
| MAX_Max_Mnt_SANGER_5_FBgn0017578_B1H\|MYC_known17 | CACGTGG | CCACGTG |
| MTF1_MTF1_f1_HocoMoco | AGTGCCGTGTGCAAAAC | GTTTTGCACACGGCACT |
| PAX2_PAX2_si_HocoMoco | GCATGAC | GTCATGC |
| SIX5_known4 | ATAAGTGATACCCTATC | GATAGGGTATCACTTAT |
| NOBOX_pTH5791_PBM | ACCAATTAAG | CTTAATTGGT |
| BSX_pTH6569_PBM\|ESX1_ESX1_1_SELEX\|GBX2_Gbx1_1_SELEX\|ESX1_ESX1_2_SELEX\|ESX1_2\|ESX1_3\|GBX1_3 | ACCAATTAAC | GTTAATTGGT |
| TCF4_amos_da_SANGER_10_FBgn0000413_B1H\|ATOH7_amos_da_SANGER_10_FBgn0003270_B1H | ACCATCTGCCG | CGGCAGATGGT |
| SP9_SP4_f1_HocoMoco | CGGCCCCGCCCCCCCCTGGCCCC | GGGGCCAGGGGGGGGCGGGGCCG |
| NPAS3_EPAS1_si_HocoMoco | CCCACGTACGCAC | GTGCGTACGTGGG |
| ESRRG_ERR2_f1_HocoMoco\|NR5A1_STF1_f1_HocoMoco\|ESRRG_ERR1_f1_HocoMoco\|ESRRG_ERR3_f1_HocoMoco\|NR5A1_2 | TCAAGGTCA | TGACCTTGA |
| DOBOX5_1 | GATAATTAATCCCTTCC | GGAAGGGATTAATTATC |
| HOXC6_Hoxc8_3429_PBM | GGCAATTAA | TTAATTGCC |
| NFE2_NFE2_f2_HocoMoco | AGCATGACTCAGCA | TGCTGAGTCATGCT |
| MYC_known15 | AACCACGTGA | TCACGTGGTT |
| MXI1_disc2 | AACCACGTGG | CCACGTGGTT |
| ELF3_Elf3_PBM | ACCCGGAAAT | ATTTCCGGGT |
| RORB_MA0072.1_SELEX\|RORA_5 | TATAAGTAGGTCAA | TTGACCTACTTATA |
| ARNT2_pTH5159_PBM | ATTCATGTGC | GCACATGAAT |
| KLF4_KLF1_f1_HocoMoco | CAGGGTGTGGC | GCCACACCCTG |
| HOXA4_zen2_SOLEXA_2_FBgn0004054_B1H | GTCATTAAGA | TCTTAATGAC |
| RARA_1 | CAGGTGACCTTTGAGA | TCTCAAAGGTCACCTG |
| NRF1_disc3 | CCCCGCCCGC | GCGGGCGGGG |
| FOXD1_Foxg1_1_SELEX\|FOXG1_3 | ATAAACAAGTGTAAACA | TGTTTACACTTGTTTAT |
| GCM1_pTH9386_PBM\|GCM1_pTH9259_PBM\|GCM1_pTH8361_PBM | ACCCGCAT | ATGCGGGT |
| SP9_Sp1_SOLEXA_2.5_FBgn0020378_B1H | AAGTGGGCGTGGCC | GGCCACGCCCACTT |
| SIN3A_disc5 | CAGCACCAGG | CCTGGTGCTG |
| POU3F3_GM12878_OCT2_HudsonAlpha_ChIP-seq\|POU3F3_GM12878_POU2F2_HudsonAlpha_ChIP-seq\|NANOG_disc1\|TATA_disc9 | ATATGCAAAT | ATTTGCATAT |
| E2F6_E2F6_f1_HocoMoco | CCTTCCCGCCCA | TGGGCGGGAAGG |

TABLE 5-continued

Transcription Factor Binding Sites of Synthetic Promoters

| Name | Binding Site Sequence | Reverse Complement |
|---|---|---|
| NR2F2_COT2_f1_HocoMoco\|RXRA_disc1 | CAAAGGTCAA | TTGACCTTTG |
| NR4A2_NR4A3_f1_HocoMoco | CAAAGGTCAG | CTGACCTTTG |
| JUN_MA0489.1_ChIP-seq | AGGAGATGACTCAT | ATGAGTCATCTCCT |
| HOXC5_Ipf1_3815_PBM | CTAATGGC | GCCATTAG |
| ENSG00000250096_RUNX2_2_SELEX\|ENSG00000250096_RUNX3_3_SELEX\|RUNX2_5\|RUNX3_3 | TAACCGCAAAAACCGCAA | TTGCGGTTTTTGCGGTTA |
| JUN_K562_JUND_UChicago_ChIP-seq | AAGTATGAGTCATCA | TGATGACTCATACTT |
| WT1_1 | CCCTCCCCC | GGGGGAGGG |
| HNF1A_3 | ATTTTAGTTAACTAAGG | CCTTAGTTAACTAAAAT |
| DRGX_MA0467.1_ChIP-seq | AAGAGGATTAG | CTAATCCTCTT |
| FOSL1_K562_CFOS_UChicago_ChIP-seq | GAGGATGAGTCACCA | TGGTGACTCATCCTC |
| MYB_V$VMYB_02_Transfac | GCCGTTAGA | TCTAACGGC |
| AR_NR3C1_1_SELEX\|NR3C1_known18 | GGGAACATTATGTACCC | GGGTACATAATGTTCCC |
| HOXA5_1 | TGCCAACTCCCCCATTAGTGCTCGACTCCA | TGGAGTCGAGCACTAATGGGGGAGTTGGCA |
| OBOX5_2 | AAGAGGGATTAATTATC | GATAATTAATCCCTCTT |
| PHOX2A_1 | CAGCATTAATTAGTAG | CTACTAATTAATGCTG |
| SOX17_Sox17_2837_PBM | AGGATGAAT | ATTCATCCT |
| ALX1_CG33980_SOLEXA_2_0_FBgn0053980_B1H | CTTAATTAGC | GCTAATTAAG |
| FOXD1_Mw164_ChIP-seq | CTGTTTAC | GTAAACAG |
| GATA_known16 | CTTTATTTCTTATCTCTAAAAA | TTTTTAGAGATAAGAAATAAAG |
| FOSL2_FOSL2_f1_HocoMoco | ATGACTCATCC | GGATGAGTCAT |
| GATA_known7 | AGATAAGGCCT | AGGCCTTATCT |
| NFE2_K562_NFE2_Stanford_ChIP-seq | AAAATTGCTGAGTCATG | CATGACTCAGCAATTTT |
| MYF_1 | CAGCAGCTGCTG | CAGCAGCTGCTG |
| ZEB1_Mv136_ChIP-seq | CACACACCTG | CAGGTGTGTG |
| RORB_MA0071.1_SELEX\|RORA_4 | ATCAAGGTCA | TGACCTTGAT |
| ZBTB33_MA0527.1_ChIP-seq | CAGATCTCGCGAGAG | CTCTCGCGAGATCTG |
| ZEB1_ZEB1_do_HocoMoco\|SNAI2_esg_SANGER_2.5_FBgn0001981_B1H | ACAGGTG | CACCTGT |
| CTCF_HeLa-S3_CTCF_UT-A_ChIP-seq | GCCACCAGGGGCAC | GTGCCCCTGGTGGC |
| AL662830.5_PBX1_do_HocoMoco | AATTTGATTGATGGG | CCCATCAATCAAATT |
| BRCA1_known1 | CAACAGAA | TTCTGTTG |
| NKX2-5_Nkx2-9_3082_PBM | AGCACTTAAG | CTTAAGTGCT |
| HOXD3_1 | AGGTTAATTAACTCAA | TTGAGTTAATTAACCT |
| DMRTA2_pTH9188_PBM | AATGTATCAAT | ATTGATACATT |
| TP53_Tp53_1_SELEX\|TP53_5 | ACATGTCCATGGACATGT | ACATGTCCATGGACATGT |
| MITF_TFEB_f1_HocoMoco | CACGTGACC | GGTCACGTG |
| POU3F3_pTH9256_PBM\|POU3F3_pTH9297_PBM | ATAATTCATA | TATGAATTAT |

TABLE 5-continued

Transcription Factor Binding Sites of Synthetic Promoters

| Name | Binding Site Sequence | Reverse Complement |
|---|---|---|
| ZKSCAN3_ZNF306_1_SELEX\|ZKSCAN3_1 | TCGAGGCTAGACCA | TGGTCTAGCCTCGA |
| REST_HTB-11_NRSF_HudsonAlpha_ChIP-seq\|REST_HepG2_NRSF_HudsonAlpha_ChIP-seq | TCAGCACCATGGACA | TGTCCATGGTGCTGA |
| SOX1_Sox1_2631_PBM | AAAGATGAAT | ATTCATCTTT |
| NPAS2_pTH5056_PBM | GCCACGTGGC | GCCACGTGGC |
| SOX9_SOX8_8_SELEX\|SOX8_9 | AATCAATTGCAGTGATT | AATCACTGCAATTGATT |
| GCM1_GCM1_3_SELEX\|GCM1_4 | CATGCGGGTAC | GTACCCGCATG |
| HES4_I$HAIRY_01_Transfac | ATGGCGCGTGCCGC | GCGGCACGCGCCAT |
| EN2_EN1_1_SELEX\|EN2_EN2_2_SELEX\|EN1_4\|EN2_3 | CCCAATTAGC | GCTAATTGGG |
| ZNF628_1 | CAAGGTTGGTTGC | GCAACCAACCTTG |
| CTCF_AG04449_CTCF_UW_ChIP-seq | CCACCAGGGGCGCCG | CGGCGCCCCTGGTGG |
| SIX5_disc4 | AAAACTACAA | TTGTAGTTTT |
| FOXD1_fkh_NAR_FBgn0000659_B1H\|FOXD1_Mf15_ChIP-seq\|FOXD1_MA0446.1_B1H | TGTTTGCTTAA | TTAAGCAAACA |
| DMRT3_1 | AAAATGTATCAAATT | AATTTGATACATTTT |
| NRF1_MA0506.1_ChIP-seq | GCGCCTGCGCA | TGCGCAGGCGC |
| SCRT2_scrt_SANGER_2.5_FBgn0004880_B1H | ACCACCTGTTG | CAACAGGTGGT |
| UBP1_pTH8565_PBM | AACCGGTTA | TAACCGGTT |
| ETV6_ETV6_2_SELEX\|ETV6_2 | AGCGGAAGTG | CACTTCCGCT |
| FOXA_known3 | ATAAACAAACAGA | TCTGTTTGTTTAT |
| FOXD1_FOXJ3_si_HocoMoco | AAAAAATAAACAA | TTGTTTATTTTT |
| HMBOX1_HM BOX1_1_SELEX\|HMBOX1_2 | ACTAGTTAAC | GTTAACTAGT |
| FOXD1_MA0458.1_B1H\|FOXD1_slp1_NAR_FBgn0003430_B1H | AATGTAAACAA | TTGTTTACATT |
| SOX9_SOX8_5_SELEX\|SOX8_6 | TGAATGTGCAGTCA | TGACTGCACATTCA |
| NFY_known1 | GTGATTGGTTA | TAACCAATCAC |
| JUN_HepG2_JUND_Stanford_ChIP-seq | AAGGTGACGTCATCA | TGATGACGTCACCTT |
| HES4_h_SANGER_5_FBgn0001168_B1H | GGCACGCGCC | GGCGCGTGCC |
| JUN_V$VJUN_01_Transfac | CCGATGACGTCATCCC | GGGATGACGTCATCGG |
| AHR::ARNT_1 | GGGCACGCAACCCTTA | TAAGGGTTGCGTGCCC |
| NFY_known4 | CAGCCAATGAG | CTCATTGGCTG |
| TCF4_V$E47_01_Transfac | CCGGCAGGTGTCCGC | GCGGACACCTGCCGG |
| AP1_known7 | CCCCTTGAGTCA | TGACTCAAGGGG |
| MAFK_MA0495.1_ChIP-seq | AAAAATTGCTGACTCAGC | GCTGAGTCAGCAATTTT |
| KLF4_luna_SANGER_5_FBgn0040765_B1H | GGCAACGCCC | GGGCGTTGCC |
| MAFB_Mafb_2914_PBM | AAATTGCTGACGT | ACGTCAGCAATTT |
| IRF4_IRF4_si_HocoMoco | AAAAAAGAAAATGAAA | TTTCATTTTCTTTTTT |
| HLTF_1 | AACCTTATAT | ATATAAGGTT |
| NHLH2_MA0048.1_SELEX\|NHLH1_3 | ACGCAGCTGCGC | GCGCAGCTGCGT |

TABLE 5-continued

Transcription Factor Binding Sites of Synthetic Promoters

| Name | Binding Site Sequence | Reverse Complement |
|---|---|---|
| ARID3C_I$DRI_01_Transfac | TATTAATCGA | TCGATTAATA |
| HES4_MA0449.1_B1H\|HES5_pTH5450_PBM\|TCFL5_pTH4576_PBM\|HES4_h_NAR_FBgn0001168_B1H | GGCACGTGCC | GGCACGTGCC |
| POU2F2_known7 | AAATATGCAAATCAC | GTGATTTGCATATTT |
| AR_V$GRE_C_Transfac\|NR3C1_known2 | CAGAACAGATTGTACC | GGTACAATCTGTTCTG |
| LBX2_MA0232.1_B1H\|GBX2_Exex_SOLEXA_FBgn0041156_B1H\|DLX1_DII_SOLEXA_FBgn0000157_B1H | TAATTA | TAATTA |
| FOXD1_FOXJ3_U_HocoMoco | TAAACAAAACAA | TTGTTTTGTTTA |
| YY1_known6 | GATGGC | GCCATC |
| HIVEP3_ZEP2_si_HocoMoco | GGGGTTTCCCTACC | GGTAGGGAAACCCC |
| ATF1_V$CREB_01_Transfac\|ATF3_known2\|ATF2_3\|ATF3_known15 | TGACGTCA | TGACGTCA |
| HNF4_disc2 | AAGTCCAGT | ACTGGACTT |
| HLX_H2.0_SOLEXA_FBgn0001170_B1H | TTAATAAA | TTTATTAA |
| CR936877.3_RXRG_2_SELEX\|CR936877.3_RXRA_4_SELEX\|RXRA_known13\|RXRG_2 | GAGGTCATGACCCC | GGGGTCATGACCTC |
| PLAG1_PLAG1_f1_HocoMoco | CCCCTCCTGATGCCCCC | GGGGGCATCAGGAGGGG |
| TBPL2_V$TBP_01_Transfac\|TATA_known3 | TATAAATA | TATTTATA |
| SREBF2_V$SREBP1_01_Transfac\|SREBP_known1 | GATCACGTGAC | GTCACGTGATC |
| FOXD1_FOXG1_2_SELEX\|FOXG1_2 | ACGGACACAATG | CATTGTGTCCGT |
| GMEB2_pTH3084_PBM\|GMEB1_pTH9298_PBM\|GMEB1_pTH9282_PBM | GTACGTCA | TGACGTAC |
| NR2F2_2 | CTCGTGACCTTTGAGA | TCTCAAAGGTCACGAG |
| BATF_disc3 | AAATGACTGG | CCAGTCATTT |
| GATA2_V$GATA1_04_Transfac\|GATA_known6 | ATCAGATAAGGGG | CCCCTTATCTGAT |
| FOSL1_pTH5077_PBM | TGATGACGCAA | TTGCGTCATCA |
| GATA_known13 | AGATAG | CTATCT |
| RELA_GM19099_NFKB_Stanford_ChIP-seq | AGGGGATTTCCAA | TTGGAAATCCCCT |
| NFE2_disc4 | CCGCTGACTCC | GGAGTCAGCGG |
| MAFA_MAF_f1_HocoMoco | GTCAGCAA | TTGCTGAC |
| ALX1_Isx_3445_PBM | CAATTAGC | GCTAATTG |
| E2F1_V$E2F_03_Transfac\|E2F_known9 | TTTCGCGCCAAA | TTTGGCGCGAAA |
| ATF1_V$CREB_Q2_Transfac\|ATF3_known6 | CCTTACGTCACC | GGTGACGTAAGG |
| RORB_Hr46_SANGER_5_FBgn0000448_B1H | AAGTAGGTCA | TGACCTACTT |
| FOXD1_FOXC1_1_SELEX\|FOXC1_3 | AAGTAAATAAACA | TGTTTATTTACTT |
| FOXJ1_1 | ATGTGTTTGTTTA | TAAACAAACACAT |
| SOX9_SOX9_3_SELEX\|SOX9_5 | ATCAATGTGCAGTGAT | ATCACTGCACATTGAT |
| HOXB9_1 | CGAATTTTATGGCTCC | GGAGCCATAAAATTCG |

TABLE 5-continued

Transcription Factor Binding Sites of Synthetic Promoters

| Name | Binding Site Sequence | Reverse Complement |
|---|---|---|
| TBX3_TBX5_1_SELEX\|TBX3_pTH3973_PBM\|TBX3_TBX5_si HocoMoco\|TBX22_TBX15_2_SELEX\|MGA_MGA_1_SELEX \|TBX1_TBX1_3_SELEX\|TBX3_pTH9336_PBM\|TBX3_pTH3775_PBM\|TBX3_TBX4_1_SELEX\|MGA_1\|TBX15_2\|TBX1_3\| TBX4_1\|TBX5_4 | AGGTGTGA | TCACACCT |
| CDX2_2 | AAATTTTATTACCGTT | AACGGTAATAAAATTT |
| HNF1A_V$HNF1_01_Transfac | GGTTAATGATTACCA | TGGTAATCATTAACC |
| CEBPA_CEBPE_f1_HocoMoco | AAGATTGCGCAA | TTGCGCAATCTT |
| OTP_1 | CCAATTAATTAATTACG | CGTAATTAATTAATTGG |
| HOXC5_Antp_FlyReg_FBgn0000095_B1H | AATTAT | ATAATT |
| ZNF263_T-REx-HEK293_ZNF263_UCD_ChIP-seq | CCTCTCCCTCCTCCC | GGGAGGAGGGAGAGG |
| RELA_REL_do_HocoMoco | GGGAAATCCCCA | TGGGGATTTCCC |
| RELB_RELB_si_HocoMoco | GGGAAATCCCCC | GGGGGATTTCCC |
| SHOX_PhdP_SOLEXA_FBgn0025334_B1H\|SHOX_PhdP_Cell FBgn0025334_B1H | AATTAA | TTAATT |
| BCL6_MA0463.1_ChIP-seq | TGCTTTCTAGGAAA | TTTCCTAGAAAGCA |
| HOXC5_MA0132.1_SELEX\|PDX1_3 | AATTAG | CTAATT |
| PAX5_Poxn_SOLEXA_5_FBgn0003130_B1H | AGCGTGACG | CGTCACGCT |
| SOX18_1 | TTCAATTGTTCTAAAA | TTTTAGAACAATTGAA |
| ESRRA_disc2 | AGCCCAAGGTCAC | GTGACCTTGGGCT |
| YY1_disc1 | GCCGCCATCTTGGGTGC GGGCAA | TTGCCCGCACCCAAGAT GGCGGC |
| HOXA13_1 | AAACCTCGTAAAATTT | AAATTTTACGAGGTTT |
| HOXC10_Hoxd9_1_SELEX\|HOXD9_1 | CCCATAAAA | TTTTATGGG |
| BARHL2_BARHL2_2_SELEX\|BARHL2_3 | AGCAATTAAC | GTTAATTGCT |
| NR2F2_Mv104_ChIP-seq\|NR2C2_disc2 | ACCTTTGACC | GGTCAAAGGT |
| DMRT2_pTH9261_PBM | AATTGATACA | TGTATCAATT |
| ATF1_ATF1_si_HocoMoco | CTGACGTCAC | GTGACGTCAG |
| DMRTC2_pTH9215_PBM\|DMRT1_pTH9197_PBM\|DMRTA 2_pTH9198_PBM | AATGTATCAA | TTGATACATT |
| HNF1_4 | AGCAGTTAATAATTAAC CATA | TATGGTTAATTATTAACT GCT |
| MEOX2_MEOX1_1_SELEX\|MEOX1_2 | GCTAATTAAC | GTTAATTAGC |
| NKX2-4_1\|NKX2-1_3 | AATTTCAAGTGGCTTA | TAAGCCACTTGAAATT |
| HOXC8_1 | ACGTTAATTACCCCAA | TTGGGGTAATTAACGT |
| CTCF_disc2 | ACCAGGGGGCG | CGCCCCCTGGT |
| GATA2_K562b_GATA1_UCD_ChIP-seq | GCAGATAAGGA | TCCTTATCTGC |
| HOMEZ_1 | AAAACATCGTTTTTAAG | CTTAAAAACGATGTTTT |
| AHR::ARNT_2 | GGGGATCGCGTGACAA CCC | GGGTTGTCACGCGATCC CC |
| HOXC4_1 | CGAATTAATTAACAATA | TATTGTTAATTAATTCG |
| GMEB1_Gmeb1_1745_PBM\|GMEB1_pTH8318_PBM | TGACGTACA | TGTACGTCA |

TABLE 5-continued

Transcription Factor Binding Sites of Synthetic Promoters

| Name | Binding Site Sequence | Reverse Complement |
|---|---|---|
| ETV5_GM12878_ETS1_HudsonAlpha_ChIP-seq | GAACTACAATTCCCAGAAGGC | GCCTTCTGGGAATTGTAGTTC |
| POU3F3_PO3F1_f1_HocoMoco | CATTGTAATGCAAA | TTTGCATTACAATG |
| LHX1_LHX3_f1_HocoMoco | AAAATTAATTAAT | ATTAATTAATTTT |
| RXRA_known8 | AGGTCACGGAGAGGTCA | TGACCTCTCCGTGACCT |
| OBOX1_1 | GTAGTTAATCCCCTTAA | TTAAGGGGATTAACTAC |
| NR3C1_known7 | CCACGAAGAACACCATGTCCCCACCCC | GGGGTGGGGACATGGTGTTCTTCGTGG |
| KLF14_KLF13_1_SELEX|KLF13_1 | ATGCCACGCCCCTTTTG | CAAAAGGGGCGTGGCAT |
| NHLH2_HLH4C_da_SANGER_5_4_FBgn0011277_B1H|TCF4_HLH4C_da_SANGER_5_4_FBgn0000413_B1H | CCACCTGAGCCC | GGGCTCAGGTGG |
| NR3C1_known4 | AGAACACCCTGTACC | GGTACAGGGTGTTCT |
| MEIS1_MEIS3_1_SELEX|ME153_2 | CCTGTCAA | TTGACAGG |
| PRDM16_V$EVI1_01_Transfac|RUNX1_2 | AGATAAGATAAGATAA | TTATCTTATCTTATCT |
| FOXD1_FOXB1_1_SELEX|FOXB1_1 | GAATGACACAGCGA | TCGCTGTGTCATTC |
| POU3F3_MA0254.1_DNaseI | TATGCA | TGCATA |
| FOSL1_MA0476.1_ChIP-seq | AATGAGTCACA | TGTGACTCATT |
| E2F1_E2F1_3_SELEX | TTTTGGCGCCAAAA | TTTTGGCGCCAAAA |
| BARHL2_CG11085_Cell_FBgn0030408_B1H|BSX_Bsh_Cell_FBgn0000529_B1H | CCAATTAAA | TTTAATTGG |
| ALX1_CG9876_Cell_FBgn0034821_B1H|SHOX_Pph13_Cell_FBgn0023489_B1H | ACTAATTA | TAATTAGT |
| FOXH1_MA0479.1_ChIP-seq | TCCAATCCACA | TGTGGATTGGA |
| GATA2_V$GATA6_01_Transfac|GATA_known9 | AAAGATAAGC | GCTTATCTTT |
| DMRT2_1 | ACAATGTATCAATTTG | CAAATTGATACATTGT |
| DMRTC2_pTH9250_PBM|DMRTA2_pTH9300_PBM | AATGTATC | GATACATT |
| YY2_V$YY1_02_Transfac|YY1_known2 | AGCAGCCAAGATGGCCGCGG | CCGCGGCCATCTTGGCTGCT |
| AC226150.2_pTH5972_PBM | CTTGTCAA | TTGACAAG |
| TBPL2_Mv129_ChIP-seq | TATGCAAATA | TATTTGCATA |
| NHLH2_NHLH1_2_SELEX|NHLH2_NHLH1_1_SELEX|NHLH1_4|NHLH1_5 | CGCAGCTGCG | CGCAGCTGCG |
| PAX9_MA0014.2_ChIP-seq | GAGGGCAGCCAAGCGTGAC | GTCACGCTTGGCTGCCCTC |
| ENSG00000250811_tgo_sim_SANGER_5_F Bgn0004666_61H|ARNT2_tgo_trh_SANGER_5_FBgn0015014_B1H|ARNT2_tgo_sim_SANGER_5_FBgn0015014_B1H | GGTCACGTAC | GTACGTGACC |
| ETS_known1 | AAAACAGGAAGTACGT | ACGTACTTCCTGTTTT |
| NR2E3_pTH5877_PBM | GAGATCAA | TTGATCTC |
| HNF4_known5|PPARA_4|HNF4_known6|HNF4_known7 | GGGTCAAAGGTCA | TGACCTTTGACCC |
| FOXL1_3 | ACCTTTGTTTACATTTA | TAAATGTAAACAAAGGT |
| HINFP_H|NFP1_2_SELEX|HINFP_3 | GCGGACGTTGCAACGTCCGC | GCGGACGTTGCAACGTCCGC |

TABLE 5-continued

Transcription Factor Binding Sites of Synthetic Promoters

| Name | Binding Site Sequence | Reverse Complement |
|---|---|---|
| CCNT2_disc1 | CTGGGGGGGGCAGATAAGGCA | TGCCTTATCTGCCCCCCCCAG |
| SP9_CG5669_SOLEXA_5_FBgn0039169_B1H | AGTGGGCGGGGCCAA | TTGGCCCCGCCCACT |
| NFYA_MA0313.1_COMPILED | ACCAA | TTGGT |
| TEF_HLF_1_SELEX\|HLF_3 | CATTACGTAACC | GGTTACGTAATG |
| SIX6_Six3_1732_PBM | GTATCAC | GTGATAC |
| TEF_DBP_1_SELEX\|DBP_2 | CATTACGTAACA | TGTTACGTAATG |
| SPI1_disc2\|BCL_disc4\|PAX5_disc3\|RXRA_disc4 | GGAAGTGAAA | TTTCACTTCC |
| PAX5_pTH8981_PBM | ACCGTGACCAC | GTGGTCACGGT |
| E2F_known19 | GCCCGTTTCGCGCCAA | TTGGCGCGAAACGGGC |
| CTCFL_disc1 | CAGGGGGCGC | GCGCCCCTG |
| MEF2B_MEF2A_f1_HocoMoco | GCTATAAATAGAAC | GTTCTATTTATAGC |
| POU2F2_known13 | TACTGATTATGCATATTTTAA | TTAAAATATGCATAATCAGTA |
| ZNF35_Zfp105_2634_PBM | CAATAAACAA | TTGTTTATTG |
| POU3F3_V$TST1_01_Transfac\|CCDC6_1 | GAGGAATTAAAATAC | GTATTTTAATTCCTC |
| ARID5A_pTH5121_PBM | GCAATATCGA | TCGATATTGC |
| MAFK_pTH5098_PBM | AATTGCTGAC | GTCAGCAATT |
| NFKB2_NFKB2_1_SELEX\|NFKB1_NFKB1_1_SELEX\|NFKB_known10\|NFKB_known11 | AGGGGAATCCCCT | AGGGGATTCCCCT |
| TLX3_Tlx2_3498_PBM\|DBX2_pTH6051_PBM\|LHX1_Lim3_Cell_FBgn0002023_B1H\|DBX2_Dbx1_3486_PBM\|EN2_en_FlyReg_FBgn0000577_B1H | ATTAATTA | TAATTAAT |
| NPAS2_CLOCK_1_SELEX\|CLOCK_1 | AACACGTGTT | AACACGTGTT |
| ATF1_V$TAXCREB_02_Transfac\|ATF3_known5 | ATGACGCATACCCCC | GGGGGTATGCGTCAT |
| JUN_kay_Jra_SANGER_5_FBgn0001291_B1H\|JUN_MA0491.1_ChIP-seq | GATGAGTCACC | GGTGACTCATC |
| E2F4_K562b_E2F4_UCD_ChIP-seq | GGCGGGAAATTGGAA | TTCCAATTTCCCGCC |
| BARHL2_BARHL2_4_SELEX\|BARHL2_Barhl1_1_SELEX\|BARHL2_5\|BARHL1_2 | ACCGTTTAGC | GCTAAACGGT |
| DMRTC2_1 | CAACAATGTAACAA | TTGTTACATTGTTG |
| RARG_RARA_3_SELEX\|RARA_4 | AGGTCATGCAAAGGTCA | TGACCTTTGCATGACCT |
| FOXA_known2 | AAAAACAAACA | TGTTTGTTTTT |
| NFIL3_MA0025.1_SELEX | ACGTTACATAA | TTATGTAACGT |
| POU3F3_V$OCT1_06_Transfac\|POU2F2_known6 | CAAAATGACATGCA | TGCATGTCATTTTG |
| TFCP2_3 | CCAGCTCAAACCAGC | GCTGGTTTGAGCTGG |
| GCM1_1 | AATGATGCGGGTACGA | TCGTACCCGCATCATT |
| HNF4_disc4 | AGCAAACAG | CTGTTTGCT |
| ARNT2_tgo_tai_SANGER_5_FBgn0015014_B1H\|BHLHE40_BHE40_f2_HocoMoco | GCACGTGAC | GTCACGTGC |
| STAT3_MCF10A-Er-Src_STAT3_Harvard#Weissman_ChIP-seq\|STAT3_MCF10A-Er-Src_STAT3_Stanford_ChIP-seq | CACTTCCGGGAAATG | CATTTCCCGGAAGTG |

TABLE 5-continued

Transcription Factor Binding Sites of Synthetic Promoters

| Name | Binding Site Sequence | Reverse Complement |
| --- | --- | --- |
| TBX3_TBX3_f1_HocoMoco | AGGTAGAGAATTAGGTGATAAAAA | TTTTTATCACCTAATTCTCTACCT |
| SREBF2_V$SREBP1_02_Transfac | GTGGGGTGATA | TATCACCCCAC |
| HOXC10_Hoxd11_3873_PBM\|HOXC10_Hoxd10_2368_PBM | GTCATAAA | TTTATGAC |
| CR936877.3_Rxra_1035_PBM | AGGGGTCACG | CGTGACCCCT |
| EOMES_Eomes_0921_PBM\|EOMES_TBR1_1_SELEX\|TBR1_1 | AGGTGTGAAA | TTTCACACCT |
| PAX9_PAX8_f1_HocoMoco | CCCGCTTCAGTGAC | GTCACTGAAGCGGG |
| CTCF_disc8 | CCACAGGCAGGTGC | GCACCTGCCTGTGG |
| ESR2_ESR2_si_HocoMoco | AGGTCAC | GTGACCT |
| POU3F3_POU3F2_2_SELEX\|POU3F3_POU3F1_1_SELEX\|POU3F1_2\|POU3F2_6 | TAATTTGCATAA | TTATGCAAATTA |
| CEBPA_pTH5253_PBM | TTGCGAAA | TTTCGCAA |
| TEAD3_TEAD3_1_SELEX\|TEAD3_1 | ACATTCCTCGCATTCCA | TGGAATGCGAGGAATGT |
| HOXC5_Antp_Cell_FBgn0000095_B1H\|EMX2_Ems_Cell_FBgn0000576_B1H\|HOXG_Antp_SOLEXA_FBgn0000095_B1H\|HOXC5_Ubx_SOLEXA_FBgn0003944_B1H | TCATTAAA | TTTAATGA |
| SMC3_disc2 | ACCAGCAGG | CCTGCTGGT |
| SOX11_SOX4_f1_HocoMoco | CGCTTTGTTCTC | GAGAACAAAGCG |
| RARG_RARA_1_SELEX\|RARA_2 | AAAGGTCATTTGAGGTCA | TGACCTCAAATGACCTTT |
| GATA2_MA0482.1_ChIP-seq | GGGAGATAAGA | TCTTATCTCCC |
| MYOD1_MYOG_f1_HocoMoco | GCAGCAGCTGTCA | TGACAGCTGCTGC |
| FOXO1_2 | AATGTAAACAACAC | GTGTTGTTTACATT |
| NFAT_2 | AATTTTCCAC | GTGGAAAATT |
| ZNF143_disc3 | ACTACAACTCCCAGCAGC | GCCTGCTGGGAGTTGTAGT |
| AR_MCR_f1_HocoMoco | AAGAACAGGTTGTTGTA | TACAACAACCTGTTCTT |
| TEF_Hlf_1_SELEX\|HLF_4 | GATTACGTAACC | GGTTACGTAATC |
| EVX2_pTH6287_PBM | ACTAATTACC | GGTAATTAGT |
| MZF1_MA0056.1_SELEX\|MZF1_3 | TCCCCA | TGGGGA |
| RFX8_RFX1_f1_HocoMoco | GTTGCCAGGGAA | TTCCCTGGCAAC |
| ZNF143_ZNF143_1_SELEX\|ZNF143_known2 | CAATGCATTGTGGGTA | TACCCACAATGCATTG |
| AP1_disc2 | GCCAATCAGA | TCTGATTGGC |
| BHLHA15_dimm_da_SANGER_5_FBgn0023091_B1H\|TCF4_dimm_da_SANGER_5_FBgn0000413_B1H | ACCATATGGCG | CGCCATATGGT |
| NR3C1_known3 | AGAACATCATGTACT | AGTACATGATGTTCT |
| GATA_known12 | GGATA | TATCC |
| FOXD1_V$_FOXD3_01_Transfac\|FOXD3_1 | AAACAAACAATC | GATTGTTTGTTT |
| EGR1_known7 | AATGCGGGGCGGA | TCCGCCCCGCATT |
| CR936877.3_RXRA_f1_HocoMoco\|PPARA_PPARA_f2_HocoMoco\|NR2C2_NR2C2_a_HocoMoco | AGGTCAAAGGTCA | TGACCTTTGACCT |

TABLE 5-continued

Transcription Factor Binding Sites of Synthetic Promoters

| Name | Binding Site Sequence | Reverse Complement |
|---|---|---|
| FOXO6_FOXO3_3_SELEX\|FOXO3_6 | GTGTGGGAAA | TTTCCCCACAC |
| ENSG00000187728_Tcf21_1_SELEX\|TCF21_1 | ACAACAGCTGTTGC | GCAACAGCTGTTGT |
| REST_known3 | GCGCTGTCCGTGGTGCTGA | TCAGCACCACGGACAGCGC |
| RARG_Rara_3_SELEX\|RARA_10 | AAGGTCAAAGGTCA | TGACCTTTTGACCTT |
| BHLHE40_Bhlhb2_1_SELEX\|MITF_pTH2885_PBM\|BHLHE40_BHLHE41_1_SELEX\|ARNT2_ARNTL_LSELEX\|MYC_disc1\|ATF3_disc1\|NFE2_disc2\|SIRT6_disc1\|ARNTL_1\|BHLHE41_2\|BHLHE40_known4 | GTCACGTGAC | GTCACGTGAC |
| HOXA3_3 | ACTAATTACCTCAA | TTGAGGTAATTAGT |
| LMX1A_Lmx1a_2238_PBM\|LMX1A_LMX1B_1_SELEX\|LMX1A_LMX1A_1_SELEX\|LHX1_Lhx4_1_SELEX\|HOXA1_pTH5486_PBM\|SHOX_Uncx4_PBM\|HOXB2_pTH5491_PBM\|LMX1A_2\|LMX16_2\|LHX4_2 | TTAATTAA | TTAATTAA |
| SOX1_SOX2_f1_HocoMoco | ATTTGCATAACAATGG | CCATTGTTATGCAAAT |
| IRF5_IRF5_f1_HocoMoco | TAAAGGAAAGCCAAAAGTGA | TCACTTTTGGCTTTCCTTTA |
| IRF_known12 | ATAAACCGAAACCAA | TTGGTTTCGGTTTAT |
| SRF_H1-hESC_SRF_HudsonAlpha_ChIP-seq | CCATATAAGGCAAA | TTTGCCTTATATGG |
| ATF3_known11 | ATGACG | CGTCAT |
| MYOG_1 | CAGCTGCC | GGCAGCTG |
| LHX8_pTH6556_PBM | GTAATCAA | TTGATTAC |
| FOXO6_foxo_SANGER_10_FBgn0038197_B1H | TCGTAAACA | TGTTTACGA |
| PRRX2_1 | AGGTTAATTGGTTAAA | TTTAACCAATTAACCT |
| SOX3_1 | AAACAATGACATTGTTT | AAACAATGTCATTGTTT |
| CTCF_GM12878_CTCF_Broad_ChIP-seq | GCCCCCTGGTGGCCA | TGGCCACCAGGGGGC |
| IRX3_2 | AATATACATGTAATATT | AATATTACATGTATATT |
| SIX5_disc3 | AAACTACATTTCCCA | TGGGAAATGTAGTTT |
| NFIA_NFIB_1_SELEX\|NFIB_1 | CTGGCACTGTGCCAA | TTGGCACAGTGCCAG |
| HOXC9_I$ABDB_01_Transfac | GCGTTTATGGCGAC | GTCGCCATAAACGC |
| TFAP2_disc2 | CATGCCCTGGGGCCA | TGGCCCCAGGGCATG |
| IRF2_IRF2_f1_HocoMoco | GGAAAGTGAAAGCA | TGCTTTCACTTTCC |
| STAT4_MA0518.1_ChIP-seq | CCATTTCCTGGAAA | TTTCCAGGAAATGG |
| HOXC10_HOXC10_3_SELEX\|HOXC10_4 | ATTTTACGAC | GTCGTAAAAT |
| PBX3_known1 | CTACCATCAATC | GATTGATGGTAG |
| POU2F2_disc2 | CCCCCTCACCTGC | GCAGGTGAGGGGG |
| CTCF_HMF_CTCF_UW_ChIP-seq | CCACCAGAGGG | CCCTCTGGTGG |
| ZNF143_V$STAF_02_Transfac | ATTTCCCATCATGCCTTGCGA | TCGCAAGGCATGATGGGAAAT |
| TCF3_5 | CACCTGCC | GGCAGGTG |
| RARG_RARA_2_SELEX\|RARA_3 | CATTGACCTTTTGACCTC | GAGGTCAAAGGTCAATG |
| NFIA_NFIX_3_SELEX | AGTGCCAAT | ATTGGCACT |

TABLE 5-continued

Transcription Factor Binding Sites of Synthetic Promoters

| Name | Binding Site Sequence | Reverse Complement |
|---|---|---|
| NFIA_NFIX_2_SELEX | CGTGCCAAG | CTTGGCACG |
| SIN3A_disc1 | TCAGCACCACGGACA | TGTCCGTGGTGCTGA |
| ZSCAN16_ZNF435_1_SELEX\|ZSCAN16_1 | AGGTGTTCTGTTAACACT | AGTGTTAACAGAACACCT |
| EP300_disc7 | ATGACACA | TGTGTCAT |
| ZNF652_Zfp652_1_SELEX\|ZNF652_1 | AGAAAGGGTTAAT | ATTAACCCTTTCT |
| ARID3C_retn_SANGER_5_FBgn0004795_B1H | AATCAAAA | TTTTGATT |
| HOXD11_1 | AGGATTTTACGACCTTA | TAAGGTCGTAAAATCCT |
| AR_MA0007.2_ChIP-seq | AAGAACAGAATGTTC | GAACATTCTGTTCTT |
| ZBTB7B_ZBT7B_si_HocoMoco | CGGAGAGGGGGAGGGGGGGGC | GCCCCCCCCTCCCCCTCCG |
| TCF7L2_known3 | AACATCAAGG | CCTTTGATGTT |
| HOXB3_1 | TCCAACTAATTAGCTCA | TGAGCTAATTAGTTGGA |
| POU1F1_PIT1_f1_HocoMoco | ATATATTCATGAG | CTCATGAATATAT |
| PAX6_PAX6_1_SELEX\|PAX6_5 | TGTGCAGTCATGCGTGAAA | TTTCACGCATGACTGCACA |
| TFDP1_TFDP1_f1_HocoMoco | AAATGGCGGGAAAC | GTTTCCCGCCATTT |
| NKX2-5_Nkx2-4_3074_PBM\|NKX2-5_V$NKX22_01_Transfac\|NKX3-1_Nkx3-1_2923_PBM\|NKX2-5_Nkx2-6_3437_PBM\|NKX2-2_1 | AACCACTTAA | TTAAGTGGTT |
| HEY1_HEY2_f1_HocoMoco | GGGGGCACGTGGCATTA | TAATGCCACGTGCCCCC |
| E2F7_E2F7_1_SELEX\|E2F7_1 | TTTTCCCGCCAAAA | TTTTGGCGGGAAAA |
| IKZF2_3 | ATAAGGAAAAA | TTTTTCCTTAT |
| TCF7L1_TF7L2_f1_HocoMoco | AAGATCAAAGGG | CCCTTTGATCTT |
| STAT1_Mv125_ChIP-seq | AAACGAAACT | AGTTTCGTTT |
| GCM1_GCM1_1_SELEX\|GCM1_2 | CATGCGGGTA | TACCCGCATG |
| SOX17_3 | ATAAACAATTAATCA | TGATTAATTGTTTAT |
| ONECUT3_ONEC2_si_HocoMoco | AAAAAAAATCAATAACAAGAC | GTCTTGTTATTGATTTTTTT |
| NR2C2_Hr78_SANGER_5_FBgn0015239_B1H\|CR936877.3_H1-hESC_RXRA_HudsonAlpha_ChIP-seq | AGAGGTCA | TGACCTCT |
| HNF1A_1 | GGTTAATAATTAAC | GTTAATTATTAACC |
| NFE2_MA0150.2_ChIP-seq | CAGCATGACTCAGCA | TGCTGAGTCATGCTG |
| HMGA1_1 | AATTTCC | GGAAATT |
| T_V$BRACH_01_Transfac\|T_1 | AATTTCACACCTAGGTGTGACTAG | CTAGTCACACCTAGGTGTGAAATT |
| FOXD1_pTH8896_PBM\|FOXD1_YCR065W_570_DeBoer11\|FOXD1_MA0317.1_PBM,\|FOXD3_pTH9057_PBM | ATAAACAA | TTGTTTAT |
| SIX5_known 2 | AAAAATGATACCCCATC | GATGGGGTATCATTTTT |

TABLE 5-continued

Transcription Factor Binding Sites of Synthetic Promoters

| Name | Binding Site Sequence | Reverse Complement |
|---|---|---|
| EN2_MA0229.1_B1H\|EN2_Inv_Cell_FBgn0001269_B1H | TAATTAGA | TCTAATTA |
| RUNX2_2 | AAACCACA | TGTGGTTT |
| MEOX2_Btn_Cell_FBgn0014949_B1H\|HOXC5_Dfd_SOLEXA_FBgn0000439_B1H\|HOXC5_Zen_SOLEXA_F_Bgn0004053_B1H\|HOXC5_Dfd_Cell_FBgn0000439_B1H | CTTAATGA | TCATTAAG |
| MEF2_known9 | ATGCTAAAAATAGATTG | CAATCTATTTTTAGCAT |
| SP100_1 | ATTTTACGGAAAAT | ATTTTCCGTAAAAT |
| NKX2-5_NKX22_si_HocoMoco | AAACCACTTAAA | TTTAAGTGGTTT |
| MZF1_V$MZF1_01_Transfac\|MZF1_1 | AGTGGGGA | TCCCCACT |
| TLX3_V$NCX_01_Transfac\|TLX2_1 | CCAATTACCG | CGGTAATTGG |
| GATA2_GATA4_a_HocoMoco | ACAGATAAC | GTTATCTGT |
| CDX2_1 | AAAGTTTTATTGCC | GGCAATAAAACTTT |
| AR_AR_1_SELEX\|NR3C1_known15 | AGGTACACGGTGTACCC | GGGTACACCGTGTACCT |
| ZEB1_MA0103.2_ChIP-seq | CAGGTGAGG | CCTCACCTG |
| NKX3-1_NKX31_si_HocoMoco | AATAAGTATATAA | TTATATACTTATT |
| HOXC12_1 | GAAATTTTACGACCTAA | TTAGGTCGTAAAATTTC |
| SP9_SP3_1_SELEX\|KLF14_KLF16_1_SELEX\|KLF16_1\|SP1_known9 | GCCACGCCCCC | GGGGGCGTGGC |
| RFX8_RFX2_2_SELEX\|RFX8_RFX4_2_SELEX\|RFX8_Rfx2_2_SELEX\|RFX2_2\|RFX5_known7\|RFX2_4 | CGTTGCCTAGCAACG | CGTTGCTAGGCAACG |
| GRHL1_GRHL1_1_SELEX\|GRHL1_1 | AACCGGTTAAACCGGTT | AACCGGTTTAACCGGTT |
| BARX1_pTH6449_PBM\|BARX1_Barx2_3447_PBM\|HMX1_Hmx3_3490_PBM | AGCAATTAA | TTAATTGCT |
| PKNOX2_hth_SOLEXA_2_FBgn0001235_B1H | CTGTCAAA | TTTGACAG |
| CDX2_CDX2_1_SELEX\|CDX2_CDX1_1_SELEX\|CDX1_2\|CDX2_3 | GCAATAAAA | TTTTATTGC |
| PRDM16_V$EVI1_06_Transfac\|RUNX1_1 | ACAAGATAA | TTATCTTGT |
| ZIC4_ZIC3_1_SELEX\|ZIC3_3 | GACCCCCGCTGCGC | GCGCAGCGGGGGTC |
| NFY_known3 | ATCAGCCAATCAGAGC | GCTCTGATTGGCTGAT |
| BX088580.2_SRP000712_Oct4_ChIP-seq\|POU5F1_disc1\|POU5F1_known2 | ATTTGCATAACAATG | CATTGTTATGCAAAT |
| ESR2_ESR1_1_SELEX\|ESRRA_known6 | AAGGTCACGGTGACCTG | CAGGTCACCGTGACCTT |
| SOX2_SOX21_2_SELEX\|SOX9_SOX8_1_SELEX\|SOX9_SOX9_2_SELEX\|SOX21_3\|SOX8_2\|SOX9_4 | AACAATGTGCAGTGTT | AACACTGCACATTGTT |
| PTF1A_Fer2_da_SANGER_5_FBgn0038402_B1H\|TCF4_Fer2_da_SANGER_5_F_Bgn0000413_B1H | CCAGCTGACG | CGTCAGCTGG |
| RORB_RORA_1_SELEX\|RORA_6 | CAAAGGTCAAATTGAGGTCA | TGACCTCAATTTGACCTTTG |
| YY2_GM12892_YY1_HudsonAlpha_ChIP-seq | AAGATGGCGGCCGCC | GGCGGCCGCCATCTT |
| SPIC_Sfpi1_1034_PBM\|SP11_disc1 | AAGAGGAAGT | ACTTCCTCTT |
| ARID3C_MA0151.1_SELEX\|ARID3A_1 | ATTAAA | TTTAAT |
| NOBOX_Og2x_3719_PBM | GCCAATTAA | TTAATTGGC |
| ELF1_disc2 | CGCTTCCGGC | GCCGGAAGCG |

TABLE 5-continued

Transcription Factor Binding Sites of Synthetic Promoters

| Name | Binding Site Sequence | Reverse Complement |
|---|---|---|
| PKNOX1_1 | AAAGACCTGTCAATCC | GGATTGACAGGTCTTT |
| NHLH2_pTH3037_PBM | CACAGCTGCG | CGCAGCTGTG |
| NR2C2_disc3 | ACCCCGGA | TCCGGGGT |
| HOXB8_1 | ACCGGCAATTAATAAA | TTTATTAATTGCCGGT |
| NR2C2_NR2C2_1_SELEX\|NR2F2_NR2F6_2_SELEX\|NR2F2_NR2F6_3_SELEX\|NR2F2_Nr2f6_2_SELEX\|NR2C2_known1\|NR2F6_2\|NR2F6_3\|NR2F6_5 | GAGGTCAAAGGTCA | TGACCTTTGACCTC |
| TBX1_TBX1_4_SELEX | TCTCACACCTCTGAGGTGTGAAA | TTTCACACCTCAGAGGTGTGAGA |
| TBPL2_V$TATA_01_Transfac\|TATA_known2\|TATA_known5 | CCCCGCCTTTTATAC | GTATAAAAGGCGGGG |
| NR2C2_Mv97_ChIP-seq | AAGTGCTTCCGGGTC | GACCCGGAAGCACTT |
| SOX11_SOX4_1_SELEX\|SOX4_2 | AACACTGCAATTGTTC | GAACAATTGCAGTGTT |
| TFAP2A_AP2D_a_HocoMoco | ACGCGCCTCGGGCG | CGCCCGAGGCGCGT |
| SOX9_SOX10_1_SELEX\|SOX9_SOX8_6_SELEX\|SOX10_3\|SOX8_7 | AACAATTGCAGTGTT | AACACTGCAATTGTT |
| ZIC4_MA0118.1_SELEX | GACCCCCCA | TGGGGGGTC |
| MAFK_HepG2_MAFK_Stanford_ChIP-seq | TGCTGACTCAGCA | TGCTGAGTCAGCA |
| BRCA1_BRCA1_f1_HocoMoco | CAACCCAAA | TTTGGGTTG |
| MGA_MGA_2_SELEX\|MGA_2 | AGGTGTGAAGTCACACCT | AGGTGTGACTTCACACCT |
| LHX9_1 | CCCATTAATTAATCACC | GGTGATTAATTAATGGG |
| SOX13_SOX5_a_HocoMoco | TAACAATA | TATTGTTA |
| LMX1A_CG4328_Cell_FBgn0036274_B1H | ATTTATTG | CAATAAAT |
| FOXD1_V$FREAC3_01_Transfac\|FOXC1_1 | GGTAAGTAAATAAACA | TGTTTATTTACTTACC |
| SOX1_Sox1_3_SELEX\|SOX2_SOX21_3_SELEX\|SOX1_SOX14_3_SELEX\|SRY_SRY_3_SELEX\|SOX14_4\|SOX21_4\|SRY_7\|SOX1_4 | TCAATAACATTGA | TCAATGTTATTGA |
| STAT3_V$STAT3_01_Transfac\|STAT3_V$STAT3_01_Transfac\|STAT_known3 | AATCATTTCCGGGAAATGCCA | TGGCATTTCCCGGAAATGATT |
| TFAP2_known9 | ATTCCCTGAGGGGAA | TTCCCCTCAGGGAAT |
| HOXC10_Hoxc10_2_SELEX\|HOXC10_HOXC10_2_SELEX\|HOXC10_3\|HOXC10_6 | GTAATAAAA | TTTTTATTAC |
| KLF4_KLF4_f2_HocoMoco | GCCCCGCCCA | TGGGCGGGGC |
| T_3 | TCACACCTAGGTGTGA | TCACACCTAGGTGTGA |
| EBF1_EBF1_1_SELEX\|EBF1_known4 | ATTCCCAAGGGAAT | ATTCCCTTGGGAAT |
| STAT1_HeLa-S3_STAT1_Stanford_ChIP-seq | ATGGGATTTCCGGGAAATGGG | CCCATTTCCCGGAAATCCCAT |
| HOXD1_1 | TAAACTAATTAGCTGTA | TACAGCTAATTAGTTTA |
| BARX1_1 | AAAGTAATTAGTGAAT | ATTCACTAATTACTTT |
| ZBTB33_disc2 | CTCGCGGGACC | GGTCCCGCGAG |
| GATA2_GATA6_f2_HocoMoco | AAGATAA | TTATCTT |
| MEF2B_Mf26_ChIP-seq | CTAAAAATAA | TTATTTTTAG |

TABLE 5-continued

Transcription Factor Binding Sites of Synthetic Promoters

| Name | Binding Site Sequence | Reverse Complement |
|---|---|---|
| HESX1_HESX1_2_SELEX\|HESX1_2 | CTAATTGGCAATTAA | TTAATTGCCAATTAG |
| DLX5_1 | CAGAGCTAATTACCCC | GGGGTAATTAGCTCTG |
| ELF1_Eip74EF_FlyReg_FBgn0000567_B1H\|EP300_disc10 | AACAGGAAGT | ACTTCCTGTT |
| PKNOX2_PKNX1_si_HocoMoco | AGCTTGATTGATG | CATCAATCAAGCT |
| MEF2B_MEF2D_1_SELEX\|MEF2D_1 | ACTATAAATAGA | TCTATTTATAGT |
| JUN_pTH4337_PBM | ATGACGCAA | TTGCGTCAT |
| DLX1_DLX6_1_SELEX\|DLX1_DLX4_1_SELEX\|DLX1_DLX2_1_SELEX\|DLX1_DLX3_1_SELEX\|DLX1_Dlx1_1_SELEX\|DLX2_2\|DLX3_2\|DLX4_2\|DLX6_1\|DLX1_3 | CCAATTAC | GTAATTGG |
| MEOX1_1 | CTGAGGTAATTACCTC | GAGGTAATTACCTCAG |
| POU1F1_pTH3818_PBM | ATAATTAATA | TATTAATTAT |
| ELF3_ELF3_f1_HocoMoco | ATTTCCTGTTTGCC | GGCAAACAGGAAAT |
| SPDEF_SPDEF_6_SELEX\|SPDEF_7 | GCAGAAAGAAGTAACA | TGTTACTTCTTTCTGC |
| EP300_disc6 | ATTACATCA | TGATGTAAT |
| POU2F2_disc1 | ATGCAAAT | ATTTGCAT |
| FOXD1_FOXI1_2_SELEX\|FOXI1_4 | ATGTTTACGGTAAACAA | TTGTTTACCGTAAACAT |
| ZBTB3_Zbtb3_1048_PBM | AATGCAGTG | CACTGCATT |
| FOXD1_FOXD2_1_SELEX\|FOXD2_1 | AAAAAATATTTACT | AGTAAATATTTTTT |
| PPARA_MA0066.1_SELEX\|RXRA_known5 | AGTAGGTCACCGTGACCTAC | GTAGGTCACGGTGACCTACT |
| HOXC13_1 | AAAGCTCGTAAAATTT | AAATTTTACGAGCTTT |
| ALX1_pTH6636_PBM | ATTGTACAAT | ATTGTACAAT |
| CDX2_Cdx2_4272_PBM | GGCAATAAA | TTTATTGCC |
| GMEB2_pTH9219_PBM | CTTACGTCA | TGACGTAAG |
| NFE2L1_NF2L1_f1_HocoMoco | AATGACT | AGTCATT |
| ESRRG_SRP000217_Esrrb_ChIP-seq | AGGTCAAGGTCACCC | GGGTGACCTTGACCT |
| C13orf38-SOHLH2_pTH5058_PBM | AGCCCGTGCG | CGCACGGGCT |
| GATA_known14 | CTGGTGGGACAGATAAG | CTTATCTGTCCCCACCAG |
| ATOH7_cato_da_SANGER_10_FBgn0024249_B1H\|TCF4_cato_da_SANGER_10_FBgn0000413_B1H | CACAGCTGAC | GTCAGCTGTG |
| MYC_known8 | CGCGCGTGGC | GCCACGCGCG |
| MLL_pTH7031_PBM | GGGGGCGTAA | TTACGCCCCC |
| HOXC5_Scr_Cell_FBgn0003339_B1H | CGTTAATGA | TCATTAACG |
| E2F_known7 | CCGCCAAA | TTTGGCGG |
| SOX18_SOX18_2_SELEX\|SOX18_3 | ATCAATGCAATTGAT | ATCAATTGCATTGAT |
| MAFBA_SANGER_5_FBgn0000964_B1H | GCTGAGTCAGCA | TGCTGACTCAGC |
| HSF_known3 | ATTCTAGAAATTTCTCC | GGAGAAATTTCTAGAAT |
| JUN_HUVEC_CJUN_Stanford_ChIP-seq | AAAGGGATGACTCAT | ATGAGTCATCCCTTT |
| AP1_disc5 | ACTCACCAC | GTGGTGAGT |
| CXXC1_pTH7032_PBM | CCGCTAA | TTAGCGG |

TABLE 5-continued

Transcription Factor Binding Sites of Synthetic Promoters

| Name | Binding Site Sequence | Reverse Complement |
| --- | --- | --- |
| MYOD1_2 | ACCACCTGTC | GACAGGTGGT |
| HNF4G_HNF4G_f1_HocoMoco | GGCCAAAGTCCA | TGGACTTTGGCC |
| KDM2B_pTH9191_PBM | GCGTAAATA | TATTTACGC |
| SOX12_1 | GTTTAGAACAATTA | TAATTGTTCTAAAC |
| MYOD1_HLH1_PBM | CAGCTGTC | GACAGCTG |
| BRCA1_disc1\|ZBTB33_disc1\|ETS_disc3\|CHD2_disc1\|NR3C1_disc3 | TCTCGCGAGA | TCTCGCGAGA |
| MAZ_1 | CCCTCCCC | GGGGAGGG |
| RARG_Rarg_2_SELEX\|RARG_8 | AAGGTCATCTAAAGGTCA | TGACCTTTAGATGACCTT |
| ETS_disc1 | AACTACAACTCCCA | TGGGAGTTGTAGTT |
| TFAP2A_AP2A_U_HocoMoco | GCCTCAGGC | GCCTGAGGC |
| ZBTB16_1 | GAACAGATCAAACTTTAGCTTCAATACAA | TTGTATTGAAGCTAAAGTTTGATCTGTTC |
| EGR3_sr_SOLEXA_5_FBgn0003499_B1H\|EGR3_sr_SANGER_5_FBgn0003499_B1H | CCCCGCCCACGCAC | GTGCGTGGGCGGGG |
| HNF4_known10 | AGTTCA | TGAACT |
| GLIS2_1 | CTGTGGGGGTCGATA | TATCGACCCCCACAG |
| CTCF_AG09309_CTCF_UW_ChIP-seq | CACCAGGGGGCGCCAG | CTGGCGCCCCTGGTG |
| EN2_EN1_4_SELEX\|EN1_7 | TAATTAAGCAATTA | TAATTGCTTAATTA |
| SMARCC1_HeLa-S3_BAF170_Stanford_ChIP-seq | GCCTGCTGGGAGTTGTAGTCC | GGACTACAACTCCCAGCAGGC |
| NFE2_V$NFE2_01_Transfac\|MAF_known2\|NFE2L2_3 | ATGACTCAGCA | TGCTGAGTCAT |
| FOXD1_V$FREAC7_01_Transfac\|FOXL1_1 | ATCTTGTTTATGTATA | TATACATAAACAAGAT |
| MEF2B_V$MEF2_02_Transfac\|MEF2_known3 | AGGTGCTATTTTTAGCACCGGA | TCCGGTGCTAAAAATAGCACCT |
| MAFB_Mafb_2_SELEX\|MAF_known11 | AATGCTGACTCAGCACA | TGTGCTGAGTCAGCATT |
| STAT3_STAT3_si_HocoMoco\|STAT3_SRP000217_Stat3_ChIP-seq | CTTCCAGGAAG | CTTCCTGGAAG |
| TEF_HLF_si_HocoMoco | CTGTTACGTAATC | GATTACGTAACAG |
| HSFY1_HSFY2_1_SELEX\|HSFY2_1 | TTCGAAACGTTCGAA | TTCGAACGTTTCGAA |
| SOX15_SOX15_1_SELEX\|SOX1_Sox1_1_SELEX\|SRY_SRY_1_SELEX\|SOX15_2\|SRY_5\|SOX1_2 | AACAATAACATTGTT | AACAATGTTATTGTT |
| NKX3-1_Nkx3-1_2923_PBM | AGCCACTTAA | TTAAGTGGCT |
| ZBTB4_ZBTB4_si_HocoMoco | CCCACCTGCCATCTAGG | CCTAGATGGCAGGTGGG |
| ZBTB6_V$Z1D_01_Transfac\|ZBTB6_1 | CGGCTCTATCATC | GATGATAGAGCCG |
| POU3F3_POU3F3_3_SELEX | ATGAATATTCAT | ATGAATATTCAT |
| GLI1_GLI2_1_SELEX\|GLI2_1 | CGTCGTGGGTGGTC | GACCACCCACGACG |
| NR3C1_known6 | CGCACAAGAACACAATGTACCCTCCCG | CGGGAGGGTACATTGTGTTCTTGTGCG |
| NKX2-3_1 | CATTAAGTACTTAAAG | CTTTAAGTACTTAATG |
| NOBOX_pTH6448_PBM | CTTAATTGGC | GCCAATTAAG |

TABLE 5-continued

Transcription Factor Binding Sites of Synthetic Promoters

| Name | Binding Site Sequence | Reverse Complement |
|---|---|---|
| AP1_disc4 | AGTCATACTGAAA | TTTCAGTATGACT |
| POU3F3_4 | ATGAATATTCAA | TTGAATATTCAT |
| ELF1_Eip74EF_SANGER_5_FBgn0000567_B1H\|ELF3_Elf3_3_876_PBM\|ELF3_Elf5_PBM\|ELF3_Ehf_3056_PBM\|ELF1_Mv63_ChIP-seq\|ELF3_Ehf_PBM\|ELF1_disc1 | ACCCGGAAGT | ACTTCCGGGT |
| NFE2L2_2 | CATGACTCAGCAG | CTGCTGAGTCATG |
| RORB_Hr46_FlyReg_FBgn0000448_B1H | AATTGGGTCA | TGACCCAATT |
| NR1H_3 | GGGGTCAGTAGAGGTCA | TGACCTCTACTGACCCC |
| SOX18_Sox18_3506_PBM\|SOX9_Sox8_1733_PBM\|SOX1_Sox14_2677_PBM\|SOX3_pTH3087_PBM\|SOX7_Sox7_3460_PBM | AAAACAAT | ATTGTTTT |
| STAT_known7 | CATTTCCG | CGGAAATG |
| IRX3_MA0233.1_B1H | AAACA | TGTTT |
| PAX5_disc1 | GGGGGCAGCCAAGCGTGAC | GTCACGCTTGGCTGCCCCC |
| FOXD1_FOXA3_f1_HocoMoco HNF4G_Hnf4a_1_SELEX\|HNF4G_HNF4A_5_SELEX\|HNF4_known20\|HNF4_known22 | GCAAAGCAAACAA ATTGGACTTTGACCCC | TTGTTTGCTTTGC GGGGTCAAAGTCCAAT |
| ZNF263_pTH2682_PBM | GGGAGCAC | GTGCTCCC |
| HES7_HE57_1_SELEX\|HES7_1 | TGGCACGTGCCA | TGGCACGTGCCA |
| RARG_Rarb_3_SELEX\|RARG_RARA_6_SELEX\|RARA_7\|RARB_3 | AGGTCAACTAAAGGTCA | TGACCTTTAGTTGACCT |
| VENTX_VENTX_2_SELEX\|VENTX_2 | CGCTAATCGGAAAACGATTAG | CTAATCGTTTTCCGATTAGCG |
| GTF2I_1 | AGAGGGAGG | CCTCCCTCT |
| TCF4_da_SANGER_10_FBgn0000413_B1H | CGCAGGTGTGC | GCACACCTGCG |
| SOX1_Sox21_3417_PBM\|SOX9_pTH1729_PBM | ATTGTTTTC | GAAAACAAT |
| E2F3_E2F3_3752_PBM | ATTGGCGCGC | GCGCGCCAAT |
| IRF_known11 | CAGTTTCGGTTCTC | GAGAACCGAAACTG |
| HOXD12_1 | AAGATTTTACGACCTTG | CAAGGTCGTAAAATCTT |
| GLI1_GLI2_2_SELEX\|GL12_2 | CAGTGTGGTCGC | GCGACCACACTG |
| NKX2-5_Bapx1_2343_PBM\|NKX2-5_pTH6327_PBM\|NKX2-5_Nkx2-3_3435_PBM\|NKX3-1_5\|NKX3-2_3\|NKX3-1_6 | ACCACTTAA | TTAAGTGGT |
| HMX1_1 | ACAAGCAATTAATGAAT | ATTCATTAATTGCTTGT |
| THRB_THB_do_HocoMoco | GAGGTCAGGTCAGGTCA | TGACCTGACCTGACCTC |
| HIC1_3 | ACTATGCCAACCTACC | GGTAGGTTGGCATAGT |
| PITX2_PITX2_si_HocoMoco | TGGGATTAAA | TTTAATCCCA |
| JUN_HeLa-S3_JUND_Stanford_ChIP-seq | AAGAATGAGTCATCA | TGATGACTCATTCTT |
| HMX1_VSHMX1_01_Transfac\|HMX3_1 | CAAGTGCGTG | CACGCACTTG |
| PRDM16_EVI1_f1_HocoMoco | AAGATAAGATAAGATA | TATCTTATCTTATCTT |
| HOXB2_HXB1_f1_HocoMoco | CCATCCATCA | TGATGGATGG |
| E2F4_HeLa-S3_E2F4_UCD_ChIP-seq | GGCGGGAAATTTGAA | TTCAAATTTCCCGCC |

TABLE 5-continued

Transcription Factor Binding Sites of Synthetic Promoters

| Name | Binding Site Sequence | Reverse Complement |
|---|---|---|
| AP1_known1 | ACTGAGTCACC | GGTGACTCAGT |
| IKZF1_V$IK1_01_Transfac\|IKZF1_1 | ACTTGGGAATACC | GGTATTCCCAAGT |
| RARG_RARG_1_SELEX\|RARG_1 | GAGGTCAAAAGGTCACA | TGTGACCTTTTGACCTC |
| PAX9_GM12878_PAX5C20_HudsonAlpha_ChIP-seq\|PAX9_GM12892_PAX5C20_HudsonAlpha_ChIP-seq\|PAX9_GM12878_PAX5N19_HudsonAlpha_ChIP-seq\|PAX9_Mv108_ChIP-seq | GCAGCCAAGCGTGAC | GTCACGCTTGGCTGC |
| GSC_Gsc_2327_PBM | GCTAATCCC | GGGATTAGC |
| HOXC6_pTH6164_PBM | AATAATTATA | TATAATTATT |
| REST_disc4 | GCACCAGGGACAGC | GCTGTCCCTGGTGC |
| POU2F2_4 | TATGAATATTCAAA | TTTGAATATTCATA |
| PKNOX2_MEIS2_do_HocoMoco | TGACAGCTGTCAA | TTGACAGCTGTCA |
| HSFY1_HSFY2_2_SELEX\|HSFY2_2 | CGTTCGAAA | TTTCGAACG |
| NR2F2_V$ARP1_01_Transfac\|NR2F2_1 | AGGGGTCAAGGGTTCA | TGAACCCTTGACCCCT |
| CTCF_HUVEC_CTCF_UW_ChIP-seq | CTCCGGCGCCCCTGGTGGC | GCCACCAGGGGCGCCGGAG |
| POU2F2_known9 | AATTAGCATAGA | TCTATGCTAATT |
| CTCF_HepG2_CTCF_UT-A_ChIP-seq | AGTGCCACCTAGTGG | CCACTAGGTGGCACT |
| CTCF_GM06990_CTCF_UW_ChIP-seq | CTCGGCGCCCCTGGTGGCC | GGCCACCAGGGGCGCCCGAG |
| PITX2_pTH5644_PBM | AGGGATTAA | TTAATCCCT |
| RXRA_known1 | CGGGTGACCTTTGACCCCTGA | TCAGGGGTCAAAGGTCACCCG |
| HOXD12_pTH6533_PBM\|CDX2_pTH6515_PBM\|CDX2_pTH5553_PBM\|HOXC5_Hoxc6_3954_PBM\|NKX6-1_4\|N KX6-1_5\|NKX6-1_6 | GTAATTAA | TTAATTAC |
| NR1I2_NR1I2_U_HocoMoco | CTGAACTTTTTTGACCTCA | TGAGGTCAAAAAAGTTCAG |
| MEOX2_Meox2_1_SELEX\|MEOX2_4 | GTAATTAC | GTAATTAC |
| TEF_TEF_1_SELEX\|TEF_Dbp_1_SELEX\|TEF_DBP_2_SELEX\|DBP_3\|DBP_4\|TEF_2 | TATTACGTAACA | TGTTACGTAATA |
| IRF2_MA0051.1_SELEX\|IRF_known10 | GGAAAGCGAAACCAAAAC | GTTTTGGTTTCGCTTTCC |
| NEUROG1_NEUROG2_2_SELEX\|NEUROG1_NEUROG2_1_SELEX\|NEUROG2_1\|NEUROG2_2 | AACATATGTC | GACATATGTT |
| AR_MA0113.2_ChIP-seq\|NR3C1_disc1 | AGAACAGAATGTTCT | AGAACATTCTGTTCT |
| GBX2_1 | AATCGCTAATTAGCGCT | AGCGCTAATTAGCGATT |
| E2F3_pTH9221_PBM | TACGCGCGTA | TACGCGCGTA |
| ATOH7_Atoh1_1_SELEX\|OLIG2_OLIG1_1_SELEX\|ATOH1_1\|OLIG1_1 | AACATATGTT | AACATATGTT |
| ARNT2_V$ARNT_01_Transfac\|ARNT_1 | GCGGGCACGTGACAAC | GTTGTCACGTGCCCGC |
| ETS1_ETS1_2_SELEX\|ETS_known15 | ACCGGAAGTACATCCGGT | ACCGGATGTACTTCCGGT |
| DM BX1_Gsc_Cell_FBgn0010323_B1H | ATTAATCC | GGATTAAT |

TABLE 5-continued

Transcription Factor Binding Sites of Synthetic Promoters

| Name | Binding Site Sequence | Reverse Complement |
|---|---|---|
| CTCF_N_HDF-Ad_CTCF_Broad_ChIP-seq | GCCACCAGATGGCACTA | TAGTGCCATCTGGTGGC |
| GATA_known10 | AGATAAAGGGA | TCCCTTTTATCT |
| LHX8_Lhx6_3432_PBM | GCTGATTAC | GTAATCAGC |
| MEF2_known7 | CGGTTTAAAAATAACC | GGTTATTTTTAAACCG |
| ONECUT1_1 | AAAAATCAATAA | TTATTGATTTTT |
| HOXB13_HXA13_f1_HocoMoco | CCAATAAAACC | GGTTTTATTGG |
| ETS1_ETS1_4_SELEX\|ETS_known17 | ACCGGAAGTACATCCGGC | GCCGGATGTACTTCCGGT |
| SOX1_pTH2677_PBM | CATTGTTA | TAACAATG |
| SOX13_SOX13_f1_HocoMoco | CATTGTTC | GAACAATG |
| FOXD1_HCM1_2157_PBM | GGTAAACAA | TTGTTTACC |
| AHR::ARNT_3 | CACGCA | TGCGTG |
| INSM1_INSM1_f1_HocoMoco | TGCCCCCTGACA | TGTCAGGGGCA |
| NFKB_disc2 | GAAATCCCCAGC | GCTGGGGATTTC |
| HNF1B_1 | GTTAAATATTAA | TTAATATTTAAC |
| SOX9_V$SOX9_B1_Transfac\|SOX9_1 | TAAGAACAATGGGA | TCCCATTGTTCTTA |
| ZNF148_Zfp281_0973_PBM | CCACCCCCCC | GGGGGGGTGG |
| HOXA2_1\|PDX1_4 | AAGGTAATTAGCTCAT | ATGAGCTAATTACCTT |
| NKX2-5_NKX21_f1_HocoMoco | AGCACTTGAG | CTCAAGTGCT |
| SRF_GM12878_SRF_HudsonAlpha_ChIP-seq | CCATGGCCAAATAAGGCAA | TTGCCTTATTTGGCCATGG |
| ZBTB7A_disc2 | AAGGGGCG | CGCCCCTT |
| GCM1_GCM1_2_SELEX\|GCM1_3 | ATGCGGGTACCCGCAT | ATGCGGGTACCCGCAT |
| TAL1_known3 | GAGACCATCTGTTCCC | GGGAACAGATGGTCTC |
| ZIC5_MA0456.1_B1H\|ZIC5_opa_NAR_FBgn0003002_B1H | CAGCGGGGGGTC | GACCCCCGCTG |
| ELF3_ELF3_2_SELEX\|ELF3_3 | AACCCGGAAGTAA | TTACTTCCGGGTT |
| ZBTB49_ZBTB49_1_SELEX\|ZBTB49_1 | TGACGTGCCAGGCGAAA | TTTCGCCTGGCACGTCA |
| TEF_MA0043.1_SELEX\|HLF_2 | GGTTACGCAATA | TATTGCGTAACC |
| FOXD1_V$HFH1_01_Transfac\|FOXD1_FOXQ1_f1_HocoMoco\|FOXQ1_1 | AAATAAACAATA | TATTGTTTATTT |
| TEF_pTH3831_PBM\|TEF_pTH5078_PBM\|NFIL3_pTH5082_PBM | TATTACGTAA | TTACGTAATA |
| STAT1_MA0137.3_ChIP-seq | TTTCCAGGAAA | TTTCCTGGAAA |
| NFE2L1_V$TCF11_01_Transfac | CGGCCAAAATGAC | GTCATTTTGGCCG |
| RFX8_RFX2_f1_HocoMoco | TGTTGCTAGGGAA | TTCCCTAGCAACA |
| TCF4_ato_da_SANGER_10_FBgn0000413_B1H\|ATOH7_ato_da_SANGER_10_FBgn0010433_B1H | CCACCTGTCAC | GTGACAGGTGG |
| KLF14_pTH2353_PBM | ACCGTTAT | ATAACGGT |
| AP1_known4 | ACTTAGTCACT | AGTGACTAAGT |
| ETV5_FLI1_f1_HocoMoco | GCCACAGGAAGTGAGGA | TCCTCACTTCCTGTGGC |

TABLE 5-continued

Transcription Factor Binding Sites of Synthetic Promoters

| Name | Binding Site Sequence | Reverse Complement |
|---|---|---|
| CEBPA_V$CEBPA_01_Transfac\|CEBPA_1 | ATATTGCAAAATCA | TGATTTTGCAATAT |
| PPARA_PPARG_f1_HocoMoco | AAGTAGGTCAAAGGTCAC | GTGACCTTTGACCTACTT |
| MEF2_known8 | AGGGTTATTTTTAGAG | CTCTAAAAATAACCCT |
| MTF1_2 | GGGCCGTGTGCAAAAA | TTTTTGCACACGGCCC |
| SIX5_known3 | AAAAGTGATACCCCATT | AATGGGGTATCACTTTT |
| NKX3-2_2 | CATAACCACTTAACAAC | GTTGTTAAGTGGTTATG |
| E2F1_E2F1_1_SELEX\|E2F_known27 | ATTGGCGCCAAA | TTTGGCGCCAAT |
| POU3F3_V$POU3F2_02_Transfac\|POU3F2_3 | ATTAACATAA | TTATGTTAAT |
| AL662830.5_exd_FlyReg_FBgn0000611_B1H | TAAAACAAAA | TTTTGTTTTA |
| DUX4_MA0468.1_ChIP-seq | TAATTTAATCA | TGATTAAATTA |
| FOXD1_FOX13_2_SELEX\|FOXD1_Foxj3_2_SELEX\|FOXD1_FOXJ2_1_SELEX\|FOXJ2_3\|FOXJ3_3\|FOXJ3_6 | GTAAACAATAAACA | TGTTTATTGTTTAC |
| HNF1B_2 | ACGGCTAGTTAACAGCT | AGCTGTTAACTAGCCGT |
| TCF12_disc4 | AACCGAAA | TTTCGGTT |
| ARID3C_pTH9384_PBM\|ARID3C_pTH5169_PBM\|ARID3C_pTH9214_PBM\|ARID3B_pTH5117_PBM | TAATTAAAA | TTTTAATTA |
| ESX1_1 | ATCCATTAATTAATTGA | TCAATTAATTAATGGAT |
| SPDEF_SPDEF_1_SELEX\|SPDEF_SPDEF_4_SELEX\|SPDEF_2\|SPDEF_5 | ACCCGGATGTA | TACATCCGGGT |
| TBX5_1 | AAAGGTGTCAAA | TTTGACACCTTT |
| CEBPA_CEBPB_f1_HocoMoco | ATTGCACAAC | GTTGTGCAAT |
| MAX_V$MAX_01_Transfac\|MYC_known2 | AAACCACGTGGTTT | AAACCACGTGGTTT |
| POU1F1_3 | GACTTAATTAATTAATC | GATTAATTAATTAAGTC |
| CTCF_GM12878_CTCF_UT-A_ChIP-seq\|CTCF_HRPEpiC_CTCF_UW_ChIP-seq | CACCAGGGGCG | CGCCCCTGGTG |
| CEBPA_CEBPA_do_HocoMoco | ATTGCACAAT | ATTGTGCAAT |
| STAT5B_V$STAT5A_01_Transfac\|STAT_known4 | GAATTCCAGGAAATA | TATTTCCTGGAATTC |
| T_BRAC_si_HocoMoco | ACATAGTGACACCTAGGTGTGAAAT | ATTTCACACCTAGGTGTCACTATGT |
| RARG_RARA_f2_HocoMoco | AGGTCACCGAGAGGTCA | TGACCTCTCGGTGACCT |
| ZSCAN10_pTH1292_PBM | AGGAAGTGCAA | TTGCACTTCCT |
| CEBPA_pTH5166_PBM | ATTACGTAAT | ATTACGTAAT |
| EGR1_disc5 | ACCGCCCA | TGGGCGGT |
| RELA_SRP001843_p65_Input_ChIP-seq | AGAGGAGAGGAGAAGAGGAGGGAGGAAGAG | CTCTTCCTCCCTCCTCTTCTCCTCTCCTCT |
| SIX5_disc1\|ZNF143_disc2 | ACTACAATTC | GAATTGTAGT |
| ZBTB33_known 1 | TTAGCAGGAA | TTCCTGCTAA |

TABLE 5-continued

Transcription Factor Binding Sites of Synthetic Promoters

| Name | Binding Site Sequence | Reverse Complement |
|---|---|---|
| BARX1_Barx1_2877_PBM\|BARHL2_BARHL2_5_SELEX\|BARHL2_Barhl1_2_SELEX\|BARHL2_6\|BARHL1_3 | AGCAATTAGC | GCTAATTGCT |
| SPZ1_2 | AGGGTAACAGC | GCTGTTACCCT |
| OTX1_1 | ATAAATTAATCCCCTCC | GGAGGGGATTAATTTAT |
| HMGA2_HMGA2_f1_HocoMoco | AATAATCGCGAATAT | ATATTCGCGATTATT |
| TFAP2A_MA0524.1_ChIP-seq | CATGGCCCCAGGGCA | TGCCCTGGGGCCATG |
| SP9_pTH4998_PBM | GGGGGCGGA | TCCGCCCCC |
| EN2_En2_1_SELEX\|EMX2_EMX2_1_SELEX\|HOXC5_HOXD8_1_SELEX\|DMBX1_ALX3_1_SELEX\|NOTO_NOTO_1_SELEX\|EMX2_EMX1_1_SELEX\|ALX3_2\|EMX1_1\|EMX2_2\|EN2_4\|HOXD8_2\|NOTO_1 | GCTAATTAGC | GCTAATTAGC |
| POU6F2_POU6F2_3_SELEX\|POU6F2_3 | GCTAATTAGA | TCTAATTAGC |
| ZNF143_disc4 | CCAGCGCCCGC | GCGGGCGCTGG |
| POU3F3_POU3F1_2_SELEX\|POU3F1_3 | ATGCATAATTTA | TAAATTATGCAT |
| HOXA5_2 | AATTAGTG | CACTAATT |
| PAX1_1 | ATATCTAGAGCGGAACGG | CCGTTCCGCTCTAGATAT |
| ATF3_disc2 | GGCGCGCGGCGGTGACGTGAC | GTCACGTCACCGCCGCGCGCC |
| PAX4_V$PAX4_01_Transfac\|PAX4_1 | GGCGGTCATGCGTGCGCGACC | GGTCGCGCACGCATGACCGCC |
| AL662830.5_V$PBX1_01_Transfac\|PBX1_1 | ATCAATCAA | TTGATTGAT |
| LHX8_1 | ACCCCTAATTAGCGGTG | CACCGCTAATTAGGGGT |
| RHOXF1_RHOXF1_2_SELEX\|RHOXF1_4 | ATAATCCC | GGGATTAT |
| E2F1_HeLa-53_E2F1_UCD_ChIP-seq | CCGCGCGCCCTCCCC | GGGGAGGGCGCGCGG |
| DLX1_DLX2_f1_HocoMoco | ATAATTAT | ATAATTAT |
| HIC1_4 | GTGCCAGCCTATGCCAAC | GTTGGCATAGGCTGGCAC |
| TBX1_TBX20_3_SELEX\|TBX20_3 | CTTTCACACCTTTTC | GAAAAGGTGTGAAAG |
| HSF2_HSF2_si_HocoMoco | AGAATGTTCTAGAA | TTCTAGAACATTCT |
| CTCF_disc1 | ACCACTAGATGGCACTATTGCA | TGCAATAGTGCCATCTAGTGGT |
| HNF4_disc5 | ACAAAGGGC | GCCCTTTGT |
| FOXD1_pTH9116_PBM | ATGTAAACAAA | TTTGTTTACAT |
| DLX1_DLX5_1_SELEX\|DLX5_2 | ATAATTAC | GTAATTAT |
| POU3F3_Oct-1_PBM\|HOXC5_Dfd_FlyReg_FBgn0000439_B1H | ATAATTAA | TTAATTAT |
| VSX2_VSX1_1_SELEX\|HOXA4_1\|VSX1_2 | ATAATTAG | CTAATTAT |
| DLX3_1 | GTCGGTAATTATCGCGA | TCGCGATAATTACCGAC |
| PAX2_3 | AGTCACGC | GCGTGACT |
| SOX1_SOX2_5_SELEX\|SOX2_6 | TATCAATAACATTGATA | TATCAATGTTATTGATA |
| SOX9_SOX8_4_SELEX\|SOX8_5 | CATCAATTGCAGTGATC | GATCACTGCAATTGATG |
| PAX2_MA0067.1_SELEX | AGTCACGG | CCGTGACT |

TABLE 5-continued

Transcription Factor Binding Sites of Synthetic Promoters

| Name | Binding Site Sequence | Reverse Complement |
|---|---|---|
| ESRRA_known5 | TATTCAAGGTCATGCGA | TCGCATGACCTTGAATA |
| NFATC1_NFATC1_2_SELEX\|NFATC1_2 | TTTCCATAATGGAAA | TTTCCATTATGGAAA |
| SMAD_1 | AGACACCAC | GTGGTGTCT |
| FOXD1_FOXB1_3_SELEX\|FOXD1_FOXC1_3_SELEX\|FOXB1_3\|FOXC1_5 | ATATTTACATA | TATGTAAATAT |
| SRF_V$SRF_C_Transfac\|SRF_known3 | CTGGCCATATATGGC | GCCATATATGGCCAG |
| TCF4_TCF4_1_SELEX\|TCF4_1 | AGCAGGTGCG | CGCACCTGCT |
| EGR1_disc6 | CCCCGGCCTCC | GGAGGCCGGGG |
| RAD21_disc9 | ACTAGACGAGATG | CATCTCGTCTAGT |
| SMAD1_SMAD1_si_HocoMoco | AGCCTGTCTGCC | GGCAGACAGGCT |
| IRF_known8 | CTTTCACTTTC | GAAAGTGAAAG |
| GMEB1_1 | CCATCGTACGTACACTC | GAGTGTACGTACGATGG |
| DMBX1_V$CART1_01_Transfac\|ALX1_1 | AACTAATTACCATTATCG | CGATAATGGTAATTAGTT |
| CREB3L2_CrebA_SANGER_5_FBgn0004396_B1H | GATTACGTGGCA | TGCCACGTAATC |
| HOXA7_1 | AGATTGG | CCAATCT |
| FOXD1_FOXF2_f1_HocoMoco | AAAAGTAAACA | TGTTTACTTTT |
| EOMES_TBX21_6_SELEX\|TBX21_6 | TCACACCTAAAAGGTGTGA | TCACACCTTTTAGGTGTGA |
| ATF3_known9 | CGATGACGTCAGAG | CTCTGACGTCATCG |
| IRX3_MA0210.1_B1H\|IRX3_MA0217.1_B1H | TAACA | TGTTA |
| USF1_H1-hESC_USF1_HudsonAlpha_ChIP-seq | CGCGGCCACGTGACC | GGTCACGTGGCCGCG |
| FOXD1_MA0030.1_SELEX\|FOXF2_2 | ATTGTTTACGTTTG | CAAACGTAAACAAT |
| RHOXF1_1 | AAGACGCTGTAAAGCGA | TCGCTTTACAGCGTCTT |
| GATA2_srp_FlyReg_FBgn0003507_B1H | ATCAACCGATAG | CTATCGGTTGAT |
| ATF7_pTH5081_PBM | GATGACGTCA | TGACGTCATC |
| MEF2_disc2 | AGGAAATGA | TCATTTCCT |
| FOXP4_CG2052_SANGER_2.5_FBgn0039905_B1H | AAAACCAAAAAAT | ATTTTTTGGTTTT |
| TFCP2_1 | CTGGGTTGTGC | GCACAACCCAG |
| SOX13_MA0087.1_SELEX\|SOX5_2 | AAACAAT | ATTGTTT |
| PITX2_Pitx3_3497_PBM\|DRGX_Crx_3485_PBM\|OTX2_Oc_SOLEXA_FBgn0004102_B1H\|RHOXF1_RHOXF1_4_SELEX\|CRX_pTH10716_PBM\|OTP_Otx2_3441_PBM\|PITX2_Pitx2_2274_PBM\|PITX2_PITX1_3_SELEX\|DRGX_Otx1_2325_PBM\|RHOXF1_6\|PITX1_4 | GGGATTAA | TTAATCCC |
| SHOX_MA0075.1_SELEX\|PRRX2_2 | AATTA | TAATT |
| ATF3_Jundm2_0911_PBM\|ATF1_Atf1_3026_PBM\|ATF3_pTH5464_PBM | GATGACGTAA | TTACGTCATC |
| ETV7_1 | CAGGAAGTAG | CTACTTCCTG |
| RARG_RARG_6_SELEX\|RARG_6 | AAGGTCAACAGAGGTCA | TGACCTCTGTTGACCTT |

TABLE 5-continued

Transcription Factor Binding Sites of Synthetic Promoters

| Name | Binding Site Sequence | Reverse Complement |
|---|---|---|
| EGR1_known3 | GTCGCCCCCAC | GTGGGGGCGAC |
| CDX2_V$CDXA_01_Transfac | ATTTATG | CATAAAT |
| E2F1_V$E2F_01_Transfac\|E2F_known1 | CAGTTTTCGCGCGTA | TACGCGCGAAAACTG |
| RELA_GM15510_NFKB_Stanford_ChIP-seq | AGGGGATTTCCAGG | CCTGGAAATCCCCT |
| SRY_V$SRY_01_Transfac\|SRY_1 | AAACAAA | TTTGTTT |
| ESRRG_MA0141.2_ChIP-seq | AGGTCAAGGTCA | TGACCTTGACCT |
| HOXC5_HXA5_si_HocoMoco\|HOXC5_HX67_si_HocoMoco | CATTAATCAA | TTGATTAATG |
| MAF_known1 | AGGCAACTTCCCTCTA | TAGAGGGAAGTTGCCT |
| YY2_K562_YY1_HudsonAlpha_ChIP-seq | ACCCAAGATGGCGGC | GCCGCCATCTTGGGT |
| PPARA_PPARA_f1_HocoMoco\|NR5A1_ftz-f1_SANGER_5_FBgn0001078_B1H\|NR2F2_svp_SANGER_5_FBgn0003651_B1H | AAGGTCA | TGACCTT |
| AP1_known6 | GAATGAGTCAGCA | TGCTGACTCATTC |
| CDX2_MA0465.1_ChIP-seq | AAGCCATAAAA | TTTTATGGCTT |
| MAFB_MA0117.1_SELEX\|MAF_known3 | GCGTCAGC | GCTGACGC |
| NFE2L1::MAFG_2 | CATGAC | GTCATG |
| HOXC5_Hoxa3_2783_PBM | AGGTCATTAA | TTAATGACCT |
| PPARA_PPARD_f1_HocoMoco | TAGGACAAAGGTCA | TGACCTTTGTCCTA |
| YY2_pho_SOLEXA_5_FBgn0002521_B1H | ACCAAAATGGCGGCC | GGCCGCCATTTTGGT |
| HNF4_known9 | GGGGCAAAGTTCAA | TTGAACTTTGCCCC |
| ELF3_ELF3_1_SELEX\|ELF3_EHF_1_SELEX\|EHF_2\|ELF3_2 | AACCCGGAAGTA | TACTTCCGGGTT |
| ELF1_ELF1_1_SELEX\|ELF1_ELF1_2_SELEX\|ELF1_ELF4_1_SELEX\|ELF1_known2\|ELF1_known3\|ELF4_1 | AACCCGGAAGTG | CACTTCCGGGTT |
| MYOD1_MYF6_f1_HocoMoco\|TFCP2_2 | CAGCTGC | GCAGCTG |
| SOX17_MA0078.1_SELEX\|SOX17_2 | CTCATTGTC | GACAATGAG |
| MAFK_K562_MAFK_Stanford_ChIP-seq | AATTGCTGACTCAGC | GCTGAGTCAGCAATT |
| ZNF740_1 | CAAGTGGGGGGGGGG | CCCCCCCCCCACTTG |
| MAX_MAX_f1_HocoMoco | ACCACGTGGCT | AGCCACGTGGT |
| PKNOX2_Pknox2_1_SELEX\|PKNOX2_Meis3_2_SELEX\|PKNOX2_Meis2_2_SELEX\|PKNOX2_PKNOX1_1_SELEX\|PKNOX2_PKNOX2_1_SELEX\|MEIS1_MEIS3_2_SELEX\|MEIS3_3\|MEIS2_4\|MEIS3_5\|PKNOX1_2\|PKNOX2_2\|PKNOX2_3 | TGACACCTGTCA | TGACAGGTGTCA |
| E2F6_HeLa-S3_E2F6_UCD_ChIP-seq\|E2F6_K562b_E2F6_UCD_ChIP-seq | GGGGCGGGAAA | TTTCCCGCCCC |
| NFKB_known6 | GGCGGGAAATTCCCC | GGGGAATTTCCCCGCC |
| RAX_1 | GTGCGCTAATTAGTCA | TGACTAATTAGCGCAC |
| PAX2_V$PAX2_01_Transfac | CCTCGTCACGCATGATGGC | GCCATCATGCGTGACGAGG |
| MYC_disc2 | ACCACGTGGCC | GGCCACGTGGT |
| PAX2_1 | CCTCGTCACGCATGATGGA | TCCATCATGCGTGACGAGG |
| E2F2_E2F2_3_SELEX\|E2F2_4 | AAAATGGCGCCATTTT | AAAATGGCGCCATTTT |

TABLE 5-continued

Transcription Factor Binding Sites of Synthetic Promoters

| Name | Binding Site Sequence | Reverse Complement |
| --- | --- | --- |
| SOX9_Sox10_1_SELEX\|SOX11_Sox11_1_SELEX\|SOX10_8\|SOX11_2 | AACAATTTCAGTGTT | AACACTGAAATTGTT |
| GATA2_T-47D_GATA3_HudsonAlpha_ChIP-seq | ACAGATTCTTATCTG | CAGATAAGAATCTGT |
| PKNOX2_MEIS1_f2_HocoMoco | CATAAAACTGTCA | TGACAGTTTTATG |
| SIX6_Six6_2267_PBM | GAATGATATCC | GGATATCATTC |
| E2F3_pTH9288_PBM | AGCGCGCGCG | CGCGCGCGCT |
| ESRRA_known2 | AGATCAAGGTCATA | TATGACCTTGATCT |
| TCF7L2_I$TCF_1_Transfac | AAGATCAAAGG | CCTTTGATCTT |
| JUN_pTH3064_PBM | TGACTCAA | TTGAGTCA |
| ESRRG_ECC-1_ERALPHA_HudsonAlpha_ChIP-seq | AGGTCACCGTGACCT | AGGTCACGGTGACCT |
| ID4_ID4_1_SELEX\|ID4_1 | GACAGGTGTA | TACACCTGTC |
| ZSCAN4_ZSCAN4_1_SELEX\|ZSCAN4_3 | TGCACACACTGAAAA | TTTTCAGTGTGTGCA |
| TFAP2_known10 | ATTGCCTGAGGCGAA | TTCGCCTCAGGCAAT |
| ESR2_ESR2_do_HocoMoco | AGGTCACCGTGACCC | GGGTCACGGTGACCT |
| SIX2_Six1_0935_PBM\|SIX6_pTH5928_PBM | ATGATACCCC | GGGGTATCAT |
| RARG_RARG_2_SELEX\|RARG_2 | AAGGTCAACTAAAGGTCA | TGACCTTTAGTTGACCTT |
| TBX1_TBX20_1_SELEX\|TBX1_TBX20_5_SELEX\|TBX20_1\|TBX20_5 | AGGTGTGAAGGTGTGA | TCACACCTTCACACCT |
| BARHL2_BARHL2_6_SELEX\|BARHL2_7 | CAATTAGCACCAATTA | TAATTGGTGCTAATTG |
| HNF4_known14 | AGGCCAAAGGTCA | TGACCTTTGGCCT |
| NR1H4_1 | CAAGGTCATTAACC | GGTTAATGACCTTG |
| NHLH2_HLH4C_da_SANGER_5_3_FBgn0011277_B1H\|TCF4_HLH4C_da_SANGER_5_3_FBgn0000413_B1H | CACCTGCTCC | GGAGCAGGTG |
| LMX1B_1 | AGTTTTTAATTAATTTG | CAAATTAATTAAAAACT |
| TCF7L2_known1 | CCTTTGAA | TTCAAAGG |
| HNF1A_2 | ACTTAGTTAACTAAAAA | TTTTTAGTTAACTAAGT |
| E2F_disc1\|HEY1_disc1 | GGTGACGTCA | TGACGTCACC |
| FOXD1_Foxj3_0982_PBM\|FOXD1_pTH6549_PBM | TGTAAACAA | TTTGTTTACA |
| EGR3_EGR3_f1_HocoMoco | ACACCCACTCT | AGAGTGGGTGT |
| SP1_pTH5421_PBM | CATGCAGC | GCTGCATG |
| AL662830.5_PBX2_f1_HocoMoco | CCATCAATCAATTTA | TAAATTGATTGATGG |
| IRX3_Mirr_Cell_F_Bgn0014343_B1H | AAAAAACA | TGTTTTTT |
| REST_disc6 | ACAGCGCT | AGCGCTGT |
| EOMES_1 | AATTTCACACCTTTTA | TAAAAGGTGTGAAATT |
| HF1H36_1 | GCCCCTCCCCCACC | GGTGGGGAGGGGC |
| NR1D2_NR1D1_f1_HocoMoco | AAAAGTAGGTCAGA | TCTGACCTACTTTT |
| BCL_disc8 | CCCCGCTGCCCGGC | GCCGGGCAGCGGGG |
| S_N3A_disc3 | ACCATGGACAG | CTGTCCATGGT |
| EOMES_EOMES_2_SELEX\|EOMES_3 | TCACACCTTAGAAGGTGTGA | TCACACCTTCTAAGGTGTGA |

TABLE 5-continued

Transcription Factor Binding Sites of Synthetic Promoters

| Name | Binding Site Sequence | Reverse Complement |
|---|---|---|
| HDAC2_disc4 | CGCGCGCGCG | CGCGCGCGCG |
| ARX_1 | GTCCATTAATTAATGGA | TCCATTAATTAATGGAC |
| HOXC10_Hoxc9_2367_PBM\|MNX1_MNX1_1_SELEX\|MNX1_2 | GGTAATTAAA | TTTAATTACC |
| LCOR_pTH8558_PBM | AATTTTGGG | CCCAAAATT |
| HOXB2_HOXA1_1_SELEX\|HOXA1_2 | GGTAATTAAC | GTTAATTACC |
| ZNF35_1 | AACAAACAACAAGAG | CTCTTGTTGTTTGTT |
| CEBPG_CEBPG_2_SELEX\|CEBPA_pTH5460_PBM\|CEBPA_CEBPB_1_SELEX\|CEBPA_CEBPB_2_SELEX\|CEBPG_CEBPG_1_SELEX\|CEBPA_Cebpb_1_SELEX\|CEBPA_CEBPE_1_SELEX\|CEBPA_CEBPD_1_SELEX\|CEBPB_disc1\|CEBPB_known8\|CEBPB_known9\|CEBPD_2\|CEBPE_1\|CEBPG_2\|CEBPG_3\|CEBPB_known 10 | ATTGCGCAAT | ATTGCGCAAT |
| YY1_phol_SANGER_5_FBgn0035997_B1H\|TATA_disc1 | CAAGATGGCG | CGCCATCTTG |
| HOXD12_HOXC12_2_SELEX\|HOXC12_3 | GGTCGTAAAAA | TTTTTACGACC |
| STAT5B_V$STAT5A_02_Transfac\|STAT_known6 | CTCTAGGAAACGCAATTCTGGGAA | TTCCCAGAATTGCGTTTCCTAGAG |
| TCF3_6 | ATCCACAGGTGCGAAAA | TTTTCGCACCTGTGGAT |
| MEF2B_MEF2A_1_SELEX\|MEF2_known12 | TCTAAAATAGA | TCTATTTTAGA |
| BATF_BATF_si_HocoMoco | ATGAGTCATA | TATGACTCAT |
| DMBX1_MA0190.1_B1H\|OTX2_MA0234.1_B1H | GGATTA | TAATCC |
| NPAS2_gce_Clk_SANGER_5_FBgn0023076_B1H\|MYCN_MA0104.3_ChIP-seq | CACGTGGC | GCCACGTG |
| FOXD1_FOXF1_f1_HocoMoco | AAAATAAACAT | ATGTTTATTTT |
| EGR3_pTH2820_PBM | CCGCCCACGC | GCGTGGGCGG |
| GLI1_GLI3_si_HocoMoco\|GLI1_GSE11062_Gli3_ChIP-seq | CTGGGTGGTCC | GGACCACCCAG |
| EP300_disc5 | AAAGAGGAAGTGAAA | TTTCACTTCCTCTTT |
| IRX3_Irx3_1_SELEX\|IRX3_3 | CTACATGACAAA | TTTGTCATGTAG |
| AL662830.5_Pbx1_3203_PBM | CCCATCAAA | TTTGATGGG |
| HAND1_1 | AATGCCAGACGCCATT | AATGGCGTCTGGCATT |
| E2F_known18 | GTTTGGCGCGAA | TTCGCGCCAAAC |
| MXI1_disc1 | CCGTCGCCATGGCAAC | GTTGCCATGGCGACGG |
| NR1H2_NR1H2_f1_HocoMoco | CGTTGACCTTTGACCTTTA | TAAAGGTCAAAGGTCAACG |
| SMAD2_SMAD3_1_SELEX\|SMAD3_3 | CGTCTAGACA | TGTCTAGACG |
| SP9_SP4_1_SELEX\|SP4_2 | AAAGGGGGCGTGGCTTA | TAAGCCACGCCCCCTTT |
| TAL1_known1 | CCGACCATCTGTTCAG | CTGAACAGATGGTCGG |
| BARHL2_pTH6503_PBM | AACCAATTAATAT | ATATTAATTGGTT |

TABLE 5-continued

Transcription Factor Binding Sites of Synthetic Promoters

| Name | Binding Site Sequence | Reverse Complement |
|---|---|---|
| GBX2_Unpg_SOLEXA_FBgn0015561_B1H\|MEOX2_Btn_SOLEXA_FBgn0014949_B1H\|SHOX_CG11294_SOLEXA_FBgn0030058_B1H\|EN2_En_SOLEXA_FBgn0000577_B1H\|VSX2_MA0181.1_B1H\|LHX1_Lim3_SOLEXA_FBgn0002023_B1H\|SHOX_MA0172.1_B1H\|HLX_Hlx1_2350_PBM\|LBX2_Lbe_SOLEXA_FBgn0011278_B1H\|HOXA4_MA0257.1_B1H\|HOXC6_MA0230.1_B1H\|LHX9_Ap_SOLEXA_FBgn0000099_B1H\|RAX2_Repo_SOLEXA_FBgn0011701_B1H\|SHOX_Otp_SOLEXA_FBgn0015524_B1H\|EMX2_E5_SOLEXA_FBgn0008646_B1H\|HOXC5_MA0238.1_B1H\|EN2_MA0220.1_B1H\|SHOX_Pph13_SOLEXA_FBgn0023489_B1H\|ALX1_CG9876_SOLEXA_FBgn0034821_B1H\|ALX1_AI_Cell_FBgn0000061_B1H\|HOXA4_Zen2_SOLEXA_FBgn0004054_B1H\|ALX1_MA0208.1_B1H\|ALX1_MA0179.1_B1H\|TLX3_MA0170.1_B1H\|LHX1_Lim1_SOLEXA_FBgn0026411_B1H\|HOXC5_MA0206.1_B1H\|SHOX_Hbn_Cell_F Bgn0008636_B1H\|NKX1-1_MA0245.1_B1H\|HOXC5_Pb_SOLEXA_FBgn0051481_B1H\|HOXC5_Ftz_SOLEXA_FBgn0001077_B1H\|HLX_MA0448.1_B1H\|ALX1_Rx_SOLEXA_FBgn0020617_B1H\|RAX2_MA0240.1_B1H\|NKX6-3_MA0191.1_B1H\|LHX1_MA0195.1_B1H\|SHOX_MA0457.1_B1H\|ALX1_CG32532_Cell_FBgn0052532_B1H\|VSX2_CG4136_Cell_FBgn0029775_B1H\|HOXC6_Lab_Cell_FBgn0002522_B1H\|LMX1A_Lmx1b_3433_PBM\|VSX2_CG4136_SOLEXA_FBgn0029775_B1H\|HOXC6_Lab_SOLEXA_FBgn0002522_B1H\|EMX2_MA0189.1_B1H\|NKX1-1_Slou_SOLEXA_FBgn0002941_B1H\|LHX1_MA0194.1_B1H\|ALX1_CG32532_SOLEXA_FBgn0052532_B1H\|SHOX_CG11294_Cell_FBgn0030058_B1H\|SHOX_MA0226.1_B1H\|LHX1_Lim1_Cell_FBgn0026411_B1H\|GBX2_MA0251.1_B1H\|EMX2_Ems_SOLEXA_FBgn0000576_B1H\|HLX_H2.0_Cell_FBgn0001170_B1H\|SHOX_MA0236.1_B1H\|LMX1A_MA0178.1_B1H | TAATTAA | TTAATTA |
| BX088580.2_POU3F4_2_SELEX\|POU3F4_3 | TAATTTATGCA | TGCATAAATTA |
| ZNF263_disc1 | CCTCCTCCCC | GGGGAGGAGG |
| HOXC10_Hoxd9_3_SELEX\|HOXD9_3 | GTCGTAAAA | TTTTACGAC |
| LM02_V$LMO2COM_01_Transfac | CAGCACCTGGCG | CGCCAGGTGCTG |
| BACH1_BACH1_si_HocoMoco | ACCATGACTCAGCA | TGCTGAGTCATGGT |
| NFE2_disc3 | CACGTGGCCC | GGGCCACGTG |
| SP9_CG5669_SANGER_10_FBgn0039169_B1H | AGGGGGCGGGGCCAA | TTGGCCCCGCCCCCT |
| OTP_OTX2_2_SELEX\|OTX2_3 | AGGATTAA | TTAATCCT |
| DRGX_OTX1_f1_HocoMoco | AGGATTAG | CTAATCCT |
| MYC_known9 | CAAGTAACACGTGACACTTG | CAAGTGTCACGTGTTACTTG |
| IRF_disc4 | AGGGGGCGGGGCCAG | CTGGCCCCGCCCCCT |
| ATF3_ATF3_f1_HocoMoco | GTGACGCCA | TGGCGTCAC |
| HES5_HES5_1_SELEX\|HES5_1 | CGGCACGTGCCA | TGGCACGTGCCG |
| HES5_HES5_2_SELEX | CGGCACGTGCCG | CGGCACGTGCCG |
| MYC_known5 | TACCACGTGTCA | TGACACGTGGTA |
| BARHL2_1 | AAAAACCAATTAAGAA | TTCTTAATTGGTTTTT |
| SOX17_1 | AACAAT | ATTGTT |
| MEF2B_MEF2D_f1_HocoMoco | GCTAAAAATAGC | GCTATTTTTAGC |
| IRF5_IRF5_2_SELEX\|IRF_known16 | AACCGAAACCA | TGGTTTCGGTT |
| RFX5_disc2 | AGCCAATCAG | CTGATTGGCT |

TABLE 5-continued

Transcription Factor Binding Sites of Synthetic Promoters

| Name | Binding Site Sequence | Reverse Complement |
|---|---|---|
| CEBPA_V$CEBPB_02_Transfac\|CEBPB_known2 | ATATTGCACAACTC | GAGTTGTGCAATAT |
| TP53_4 | ACATGCCCGGGCATGTCCGG | CCGGACATGCCCGGCATGT |
| REST_H1-hESC_NRSF_HudsonAlpha_ChIP-seq | AGCACCATGGACAGC | GCTGTCCATGGTGCT |
| MYOD1_3 | CCGAAGCAGGTGGCGAAG | CTTCGCCACCTGCTTCGG |
| ZNF740_Zfp740_1_SELEX\|ZNF740_ZNF740_1_SELEX\|ZNF740_ZNF740_2_SELEX\|ZNF740_2\|ZNF740_3\|ZNF740_4 | CCCCCCCCAC | GTGGGGGGGG |
| NOBOX_2 | CGCGCTAATTAGGTATC | GATACCTAATTAGCGCG |
| ZBTB7C_ZBTB7A_1_SELEX\|ZBTB7A_known3 | GGCGACCACCGA | TCGGTGGTCGCC |
| MYBL1_MA0100.2_ChIP-seq | CCAACTGCCA | TGGCAGTTGG |
| GFI1_1 | AAAAAATAAATCACAGCATATGCC | GGCATATGCTGTGATTTATTTTTT |
| KLF7_1 | ATAGGGGCGGGGTCGA | TCGACCCCGCCCCTAT |
| POU2F2_known10 | GATTTGCATA | TATGCAAATC |
| MYOD1_1 | CAACAGGTGGTG | CACCACCTGTTG |
| ALX1_PRRX1_f1_HocoMoco | CAGATTA | TAATCTG |
| CTCF_HMEC_CTCF_UW_ChIP-seq | CCACCAGGGGCGCCAG | CTGGCGCCCCTGGTGG |
| TCF7L2_Lef1_3504_PBM\|TCF7L1_Tcf7l2_3461_PBM | AGATCAAAGG | CCTTTGATCT |
| ZBTB7C_K562_ZBTB7A_HudsonAlpha_ChIP-seq | CCGAGACCCCTGCCC | GGGCAGGGGTCTCGG |
| TBX5_3 | AAGGTGTGAG | CTCACACCTT |
| TATA_known6 | TATTTATATATAAAGA | TCTTTATATATAAATA |
| EOMES_TBX21_5_SELEX\|TBX3_pTH3751_PBM\|TBX1_pTH3777_PBM\|EOMES_TBX21_2_SELEX\|TBX21_2\|TBX21_5 | AAGGTGTGAA | TTCACACCTT |
| OLIG2_BHLHE22_1_SELEX\|BHLHE22_1 | AAACATATGTTT | AAACATATGTTT |
| HOXA11_1 | ATGTTTTACGACTTTA | TAAAGTCGTAAAACAT |
| ETV5_ERG_2_SELEX\|ETV5_FLI1_4_SELEX\|ETV5_FLI1_2_SELEX\|ETV5_ERG_4_SELEX\|ERG_2\|ERG_4\|FLI1_2\|FLI1_4 | ACCGGAAATCCGGT | ACCGGATTTCCGGT |
| ESRRG_Esrra_1_SELEX\|ESRRA_known10 | TAGGTCAGTCAAGGTCA | TGACCTTGACTGACCTA |
| FOXD1_Foxj3_1_SELEX\|FOXJ3_5 | ACGGACACAAT | ATTGTGTCCGT |
| IRF1_MA0050.2_ChIP-seq | AAAGTGAAAGTGAAAGTAAAA | TTTTACTTTCACTTTCACTTT |
| SOX1_1 | AATCAATTCAATAATT | AATTATTGAATTGATT |
| CDC5L_CDC5L_si_HocoMoco | ATTATGTTAAATCAC | GTGATTTAACATAAT |
| SIX5_disc2\|ZNF143_disc1 | GGGAATTGTA | TACAATTCCC |
| GATA_known11 | AGATAAG | CTTATCT |
| HNF4G_Mv81_ChIP-seq\|HNF4G_MA0114.2_ChIP-seq | CTGGACTTTGGACTC | GAGTCCAAAGTCCAG |
| HOXC10_Hoxa10_2318_PBM\|HOXC10_Hoxa11_2218_PBM | GGTCATAAA | TTTATGACC |
| DMRTC2_pTH9387_PBM | AAATGTAA | TTACATTT |

TABLE 5-continued

Transcription Factor Binding Sites of Synthetic Promoters

| Name | Binding Site Sequence | Reverse Complement |
|---|---|---|
| FOXO6_FOXO1_1_SELEX\|FOXP4_pTH5656_PBM\|FOXD1_FOXJ3_1_SELEX\|FOXP4_pTH1288_PBM\|FOXD1_Foxj3_3_SELEX\|FOXD1_Foxk1_2323_PBM\|FOXD1_pTH5501_PBM\|FOXD1_Foxa2_2830_PBM\|FOXO6_FOXO3_2_SELEX\|KIAA0415_FKH2_4517_PBM\|FOXD1_pTH6638_PBM\|FOXO6_pTH3749_PBM\|FOXD1_pTH6729_PBM\|FOXD1_pTH6734_PBM1 FOXD1_slp2_SANGER_5_FBgn0004567_B1H\|FOXD1_FOXJ2_2_SELEX\|FOXJ2_4\|FOXJ3_2\|FOXO1_3\|FOXO3_5\|FOXJ37 | GTAAACAA | TTGTTTAC |
| LBX2_1 | TCGCATTAATTAATGCA | TGCATTAATTAATGCGA |
| YY2_GM12878_YY1_HudsonAlpha_ChIP-seq | CAAGATGGCGGCCGC | GCGGCCGCCATCTTG |
| GATA2_V$GATA1_06_Transfac | ATAGATAAGA | TCTTATCTAT |
| MYC_known19 | CCCGACCACGTGGTCA | TGACCACGTGGTCGGG |
| REST_V%NRSF_01_Transfac\|REST_known1 | GGCGCTGTCCGTGGTGCTGAA | TTCAGCACCACGGACAGCGCC |
| SP9_Sp1_SANGER_5_FBgn0020378_B1H | GCCACGCCCAC | GTGGGCGTGGC |
| NR3C1_disc4 | AACCAAGATGGCGGC | GCCGCCATCTTGGTT |
| EGR1_known6 | CAGATGCCGCCCACGCATTATTC | GAATAATGCGTGGGCGGCATCTG |
| PKNOX2_V$ME1S1_01_Transfac\|MEIS1_1 | CAGTGACAGGTC | GACCTGTCACTG |
| ZNF524_ZNF524_2_SELEX\|ZNF524_2 | CTCGAACCCGTGCC | GGCACGGGTTCGAG |
| SMAD4_Med_FlyReg_FBgn0011655_B1H | ATTGCCCGCCGC | GCGGCGGGCAAT |
| E2F3_MA0469.1_ChIP-seq | CTCCCGCCCCCACTC | GAGTGGGGGCGGGAG |
| POU3F3_V$OCT1_07_Transfac | AATTAGCATACA | TGTATGCTAATT |
| IRF4_1 | CGTATCGAAACCAAA | TTTGGTTTCGATACG |
| MYC_disc8 | ACCGCGTG | CACGCGGT |
| CUX1_CUX1_2_SELEX\|CUX1_9 | ATCGATAACCTGATCGAT | ATCGATCAGGTTATCGAT |
| ETS_known8 | CGGAAG | CTTCCG |
| SOX13_Sox5_3459_PBM | AGAACAAT | ATTGTTCT |
| NR1D2_Eip75B_SANGER_5_FBgn0000568_B1H | TATGTGGGTCA | TGACCCACATA |
| KLF4_CG9895_SANGER_10_FBgn0034810_B1H | AATGGGCGTGGC | GCCACGCCCATT |
| HEY1_Hey_SANGER_5_FBgn0027788_B1H | CAGCCGACACGTGCCCC | GGGGCACGTGTCGGCTG |
| PKNOX2_Meis1_2335_PBM | AGCTGTCAA | TTGACAGCT |
| CTCF_HSMM_CTCF_Broad_ChIP-seq | CCACCAGAGGGCGCTATA | TATAGCGCCCTCTGGTG |
| DMRT2_pTH9189_PBM | TAATACATTA | TAATGTATTA |
| MEIS1_3 | AAAGACCTGTCAATAC | GTATTGACAGGTCTTT |
| TGIF1_2 | ACGCAGCTGTCAATATC | GATATTGACAGCTGCGT |
| HSF2_1 | AGAATATTCG | CGAATATTCT |
| HNF4G_MA0484.1_ChIP-seq | AGAGTCCAAAGTCCA | TGGACTTTGGACTCT |
| FOXA_known7 | AAAAGTAAACAAGAC | GTCTTGTTTACTTTTT |
| NR2C2_MA0504.1_ChIP-seq | AGGGGTCAGAGGTCA | TGACCTCTGACCCCT |

TABLE 5-continued

Transcription Factor Binding Sites of Synthetic Promoters

| Name | Binding Site Sequence | Reverse Complement |
| --- | --- | --- |
| AR_PRGR_do_HocoMoco | AGAACAGTCTGTA | TACAGACTGTTCT |
| AIRE_AIRE_f2_HocoMoco | ATTGGTTATATTGGTTAA | TTAACCAATATAACCAAT |
| DLX1_1 | ATTAATTACCTCAG | CTGAGGTAATTAAT |
| PAX5_known4 | AGAGCACTGAAGCGTAACCG | CGGTTACGCTTCAGTGCTCT |
| PROP1_1 | CGAATTAATTAAGAAAC | GTTTCTTAATTAATTCG |
| SOX14_1 | GATAATTATAATTAGC | GCTAATTATAATTATC |
| ETV5_Elk3_PBM\|ETV5_Elk4_PBM\|ELF1_Elf2_PBM\|ETV5_FIi1_PBM\|ENSG00000235187_Etv3_PBM\|ETV5_Erg_PBM\|ETV6_Etv6_PBM\|ENSG00000235187_Gm4881_PBM\|ETV5_Elk1_PBM\|ETV5_Gabpa_2829_PBM\|ELF1_Elf4_PBM\|ETV5_Ets1_PBM | AACCGGAAGT | ACTTCCGGTT |
| DMRT1_1 | GCAACAATGTATCAA | TTGATACATTGTTGC |
| ARNT2_dys_tgo_SANGER_5_FBgn0015014_B1H\|NPAS4_dys_tgo_SANGER_5_FBgn0039411_B1H | AAATCGTGACT | AGTCACGATTT |
| NFYA_NFYA_f1_HocoMoco\|NFYB_NFYB_f1_HocoMoco | CAGCCAATCAGAG | CTCTGATTGGCTG |
| DMRTA2_1 | GACACTGTAACAAA | TTTTGTTACAGTGTC |
| FOXA_disc1\|HDAC2_disc2 | TAAGTAAACA | TGTTTACTTA |
| BBX_1 | CACTTCATTGAATTA | TAATTCAATGAAGTG |
| HOXC6_1 | CAAATTAATTAATAAA | TTTTATTAATTAATTTG |
| ETS_disc4 | AACCGGAAGC | GCTTCCGGTT |
| ALX1_PRRX1_2_SELEX\|ALX1_ISX_2_SELEX\|MSX1_Msx3_2_SELEX\|DMBX1_Alx4_1744_PBM\|LHX9_LHX9_1_SELEX\|RAX2_RAXL1_1_SELEX\|SHOX_pTH5805_PBM\|MSX1_MSX2_2_SELEX\|DMBX1_Cart1_1275_PBM\|BSX_BSX_1_SELEX\|SHOX_Shox2_2641_PBM\|MSX1_MSX1_2_SELEX\|SHOX_PRRX2_1_SELEX\|SHOX_SHOX2_1_SELEX\|ALX1_Vsx1_1_SELEX\|SHOX_pTH5666_PBM\|BSX_2\|ISX_3\|LHX9_2\|MSX1_4\|MSX2_4\|MSX2_6\|PRRX1_3\|PRRX2_4\|RAX2_1\|SHOX2_2\|VSX1_4 | CCAATTAA | TTAATTGG |
| STAT_known8\|STAT_known9 | TATTTCCA | TGGAAATA |
| MYB_4 | CAACTGCCA | TGGCAGTTG |
| CR936877.3_MA0016.1_SELEX | CCGTGACCCC | GGGGTCACGG |
| RAD21_disc6 | GCCACCCTCTGGTGGCC | GGCCACCAGAGGGTGGC |
| ONECUT3_MA0235.1_B1H | AAATCAA | TTGATTT |
| NKX2-1_1 | ACACTTGAGT | ACTCAAGTGT |
| POU2F2_known14 | ATGTATTAATTAAGTA | TACTTAATTAATACAT |
| SCRT1_CG17181_SOLEXA_5_FBgn0035144_B1H | AACCACCTGTTGACC | GGTCAACAGGTGGTT |
| ENSG00000234254_V$TGIF_01_Transfac\|TGIF1_1 | AGCTGTCAGAA | TTCTGACAGCT |
| MITF_TFE3_f1_HocoMoco | CCACATGACC | GGTCATGTGG |
| AR_ECC-1_GR_HudsonAlpha_ChIP-seq | AGGGAACAGAATGTTCTGGGC | GCCCAGAACATTCTGTTCCCT |
| TEF_1 | ATGTTAACATAA | TTATGTTAACAT |
| HIC1_HIC2_1_SELEX\|HIC2_1 | ATGCCCACC | GGTGGGCAT |
| IRX5_1 | AATTTTACATGTATATA | TATATACATGTAAAATT |

TABLE 5-continued

Transcription Factor Binding Sites of Synthetic Promoters

| Name | Binding Site Sequence | Reverse Complement |
|---|---|---|
| ETV5_Gabpa_PBM1ETV5_ELK1_f1_HocoMoco\|ETV5_Ets97D_SANGER_10_FBgn0004510_B1H\|ETV5_Etv5_PBM\|ELK4_1 | ACCGGAAGT | ACTTCCGGT |
| HOXC10_Hoxd9_2_SELEX\|HOXD9_2 | GCAATAAAAA | TTTTTATTGC |
| SIX5_Six4_2860_PBM | ATGATACCC | GGGTATCAT |
| HOXC5_PDX1_1_SELEX\|PDX1_5 | GTAATTAACGGTAATTAA | TTAATTACCGTTAATTAC |
| MYC_disc9 | CGCCCACGTC | GACGTGGGCG |
| MYOD1_MA0545.1_ChIP-seq | GAACAGCTGTC | GACAGCTGTTC |
| PITX2_Ptx1_Cell_FBgn0020912_B1H\|DMBX1_Gsc_SOLEXA_FBgn0010323_B1H\|PITX2_MA0201.1_B1H\|OTX2_Oc_Cell FBgn0004102_B1H | GGATTAA | TTAATCC |
| FOXD1_pTH2673_PBM\|FOXD1_pTH3796_PBM\|FOXD1_pTH2808_PBM | TATGTAAACA | TGTTTACATA |
| GZF1_1 | TATAGACGCGCA | TGCGCGTCTATA |
| NFY_known5 | CCTTAGCCAATCA | TGATTGGCTAAGG |
| ZBTB14_3 | TCAGGCGCGCGCGCCA | TGGCGCGCGCGCCTGA |
| HOXC10_HXA9_f1_HocoMoco | TCATAAAACTGTCA | TGACAGTTTTATGA |
| TCF7L2_TCF7_f1_HocoMoco | AGAACAAAGCGC | GCGCTTTGTTCT |
| CREB3L1_CREB3_1_SELEX | CGGTGACGTCATCA | TGATGACGTCACCG |
| DMRT1_pTH9446_PBM | TGTATCAA | TTGATACA |
| LBX2_Lbe_Cell_FBgn0011278_B1H | GTTAACTA | TAGTTAAC |
| POU2F2_known8 | CTCATTTGCATAC | GTATGCAAATGAG |
| ZSCAN26_1 | TTATGTACTAATAA | TTATTAGTACATAA |
| MTF1_Mtf1_2377_PBM | CGTGCGCAA | TTGCGCACG |
| POU3F3_POU3F3_2_SELEX\|POU3F3_3 | ATGCATAAATTA | TAATTTATGCAT |
| MZF1_MA0057.1_SELEX\|MZF1_4 | GGAGGGGAA | TTCCCCCTCC |
| BHLHE40_MA0464.1_ChIP-seq | CTCACGTGCAC | GTGCACGTGAG |
| NHLH2_HEN1_si_HocoMoco | AGGGACGCAGCTGCTCCCCA | TGGGGAGCAGCTGCGTCCCT |
| LHX8_Lhx6_2272_PBM | CTAATCAA | TTGATTAG |
| ARID3C_ARI3A_do_HocoMoco | AATTAATCGAAATCAAATTAAA | TTTAATTTGATTTCGATTAATT |
| JDP2_1 | ACGATGACGTCATCGG | CCGATGACGTCATCGT |
| MAX_HeLa-S3_MAX_Stanford_ChIP-seq\|MYC_NB4_CMYC_Stanford_ChIP-seq | AGCACGTGGCC | GGCCACGTGCT |
| TEAD2_1 | CCGCCGC | GCGGCGG |
| YY2_YY2_2_SELEX\|YY2_2 | AAAATGGCGGT | ACCGCCATTTT |
| AHR_tgo_ss_SANGER_5_FBgn0003513_B1H\|ARNT2_tgo_ss_SANGER_5_FBgn0015014_B1H | GTCACGCA | TGCGTGAC |
| LHX8_LHX6_3_SELEX\|LHX6_5 | TGATTGCAATCA | TGATTGCAATCA |

TABLE 5-continued

Transcription Factor Binding Sites of Synthetic Promoters

| Name | Binding Site Sequence | Reverse Complement |
|---|---|---|
| EMX2_MA0219.1_B1H\|HOXC5_MA0166.1_B1H\|MEOX2_MA0215.1_B1H\|BSX_Bsh_SOLEXA_FBgn0000529_B1H\|HOXC5_MA0203.1_B1H\|HOXC5_MA0225.1_B1H\|HOXC5_Scr_SOLEXA_FBgn0003339_B1H\|HOXC5_Hoxc5_2630_PBM\|HOXC5_MA0186.1_B1H | TCATTAA | TTAATGA |
| TCF12_disc6 | ATTCCAGGC | GCCTGGAAT |
| VDR_1 | GGGTCAAGGGGGTGA | TCACCCCCTTGACCC |
| RAD21_disc5 | CGCTGCCCTCTGC | GCAGAGGGCAGCG |
| TP73_GSE15704_TP73_rapamycin_ChIP-seq\|TP53_MA0106.2_ChIP-seq | ACATGCCCAGACATG | CATGTCTGGGCATGT |
| YY1_known5 | AAAATGGCGGC | GCCGCCATTTT |
| NFIA_NFIA_1_SELEX\|NFIA_NFIX_LSELEX\|NFIA_1\|NFIX_1 | TTGGCACCGTGCCAA | TTGGCACGGTGCCAA |
| MEF2B_V$RSRFC4_01_Transfac | AAGCTATAAATAGAAT | ATTCTATTTATAGCTT |
| NANOG_disc4 | TGCATATCAA | TTGATATGCA |
| EVX2_eve_FlyReg_FBgn0000606_B1H | AAATAATTAACG | CGTTAATTATTT |
| HOXD8_1 | TAATTAATTAATGGCTA | TAGCCATTAATTAATTA |
| GTF2A_1 | GGTCCTTTTATA | TATAAAAGGACC |
| JUN_MA0492.1_ChIP-seq | AAAGATGATGTCATC | GATGACATCATCTTT |
| ETV5_H1-hESC_GABP_HudsonAlpha_ChIP-seq | AACCGGAAGTG | CACTTCCGGTT |
| GATA2_Mw145_ChIP-seq | TCTTATCA | TGATAAGA |
| ARNT2_ss_tgo_SANGER_10_FBgn0015014_B1H\|AHR_ss_tgo_SANGER_10_FBgn0003513_B1H | CATTGCGTGAC | GTCACGCAATG |
| NFE2L1:: MAFG_1 | CATAATTGCTGAGTCATTTTAG | CTAAAATGACTCAGCAATTATG |
| MEF2_known6 | CGGTTTAAAAATAACCCA | TGGGTTATTTTTAAACCG |
| ELF1_I$E74A_01_Transfac | CCTCACTTCCGGGTTCG | CGAACCCGGAAGTGAGG |
| NKX2-5_Titf1_1722_PBM | CCACTTAA | TTAAGTGG |
| EBF1_known3 | ACCCAAGGGA | TCCCTTGGGT |
| POU3F3_V$OCT1_01_Transfac | CCGAAATTTGCATATTGAA | TTCAATATGCAAATTTCGG |
| RARG_RARB_a_HocoMoco | GAGGTCAGGGC | GCCCTGACCTC |
| SP4_1 | GAGAAGGGGCGGGACC | GGTCCCGCCCCCTTCTC |
| PPARA_2 | CCTGACCCCAATGACCCGA | TCGGGTCATTGGGGTCAGG |
| HOXB4_1 | CGCGTTAATTAATTACC | GGTAATTAATTAACGCG |
| TCF4_TCF4_2_SELEX\|TCF4_2 | CACACCTGCA | TGCAGGTGTG |
| MYOD1_V$MYOD_Q6_Transfac | AGCACCTGTC | GACAGGTGCT |
| PHOX2B_1 | CCTATTAATTAATTCCG | CGGAATTAATTAATAGG |
| MEIS1_2 | AAGGAGCTGTCAATAC | GTATTGACAGCTCCTT |
| ETV5_ETV2_1_SELEX\|ETV2_1 | AACCGGAAATA | TATTTCCGGTT |
| FOXM1_FOXM1_f1_HocoMoco | AAAACAAACAAC | GTTGTTTGTTTT |

TABLE 5-continued

Transcription Factor Binding Sites of Synthetic Promoters

| Name | Binding Site Sequence | Reverse Complement |
| --- | --- | --- |
| HNF4G_Mv82_ChIP-seq | AGTCCA | TGGACT |
| BHLHA15_pTH4582_PBM | ACATATGG | CCATATGT |
| EBF1_V$OLF1_01_Transfac\|EBF1_known1 | ACAACCTCCCTGGGGAGTTGTG | CACAACTCCCCAGGGAGGTTGT |
| DMBX1_DMBX1_1_SELEX\|DMBX1_2 | GCGGATTAAC | GTTAATCCGC |
| LBX2_LBX2_2_SELEX\|HESX1_HESX1_1_SELEX\|NKX1-1_Nkx1-1_3856_PBM\|HESX1_1\|LBX2_3 | GCCAATTAGC | GCTAATTGGC |
| REST_disc9 | GCACCTCGCACAGC | GCTGTGCGAGGTGC |
| YY2_YY1_1_SELEX\|YY1_known7 | ATAATGGCGGC | GCCGCCATTAT |
| MECP2_M_ECP2_f1_HocoMoco | CCCGGAG | CTCCGGG |
| MAFK_Mafk_3106_PBM | ATTTTGCTGA | TCAGCAAAAT |
| TAL1_disc2 | AGATAAGAG | CTCTTATCT |
| TWIST2_TWST1_f1_HocoMoco | ACCCAGGTGG | CCACCTGGGT |
| YY1_known1 | GAACACCATTTTGAAC | GTTCAAAATGGTGTTC |
| NR2E3_MA0164.1_SELEX\|NR2E3_1 | AAGCTTG | CAAGCTT |
| EOMES_TBR1_2_SELEX\|TBX3_TBX2_2_SELEX\|TBR1_2\|TBX2_2 | AAGGTGTGAAA | TTTCACACCTT |
| LHX6_2 | AACCGCTAATTAGTGGA | TCCACTAATTAGCGGTT |
| ASCL2_Ascl2_1_SELEX\|ASCL2_2 | AGCAGCTGCT | AGCAGCTGCT |
| MYB_3 | AGGGCCAGTTG | CAACTGGCCCT |
| GATA2_Gata5_3768_PBM | AGAGATAAG | CTTATCTCT |
| AP1_known9 | ATGACTCA | TGAGTCAT |
| SP9_SP1_f2_HocoMoco | CCGGCCCCGCCCCCTCCCC | GGGGAGGGGGCGGGGCCGG |
| RARG_RARA_4_SELEX\|RARA_5 | AGGGTCAAAGGTCA | TGACCTTTGACCCT |
| ZFHX2_pTH5642_PBM\|NOTO_pTH6268_PBM | GTTAATTAAC | GTTAATTAAC |
| UBP1_SRP000217_Tcfc2p11_ChIP-seq\|UBP1_SRP000217_Tcfcp2l1_ChIP-seq | CCGGTTCAAACCGGTTCTGGC | GCCAGAACCGGTTTGAACCGG |
| ESRRG_ESRRG_1_SELEX\|ESRRG_1 | AAGGTCATTTCAAGGTCA | TGACCTTGAAATGACCTT |
| CDX2_Cdx1_2245_PBM | GGTAATAAA | TTTATTACC |
| FOXO6_V$FOXO1_02_Transfac | AACGTAAACAACAC | GTGTTGTTTACGTT |
| MAFK_MAFG_si_HocoMoco | AGTCATG | CATGACT |
| MAZ_MAZ_f1_HocoMoco | CCCTCCCTCCCCCCCC | GGGGGGGGAGGGAGGG |
| TCF3_2 | AATAACAGGTGTTCAC | GTGAACACCTGTTATT |
| FOXO6_FOXO6_3_SELEX\|FOXO6_3 | GTCGTGTGGGAAA | TTTCCCACACGAC |
| ESRRG_ESRRG_2_SELEX\|ESRRG_2 | AAGGTCAGTCAAGGTCA | TGACCTTGACTGACCTT |
| SIN3A_disc2 | GGCCACGTGA | TCACGTGGCC |
| SOX7_SOX7_3_SELEX\|SOX7_4 | CATGACTGAAATTCATC | GATGAATTTCAGTCATG |
| TBPL2_MA0386.1_PBM\|TBPL2_YER148W_798_DeBoer11 | ATCGAATATATATATCTAGTC | GACTAGATATATATATTCGAT |

TABLE 5-continued

Transcription Factor Binding Sites of Synthetic Promoters

| Name | Binding Site Sequence | Reverse Complement |
| --- | --- | --- |
| HOXC5_V$HOX13_01_Transfac | TGCCAACTTCCCCATTA | TGGAGGCGACCACTAAT |
| | GTGGTCGCCTCCA | GGGGAAGTTGGCA |
| EMX2_1 | ACCACTAATTAGTGGAC | GTCCACTAATTAGTGGT |
| ATF3_Mv43_ChIP-seq\|TCF7L2_disc1 | ATGAGTCATC | GATGACTCAT |
| NR1H4_3 | AGGGTTAATAAA | TTTATTAACCCT |
| RAD21_disc4 | ACCTGGTGGC | GCCACCAGGT |
| CBFB_PEBB_f1_HocoMoco | CAAACCACAGA | TCTGTGGTTTG |
| STAT_disc5 | AAATTCCTG | CAGGAATTT |
| HNF4G_VSHNF4_01_B_Transfac | GGGGTCAAAGGTCAC | GTGACCTTTGACCCC |
| NKX2-5_MA0503.1_ChIP-seq | AGCCACTCAAG | CTTGAGTGGCT |
| TFCP2_VSCP2_01_Transfac | CTGGGTAGAGC | GCTCTACCCAG |
| GRHIA_GRHL1_2_SELEX\|TFCP2_TFCP2_1_SELEX\|GRHL1_2\|TFCP2_4 | AAACCGGTTT | AAACCGGTTT |
| NANOGP1_NANOG_f1_HocoMoco | CCATTAAA | TTTAATGG |
| NKX2-5_Nkx2-5_3436_PBM | GCCACTTAAA | TTTAAGTGGC |
| NKX2-5_NKX32_f1_HocoMoco | AGTTAAGTGGA | TCCACTTAACT |
| PAX4_5 | GAAAAATTTCCAATACTCCACTCCCCCCCC | GGGGGGGGAGTGGAGTATTGGAAATTTTC |
| NR2F2_NR2F1_4_SELEX\|HNF4_known26 | CAAAGGTCAAGGG | CCCTTGACCTTTG |
| HNF1_1 | GGTTAATAATTACCA | TGGTAATTATTAACC |
| THRB_THB_f1_HocoMoco | GGTCAGGTCA | TGACCTGACC |
| IRF8_IRF8_1_SELEX\|RF_known19 | ACGAAACCGAAACT | AGTTTCGGTTTCGT |
| ONECUT3_ONECUT3_1_SELEX\|ONECUT3_1 | AAAAAATCAATAAT | ATTATTGATTTTTT |
| GLIS3_lmd_SANGER_5_FBgn0039039_B1H | ACGACCCCCACAG | CTGTGGGGGTCGT |
| E4F1_E4F1_f1_HocoMoco | CGTGACGTC | GACGTCACG |
| SOX10_1 | CTTTGTC | GACAAAG |
| ETV5_ETS2_f1_HocoMoco | CCACTTCCCGC | GCGGGAAGTGG |
| CHD2_disc2\|E2F_disc5 | AAAGGCGC | GCGCCTTT |
| LHX5_1 | AGTATTTAATTAATTCG | CGAATTAATTAAATACT |
| NR1H4_2 | AGGTCATTAACCC | GGGTTAATGACCT |
| YY1_known3 | AGATGGCCG | CGGCCATCT |
| ETV5_K562_GABP_HudsonAlpha_ChIP-seq | CACTTCCGGTTCC | GGAACCGGAAGTG |
| CUX1_V$CDP_01_Transfac\|CUX1_1 | ATCGATTATTGG | CCAATAATCGAT |
| PLAGL1_Plagl1_0972_PBM | GGGGCCCCCC | GGGGGGCCCC |
| HOXC10_Hoxa11_1_SELEX\|HOXA11_2 | AATTTTACGACC | GGTCGTAAAATT |
| SMAD1_Mad_FlyReg_FBgn0011648_B1H | CGGCCGACGC | GCGTCGGCCG |
| CTCF_HCPEpiC_CTCF_UW_ChIP-seq\|CTCF_HepG2_CTCF_UW_ChIP-seq | CGCCCCCTGGTGGC | GCCACCAGGGGCG |
| IRX3_Ara_Cell_FBgn0015904_B1H | AAATAACA | TGTTATTT |

TABLE 5-continued

Transcription Factor Binding Sites of Synthetic Promoters

| Name | Binding Site Sequence | Reverse Complement |
|---|---|---|
| FOXO6_pTH3731_PBM\|FOXO6_pTH3477_PBM | TCGTAAACAA | TTGTTTACGA |
| GFI1B_GFI1_f1_HocoMoco | AAATCACAGC | GCTGTGATTT |
| PKNOX2_MEIS2_1_SELEX\|MEIS2_1 | TTGACAGCTGTCAA | TTGACAGCTGTCAA |
| RFX8_MA0510.1_ChIP-seq | CTCCCTGGCAACAGC | GCTGTTGCCAGGGAG |
| NRF1_NRF1_1_SELEX\|NRF1_known2 | TGCGCATGCGCA | TGCGCATGCGCA |
| PLAGL1_PLAL1_si_HocoMoco | CGGGGGGCCC | GGGCCCCCCG |
| IRF3_IRF3_1_SELEX\|IRF_known14 | CAGTTTCGGTTTCCGTTTCCC | GGGAAACGGAAACCGAAACTG |
| AL662830.5_MA0070.1_SELEX\|PBX1_4 | CCATCAATCAAA | TTTGATTGATGG |
| IRF_known9 | GAAAGCGAAACC | GGTTTCGCTTTC |
| SETDB1_disc1 | CGGGGCATTCTGGGAATGTAGTCC | GGACTACAATTCCCAGAATGCCCCG |
| GLIS3_lmd_SOLEXA_5_FBgn0039039_B1H | CAGACCCCCCACAGA | TCTGTGGGGGGTCTG |
| PRDM1_Mv112_ChIP-seq | AAAGTGATA | TATCACTTT |
| LHX9_LHX9_2_SELEX\|LHX9_3 | TAATTGCCAATTA | TAATTGGCAATTA |
| HNF4G_HNF4A_f1_HocoMoco | AGGCCAAAGTCCA | TGGACTTTGGCCT |
| TP53_V$P53_02_Transfac\|TP53_2 | AGACATGCCT | AGGCATGTCT |
| POU6F2_V$POU6F1_01_Transfac\|POU6F1_1 | ATAAATTATGC | GCATAATTTAT |
| GATA2_V$GATA3_01_Transfac\|GATA_known3 | CCCTATCTC | GAGATAGGG |
| ESRRG_MA0592.1_ChIP-seq | CCAAGGTCACA | TGTGACCTTGG |
| HMGN3_disc1 | CGCTGACTCA | TGAGTCAGCG |
| RXRA_known9 | ATTAAGGGGTCACGACA | TGTCGTGACCCCTTAAT |
| AP1_disc9 | ACTCATGC | GCATGAGT |
| NFIL3_NFIL3_si_HocoMoco | ATGCATTACATAAC | GTTATGTAATGCAT |
| SOX17_SOX17_f2_HocoMoco | CAACAATCTTCATTGTCC | GGACAATGAAGATTGTTG |
| SRF_SRF_1_SELEX\|SRF_known9 | ACCATATATGGC | GCCATATATGGT |
| MYBL1_MYBL1_2_SELEX\|MYBL1_3 | ACCGTTAACGGT | ACCGTTAACGGT |
| TFE_1 | TCACATGA | TCATGTGA |
| SREBF2_pTH5161_PBM | ATCACGCGA | TCGCGTGAT |
| PAX3_V$PAX3_01_Transfac\|PAX3_2 | TCGTCACGCTTCA | TGAAGCGTGACGA |
| PRDM16_MA0029.1_SELEX\|RUNX1_8 | AAGATAAGATAACA | TGTTATCTTATCTT |
| NFE2_disc1 | ATGACTCAGC | GCTGAGTCAT |
| SRF_pTH10822_PBM | CATATAAGG | CCTTATATG |
| RBPJ_SUH_f1_HocoMoco | CGTGGGAAA | TTTCCCACG |
| MSX1_MSX2_f1_HocoMoco | ACAATTA | TAATTGT |
| MAFK_MAFG_1_SELEX\|MAFG_1 | AAATTGCTGAGTCAGCATATT | AATATGCTGACTCAGCAATT |
| FOXD1_V$FOXJ2_02_Transfac\|FOXJ2_2 | AAAAATATTATTAT | ATAATAATATTTTT |
| RUNX1_RUNX1_f1_HocoMoco | TAACCACAAA | TTTGTGGTTA |

TABLE 5-continued

Transcription Factor Binding Sites of Synthetic Promoters

| Name | Binding Site Sequence | Reverse Complement |
|---|---|---|
| ETS1_V$CETS1P54_02_Transfac | CCACCGGAAATTA | TAATTTCCGGTGG |
| RFX5_known3 | AGTTACTAGGCAAA | TTTGCCTAGTAACT |
| HOXC5_MA0256.1_B1H\|EVX2_MA0221.1_B1H | CTAATGA | TCATTAG |
| ESRRG_ESRRA_3_SELEX\|ESRRG_ESRRA_6_SELEX\|ESRRA_known9 | CAAGGTCATTTCAAGGTCA | TGACCTTGAAATGACCTTG |
| TFAP2A_TFAP2C_1_SELEX\|TFAP2A_TFAP2C_4_SELEX\|TFAP2A_TFAP26_1_SELEX\|TFAP26_21TFAP2_known14\|TFAP2_known17 | TGCCCCAGGGCA | TGCCCTGGGGCA |
| SOX15_SOX15_3_SELEX\|SOX1_SOX2_2_SELEX\|SOX1_SOX14_2_SELEX\|SOX1_SOX2_6_SELEX\|SOX1_Sox1_2_SELEX\|SOX14_3\|SOX15_4\|SOX2_3\|SOX2_7\|SOX1_3 | ATGAATAACATTCAT | ATGAATGTTATTCAT |
| POU3F3_pTH9290_PBM | AATTTGCATA | TATGCAAATT |
| MLX_Mio_bigmax_SANGER_5_FBgn0039509_B1H | ATCACGTG | CACGTGAT |
| CDX2_Cad_Cell_FBgn0000251_B1H\|HOXB13_pTH6143_PBM\|CDX2_Cad_SOLEXA_FBgn0000251_B1H | TAATAAAA | TTTTATTA |
| INSM1_MA0155.1_COMPILED\|INSM1_1 | CGCCCCTGACA | TGTCAGGGGCG |
| MYBL1_Myb_1047_PBM | TAACGGTCAA | TTGACCGTTA |
| ARNT2_ARNT2_si_HocoMoco | GCCTCCCACGCC | GGCGTGGGAGGC |
| GATA2_V$GATA3_03_Transfac | AAAGATCTTA | TAAGATCTTT |
| CEBPA_HepG2_CEBPB_Stanford_ChIP-seq | ATTGTGCAATC | GATTGCACAAT |
| YY2_MA0095.2_ChIP-seq\|YY2_TYY1_J2_HocoMoco | CAAGATGGCGGC | GCCGCCATCTTG |
| CEBPA_MA0466.1_ChIP-seq | ATTGTGCAATA | TATTGCACAAT |
| ZBTB7A_known2 | AAGCCCCCCAAAAAT | ATTTTTGGGGGCTT |
| MEF2B_V$MEF2_03_Transfac\|MEF2_known4 | TGTGGTTCTAAAATAGAACAA | TTGTTCTATTTTAGAACCACA |
| EGR1_known4 | CCCGCCCCGCCCC | GGGGCGGGGCGGG |
| GATA1_GATAe_SANGER_5_FBgn0038391_B1H | CTTATCA | TGATAAG |
| PAX2_PAX2_f1_HocoMoco | GTTCAGTCATGCGTGACA | TGTCACGCATGACTGAAC |
| PAX4_6 | GTGGGCTAATTAGTTCA | TGAACTAATTAGCCCAC |
| ARNT2_tgo_cyc_SANGER_5_FBgn0023094_B1H\|BHLHE40_Bhlhb2_1274_PBM\|ARNT2_tgo_cyc_SANGER_5_FBgn0015014_B1H | GTCACGTGA | TCACGTGAC |
| EN2_EN1_2_SELEX\|EN1_5 | TAATTGACCAATTA | TAATTGGTCAATTA |
| NR5A2_1 | CTGACCTTGAAC | GTTCAAGGTCAG |
| YY2_YY2_3_SELEX | ATGGCGGCATGG | CCATGCCGCCAT |
| MAFK_MAFK_3_SELEX\|MAF_known8 | AAAATTGCTGAC | GTCAGCAATTTT |
| ZBTB42_ZNF238_1_SELEX\|ZBTB18_2 | AATCCAGATGTTG | CAACATCTGGATT |
| TA L2_TAL1_f1_Hoco Moco | GAACAGATGGTC | GACCATCTGTTC |
| CPEB1_CPEB1_1_SELEX\|CPEB1_1 | AATAAAAA | TTTTTATT |
| TCF7L2_pan_FlyReg_FBgn0085432_B1H\|TCF7L1_Tcf3_3787_PBM | CTTTGATC | GATCAAAG |
| ETS_known6 | ACCGGAAGTGCA | TGCACTTCCGGT |
| TCF7L1_MA0523.1_ChIP-seq | AAAGATCAAGGAA | TTCCTTGATCTTT |

TABLE 5-continued

Transcription Factor Binding Sites of Synthetic Promoters

| Name | Binding Site Sequence | Reverse Complement |
|---|---|---|
| ETV5_ETV5_f1_HocoMoco | GACAGGAAGTAAC | GTTACTTCCTGTC |
| ETV5_ERG_f1_HocoMoco | ACCGGAAATCC | GGATTTCCGGT |
| MZF1_MZF1_f1_HocoMoco | GGTGGGGAA | TTCCCCACC |
| RUNX_2 | ACGTTTGTGGTTAGC | GCTAACCACAAACGT |
| PBX1_5 | TCACCCATCAATAATCA | TGATTATTGATGGGTGA |
| EGR3_EGR4_f1_HocoMoco | GCCCTGCCGCC | GGCGGCAGGGC |
| POU3F3_POU3F2_1_SELEX\|POU3F2_5 | TAATTTATGCATA | TATGCATAAATTA |
| LHX2_1 | GTTCACTAATTAGTTTA | TAAACTAATTAGTGAAC |
| MYOD1_V$MYOD_01_Transfac | CAACACCTGTCC | GGACAGGTGTTG |
| GATA2_Mv73_ChIP-seq | CTGGTGGGGCAGATAAGGA | TCCTTATCTGCCCCACCAG |
| TCF4_GM12878_TCF12_HudsonAlpha_ChIP-seq | ACAGCTGCTGC | GCAGCAGCTGT |
| TCF7L2_known4 | CATCAAAGGG | CCCTTTGATG |
| HNF4_known8 | AAAGTCCAA | TTGGACTTT |
| FOXO6_N$DAF16_01_Transfac | GTGTTGTTTACAAC | GTTGTAAACAACAC |
| HMBOX1_1 | GAAAACTAGTTAACATC | GATGTTAACTAGTTTTC |
| CTCF_NHEK_CTCF_UW_ChIP-seq | CCACCAGGGGCGC | GCGCCCCTGGTGG |
| ALX1_2 | CGAATTAATTAATCACC | GGTGATTAATTAATTCG |
| ELF1_MA0473.1_ChIP-seq | CACTTCCTGGTTC | GAACCAGGAAGTG |
| EOMES_TBX21_1_SELEX\|TBX21_1 | GGTGTGAATTCACACC | GGTGTGAATTCACACC |
| AL662828.6_V$ATF6_01_Transfac\|ATF6_1 | CCACGTCA | TGACGTGG |
| ATF3_pTH2684_PBM | ACGTCATCA | TGATGACGT |
| E2F_known22 | GCGCCAAA | TTTGGCGC |
| POU5F1_known1 | ATTGTCATGCTAATG | CATTAGCATGACAAT |
| ELF1_GM12878_ELF1_HudsonAlpha_ChIP-seq | CCACTTCCGGGTTCG | CGAACCCGGAAGTGG |
| MAF_known4 | AAATTTGCTGACTTAGC | GCTAAGTCAGCAAATTT |
| HEY1_disc2 | GCCCCGCTGCCGCCGC | GCGGCGGCAGCGGGGC |
| FOXD1_HepG2_FOXA2_HudsonAlpha_ChIP-seq | CTCTGTTTACTTTGC | GCAAAGTAAACAGAG |
| HNF1A_MA0046.1_COMPILED | GGTAATTATTAACC | GGTTAATAATTACC |
| HMGA2_HMGA1J1_HocoMoco | AAAATAC | GTATTTT |
| SOX18_SOX18_f1_HocoMoco | GAACCCATTGTTCTTTTC | GGAAAAGAACAATGGGTTC |
| SRF_known6 | ATGGCCATATAAGGAGATG | CATCTCCTTATATGGCCAT |
| TGIF2LY_TGIF2LX_1_SELEX\|ENSG00000234254_TGIF1_1_SELEX\|ENSG00000234254_TGIF2_1_SELEX\|TGIF1_3\|TGIF2LX_1\|TGIF2_2 | TGACAGCTGTCA | TGACAGCTGTCA |
| GFI1B_sens_SANGER_10_FBgn0002573_B1H | AAATCACGGC | GCCGTGATTT |
| SIX5_Mv123_ChIP-seq\|ETS_disc5 | ACAACTCC | GGAGTTGT |
| RFX8_H1-hESC_RFX5_Stanford_ChIP-seq | TCACCTGTTGCTAGGCAGA | TCTGCCTAGCAACAGGTGA |

TABLE 5-continued

Transcription Factor Binding Sites of Synthetic Promoters

| Name | Binding Site Sequence | Reverse Complement |
|---|---|---|
| GBX2_GBX1_1_SELEX\|HOXA4_Hoxa2_1_SELEX\|HOXC5_HOXB3_1_SELEX\|LHX8_LHX6_1_SELEX\|GBX1_2\|HOXB3_2\|HOXA2_3\|LHX6_3 | ACTAATTAGC | GCTAATTAGT |
| EGR3_V$EGR2_01_Transfac\|EGR1_known2 | ACGCCCACGCAA | TTGCGTGGGCGT |
| ZBTB4_ZBTB4!METH_f1_HocoMoco | CAATAGCGGTGGTGG | CCACCACCGCTATTG |
| SP1_known6\|SP1_known7 | CCCCGCCCCC | GGGGGCGGGG |
| EGR3_V$EGR3_01_Transfac\|EGR3_V$EGR1_01_Transfac\|EGR1_known1\|EGR3_1 | ACGCCCACGCAT | ATGCGTGGGCGT |
| SP5_pTH9394_PBM | ACACGCCCCT | AGGGGCGTGT |
| HOXD12_Hoxc12_3480_PBM\|HOXD12_Hoxd12_3481_PBM\|HOXC10_Hoxb9_3413_PBM\|HOXC10_Hoxc11_3718_PBM | GGTCATAAAA | TTTTATGACC |
| RAD21_disc1 | GGCCACCAGATGGCACTATA | TATAGTGCCATCTGGTGGCC |
| HHEX_pTH6423_PBM | GGGCAATAGA | TCTATTGCCC |
| PPARA_V$PPARA_01_Transfac\|PPARA_1 | CAAAACTAGGTCAAAGGTCA | TGACCTTTGACCTAGTTTTG |
| GLI1_GLI1_f1_HocoMoco | AGACCACCCAG | CTGGGTGGTCT |
| SMAD2_SMAD3_f1_HocoMoco | GGCCAGACAC | GTGTCTGGCC |
| GLI1_GLI2_f1_HocoMoco\|GLI1_Ci_SANGER_5_FBgn0004859_81H | AGACCACCCAC | GTGGGTGGTCT |
| SPIC_MA0080.3_ChIP-seq\|SPIC_GSE11329_Sfpi1_ChIP-seq | AAAAAGAGGAAGTGA | TCACTTCCTCTTTTT |
| FOXD1_MA0040.1_SELEX\|FOXQ1_2 | AATAAACAATA | TATTGTTTATT |
| HEY1_pTH5102_PBM\|NPAS2_tai_Clk_SANGER_5_FBgn0023076_B1H | GACACGTGC | GCACGTGTC |
| USF1_pTH4376_PBM | CCCACGTGATA | TATCACGTGGG |
| CBX5_1 | AATATTCAACAG | CTGTTGAATATT |
| TFAP2A_TFAP2A_5_SELEX | TGCCCTAGGGCA | TGCCCTAGGGCA |
| NFYC_NFYC_f1_HocoMoco | CAGCCAATCAGCGC | GCGCTGATTGGCTG |
| FOXD1_MA0033.1_SELEX\|FOXL1_2 | TATACATA | TATGTATA |
| ETV5_GM12878_GABP_HudsonAlpha_ChIP-seq | CACTTCCGGCG | CGCCGGAAGTG |
| RARG_RARG_5_SELEX\|RARG_5 | AAGGTCAAGCAAAGGTCA | TGACCTTTGCTTGACCTT |
| HOXC5_Abd-A_FlyReg_FBgn0000014_81H\|HOXC5_HXD4_f1_HocoMoco | TCAATTAA | TTAATTGA |
| FOXD1_FOXI1_f1_HocoMoco | AACCAATCAGAG | CTCTGATTGGTT |
| ETV5_ELK1_3_SELEX\|ETS_known13 | CACTTCCGCCGGAAGTG | CACTTCCGGCGGAAGTG |
| SPIC_SPIB_f1_HocoMoco | AAAAAGAGGAAG | CTTCCTCTTTTT |
| POU4F1_POU4F2_1_SELEX\|POU4F1_POU4F3_1_SELEX\|POU4F1_POU4F2_2_SELEX\|POU4F2_1\|POU4F2_2\|POU4F3_2 | ATGCATAATTAATGAG | CTCATTAATTATGCAT |
| HDX_Hdx_3845_PBM | GAAATCA | TGATTTC |
| GCM1_pTH9341_PBM\|GCM1_pTH9357_PBM\|GCM1_GCM2_1_SELEX\|GCM2_1 | TACCCGCATA | TATGCGGGTA |
| MSX2_1 | AGCGCTAATTGGTCTTC | GAAGACCAATTAGCGCT |

TABLE 5-continued

Transcription Factor Binding Sites of Synthetic Promoters

| Name | Binding Site Sequence | Reverse Complement |
|---|---|---|
| STAT5B_STA5A_do_HocoMoco | AATTCCTGGAAA | TTTCCAGGAATT |
| PKNOX2_MEIS2_2_SELEX\|MEIS2_2 | GCTGTCAA | TTGACAGC |
| AL662830.5_V$PBX1_02_Transfac\|PBX1_2 | AATTTGATTGATGTG | CACATCAATCAAATT |
| LHX8_Lhx8_1_SELEX\|LHX8_2 | CTAATTAGCGCTAATTAA | TTAATTAGCGCTAATTAG |
| RFX8_RFX1_4537_PBM | GTAGCAACCA | TGGTTGCTAC |
| BCL6B_BCL66_1_SELEX\|BCL6B_2 | TGAATTCCTAGAAAGCA | TGCTTTCTAGGAATTCA |
| JUN_HepG2_CJUN_Stanford_ChIP-seq | GAGGATGACGTCATC | GATGACGTCATCCTC |
| ATOH7_MA0461.1_ChIP-seq | CAGATGGC | GCCATCTG |
| MYBL1_MYBL1_1_SELEX\|MYBL1_2 | ACCGTTAAACGG | CCGTTTAACGGT |
| TLX3_TLX1_f1_HocoMoco | CGCCAAGGAGC | GCTCCTTGGCG |
| ETS_known5 | AATTACTTCCTGTC | GACAGGAAGTAATT |
| STAT_disc4 | ATTGCACAA | TTGTGCAAT |
| RARG_Rara_2_SELEX\|RARA_9 | AGGTCACTCAAAGGTCA | TGACCTTTGAGTGACCT |
| XBP1_XBP1_f1_HocoMoco | GACGTGTCATTA | TAATGACACGTC |
| ESRRB_1 | AGCTCAAGGTCA | TGACCTTGAGCT |
| MYOD1_MA0499.1_ChIP-seq | AGGGACAGCTGCA | TGCAGCTGTCCCT |
| CEBPA_K562_CEBPB_Stanford_ChIP-seq | GATTGTGCAATACC | GGTATTGCACAATC |
| MAFB_Mafb_3_SELEX\|MAF_known12 | AATGCTTACGTCAGCACT | AGTGCTGACGTAAGCATT |
| NPAS2_Met_Clk_SANGER_5_FBgn0023076_B1H | CACGTGTC | GACACGTG |
| HOXC10_HOXA10_2_SELEX\|HOXA10_3 | GGTAATAAAAA | TTTTTATTACC |
| ONECUT3_ONECUT1_1_SELEX\|ONECUT3_ONECUT1_2_SELEX\|ONECUT3_ONECUT2_1_SELEX\|ONECUT1_2\|ONECUT1_3\|PNECUT2_1 | AAAAAATCGATAAT | ATTATCGATTTTTT |
| EBF1_known2 | GTCCCTTGGGA | TCCCAAGGGAC |
| TERF2_pTH7805_PBM | CTAGGGTTA | TAACCCTAG |
| PAX5_known3 | CTGGAACTCAC | GTGAGTTCCAG |
| SOX1_SOX14_1_SELEX\|SOX14_2 | ACAATAACATTG | CAATGTTATTGT |
| SRF_known4 | CCCATATAAGGAGATGGC | GCCATCTCCTTATATGGG |
| CTCF_HEEpiC_CTCF_UW_ChIP-seq | CCACCAGAGGGCG | CGCCCTCTGGTGG |
| CTCF_HeLa-53_CTCF_Broad_ChIP-seq\|CTCF_SRP000217_Ctcf_ChIP-seq\|CTCF_NHLF_CTCF_Broad_ChIP-seq\|CTCF_HPAF_CTCF_UW_ChIP-seq\|CTCF_HepG2_CTCF_HudsonAlpha_ChIP-seq | AGCGCCCCTGGTGG | CCACCAGGGGCGCT |
| PAX7_1 | CGAACTAATTAGTACTA | TAGTACTAATTAGTTCG |
| NR2E3_Hr51_SANGER_5_FBgn0034012_B1H | AAAAATCAAGGT | ACCTTGATTTTT |

TABLE 5-continued

Transcription Factor Binding Sites of Synthetic Promoters

| Name | Binding Site Sequence | Reverse Complement |
|---|---|---|
| CR936877.3_RXRG_4_SELEX\|CR936877.3_RXRA_2_SELEX\|RXRA_known11 | GGGGTCATGACCCC | GGGGTCATGACCCC |
| DUXA_DUXA_1_SELEX\|DUXA_1 | CTAATTTAATCAA | TTGATTAAATTAG |
| ESR2_MA0112.2_ChIP-seq\|ESRRA_known4 | AGGTCAGGGTGACCTGGGCC | GGCCCAGGTCACCCTGACCT |
| SPDEF_SPDEF_3_SELEX\|SPDEF_4 | GCAGTAAGAAGTATAC | GTATACTTCTTACTGC |
| YY2_K562b_YY1_UCD_ChIP-seq | CAAGATGGCGGCGGC | GCCGCCGCCATCTTG |
| ZIC1_2 | CACCCCCGGGGGGG | CCCCCCCGGGGGTG |
| ESRRG_ESRRG_3_SELEX\|ESRRG_pTH2311_PBM\|ESRRG_3 | ATGACCTTGA | TCAAGGTCAT |
| SP9_pTH5423_PBM | GAGCGGGA | TCCCGCTC |
| SMARCC1_SMRC1_f1_HocoMoco | CTGAGTCAC | GTGACTCAG |
| ISL2_tup_SOLEXA_10_FBgn0003896_B1H | CTTAATTGA | TCAATTAAG |
| TFAP2A_Tcfap2b_3988_PBM | CCTGAGGCGA | TCGCCTCAGG |
| E2F3_E2F3_si_HocoMoco | CGCGCGAAAC | GTTTCGCGCG |
| TEAD1_MA0090.1_COMPILED\|TEAD1_2 | CACATTCCTCCG | CGGAGGAATGTG |
| ESRRA_known3 | ACCGTGACCTG | CAGGTCACGGT |
| KLF4_CG9895_SOLEXA_5_FBgn0034810_B1H | GGCCACGCCCA | TGGGCGTGGCC |
| RARG_RARB_1_SELEX\|RARG_Rarb_1_SELEX\|RARB_1 | AAAGGTCAAAAGGTCA | TGACCTTTTGACCTTT |
| RARG_pTH4269_PBM\|RARG_pTH2804_PBM | AGAGGTCACC | GGTGACCTCT |
| ZEB1_known5 | CACCTG | CAGGTG |
| NR2C2_pTH1284_PBM | AGAGGTCACG | CGTGACCTCT |
| E2F1_E2F1_f2_HocoMoco\|E2F4_E2F4_do_HocoMoco | AATTGGCGGGAAAA | TTTTCCCGCCAATT |
| MAFK_MAFK_2_SELEX\|MAF_known7 | AAAATGCTGACTCAGCATTTT | AAAATGCTGAGTCAGCATTTT |
| ENSG00000250096_MA0511.1_ChIP-seq | CAAACCACAAACCCC | GGGGTTTGTGGTTTG |
| EP300_disc8 | CGGCGCCCGC | GCGGGCGCCG |
| ETV5_Ets96B_SANGER_5_FBgn0039225_B1H | ACCGGAAGTAC | GTACTTCCGGT |
| RFX5_disc3 | AACTGATGA | TCATCAGTT |
| HLF_pTH9052_PBM | TATTTACGTAACA | TGTTACGTAAATA |
| FOXD1_fd64A_SANGER_5_FBgn0004895_B1H | TATAAACA | TGTTTATA |
| RFX7_1 | CCGCATAGCAACGGA | TCCGTTGCTATGCGG |
| SEF1_1 | AACACGGATATCTGTGGTC | GACCACAGATATCCGTGTT |
| NFIA_NFIX_4_SELEX | CTGGCAAATTGCCAA | TTGGCAATTTGCCAG |
| POU2F2_1\|POU2F3_1 | TCTAATTTGCATACAA | TTGTATGCAAATTAGA |
| REST_PFSK-1_NRSF_HudsonAlpha_ChIP-seq | CAGCACCATGGACAG | CTGTCCATGGTGCTG |
| GRHL1_GRHL1_3_SELEX\|GRHL1_3 | AAAACCGGTTTT | AAAACCGGTTTT |
| NR1H3_EcR_SANGER_5_FBgn0000546_B1H | ATGACCTC | GAGGTCAT |

TABLE 5-continued

Transcription Factor Binding Sites of Synthetic Promoters

| Name | Binding Site Sequence | Reverse Complement |
|---|---|---|
| SREBP_known3 | CACCCCA | TGGGGTG |
| TBX1_TBX1_5_SELEX\|TBX1_4 | TTCACACCTAGAGGTGTGAA | TTCACACCTCTAGGTGTGAA |
| REST_disc10 | AAGGTGCTG | CAGCACCTT |
| SPIC_SP\|1_1_SELEX\|SPIC_SPIB_1_SELEX\|SPIC_Spic_1_SELEX\|SPI1_known4\|SPIB_2\|SPIC_2 | AAAAAGCGGAAGTA | TACTTCCGCTTTTT |
| MAX_GM12878_MAX_Stanford_ChIP-seq | CAGTCACGTGGTC | GACCACGTGACTG |
| MYBL2_pTH3712_PBM | CGACCGTTA | TAACGGTCG |
| TFAP2A_TFAP2A_4_SELEX | AGCCTGAGGCA | TGCCTCAGGCT |
| ZNF691_1 | ATAGTGAGCACTGTTCG | CGAACAGTGCTCACTAT |
| GMEB2_GMEB2_2_SELEX\|GMEB2_2 | AACGTAACCACGTA | TACGTGGTTACGTT |
| STAT1_STAT1_f2_HocoMoco | CATTTCCCGGAAATG | CATTTCCGGGAAATG |
| NR2E1_tll_FlyReg_FBgn0003720_B1H | AAAGTCA | TGACTTT |
| RELA_GM12878_NFKB_Stanford_ChIP-seq | AAGGGGATTTCCAA | TTGGAAATCCCCTT |
| PTF1A_Fer1_SANGER_5_FBgn0037475_B1H | ACGACAGCTGACG | CGTCAGCTGTCGT |
| MSX1_V$MSX1_01_Transfac\|MSX1_1 | CAATTACGG | CCGTAATTG |
| TFAP2A_HeLa-S3_AP2ALPHA_UCD_ChIP-seq | ACTGCCTCAGGGCAT | ATGCCCTGAGGCAGT |
| GATA2_V$GATA1_03_Transfac\|GATA_known5 | AGGAAGATTACCGC | GCGGTAATCTTCCT |
| ELF3_EHF_si_HocoMoco | AAACCCGGAAGTA | TACTTCCGGGTTT |
| ZNF282_ZNF282_1_SELEX\|ZNF282_1 | CTTTCCCACAACACGAC | GTCGTGTTGTGGGAAAG |
| ZNF232_ZNF232_1_SELEX\|ZNF232_1 | ATGTTAAATGTAGATTAAG | CTTAATCTACATTTAACAT |
| ALX3_1 | CTCAGCTAATTAGTTTA | TAAACTAATTAGCTGAG |
| POU3F3_pTH9245_PBM | ATGCTAATTA | TAATTAGCAT |
| PRDM16_V$EVI1_05_Transfac\|PRDM16_V$EVI1_03_Transfac\|RUNX1_4\|RUNX1_6 | AGATAAGATAA | TTATCTTATCT |
| HOXB13_Hoxb13_3479_PBM\|HOXB13_Hoxc13_3127_PBM | GCTCATAAAA | TTTTATGAGC |
| NR2F2_COT2_f2_HocoMoco | AAGGTCAAAGGTCAA | TTGACCTTTGACCTT |
| IRF9_IRF9_f1_HocoMoco | AGTTTCGCTTTC | GAAAGCGAAACT |
| EGR3_Egr3_1_SELEX\|EGR3_3 | AAATGCGTGGGCGTA | TACGCCCACGCATTT |
| DNMT1_pTH7029_PBM | CCCCGCGGCC | GGCCGCGGGG |
| FOXD1_Foxc1_2_SELEX\|FOXC1_7 | ATAAACA | TGTTTAT |
| GCM1_pTH7965_PBM\|GCM1_Gcm1_3732_PBM | ACCCGCATC | GATGCGGGT |
| SRF_V$SRF_01_Transfac\|SRF_known1 | ATGCCCATATATGGTAAT | ATTACCATATATGGGCAT |
| PAX9_pTH8556_PBM | CATGACCACC | GGTGGTCATG |
| TLX2_2 | AAGTTATTAATTAATTA | TAATTAATTAATAACTT |
| ZNF691_Zfp691_0895_PBM | AGGAGCAC | GTGCTCCT |
| ETV5_Ets65A_SANGER_10_FBgn0005658_B1H | ATTTCCGG | CCGGAAAT |

TABLE 5-continued

Transcription Factor Binding Sites of Synthetic Promoters

| Name | Binding Site Sequence | Reverse Complement |
| --- | --- | --- |
| SOX17_Sox17_2_SELEX\|SOX17_5 | ATGAATGAAATTCAT | ATGAATTTCATTCAT |
| ATF5_ATF4_1_SELEX\|ATF4_2 | GGATGATGCAATA | TATTGCATCATCC |
| XBP1_V$HTF_01_Transfac | ATTAAATGACACGTCATCTTTCTG | CAGAAAGATGACGTGTCATTTAAT |
| SIX6_pTH5437_PBM | TAGGGGATAA | TTATCCCCTA |
| TP63_TP63_1_SELEX\|TP63_1 | AACATGTTGGGACATGTC | GACATGTCCCAACATGTT |
| ZBTB33_disc4 | AACCTCGC | GCGAGGTT |
| TBX3_TBX4_2_SELEX\|TBX3_TBX5_2_SELEX\|TBX4_2\|TBX5_5 | AGGTGTGAAATTTCACACCT | AGGTGTGAAATTTCACACCT |
| GATA_disc2 | GTGTGAGTCA | TGACTCACAC |
| RFX3_1 | TGTGACCCTTAGCAACCGATTAA | TTAATCGGTTGCTAAGGGTCACA |
| AP1_disc6 | AAAACCCGGAGCGGA | TCCGCTCCGGGTTTT |
| ZFHX3_ZFHX3_f1_HocoMoco | ATTAATAATTA | TAATTATTAAT |
| HOXC10_HOXD11_2_SELEX\|HOXD11_3 | GGTAATAAAA | TTTTATTACC |
| HOXA4_Ind_Cell_FBgn0025776_B1H | CACTAATTA | TAATTAGTG |
| NKX2-6_1 | AATGTTAAGTGGCTTA | TAAGCCACTTAACATT |
| SP9_SP1_f1_HocoMoco\|SP9_MA0079.3_ChIP-seq | GCCCCGCCCCC | GGGGGCGGGGC |
| BARHL2_CG11085_SOLEXA_FBgn0030408_B1H | ACCAATTAAA | TTTAATTGGT |
| TEF_pTH4377_PBM | AATTTATGTAATA | TATTACATAAATT |
| SRF_disc2 | GAGGGGCCGGC | GCCGGCCCCTC |
| IRF_known7 | GAAAGTGAAACTGAA | TTCAGTTTCACTTTC |
| PRDM16_V$EVI1_04_Transfac\|RUNX1_5 | AGATAAGATAAGATA | TATCTTATCTTATCT |
| STAT5B_V$STAT56_01_Transfac\|STAT_known5 | AAATTCCAGGAAATC | GATTTCCTGGAATTT |
| TP53_V$P53_01_Transfac\|TP53_P53_f2_HocoMoco | AGACATGCCCGGGCATGTCC | GGACATGCCCGGGCATGTCT |

TABLE 5-continued

Transcription Factor Binding Sites of Synthetic Promoters

| Name | Binding Site Sequence | Reverse Complement |
|---|---|---|
| EGR3_GM12878_EGR1_HudsonAlpha_ChIP-seq | CCCCCCCCCCGCCCCCGCAC | GTGCGGGGGCGGGGGGGGGG |
| IRF3_IRF3_f1_HocoMoco | GGAAAGCGAAACTGAAA | TTTCAGTTTCGCTTTCC |
| NFIL3_2 | ATGTTACATAA | TTATGTAACAT |
| CUX1_V$CDPCR1_01_Transfac\|CUX1_3 | AATCGATCGC | GCGATCGATT |
| OVOL1_ovo_FlyReg_FBgn0003028_B1H | AGTAACGG | CCGTTACT |
| PPARA_V$PPARG_03_Transfac\|PPARA_3 | AACTAGGGCAAAGGTCA | TGACCTTTGCCCTAGTT |
| ZEB1_V$AREB6_02_Transfac\|ZEB1_known2 | ATTCACCTGTAC | GTACAGGTGAAT |
| VDR_pTH5509_PBM | ATGAACC | GGTTCAT |
| HNF4G_V$HNF4_01_Transfac | ACAGGGTCAAAGGTCACGA | TCGTGACCTTTGACCCTGT |
| RARG_RARA_S_SELEX\|RARA_6 | AAAGGTCATGTGAGGTCA | TGACCTCACATGACCTTT |
| FOXA2_FOXA2_f1_HocoMoco | CTAAGTAAACAA | TTGTTTACTTAG |
| ATF3_known10 | CTCTGACGTCA | TGACGTCAGAG |
| MYPOP_pTH3456_PBM | TGGCGCAAAA | TTTTGCGCCA |
| TWIST2_MA0249.1_DNaseI\|TWIST_twi_FlyReg_FBgn0003900_B1H | CAACATATGCGA | TCGCATATGTTG |
| GBX2_MA0224.1_B1H\|DLX1_DII_Cell_FBgn0000157_B1H\|GBX2_Exex_Cell_FBgn0041156_B1H\|DLX1_MA0187.1_B1H | GTAATTA | TAATTAC |
| IRX3_Irx3_2226_PBM | ATTACATG | CATGTAAT |
| PPARA_V$PPARG_02_Transfac\|RXRA_known2 | AAGTAGGTCACCGTGACCTACTT | AAGTAGGTCACGGTGACCTACTT |
| NR2E1_NR2E1_1_SELEX\|NR2E1_Nr2e1_1_SELEX\|NR2E1_1\|NR2E1_3 | AAAAGTCAA | TTGACTTTT |
| HOXC5_Hoxb4_2627_PBM\|HOXC5_Hoxb5_3122_PBM\|HOXC5_Hoxb3_1720_PBM\|HOXC5_Hoxc4_3491_PBM\|HOXC5_Hoxa3_2783_PBM | GGTCATTAA | TTAATGACC |
| FOXA2_V$HNF36_01_Transfac | TAAATAAACATTTCA | TGAAATGTTTATTTA |
| AP1_known2 | GGTGACTCAGA | TCTGAGTCACC |
| FEZF2_CG31670_SOLEXA_5_FBgn0031375_B1H | CAAAAAGAGCAACCA | TGGTTGCTCTTTTTG |
| ARNT2_pTH5111_PBM | AAGCACGTGATT | AATCACGTGCTT |
| MYBL2_MYBL2_3_SELEX\|MYBL2_3 | ATAACCGTTAA | TTAACGGTTAT |
| HNF4_disc3 | AGTCCAAAG | CTTTGGACT |
| HOXC5_Hoxb6_3428_PBM | GCCATTA | TAATGGC |
| FOXD1_FOXA1_f1_HocoMoco\|EP300_disc3\|FOXA_known | CAAAGTAAACA | TGTTTACTTTG |

TABLE 5-continued

Transcription Factor Binding Sites of Synthetic Promoters

| Name | Binding Site Sequence | Reverse Complement |
|---|---|---|
| 5 | | |
| CREB3L2_CREB3L1_5_SELEX\|CREB3L2_CREB3L1_3_SELEX\|<br>CREB3L2_Creb3l2_2_SELEX\|CREB3L2_CREB3L1_2_SELEX\|C<br>REB3L1_2\|CREB3L1_3\|CREB3L2_2 | TGCCACGTGGCA | TGCCACGTGGCA |
| E2F_disc2\|EGR1_disc3 | GCGCATGCGC | GCGCATGCGC |
| FOXD1_ECC-1_FOXA1_HudsonAlpha_ChIP-seq | CCCTAAGTAAACAAA | TTTGTTTACTTAGGG |
| TP53_1 | GGACATGCCCGGGCATGTCC | GGACATGCCCGGGCATGTCC |
| FOXD1_FOXC1_f1_HocoMoco | CGTTGTTTACTTAAG | CTTAAGTAAACAACG |
| PKNOX2_Mrg2_2302_PBM\|PKNOX2_Mrg1_2246_PBM | ACCTGTCAA | TTGACAGGT |
| SCRT2_scrt_SOLEXA_2.5_2_FBgn0004880_B1H | ACCACCTGTTGCA | TGCAACAGGTGGT |
| MYBL1_MYB_f1_HocoMoco | CAGTTGG | CCAACTG |
| MEIS1_pTH5781_PBM | ACCTGTCAT | ATGACAGGT |
| TP73_P73_si_HocoMoco | CAGACCTGCCCC | GGGGCAGGTCTG |
| JUN_HepG2_JUND_HudsonAlpha_ChIP-seq | GAGGATGAGTCAC | GTGACTCATCCTC |

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

SEQUENCE LISTING

The patent contains a lengthy sequence listing. A copy of the sequence listing is available in electronic form from the USPTO web site (https://seqdata.uspto.gov/?pageRequest=docDetail&DocID=US11718860B2). An electronic copy of the sequence listing will also be available from the USPTO upon request and payment of the fee set forth in 37 CFR 1.19(b)(3).

What is claimed is:

1. An engineered nucleic acid comprising a promoter that comprises the following sequence: TFBS-AGA-TFBS-TCG-TFBS-GAC-TFBS-CTA-TFBS-ACT-TFBS-TGC-TFBS-GTA-TFBS, wherein TFBS comprises the following sequence: CCACGTGC (SEQ ID NO: 12265).

2. The engineered nucleic acid of claim 1, wherein the promoter is operably linked to a nucleotide sequence encoding a therapeutic protein.

3. The engineered nucleic acid of claim 1, wherein the promoter comprises the following sequence:

(SEQ ID NO: 12266)
CCACGTGCAGACCACGTGCTCGCCACGTGCGACCCACGTGCCTACCACG
TGCACTCCACGTGCTGCCCACGTGCGTACCACGTGCG.

4. A cell comprising the engineered nucleic acid of claim 1.

5. An oncolytic virus comprising the engineered nucleic acid of claim 1.

6. The oncolytic virus of claim 5, wherein the oncolytic virus is an oncolytic herpes simplex virus.

7. An engineered nucleic acid comprising a promoter that comprises a nucleotide sequence identified by SEQ ID NO: 41, or a nucleotide sequence at least 95% identical to a nucleotide sequence identified by SEQ ID NO: 41.

* * * * *

UNITED STATES PATENT AND TRADEMARK OFFICE
CERTIFICATE OF CORRECTION

| | | |
|---|---|---|
| PATENT NO. | : 11,718,860 B2 | Page 1 of 1 |
| APPLICATION NO. | : 16/493340 | |
| DATED | : August 8, 2023 | |
| INVENTOR(S) | : Timothy Kuan-Ta Lu et al. | |

It is certified that error appears in the above-identified patent and that said Letters Patent is hereby corrected as shown below:

In the Specification

At Column 1, Lines 16-20, the paragraph under the heading "FEDERALLY SPONSORED RESEARCH":
"This invention was made with Government support under Grant No. W911NF-11-2-0056 awarded by the Army Research Office and under Grant No. P50 GM098792 awarded by the National Institutes of Health. The Government has certain rights in the invention."

Should read:
-- This invention was made with government support under W911NF-11-2-0056 awarded by the U.S. Army Research Office, and GM098792 awarded by the National Institutes of Health. The government has certain rights in the invention. --

Signed and Sealed this
Twenty-eighth Day of November, 2023

Katherine Kelly Vidal
*Director of the United States Patent and Trademark Office*